United States Patent
Cuevas Marchante et al.

(10) Patent No.: US 12,410,148 B2
(45) Date of Patent: Sep. 9, 2025

(54) ANTIBODY DRUG CONJUGATES

(71) Applicant: Pharma Mar, S.A., Madrid (ES)

(72) Inventors: Carmen Cuevas Marchante, Madrid (ES); Juan Manuel Dominguez Correa, Madrid (ES); Andres Francesch Solloso, Madrid (ES); Maria Garranzo Garcia-Ibarrola, Madrid (ES); Maria Jose Munoz Alonso, Madrid (ES); Francisco Sanchez Madrid, Madrid (ES); Juan Manuel Zapata Hernandez, Madrid (ES); Alicia Garcia Arroyo, Madrid (ES); Maria Angeles Ursa Pecharroman, Madrid (ES)

(73) Assignee: PARMA MAR, S.A., Madrid (ES)

( * ) Notice: Subject to any disclaimer, the term of this patent is extended or adjusted under 35 U.S.C. 154(b) by 787 days.

(21) Appl. No.: 17/553,745

(22) Filed: Dec. 16, 2021

(65) Prior Publication Data

US 2022/0168436 A1     Jun. 2, 2022

Related U.S. Application Data

(62) Division of application No. 14/894,685, filed as application No. PCT/EP2014/061392 on Jun. 2, 2014, now Pat. No. 11,224,663.

(30) Foreign Application Priority Data

May 31, 2013  (GB) ...................... 1309807

(51) Int. Cl.
*A61K 47/68* (2017.01)
*C07D 309/30* (2006.01)
(Continued)

(52) U.S. Cl.
CPC ........ *C07D 309/32* (2013.01); *A61K 47/6803* (2017.08); *A61K 47/6849* (2017.08);
(Continued)

(58) Field of Classification Search
None
See application file for complete search history.

(56) References Cited

U.S. PATENT DOCUMENTS 7,662,387 B2 * 2/2010 Law ................... A61K 47/6849
                                                     424/178.1

FOREIGN PATENT DOCUMENTS

EP          1864682 A1    12/2007
WO       2004010957 A2     2/2004
(Continued)

OTHER PUBLICATIONS

ADC Review, What Are Cytotoxic Agents, Mar. 23, 2019.
(Continued)

*Primary Examiner* — Karl J Puttlitz
(74) *Attorney, Agent, or Firm* — Ballard Spahr LLP

(57) ABSTRACT

Drug conjugates of formula $[D-(X)_b-(AA)_w-(L)-]_n-Ab$ wherein:
D is a drug moiety having the following formula (I) or a pharmaceutically acceptable salt, ester, solvate, tautomer or stereoisomer thereof, wherein:

(I)

(Continued)

A is selected from

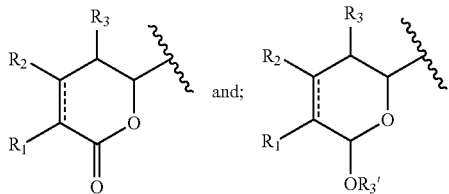

and;

$R_1$, $R_2$ and $R_3$ is H, $OR_a$, $OCOR_a$, $OCOOR_a$, alkyl, alkenyl, alkynyl, etc; $R_3'$ is, $COR_a$, $COOR_a$, $CONR_aR_b$, etc; each of $R_4$ to $R_{10}$ and $R_{12}$ is alkyl, alkenyl or alkynyl; $R_{11}$ is H, $COR_a$, $COOR_a$, alkyl, alkenyl or alkynyl, or $R_{11}$ and $R_{12}$+N+C atoms to which they are attached may form a heterocyclic group; each of $R_{13}$ and $R_{14}$ is H, $COR_a$, $COOR_a$, alkyl, alkenyl or alkynyl; each $R_a$ and $R_b$ is H, alkyl, alkenyl, alkynyl, etc.;

each dotted line represents an optional additional bond;

X is an extending group; AA is an amino acid unit; L is a linker group; w is 0 to 12; b is 0 or 1; Ab is a moiety comprising at least one antigen binding site, and n is the ratio of the group [D-(X)$_b$-(AA)$_w$-(L)-] to the moiety comprising at least one antigen binding site and is in the range from 1 to 20, are useful in the treatment of cancer.

8 Claims, 38 Drawing Sheets

(51) Int. Cl.
  *C07D 309/32* (2006.01)
  *C07D 405/12* (2006.01)
(52) U.S. Cl.
  CPC ........ *A61K 47/6855* (2017.08); *C07D 309/30* (2013.01); *C07D 405/12* (2013.01)

(56) References Cited

FOREIGN PATENT DOCUMENTS

| WO | 2005037992 | A2 | 4/2005 | |
|---|---|---|---|---|
| WO | 2006060533 | A2 | 6/2006 | |
| WO | WO-2007144423 | A1 * | 12/2007 | ........... A61K 31/366 |
| WO | 2009080761 | A1 | 7/2009 | |
| WO | 2009080769 | A1 | 7/2009 | |
| WO | 2009143313 | A1 | 11/2009 | |
| WO | 2010009124 | A2 | 1/2010 | |
| WO | 2010149688 | A2 | 12/2010 | |

OTHER PUBLICATIONS

Avilés, P., et al. (2018). MI130004, a novel antibody-drug conjugate combining trastuzumab with a molecule of marine origin, shows outstanding In Vivo activity against HER2-expressing tumors. Molecular cancer therapeutics, 17(4), 786-794.
Dominguez et al., CD13 as a new tumor target for antibod••drug conjugates: validation with the conjugate MI130110, Journal of Hematology & Oncology, (2020) 13;32.
Jain, N., Smith, S. W., Ghone, S., & Tomczuk, B. (2015). Current ADC linker chemistry. Pharmaceutical research, 32(11), 3526-3540.
Kudo, N., et al. (1999). Leptomycin B inactivates CRM1/exportin 1 by covalent modification at a cysteine residue in the central conserved region. Proceedings of the National Academy of Sciences, 96(16), 9112-9117.
M Gromek, S., & J Balunas, M. (2014). Natural products as exquisitely potent cytotoxic payloads for antibody-drug conjugates. Current Topics in Medicinal Chemistry, 14(24), 2822-2834.
Pera, B., et al. (2013). New interfacial microtubule inhibitors of marine origin, PM050489/PM060184, with potent antitumor activity and a distinct mechanism. ACS chemical biology, 8(9), 2084-2094.
Tolcher, A. W. (2016). Antibody drug conjugates: lessons from 20 years of clinical experience. Annals of Oncology, 27(12), 2168-2172.
Dumontet, C, "Microtubule binding agents: a dynamic target for cancer therapeutics," Nature Reviews Drug Discovery, 9(10): 790-803 (2010).
Flygare et al., Chemical Biology and Drug Design, vol. 81(1), 2013, pp. 113-121.
Garranzo et al., "PharmaMar Payloads: the essential link for ADCs," PharmaMar, poster presented during the ADC World Congress, Frankfurt, Germany, Feb. 17-21, 2014.
Gromek S. & M.J. Balunas, "Natural Products as Exquisitely Potent Cytotoxic Payloads for Antibody-Drug Conjugates," Current Topics in Medicinal Chemistry, 14:2822-2834 (2014).
Hernandez Baltazar, E. and Gonzalez Christian, J. Antibody-Drug Conjugates: The state of the art. Rev. mex. science. farm [online]. 2011, vol. 42, n.3 [cited Jul. 7, 2023], pp. 7-16. Available at: <http://www.scielo.org.mx/scielo.php?script=sci_arttext&pid=S1870-01952011000300002&lng=es&nrm=iso>. ISSN 1870-0195.
Tumors MV Nora De Souza (The Scientific World Journal, 2004, 4, 415-436 (Year: 2004).
Pharma Mar S.A.U., Search Report under Section 17(5) for Application No. GB1309807.4, 5 pages, Dec. 2, 2013.
"PharmaMar Payloads: the essential link for ADCs", communication to the World ADC Congress, Feb. 17-20, 2014, Frankfurt, Germany.
Prota, A.E et al "A new tubulin-binding site and phamacophore for microtubule-destabilizing anticaner drugs," PNAS, vol. 111(38), 13817-13821 (2014).
Aviles et al. entitled "MI130110, a new antibody-drug conjugate combining an anti-CD13 antibody and a payload [PM050489] of marine origin shows remarkable in vivo activity", European J. Cancer, 69(1):S130-S131, Dec. 2016 (Poster and Abstract).

* cited by examiner

Statistical significance (student's t test): * $p < 0.05$,  $p < 0.01$, * $p < 0.001$ Statistical significance (student's t test): * $p < 0.05$,  $p < 0.01$, * $p < 0.001$ Statistical significance (student's t test): * $p < 0.05$,  $p < 0.01$, * $p < 0.001$ Statistical significance (student's t test): *** p < 0.001

Statistical significance (student's t test): *** $p < 0.001$

Statistical significance (student's t test): * $p < 0.05$,  $p < 0.01$, * $p < 0.001$ Statistical significance (student's t test): * $p < 0.05$,  $p < 0.01$, * $p < 0.001$ Statistical significance (student's t test): * $p < 0.001$ Statistical significance (student's t test): * $p < 0.001$ Statistical significance (student's t test): * $p < 0.001$ Statistical significance (student's t test):  $p < 0.01$, *** $p < 0.001$ Statistical significance (student's t test): * $p < 0.05$,  $p < 0.01$, * $p < 0.001$ Statistical significance (student's t test): * $p < 0.05$,  $p < 0.01$, * $p < 0.001$ Statistical significance (student's t test): * $p < 0.05$,  $p < 0.01$, * $p < 0.001$ Statistical significance (student's t test): * $p < 0.05$,  $p < 0.01$, * $p < 0.001$ Statistical significance (student's t test): * $p < 0.05$,  $p < 0.01$, * $p < 0.001$ Statistical significance (student's t test): * p < 0.05,  p < 0.01, * p < 0.001

Statistical significance (student's t test): *** p < 0.001

ANTIBODY DRUG CONJUGATES

FIELD OF THE INVENTION

The present invention relates to novel drug conjugates, drug linker compounds, to methods for their preparation, pharmaceutical compositions containing said drug conjugates and their use as antitumoral agents.

BACKGROUND TO THE INVENTION

International publications numbers WO-A-2007/1 44423 and WO-A-2009/080761 disclose novel dihydropyran-2-one and tetrahydropyran-2-one derivatives which demonstrate very promising anti-tumor activity. PM060184 disclosed in WO-A-2007/1 44423 is currently in Phase I clinical trials for the prevention and treatment of solid tumors.

The treatment of cancer has progressed significantly in recent years with the development of pharmaceutical entities that target and kill cancer cells more efficiently. Researchers have taken advantage of cell-surface receptors and antigens selectively expressed by target cells such as cancer cells to develop pharmaceutical entities based on antibodies that bind, in the example of tumors, the tumor-specific or tumor-associated antigens. In order to achieve this, cytotoxic molecules such as chemotherapeutic drugs, bacteria and plant toxins and radionuclides have been chemically linked to monoclonal antibodies that bind tumor-specific or tumor-associated cell surface antigens (see, for example, International Patent Applications WO-A-2004/010957, WO-A-2006/060533 and WO-A-2007/024536). Such compounds are typically referred to as drug, toxin and radionuclide "conjugates". Tumor cell killing occurs upon binding of the drug conjugate to a tumor cell and release or/and activation of the cytotoxic activity of the drug moiety. The selectivity afforded by drug conjugates minimizes toxicity to normal cells, thereby enhancing tolerability of the drug in the patient. Three examples of drug antibody conjugates of this type that have received marketing approval are: Gemtuzumab ozogamicin for acute myelogenous leukemia, Brentuximab vedotin for relapsed and refractory Hodgkin lymphoma and anaplastic large cell lymphoma, and ado-Trastuzumab emtansine for breast cancer, especially HER2+.

The effectiveness of drugs for cancer chemotherapy generally relies on differences in growth rates, biochemical pathways, and physiological characteristics between cancer and normal tissues. Consequently, most standard chemotherapeutics are relatively nonspecific and exhibit dose-limiting toxicities that contribute to suboptimal therapeutic effects. One approach to selectively target malignant cells and not healthy tissues is to use specific monoclonal antibodies (mAbs) that recognize tumor-associated antigens expressed on the surface of tumor cells [Meyer, D. L. & Senter, P. D. (2003) Recent advances in antibody drug conjugates for cancer therapy. Annu. Rep. Med. Chem., 38, 229-237; Chari, R. V. (2008) Targeted cancer therapy: conferring specificity to cytotoxic drugs. Acc. Chem. Res. 41, 98-107]. mAbs and derivatives are currently the fastest growing class of therapeutic molecules. More than 30 G-type immunoglobulins (IgG) and related agents have been approved over the past 25 years mainly for cancers and inflammatory diseases. In oncology, mAbs are often combined with cytotoxic drugs to enhance their therapeutic efficacy. Alternatively, small anti-neoplastic molecules can be chemically conjugated to mAbs, used both as carriers (increased half-life) and as targeting agents (selectivity).

Considerable effort has been directed toward the use of monoclonal antibodies (mAbs) for targeted drug delivery due to their high selectivities for tumor-associated antigens, favorable pharmacokinetics, and relatively low intrinsic toxicities. The mAb-drug conjugates (ADCs) are formed by covalently linking anticancer drugs to mAbs, usually through a conditionally stable linker system. Upon binding to cell surface antigens, mAbs used for most ADCs are actively transported to lysosomes or other intracellular compartments, where enzymes, low pH, or reducing agents facilitate drug release.

Antigens must have high tumor cell selectivity to limit toxicity and off-target effects. A plethora of tumor-associated antigens have been investigated in pre-clinical models and in clinical trials including antigens over-expressed in B-cells (e.g., CD20, CD22, CD40, CD79), T-cells (CD25, CD30), carcinoma cells (HER2, EGFR, EpCAM, EphB2, PSMA), endothelial (endoglin), or stroma cells (fibroblast activated protein), to name a few [Teicher B A. Antibody-drug conjugate targets. Curr Cancer Drug Targets 9(8):982-1004, 2009]. A major and critical property for ADC targets is their ability to be internalized; this can be an intrinsic feature of the antigen by itself, or it can be induced by the binding of the antibody to its antigen. Indeed, ADC internalization is crucial to reduce toxicity associated with an extracellular delivery of the drug payload.

Regarding the conjugated small molecules and in contrast to the vast variety of putative antigen targets, a limited number of families of cytotoxic drugs used as payloads in ADCs are currently actively investigated in clinical trials: calicheamycin (Pfizer), duocarmycins (Synthon), pyrrolobenzodiazepines (Spirogen), irinotecan (Immunomedics), maytansinoids (DM1 and DM4; ImmunoGen+Genentech/Roche, Sanofi-Aventis, Biogen Idee, Centocor/Johnson & Johnson, Millennium/Takeda), and auristatins (MMAE and MMAF; Seattle Genetics+Genentech/Roche, MedImmune/AstraZeneca, Bayer-Schering, Celldex, Progenies, Genmab). Calicheamycin duocarmycins and pyrrolobenzodiazepines are DNA minor groove binders, irinotecan is a Topoisomerase I inhibitor, whereas maytansinoids and auristatins are tubulin depolymerization agents. One of their common features is their high free drug potency (10-9 to 10-1 1 M) in comparison, for example, to doxorubicin (10-7 M) used in the first generation ADCs. Another key element for success is the clear knowledge of a "permissive" position for the linker attachment that allows the release of active metabolites, similar to traditional prodrugs.

Interestingly, a representative of three of these cytotoxic-derived ADCs has reaches late stage clinical trials. Trastuzumab emtansine (T-DM1), trastuzumab linked to a maytansinoid hemi-synthetic drug by a stable linker (FDA approval on Feb. 22, 2013 for advanced HER2 positive breast cancer); Inotuzumab ozogamicin (CMC-544), a humanized anti-CD22 mAb (G5/44, IgG4) conjugated to calicheamycin with an acid labile linker (acetylphenoxybutanoic) (B-cell non-Hodgkin's lymphoma); Brentuximab vedotin, a humanized anti-CD30 mAb linked to monomethyl auristatin E (MMAE), via a maleimidecaproyl-valyl-citrullinyl-p-aminobenzylcarbamate linker (FDA approval on Aug. 19, 2011 for anaplastic large cell lymphoma and Hodking's lymphoma).

Linkers represent the key component of ADC structures. Several classes of second generation linkers have been investigated, including acid-labile hydrazone linkers (lysosomes) (e.g. gemtuzumab and inotuzumab ozogamicin); disulfide-based linkers (reductive intracellular environment); non-cleavable thioether linkers (catabolic degradation in lysosomes) (e.g., trastuzumab emtansine); peptide linkers (e.g. citruline-valine) (lysosomal proteases like cathepsin-B) (e.g. brentuximab vedotin): see, for example, WO-A-2004/010957, WO-A-2006/060533 and WO-A-2007/024536. Purification of antibody-drug conjugates by size exclusion chromatography (SEC) has also been described [see, e.g., Liu et al., Proc. Natl. Acad. Set (USA), 93: 8618-8623 (1996), and Chari et al., Cancer Research, 52: 127-131 (1992)].

Trastuzumab (Herceptin) is a monoclonal antibody that interferes with the HER2/neu receptor. Its main use is to treat certain breast cancers. The HER receptors are proteins that are embedded in the cell membrane and communicate molecular signals from outside the cell (molecules called EGFs) to inside the cell, and turn genes on and off. The HER proteins stimulate cell proliferation. In some cancers, notably certain types of breast cancer, HER2 is over-expressed, and causes cancer cells to reproduce uncontrollably.

The HER2 gene is amplified in 20-30% of early-stage breast cancers, which makes it overexpress epidermal growth factor (EGF) receptors in the cell membrane. In some types of cancer, HER2 may send signals without growth factors arriving and binding to the receptor, making its effect in the cell constitutive; however, trastuzumab is not effective in this case.

The HER2 pathway promotes cell growth and division when it is functioning normally; however when it is over-expressed, cell growth accelerates beyond its normal limits. In some types of cancer the pathway is exploited to promote rapid cell growth and proliferation and hence tumor formation. In cancer cells the HER2 protein can be expressed up to 100 times more than in normal cells (2 million versus 20,000 per cell). This overexpression leads to strong and constant proliferative signaling and hence tumor formation. Overexpression of HER2 also causes deactivation of checkpoints, allowing for even greater increases in proliferation.

SUMMARY OF THE INVENTION

There is a need for novel active drug conjugates that are not based on the families of cytotoxic drugs that have been used as payloads to date. The present invention addresses this need. It further provides novel drug linker compounds for use in the preparation of drug conjugates of the present invention, processes for the preparation of the novel drug conjugates of the present invention, pharmaceutical compositions containing said drug conjugates and their use as antitumoral agents, as well as a kit comprising the drug conjugate of the present invention for use in the treatment of cancer.

In a first aspect of the present invention there is provided a drug conjugate comprising a drug moiety covalently attached to the rest of the drug conjugate, the compound having formula $[D-(X)_b-(AA)_w-(L)-]_n-Ab$ wherein:
D is a drug moiety having the following formula (I) or a pharmaceutically acceptable salt, ester, solvate, tautomer or stereoisomer thereof, wherein:

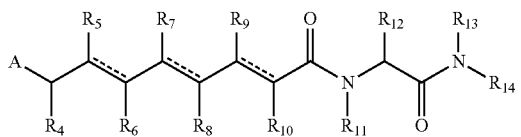

(I)

A is selected from

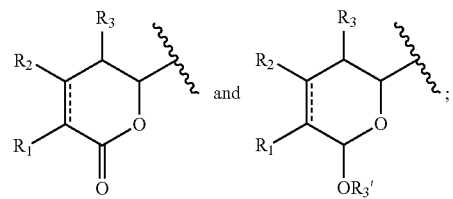

each of R1, $R_2$ and $R_3$ is independently selected from hydrogen, $OR_a$, $OCOR_a$, $OCOOR_a$, $NR_aR_b$, $NR_aCOR_b$, $NR_aC(=NR_a)NR_aR_b$, substituted or unsubstituted C1-C12 alkyl, substituted or unsubstituted C2-C12 alkenyl and substituted or unsubstituted $C_2$-C1$_2$ alkynyl, wherein the optional substituents are one or more substituents $R_x$;

$R_{3'}$ is selected from hydrogen, CORa, COORa, CONRaR$_b$, $S(O)R_a$, $SO_2Ra$, $P(O)(R_a)R_b$, substituted or unsubstituted C1-C1$_2$ alkyl, substituted or unsubstituted $C_2$-Ci$_2$ alkenyl and substituted or unsubstituted $C_2$-Ci$_2$ alkynyl, wherein the optional substituents are one or more substituents $R_x$;

each of $R_4$, R5, R-6, $R_7$, Rs, R9, R10 and R1$_2$ is independently selected from the group consisting of hydrogen, substituted or unsubstituted C1-C1$_2$ alkyl, substituted or unsubstituted $C_2$-Ci$_2$ alkenyl and substituted or unsubstituted $C_2$-Ci$_2$ alkynyl, wherein the optional substituents are one or more substituents $R_x$;

R11 is selected from the group consisting of hydrogen, $COR_a$, $COOR_a$, substituted or unsubstituted C1-C1$_2$ alkyl, substituted or unsubstituted $C_2$-Ci$_2$ alkenyl and substituted or unsubstituted $C_2$-Ci$_2$ alkynyl, or R11 and R1$_2$ together with the corresponding N atom and C atom to which they are attached may form a 5- to 14-membered substituted or unsubstituted unsaturated or saturated heterocyclic group having one or more rings and optionally comprising one or more further heteroatoms selected from oxygen, nitrogen and sulphur atoms in said ring(s) in addition to the nitrogen atom of the NR11, wherein the optional substituents are one or more substituents $R_x$;

each of $R_{13}$ and R1$_4$ is independently selected from the group consisting of hydrogen, CORa, COORa, substituted or unsubstituted C1-C1$_2$ alkyl, substituted or unsubstituted $C_2$-Ci$_2$ alkenyl, substituted or unsubstituted $C_2$-Ci$_2$ alkynyl and substituted or unsubstituted $C_4$-C12 alkenynyl, wherein the optional substituents are one or more substituents $R_x$;

each of $R_a$ and $R_b$ is independently selected from the group consisting of hydrogen, substituted or unsubstituted C1-C12 alkyl, substituted or unsubstituted C2-C12 alkenyl, substituted or unsubstituted C2-C12 alkynyl, substituted or unsubstituted aryl groups having from 6 to 18 carbon atoms in one or more rings, and 5- to 14-membered substituted or unsubstituted unsaturated or saturated heterocyclic groups having one or more rings, wherein the optional substituents are one or more substituents $R_x$;

substituents $R_x$ are selected from the group consisting of $C_1$-$C_{12}$ alkyl groups which may be optionally substituted with at least one group $R_y$, $C_2$-Ci$_2$ alkenyl groups which may be optionally substituted with at least one group $R_y$, $C_2$-Ci$_2$ alkynyl groups which may be optionally substituted with at least one group $R_y$, halogen atoms, oxo groups, thio groups, cyano groups, nitro groups, $OR_y$, $OCOR_y$, $OCOOR_y$, $COR_y$, $COOR_y$, $OCON R_yR_z$, $CON R_yR_z$, $S(0)R_y$, $SO_2R_y$, $P(O)(R_y)$ $OR_z$, $NR_yR_z$, $NR_yCOR_z$, $NR_yC(=0)N$ $R_yR_z$, $NR_yC(=N R_y)NR_yR_z$, aryl groups having from 6 to 18 carbon atoms in one or more rings which may optionally be substituted with one or more substituents which may be the same or different selected from the group consisting of $R_y$, ORy, OCORy, OCOORy, $NR_yR_z$, NRyCORz and $NR_yC(=N\ R_y)NR_yR_z$, aralkyl groups comprising an alkyl group having from 1 to 12 carbon atoms substituted with an optionally substituted aryl group as defined above, aralkyloxy groups comprising an alkoxy group having from 1 to 12 carbon atoms substituted with an optionally substituted aryl group as defined above, and a 5- to 14-membered saturated or unsaturated heterocyclic group having one or more rings and comprising at least one oxygen, nitrogen or sulphur atom in said ring(s), said heterocyclic group optionally being substituted with one or more substituents $R_y$, and where there is more than one optional substituent on any given group the optional substituents $R_y$ may be the same or different;

each $R_y$ and $R_z$ is independently selected from the group consisting of hydrogen, $C_1$. $C_{12}$ alkyl groups, $C_1$-$C_{12}$ alkyl groups that are substituted with at least one halogen atom, aralkyl groups comprising a $C_1$-$C_{12}$ alkyl group that is substituted with an aryl group having from 6 to 18 carbon atoms in one or more rings and heterocycloalkyl groups comprising a $C_1$-$C_{12}$ alkyl group that is substituted with a 5- to 14-membered unsaturated or saturated heterocyclic group having one or more rings and comprising at least one oxygen, nitrogen or sulphur atom in said ring(s);

each dotted line represents an optional additional bond;

each wavy line indicates a point of covalent attachment of the group A to the rest of the drug moiety;

X is an extending group;

each AA is independently an amino acid unit;

L is a linker group;

w is an integer ranging from 0 to 12;

b is an integer of 0 or 1;

Ab is a moiety comprising at least one antigen binding site; and n is the ratio of the group [D-$(X)_b$-$(AA)_w$-(L)-] to the moiety comprising at least one antigen binding site and is in the range from 1 to 20

As we shall explain and exemplify in greater detail below, the drug conjugates of formula [D-$(X)_b$-$(AA)_w$-(L)-]$_n$-Ab of the present invention represent a breakthrough in addressing the problems outlined above of requiring further drug conjugates in addition to those based on the three main families of cytotoxic drugs that have been used as payloads to date, that show excellent antitumor activity.

In a preferred embodiment of the first aspect of the present invention, there is provided a drug conjugate according to claim 1, or a pharmaceutically acceptable salt, ester, solvate, tautomer or stereoisomer thereof, wherein D is a drug moiety selected from formulas (Ia) and (Ib):

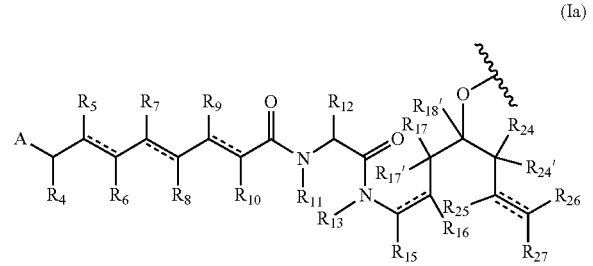

(Ia)

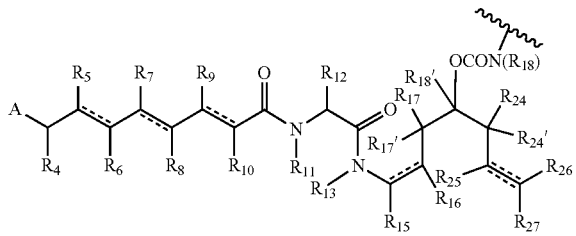

(Ib)

wherein the wavy lines of (Ia) and (Ib) indicate the point of covalent attachment to $(X)_b$ if any, or $(AA)_W$ if any, or the linker group L;

A is selected from

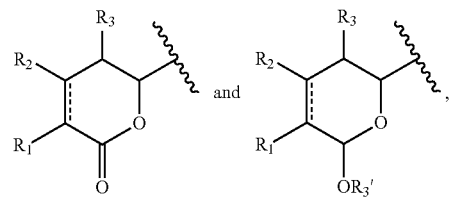

wherein the wavy lines of the moiety A indicate the point of covalent attachment to the rest of the drug moiety;

each of R1, R2, R3, R3', $R_4$, R5, R6, R7, Rs, R9, Rio, Rn, Ri2, Ri3, Ra, Rb, Rx, Ry and Rz is as defined in the first aspect of the present invention;

each of $R1_5$, R16, R17, $R_{77}$, R18', $R_{24}$, $R_{24}'$, R25 and $R_26$ is independently selected from the group consisting of hydrogen, substituted or unsubstituted C1-C12 alkyl, substituted or unsubstituted C2-C12 alkenyl and substituted or unsubstituted C2-C12 alkynyl, wherein the optional substituents are one or more substituents $R_x$;

$R_{18}$ is selected from the group consisting of hydrogen, $C_1$-$C_{12}$ alkyl groups which may optionally be substituted with at least one group $R_x$, aryl groups having from 6 to 18 carbon atoms in one or more aromatic rings, said aryl groups optionally being substituted with one or more substituents $R_x$, and 5- to 14-membered substituted or unsubstituted unsaturated or saturated heterocyclic groups having one or more rings, wherein the optional substituents are one or more substituents $R_x$;

$R_{27}$ is selected from hydrogen, substituted or unsubstituted $C_1$-$C_{12}$ alkyl and halogen;

and each dotted line represents an optional additional bond, but when a triple bond exists between the C atom to which $R_{25}$ is attached and the C atom to which $R_{26}$ and $R_{27}$ are attached, then $R_{25}$ and either $R_{26}$ or $R_{27}$ are absent.

In a second aspect of the present invention, there is provided a compound of formula D-X-(AA)»-.|.; or of formula D-X-$(AA)_W$-H, wherein:

|$_{-1}$ is a linker selected from the group of formulas consisting of:

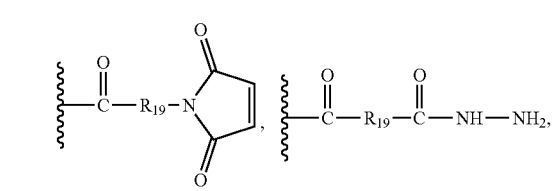

-continued

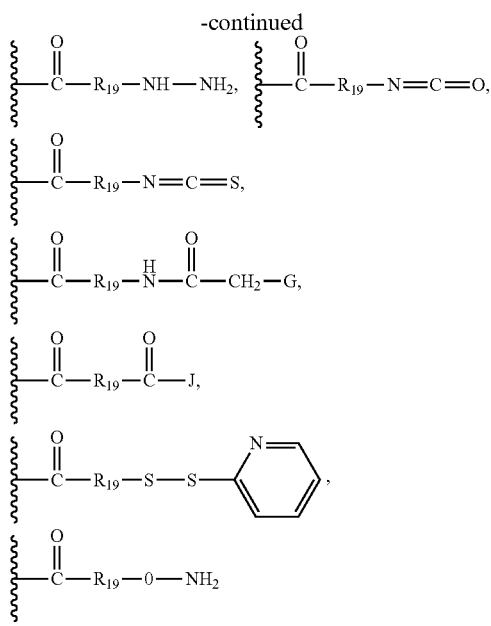

each of the wavy lines indicates the point of covalent attachment to $(AA)_w$ if any, or to X;
G is selected from halo, —O-mesyl and —O-tosyl;
J is selected from halo, hydroxy, —N-succinimidoxy, -0-(4-nitrophenyl), —O-pentafluorophenyl, —O-tetrafluorophenyl and –0-C(0)-OR$_2$°;
Rig is selected from —C1-C12 alkylene-, —C$_3$-C$_8$ carbocyclo, -0-(Ci-Ci$_2$ alkylene), —C$_6$-C18 arylene in one or more rings which may optionally be substituted with one or more substituents R$_x$, —C1-C12 alkylene-C$_6$-Ci$_8$ arylene- wherein the arylene group is in one or more rings which may optionally be substituted with one or more substituents R$_x$, —C$_6$-Ci$_8$ arylene-Ci-Ci2 alkylene- wherein the arylene group is in one or more rings which may optionally be substituted with one or more substituents R$_x$, —C1-C12 alkylene-(C$_3$-C$_8$ carbocyclo)-, —(C$_3$-C$_8$ carbocyclo)-Ci-Ci$_2$ alkylene-, —C5-C14 heterocyclo- wherein said heterocyclo group may be a saturated or unsaturated group having one or more rings and comprising at least one oxygen, nitrogen or sulphur atom in said ring(s), said group optionally being substituted with one or more substituents R$_x$, —C1-C12 alkylene-(C$_5$-Ci$_4$ heterocyclo)- wherein said heterocyclo group may be a saturated or unsaturated group having one or more rings and comprising at least one oxygen, nitrogen or sulphur atom in said ring(s), said group optionally being substituted with one or more substituents R$_x$, —(C5-C14 heterocyclo)-C1-C12 alkylene-, wherein said heterocyclo group may be a saturated or unsaturated group having one or more rings and comprising at least one oxygen, nitrogen or sulphur atom in said ring(s), said group optionally being substituted with one or more substituents R$_x$, —(OCH$_2$CH$_2$) r- and —CH2-(OCH$_2$CH2)r-, wherein each of the above alkylene substituents whether alone or attached to another moiety the carbon chain may optionally be substituted by one or more substituents R$_x$;
R2$_0$ is a C1-C12 alkyl or an aryl group having from 6 to 18 carbon atoms in one or more aromatic rings, said aryl groups optionally being substituted with one or more substituents R$_x$;
r is an integer ranging from 1-10; and
each of D, X, AA and w is as defined in the first aspect of the invention.

In a third aspect of the present invention, there is provided a drug conjugate according to the first aspect of the invention, for use as a medicament.

In a fourth aspect of the present invention, there is provided a drug conjugate according to the first aspect of the invention for use in the treatment of cancer, and more preferably a cancer selected from lung cancer, colorectal cancer, breast cancer, pancreas carcinoma, kidney cancer, leukaemia, multiple myeloma, lymphoma and ovarian cancer. Most preferred cancers are selected from colorectal cancer, breast cancer, leukaemia, lymphoma, and ovarian cancer.

In a fifth aspect of the present invention, there is provided a pharmaceutical composition comprising a drug conjugate according to the first aspect of the invention and a pharmaceutically acceptable carrier.

In a sixth aspect of the present invention, there is provided a method for the prevention or treatment of cancer, comprising administering an effective amount of a drug conjugate according to the first aspect of the present invention to a patient in need thereof. Preferably, the cancer is selected from lung cancer, colorectal cancer, breast cancer, pancreas carcinoma, kidney cancer, leukaemia, multiple myeloma, lymphoma and ovarian cancer. Most preferred cancers are selected from colorectal cancer, breast cancer, leukaemia, lymphoma, and ovarian cancer.

In a seventh aspect of the present invention, there is provided the use of a drug conjugate according to the first aspect of the present invention in the preparation of a medicament for the treatment of cancer, and more preferably a cancer selected from lung cancer, colorectal cancer, breast cancer, pancreas carcinoma, kidney cancer, leukaemia, multiple myeloma, lymphoma and ovarian cancer. Most preferred cancers are selected from colorectal cancer, breast cancer, leukaemia, lymphoma, and ovarian cancer.

In an eighth aspect of the present invention, there is provided a kit comprising a therapeutically effective amount of a drug conjugate according to the first aspect of the invention and a pharmaceutically acceptable carrier. The kit is for use in the treatment of cancer, and more preferably a cancer selected from lung cancer, colorectal cancer, breast cancer, pancreas carcinoma, kidney cancer, leukaemia, multiple myeloma, lymphoma and ovarian cancer. Most preferred cancers are selected from colorectal cancer, breast cancer, leukaemia, lymphoma, and ovarian cancer.

In a ninth aspect of the present invention there is provided a process for the preparation of a drug conjugate according to the first aspect of the present invention comprising conjugating a moiety Ab comprising at least one antigen binding site and a drug D of formula (I), (Ia) or (Ib), Ab and D being as defined in the first aspect of the present invention.

DETAILED DESCRIPTION OF PREFERRED EMBODIMENTS

In the compounds of the present invention, the alkyl groups in the definitions of R$_1$, R2, R3, R3', R$_4$, R5, R6, R7, Re, R9, R-10, R11, RI2, R$_{13}$, R1$_4$, R$_{15}$, R$_{16}$, R$_{17}$, RI7', R$_{18}$, RI8', R20, R2$_4$, R2$_4$', R25, R26, R27, R$_a$, Rb, Rx, R$_y$, and Rz may be straight chain or branched alkyl chain groups having from 1 to 12 carbon atoms, and they are preferably an alkyl group having from 1 to 6 carbon atoms, more preferably a methyl group, an ethyl group or an I-propyl group, and most preferably a methyl group. In the definitions of M and Q, they may be straight chain or branched alkyl chain groups having from 1 to 6 carbon atoms.

In the compounds of the present invention, the alkenyl groups in the definitions of $R_1$, R2, R3, R3', $R_4$, R5, R6, R7, Re, R9, $R_{10}$, R11, R12, $R_{13}$, $R1_4$, $R_{15}$, $R_{16}$, $R_{17}$, R17', R18', $R2_4$, $R_{24'}$, R25, R26, $R_a$, Rb and $R_x$ are branched or unbranched, and may have one or more double bonds and from 2 to 12 carbon atoms. Preferably, they have from 2 to 6 carbon atoms, and more preferably they are branched or unbranched alkenyl groups having 2, 3 or 4 carbon atoms.

In the compounds of the present invention, the alkynyl group in the definitions of $R_1$, R2, R3, R3', $R_4$, R5, R6, R7, Re, R9, RI0, R11, R12, R13, $RI_4$, RI5, RI6, $R_{17}$, RI7', RI8', $R2_4$, $R_{24'}$, R25, R26, $R_a$, Rb and $R_x$ are branched or unbranched, and may have one or more triple bonds and from 2 to 12 carbon atoms. Preferably, they have from 2 to 6 carbon atoms, and more preferably they are branched or unbranched alkynyl groups having 2, 3 or 4 carbon atoms.

In the compounds of the present invention, the alkenynyl groups in the definitions of $R_{13}$ and $R_{14}$ are branched or unbranched, and may have one or more double bonds and one or more triple bonds. Preferably, they have from 4 to 12 carbon atoms, and more preferably they are branched or unbranched alkynyl groups having from 6 to 10 carbon atoms.

In the compounds of the present invention, the halogen substituents in the definitions of R27, Rx, $R_y$ and $R_z$ include F, Cl, Br and I, preferably Cl.

In the compounds of the present invention, the 5- to 14-membered saturated or unsaturated heterocyclic groups in the definitions of $R_x$, $R_a$, Rb, R18, and the heterocyclic groups that may be formed by R11 and $R1_2$ together with the nitrogen atom and carbon atom to which they are attached are heterocyclic groups having one or more rings, comprising at least one oxygen, nitrogen or sulphur atom in said ring(s). The heterocyclic groups are groups which may be heteroaromatic groups or heteroalicyclic groups, the latter of which may be partially unsaturated, both the aromatic and the alicyclic heterocyclic groups containing from 1 to 3 separated or fused rings. Preferably the heteroaromatic and heteroalicyclic groups contain from 5 to 10 ring atoms. Suitable heteroaromatic groups in the compounds of the present invention contain one, two or three heteroatoms selected from N, O or S atoms and include, for example, quinolyl including 8-quinolyl, isoquinolyl, coumarinyl including 8-coumarinyl, pyridyl, pyrazinyl, pyrazolyl, pyrimidinyl, furyl, pyrrolyl, thienyl, thiazolyl, isothiazolyl, triazolyl, tetrazolyl, isoxazolyl, oxazolyl, imidazolyl, indolyl, isoindolyl, indazolyl, indolizinyl, phthalazinyl, pteridinyl, purinyl, oxadiazolyl, thiadiazolyl, furazanyl, pyridazinyl, triazinyl, cinnolinyl, benzimidazolyl, benzofuranyl, benzofurazanyl, benzothiophenyl, benzothiazolyl, benzoxazolyl, quinazolinyl, quinoxalinyl, naphthyridinyl and furopyridyl. Suitable heteroalicyclic groups in the compounds of the present invention contain one, two or three heteroatoms selected from N, O or S atoms and include, for example, pyrrolidinyl, tetrahydrofuranyl, dihydrofuranyl, tetrahydrothienyl, tetrahydrothiopyranyl, piperidyl, morpholinyl, thiomorpholinyl, thioxanyl, piperazinyl, azetidinyl, oxetanyl, thietanyl, homopiperidyl, oxepanyl, thiepanyl, oxazepinyl, diazepinyl, thiazepinyl, 1,2,3,6-tetrahydropyridyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo [3.1.0]hexyl, 3-azabicyclo[4.1.0]heptyl, 3H-indolyl, and quinolizinyl.

In the compounds of the present invention, the aryl groups in the definitions of $R1_8$, R20, $R_a$, Rb, and $R_x$, are single or multiple ring compounds that contain separate and/or fused aryl groups and have from 6 to 18 ring atoms and are optionally substituted. Typical aryl groups contain from 1 to 3 separated or fused rings. Preferably aryl groups contain from 6 to 12 carbon ring atoms. Particularly preferred aryl groups include substituted or unsubstituted phenyl, substituted or unsubstituted naphthyl, substituted or unsubstituted biphenyl, substituted or unsubstituted phenanthryl and substituted or unsubstituted anthryl, and most preferred substituted or unsubstituted phenyl, wherein the substituents are as indicated above depending upon whether the aryl group is one of substituent $R_2$0, R28, $R_a$ and $R_b$ or it is substituent $R_x$.

In the compounds of the present invention, the aralkyl groups in the definitions of $R_x$, $R_y$ and $R_z$ comprise an alkyl group as defined and exemplified above which is substituted with one or more aryl groups as defined and exemplified above. Preferred examples include optionally substituted benzyl, optionally substituted phenylethyl and optionally substituted naphthylmethyl.

In the compounds of the present invention, the aralkyloxy groups in the definitions of $R_x$ comprise an alkoxy group having from 1 to 12 carbon atoms which is substituted with one or more aryl groups as defined and exemplified above. Preferably, the alkoxy moiety has from 1 to 6 carbon atoms and the aryl group contains from 6 to about 12 carbon ring atoms, and most preferably the aralkyloxy group is optionally substituted benzyloxy, optionally substituted phenylethoxy and optionally substituted naphthylmethoxy.

In the compounds of the present invention, the heterocycloalkyl groups in the definitions of $R_y$ and $R_z$ comprise an alkyl group as defined and exemplified above which is substituted with one or more heterocyclyl groups as defined and exemplified above. Preferably, the heterocycloalkyl groups comprise an alkyl group having from 1 to 6 carbon atoms which is substituted with a heterocyclyl group having from 5 to 10 ring atoms in 1 or 2 ring atoms and can be aromatic, partially saturated or fully saturated. More preferably, the heterocycloalkyl groups comprise a methyl or ethyl group which is substituted with a heterocyclyl group selected from the group consisting of pyrrolidinyl, imidazolidinyl, piperidinyl, piperazinyl, morpholinyl, tetrahydrofuranyl, oxanyl, thianyl, 8-quinolyl, isoquinolyl, pyridyl, pyrazinyl, pyrazolyl, pyrimidinyl, furyl, pyrrolyl, thienyl, thiazolyl, isothiazolyl, triazolyl, tetrazolyl, isoxazolyl, oxazolyl and benzimidazole.

In the compounds of the present invention, the alkylene groups in the definition of $R_{19}$ are straight or branched alkylene groups having from 1 to 12 carbon atoms and the alkylene groups in the definitions of M and X are straight or branched alkylene groups having from 1 to 6 carbon atoms. Preferably, the alkylene groups in the definition of $R_{19}$ are straight or branched alkylene groups having from 1 to 8 carbon atoms, more preferably straight or branched alkylene groups having from 1 to 6 carbon atoms. For M, preferred are straight or branched alkylene groups having from 1 to 3 carbon atoms. In the definition of X, the alkylene groups in the definition of X are preferably straight or branched alkylene groups having from 2 to 4 carbon atoms.

In the compounds of the present invention, the carbocycio groups in the definitions of $R_{19}$ and M are cycloalkyl groups having from 3 to 8 carbon atoms which have two covalent bonds at any position on the cycloalkyl ring connecting said cycloalkyl group to the remainder of the drug conjugate. Preferably, the carbocycio groups in the definitions of $R_{19}$ and M are cycloalkyl groups having from 3 to 7 carbon atoms, and more preferably carbocycio groups having from 5 to 7 carbon atoms.

In the compounds of the present invention, the arylene groups in the definition of $R_{19}$ are aryl groups having from 6 to 18 carbon atoms in one or more rings which have two covalent bonds at any position on the aromatic ring system connecting said arylene groups to the remainder of the drug conjugate. Preferably, the arylene groups in the definition of $R_{19}$ are aryl groups having from 6 to 12 carbon atoms in one or more rings which have two covalent bonds at any position on the aromatic ring system, and most preferably they are phenylene groups.

In the compounds of the present invention, the heterocyclo groups in the definition of $R_{1g}$ are heterocyclyl groups containing from 1 to 3 separated or fused rings having from 5 to 14 ring atoms and comprising at least one oxygen, nitrogen or sulphur atom in said ring(s), wherein there are two covalent bonds at any position on the ring system of said heterocyclic groups. The heterocyclic groups are groups which may be heteroaromatic groups or heteroalicyclic groups (the latter may be partially unsaturated). Preferably, the heterocyclo groups in the definition of $R_{19}$ are heterocyclyl groups containing from 1 to 3 separated or fused rings having from 5 to 12 ring atoms and comprising at least one oxygen, nitrogen or sulphur atom in said ring(s), wherein there are two covalent bonds at any position on the ring system of said heterocyclic groups.

Where there are more than one optional substituents $R_x$ on a substituent, each substituent $R_x$ may be the same or different.

Preferred drug conjugates according to the first aspect of the present invention include:

a drug conjugate of formula $[D-(X)_b-(AA)_w-(L)-]_n-Ab$ according to the first aspect of the present invention wherein L is a linker group selected from the group consisting of:

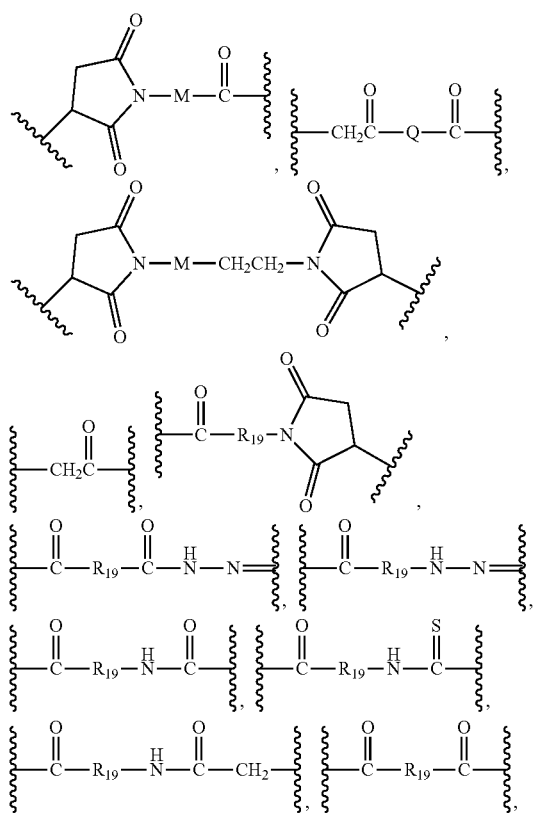

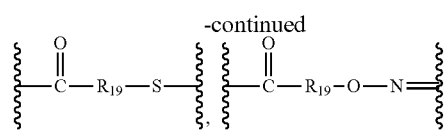

wherein the wavy lines indicate the point of covalent attachments to an Ab (the wavy line to the right) and $(AA)_w$ if any, or $(X)_b$ if any, or the drug moiety (the wavy line to the left);

Rig is selected from —C1-C12 alkylene-, —$C_3$-$C_8$ carbocyclo, -0-(Ci-$Ci_2$ alkylene), —$C_6$-C18 arylene in one or more rings which may optionally be substituted with one or more substituents $R_x$, —C1-C12 alkylene —$C_6$-$Ci_8$arylene- wherein the arylene group is in one or more rings which may optionally be substituted with one or more substituents $R_x$, —$C_6$-Ci8 arylene -Ci-Ci2 alkylene- wherein the arylene group is in one or more rings which may optionally be substituted with one or more substituents $R_x$, —C1-C12 alkylene-($C_3$-$C_8$ carbocyclo)-, —($C_3$-$C_8$carbocyclo)-Ci-Ci2 alkylene-, —C5-C14 heterocyclo- wherein said heterocyclo group may be a saturated or unsaturated group having one or more rings and comprising at least one oxygen, nitrogen or sulphur atom in said ring(s), said group optionally being substituted with one or more substituents $R_x$, —C1-C12 alkylene —($C_5$-$Ci_4$ heterocyclo)- wherein said heterocyclo group may be a saturated or unsaturated group having one or more rings and comprising at least one oxygen, nitrogen or sulphur atom in said ring(s), said group optionally being substituted with one or more substituents $R_x$, —($C_5$-$Ci_4$ heterocyclo)-C1-C12 alkylene- wherein said heterocyclo group may be a saturated or unsaturated group having one or more rings and comprising at least one oxygen, nitrogen or sulphur atom in said ring(s), said group optionally being substituted with one or more substituents $R_x$, —($OCH_2CH_2$) r-, and —$CH2$-$(OCH_2CH2)r$-, wherein each of the above alkylene substituents whether alone or attached to another moiety the carbon chain may optionally be substituted by one or more substituents $R_x$;

M is selected from the group consisting of -Ci-$C_6$ alkylene-, -Ci-$C_6$ alkylene-($C_3$-$C_8$ carbocyclo)-, —($CH_2CH_2O)_s$-, —$C_1$-$C_6$ alkylene-($C_3$-$C_8$carbocyclo)-CON(H or $C_{1-6}$alkyl)-Ci-$C_6$ alkylene-, phenylene which may optionally be substituted with one or more substituents $R_x$, phenylene-$CrC_6$ alkylene- wherein the phenylene moiety may optionally be substituted with one or more substituents $R_x$ and -Ci-$C_6$ alkylene-CON(H or $C_{1-6}$alkyl)Ci-$C_6$ alkylene-;

Q is selected from the group consisting of —N(H or $C_{1-6}$alkyl)phenylene- and —N(H or $C_{1-6}$alkyl)-$(CH_2)s$;

r is an integer ranging from 1 to 10; and s is an integer ranging from 1 to 10.

a drug conjugate of formula $[D-(X)_b-(AA)_w-(L)-]_n-Ab$ according to the first aspect of the present invention wherein L is selected from the group consisting of:

-continued

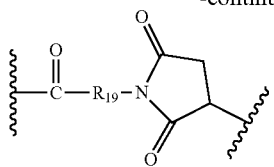

wherein:
the wavy lines indicate the point of covalent attachments to an Ab (the wavy line to the right) and $(AA)_W$ if any, or $(X)_b$ if any, or the drug moiety (the wavy line to the left);
Rig is selected from —C1-C12 alkylene-, –0-(Ci-Ci$_2$ alkylene), —C$_6$-Ci$_2$ arylene in one or more rings which may optionally be substituted with one or more substituents R$_x$, —C$_1$-C12alkylene-C$_6$-Ci2 arylene- wherein the arylene group is in one or more rings which may optionally be substituted with one or more substituents R$_x$, —C$_6$-Ci$_2$ arylene-Ci-C12 alkylene- wherein the arylene group is in one or more rings which may optionally be substituted with one or more substituents R$_x$, —C5-C12 heterocycio- wherein said heterocycio group may be a saturated or unsaturated group having one or more rings and comprising at least one oxygen, nitrogen or sulphur atom in said ring(s), said group optionally being substituted with one or more substituents R$_x$, —C1-C12 alkylene-(C5-C12 heterocycio)- wherein said heterocycio group may be a saturated or unsaturated group having one or more rings and comprising at least one oxygen, nitrogen or sulphur atom in said ring(s), said group optionally being substituted with one or more substituents R$_x$, —(C5-C12 heterocyclo)-CrCi$_2$ alkylene- wherein said heterocycio group may be a saturated or unsaturated group having one or more rings and comprising at least one oxygen, nitrogen or sulphur atom in said ring(s), said group optionally being substituted with one or more substituents R$_x$, —(OCH$_2$CH$_2$)$_r$—, and —CH2-(OCH$_2$CH2)r wherein each of the above alkylene substituents whether alone or attached to another moiety the carbon chain may optionally be substituted by one or more substituents R$_x$; and
M is selected from the group consisting of -Ci-C$_6$ alkylene-, -Ci-C$_6$ alkylene-(C$_3$-C$_8$ carbocyclo)- and phenylene which may optionally be substituted with one or more substituents R$_x$; and
r is an integer ranging from 1-6.
  a drug conjugate of formula $[D-(X)_b-(AA)_w-(L)-]_n$-Ab according to the first aspect of the present invention selected from formulas (IV) and (V):

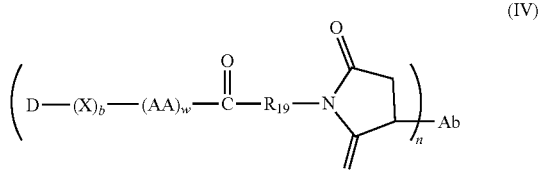
(IV)

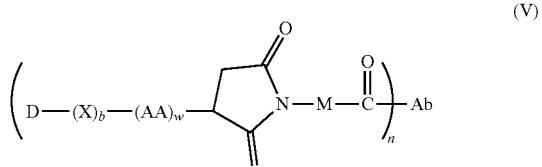
(V)

wherein:
X is an extending group as defined in the first aspect of the invention;
each AA is independently an amino acid unit as defined in the first aspect of the invention;
w is an integer ranging from 0 to 12;
b is an integer of 0 or 1;
D is a drug moiety;
Ab is a moiety comprising at least one antigen binding site;
n is the ratio of the group $[D-(X)_b-(AA)_w-(L)-]$ wherein L is as defined in formula (IV) or (V) to the moiety comprising at least one antigen binding site and is in the range from 1 to 20;
Rig is selected from —CrC$_8$ alkylene-, –0-(Ci-C$_8$ alkylene), —CrC$_8$ alkylene-C$_6$-Ci$_2$ arylene- wherein the arylene group is in one or more rings which may optionally be substituted with one or more substituents R$_x$, —C$_6$-Ci$_2$arylene-Ci-C$_8$ alkylene- wherein the arylene group is in one or more rings which may optionally be substituted with one or more substituents R$_x$, wherein each of the above alkylene substituents whether alone or attached to another moiety the carbon chain may optionally be substituted by one or more substituents R$_x$; and
M is selected from the group consisting of -Ci-C$_3$ alkylene- and -Ci-C$_3$ alkylene-(C$_5$-C$_7$ carbocyclo)-.
  a drug conjugate of formula $[D-(X)_b-(AA)_w-(L)-]_n$-Ab according to the first aspect of the present invention, selected from formulas (IV) and (V):

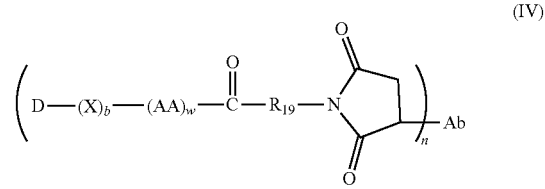
(IV)

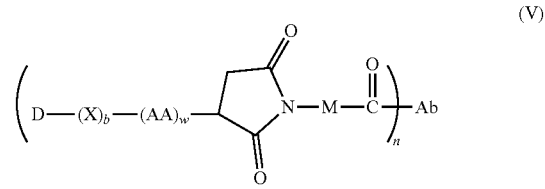
(V)

wherein:
X is an extending group;
each AA is independently an amino acid unit;
w is an integer ranging from 0 to 12;
b is an integer of 0 or 1;
D is a drug moiety;
Ab is a moiety comprising at least one antigen binding site;
n is the ratio of the group $[D-(X)_b-(AA)_w-(L)-]$ wherein L is as defined in (IV) or (V) to the moiety comprising at least one antigen binding site and is in the range from 1 to 20;
Rig is selected from -Ci-C$_6$ alkylene-, phenylene-CrC$_6$ alkylene- wherein the phenylene group may optionally be substituted with one or more substituents R$_x$ selected from the group consisting of alkyl groups having from 1 to 6 carbon atoms, alkoxy groups having from 1 to 6 carbon atoms, halogen atoms, nitro groups and cyano groups, wherein each of the above alkylene substituents whether alone or attached to another moiety in the carbon chain may optionally be substituted by one or more substituents R$_x$ selected from the group consisting of alkyl groups having from 1 to 6 carbon atoms, alkoxy groups having from 1 to 6 carbon atoms, aryl groups having from 6 to 12 carbon atoms, halogen atoms, nitro groups and cyano groups, and preferably $R_{19}$ is a -$C_1$-$C_6$ alkylene group; and M is —C1-C3 alkylene-($C_5$-$C_7$carbocyclo)-.

It is preferred that in the definition of the drug conjugate of formula $[D-(X)_b-(AA)_w-(L)-]_n$-Ab, L is as defined in the preferred definitions for said group above and $(AA)_W$ is of formula (II):

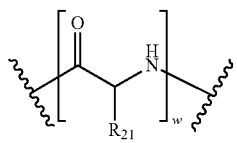

(II)

wherein the wavy lines indicate the point of covalent attachments to $(X)_b$ if any, or the drug moiety (the wavy line to the left) and to the linker (the wavy line to the right); and R21 is, at each occurrence, selected from the group consisting of hydrogen, methyl, isopropyl, isobutyl, sec-butyl, benzyl, p-hydroxybenzyl, —CH$_2$OH, —CH(OH)CH$_3$, —CH$_2$CH$_2$SCH$_3$, —CH$_2$CONH$_2$, —CH$_2$COOH, —CH$_2$CH$_2$CONH$_2$, —CH$_2$CH$_2$OOH, —(CH$_2$)$_3$NHC(=NH)NH$_2$, —(CH$_2$)$_3$NH$_2$, —(CH$_2$)$_3$NHCOCH$_3$, —(CH$_2$)$_3$NHCHO, —(CH$_2$)$_4$NHC(=NH)NH$_2$, —(CH$_2$)$_4$NH$_2$, —(CH$_2$)$_4$NHCOCH$_3$, —(CH$_2$)$_4$NHCHO, —(CH$_2$)$_3$NHCONH$_2$, —(CH$_2$)$_4$NHCONH$_2$, —CH$_2$CH$_2$CH(OH)CH$_2$NH$_2$, 2-pyridylmethyl-, 3-pyridylmethyl-, 4-pyridylmethyl-, phenyl, cyclohexyl,

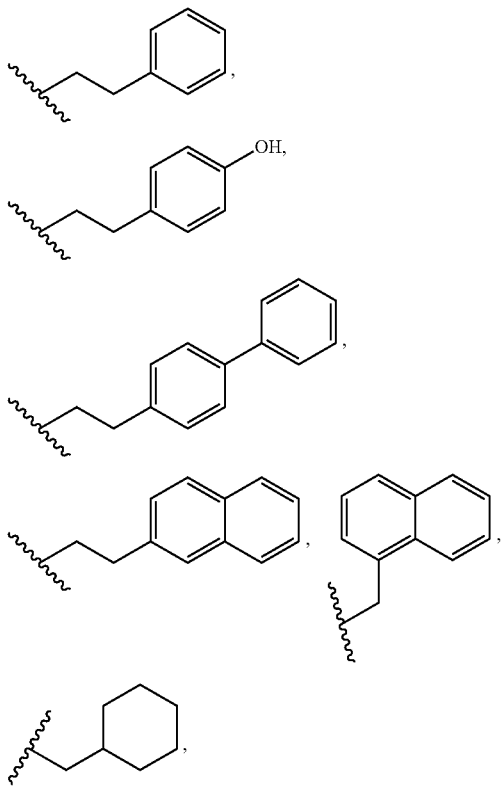

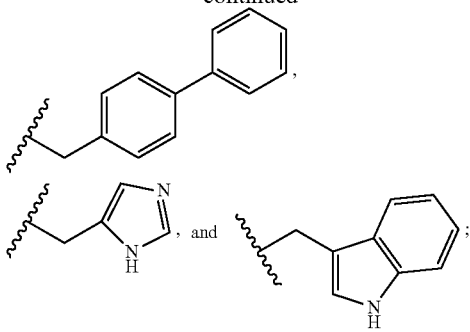

and w is an integer ranging from 0 to 12.

a drug conjugate of formula $[D-(X)_b-(AA)_w-(L)-]_n$-Ab according to the first aspect of the present invention, wherein L is as defined in the preferred definitions for said group above and $(AA)_W$ is of formula (II) wherein:

$R_{21}$ is selected, at each occurrence, from the group consisting of hydrogen, methyl, isopropyl, sec-butyl, benzyl, indolylmethyl, —(CH$_2$)$_3$NHCONH$_2$, —(CH$_2$)$_4$NH$_2$, —(CH$_2$)$_3$NHC(=NH)NH$_2$ and —(CH$_2$)$_4$NHC(=NH)NH$_2$; and w is an integer ranging from 0 to 6.

a drug conjugate of formula $[D-(X)_b-(AA)_w(L)-]_n$-Ab according to the first aspect of the present invention, wherein L is as defined in the preferred definitions for said group above, wherein w is 0 or 2, and when w is 2, then $(AA)_W$ is of formula (III) wherein:

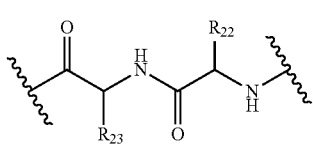

(III)

the wavy lines indicate the point of covalent attachments to $(X)_b$ if any, or the drug moiety (the wavy line to the left) and to the linker (the wavy line to the right);

$R_2$ is selected from methyl, benzyl, isopropyl, sec-butyl and indolylmethyl; and $R_{23}$ is selected from methyl, —(CH$_2$)$_4$NH$_2$, —(CH$_2$)$_3$NHCONH$_2$ and —(CH$_2$)$_3$NHC(=NH)NH$_2$.

Further, it is preferred that in the definition of the drug conjugate of formula $[D-(X)b-(AA)_w(L)-]_n$-Ab, L and AA are as defined in the preferred definitions for said groups above and X is an extending group selected from the group consisting of:

—CONH-($C_1$-$C_6$ alkylene)NH—;

—COO—CH$_2$-(phenylene which may optionally be substituted with one or more substituents $R_x$)—NH—;

—CONH-($C_1$-$C_6$ alkylene)NH—COO—CH$_2$-(phenylene which may optionally be substituted with one or more substituents $R_x$)—NH—;

—CH$_2$-(phenylene which may optionally be substituted with one or more substituents $R_x$)—NH—;

—COCH$_2$NH—COCH$_2$—NH—;

—COCH$_2$NH—;

—CONH-($C_1$-$C_6$ alkylene)S—;

—CONH-($C_1$-$C_6$ alkylene)NHCO($C_1$-$C_6$ alkylene)S—;

-($C_1$-$C_6$ alkylene)NHCO($C_1$-$C_6$ alkylene)S—;

-($C_1$-$C_6$ alkylene)S—;

-(Ci-C$_6$ alkylene)NH—; and
-(Ci-C$_6$ alkylene)NH—COO—CH$_2$-(phenylene which may optionally be substituted with one or more substituents R$_x$)—NH—.

a drug conjugate of formula [D-(X)$_b$-(AA)$_w$-(L)-]$_n$-Ab according to the first aspect of the present invention, wherein L and AA are as defined in the preferred definitions for said groups above and X is an extending group selected from the group consisting of:
—CONH—(C$_2$-C$_4$ alkylene)NH—;
—COO—CH$_2$-phenylene-NH—, wherein said phenylene group may optionally be substituted with from one to four substituents R$_x$ selected from the group consisting of alkyl groups having from 1 to 6 carbon atoms, alkoxy groups having from 1 to 6 carbon atoms, halogen atoms, nitro groups and cyano groups;
—CONH—(C$_2$-C$_4$ alkylene)NH—COO—CH$_2$-(phenylene which may optionally be substituted with from one to four substituents R$_x$ selected from the group consisting of alkyl groups having from 1 to 6 carbon atoms, alkoxy groups having from 1 to 6 carbon atoms, halogen atoms, nitro groups and cyano groups)-NH—;
—COCH$_2$NH—COCH$_2$—NH—;
—CONH—(C$_2$-C$_4$ alkylene)S—;
—CONH—(C$_2$-C$_4$ alkylene)NHCO(CrC$_3$ alkylene)S—;
—(C$_2$-C$_4$ alkylene)NHCO(C$_1$-C$_3$ alkylene)S—;
—(C2-C4 alkylene)S—;
-(C2-C4 alkylene)NH—; and
-(C2-C4 alkylene)NH—COO—CH$_2$-(phenylene which may optionally be substituted with from one to four substituents R$_x$ selected from the group consisting of alkyl groups having from 1 to 6 carbon atoms, alkoxy groups having from 1 to 6 carbon atoms, halogen atoms, nitro groups and cyano groups)-NH—.

a drug conjugate of formula [D-(X)$_b$-(AA)$_w$-(L)-]$_n$-Ab according to the first aspect of the present invention, wherein L and AA are as defined in the preferred definitions for said groups above and X is an extending group selected from the group consisting of:
—CONH(CH$_2$)$_3$NHCOOCH$_2$-phenylene-NH—;
—CONH(CH$_2$)$_3$NH—;
—CONH(CH$_2$)$_3$—S—;
—CONH(CH$_2$)$_3$NHCO(CH$_2$)$_2$S—;
—(CH$_2$)$_3$NHCO(CH$_2$)$_2$S—;
—(CH$_2$)$_3$S—;
—(CH$_2$)$_3$NH—; and
—(CH$_2$)$_3$NHCOOCH$_2$-phenylene-NH—.

A preferred drug conjugate of formula [D-(X)$_b$-(AA)$_w$-(L)-]$_n$-Ab according to the first aspect of the present invention is one wherein L, (AA)$_W$ and X are as defined above and wherein D is a compound of formula (I), (Ia) or (Ib), or a pharmaceutically acceptable salt, ester, solvate, tautomer or stereoisomer thereof, wherein R$_2$ and R$_3$ are each independently selected from hydrogen and substituted or unsubstituted Ci-C$_6$ alkyl, wherein the optional substituents are one or more substituents R$_x$, and more preferably each of R$_2$ and R$_3$ is hydrogen.

Another preferred drug conjugate of formula [D-(X)$_b$-(AA)$_w$-(L)-]$_n$-Ab according to the first aspect of the present invention is one wherein L, (AA)$_W$ and X are as defined above and wherein D is a compound of formula (I), (Ia) or (Ib), or a pharmaceutically acceptable salt, ester, solvate, tautomer or stereoisomer thereof, wherein R$_1$ is selected from hydrogen, OR$_a$ and OCOR$_a$, wherein R$_a$ is selected from hydrogen and substituted or unsubstituted Ci-C$_6$ alkyl, wherein the optional substituents are one or more substituents R$_x$, and more preferably R, is hydrogen or methoxy.

A further preferred drug conjugate of formula [D-(X)$_b$-(AA)$_w$-(L)-]$_n$-Ab according to the first aspect of the present invention is one wherein L, (AA)$_W$ and X are as defined above and wherein D is a compound of formula (I), (Ia) or (Ib), or a pharmaceutically acceptable salt, ester, solvate, tautomer or stereoisomer thereof, wherein R$_3$— is selected from hydrogen, COR$_a$, and substituted or unsubstituted Ci-C$_6$ alkyl, wherein R$_a$ is a substituted or unsubstituted Ci-C$_6$ alkyl, wherein the optional substituents are one or more substituents R$_x$, and more preferably R$_3$' is hydrogen.

A further preferred drug conjugate of formula [D-(X)$_b$-(AA)$_w$-(L)-]$_n$-Ab according to the first aspect of the present invention is one wherein L, (AA)$_W$ and X are as defined above and wherein D is a compound of formula (I), (Ia) or (Ib), or a pharmaceutically acceptable salt, ester, solvate, tautomer or stereoisomer thereof, wherein each of R$_4$, R$_5$, R$_6$, R$_7$, Rs, R9, R10 and R12 is independently selected from hydrogen and substituted and unsubstituted C$_1$-C$_6$ alkyl, wherein the optional substituents are one or more substituents R$_x$, and more preferably each of R$_4$, R$_5$, R6, R$_7$, Rs, R9, R10 and R12 is independently selected from hydrogen, substituted and unsubstituted methyl, substituted and unsubstituted isopropyl and substituted and unsubstituted tert-butyl, wherein the optional substituents are one or more substituents R$_x$.

A further preferred drug conjugate of formula [D-(X)$_b$-(AA)$_w$-(L)-]$_n$-Ab according to the first aspect of the present invention is one wherein L, (AA)$_W$ and X are as defined above and wherein D is a compound of formula (I), (Ia) or (Ib), or a pharmaceutically acceptable salt, ester, solvate, tautomer or stereoisomer thereof, wherein each of R$_5$, R$_7$, R$_8$, R9 and R1$_0$ is hydrogen.

A further preferred drug conjugate of formula [D-(X)$_b$-(AA)$_w$-(L)-]$_n$-Ab according to the first aspect of the present invention is one wherein L, (AA)$_W$ and X are as defined above and wherein D is a compound of formula (I), (Ia) or (Ib), or a pharmaceutically acceptable salt, ester, solvate, tautomer or stereoisomer thereof, wherein each of R$_4$ and R$_6$ is methyl.

A further preferred drug conjugate of formula [D-(X)$_b$-(AA)$_w$-(L)-]$_n$-Ab according to the first aspect of the present invention is one wherein L, (AA)$_W$ and X are as defined above and wherein D is a compound of formula (I), (Ia) or (Ib), or a pharmaceutically acceptable salt, ester, solvate, tautomer or stereoisomer thereof, wherein R$_{1_2}$ is isopropyl, tert-butyl or benzyl.

A further preferred drug conjugate of formula [D-(X)$_b$-(AA)$_w$-(L)-]$_n$-Ab according to the first aspect of the present invention is one wherein L, AA and X are as defined above and wherein D is a compound of formula (I), (Ia) or (Ib), or a pharmaceutically acceptable salt, ester, solvate, tautomer or stereoisomer thereof, wherein each of R$_{11}$ and R13 is independently selected from hydrogen and substituted and unsubstituted Ci-C$_6$ alkyl, wherein the optional substituents are one or more substituents R$_x$, and more preferably each of R$_{11}$ and R$_{13}$ is hydrogen.

A further preferred drug conjugate of formula [D-(X)$_b$-(AA)$_w$-(L)-]$_n$-Ab according to the first aspect of the present invention is one wherein L, (AA)$_W$ and X are as defined above and wherein D is a compound of formula (Ia) or (Ib), or a pharmaceutically acceptable salt, ester, solvate, tautomer or stereoisomer thereof, wherein each of $R1_5$, R16, R17, $Ri_7$, $R_{18}$, $R2_4$, $R2_4'$, R25 and $R_26$ is independently selected from the group consisting of hydrogen, substituted or unsubstituted Ci-$C_6$ alkyl, substituted or unsubstituted $C_2$-$C_6$ alkenyl and substituted or unsubstituted $C_2$-$C_6$ alkynyl, wherein the optional substituents are one or more substituents $R_x$, more preferably each of $R_{1_5}$, R16, Ri7, Ri7', R18', $R2_4$, $R2_4'$, R25 and $R_26$ is independently selected from the group consisting of hydrogen and substituted or unsubstituted Ci-$C_6$ alkyl, wherein the optional substituents are selected from the group consisting of alkoxy groups having from 1 to 6 carbon atoms, hydroxyl groups, oxo groups, halogen atoms, $OCOR_y$, $OCOOR_y$, $COR_y$, $COOR_y$, OCON $R_yR_z$, CON $R_yR_z$, $NR_yR_z$, and $NR_y$-$COR_z$, wherein each of $R_Y$ and $R_z$ is selected from hydrogen atoms and alkyl groups having from 1 to 6 carbon atoms, yet more preferably each of $R1_5$, R16, R17, $Ri_7'$, $R_{18'}$, $R2_4$, $R2_{4'}$, R25 and $R_26$ is independently hydrogen or a $CrC_6$ alkyl group, and most preferably each of $R1_5$, R16, R17, $R_{17'}$, $R_{18'}$, $R2_4$, $R2_4'$, R25 and $R_{26}$ is hydrogen or methyl.

A further preferred drug conjugate of formula $[D-(X)_b-(AA)_w-(L)-]_n$-Ab according to the first aspect of the present invention is one wherein L, $(AA)_W$ and X are as defined above and wherein D is a compound of formula (Ib), or a pharmaceutically acceptable salt, ester, solvate, tautomer or stereoisomer thereof, wherein $R_{1_8}$ is selected from hydrogen, a $CrC_6$ alkyl group which may optionally be substituted with one or more substituents $R_x$, an aryl group having from 6 to 12 carbon atoms in one or more aromatic rings, said aryl groups optionally being substituted with one or more substituents $R_x$ and a 5-to 10-membered unsaturated or saturated heterocyclic group having one or more rings, said heterocyclic group optionally being substituted with one or more substituents $R_x$, wherein the substituents $R_x$ are selected from the group consisting of alkoxy groups having from 1 to 6 carbon atoms, hydroxyl groups, halogen atoms, alkylamino groups having from 1 to 6 carbon atoms and dialkylamino groups having from 1 to 6 carbon atoms, more preferably R-I8 is selected from hydrogen, a $CrC_6$ alkyl group which may optionally be substituted with at least one group $R_x$ and a phenyl group which may optionally be substituted with at least one group $R_x$, and most preferably $R_{1_8}$ is hydrogen or a phenyl group, particularly hydrogen.

A further preferred drug conjugate of formula $[D-(X)_b-(AA)_w-(L)-]_n$-Ab according to the first aspect of the present invention is one wherein L, $(AA)_W$ and X are as defined above and wherein D is a compound of formula (Ia) or (Ib), or a pharmaceutically acceptable salt, ester, solvate, tautomer or stereoisomer thereof, wherein $R_{27}$ is selected from a hydrogen atom, a halogen atom or a substituted or unsubstituted Ci-$C_6$ alkyl wherein the optional substituents are one or more substituents $R_x$, and more preferably $R_2$⁷ is selected from a hydrogen atom and a chlorine atom.

A further preferred drug conjugate of formula $[D-(X)_b-(AA)_w-(L)-]_n$-Ab according to the first aspect of the present invention is one wherein L, $(AA)_W$ and X are as defined above and wherein D is a compound of formula (I), (Ia) or (Ib), or a pharmaceutically acceptable salt, ester, solvate, tautomer or stereoisomer thereof, wherein each pair of carbon atoms linked by one or more dotted lines are bonded through double bonds.

A further preferred drug conjugate of formula $[D-(X)_b-(AA)_w-(L)-]_n$-Ab according to the first aspect of the present invention is one wherein L, $(AA)_W$ and X are as defined above and wherein D is a compound of formula (Ia) or (Ib), or a pharmaceutically acceptable salt, ester, solvate, tautomer or stereoisomer thereof, wherein:

R1 is selected from hydrogen, $OR_a$ and $OCOR_a$, wherein $R_a$ is selected from hydrogen and substituted or unsubstituted Ci-$C_6$ alkyl, wherein the optional substituents are one or more substituents $R_x$;

$R_2$ and $R_3$ are each independently selected from hydrogen and substituted or unsubstituted Ci-$C_6$ alkyl, wherein the optional substituents are one or more substituents $R_x$;

$R_3'$ is selected from hydrogen, $COR_a$, and substituted or unsubstituted Ci-$C_6$ alkyl, wherein $R_a$ is a substituted or unsubstituted Ci-$C_6$ alkyl, wherein the optional substituents are one or more substituents $R_x$;

each of $R_4$, R5, R6, R7, Rs, R9, R10 and R12 is independently selected from hydrogen and substituted and unsubstituted Ci-$C_6$ alkyl, wherein the optional substituents are one or more substituents $R_x$;

R11 and R13 are independently selected from hydrogen and substituted and unsubstituted Ci-$C_6$ alkyl, wherein the optional substituents are one or more substituents $R_x$;

each of $R1_5$, R16, R17, $R_{7'}$, R18', $R2_4$, $R2_4'$, R25 and $R_26$ is independently selected from the group consisting of: hydrogen and substituted or unsubstituted Ci-$C_6$ alkyl groups wherein the optional substituents are selected from the group consisting of alkoxy groups having from 1 to 6 carbon atoms, hydroxyl groups, oxo groups, halogen atoms, $OCOR_y$, $OCOOR_y$, $COR_y$, $COOR_y$, OCON RyRz, CON RyRz, N RyRz and N $R_y$COR z wherein each of $R_y$ and $R_z$ is selected from hydrogen atoms and alkyl groups having from 1 to 6 carbon atoms;

R18 is selected from hydrogen, a Ci-$C_6$ alkyl group which may optionally be substituted with at least one group $R_x$, an aryl group having from 6 to 12 carbon atoms in one or more aromatic rings, said aryl groups optionally being substituted with one or more substituents $R_x$ and 5- to 10-membered unsaturated or saturated heterocyclic group having one or more rings, said heterocyclic group optionally being substituted with one or more substituents $R_x$, wherein the substituents $R_x$ are selected from the group consisting of alkoxy groups having from 1 to 6 carbon atoms, hydroxyl groups, halogen atoms, alkylamino groups having from 1 to 6 carbon atoms and dialkylamino groups having from 1 to 6 carbon atoms;

$R_27$ is selected from hydrogen, halogen and substituted and unsubstituted Ci-$C_6$ alkyl wherein the optional substituents are one or more substituents $R_x$; and each dotted line represents an optional additional bond, but when a triple bond exists between the C atom to which $R_{25}$ is attached and the C atom to which $R_26$ and $R_27$ are attached, then $R_{25}$ and either $R_{26}$ or $R_{27}$ are absent.

A further preferred drug conjugate of formula $[D-(X)_b-(AA)_w-(L)-]_n$-Ab according to the first aspect of the present invention is one wherein L, $(AA)_W$ and X are as defined above and wherein D is a compound of formula (Ia) or (Ib), or a pharmaceutically acceptable salt, solvate, tautomer or stereoisomer thereof, wherein:

R1 is hydrogen or methoxy;

each of $R_2$ and $R_3$ is hydrogen;

$R_3'$ is hydrogen;

each of $R_4$, R5, R6, R7, Rs, R9, R10 and $Ri_2$ is independently selected from hydrogen, substituted or unsubstituted methyl, substituted or unsubstituted isopropyl and substituted or unsubstituted tert-butyl wherein the optional substituents are one or more substituents $R_x$;

each of R11 and $R_{13}$ is hydrogen;

each of $R1_5$, R16, R17, $R_{i7'}$, $R_{18'}$, $R2_4$, $R2_4'$, R25 and $R_{26}$ is independently selected from the group consisting of:

hydrogen and substituted or unsubstituted $Ci$-$C_6$ alkyl groups wherein the optional substituents are selected from the group consisting of alkoxy groups having from 1 to 6 carbon atoms, hydroxyl groups, oxo groups, halogen atoms, $OCOR_y$, $OCOOR_y$, $CORy$, $COOR_y$, $OCON$ $RyR_z$, $CON$ $RyR_z$, $N$ $RyR_z$ and $N$ $R_yCOR_z$ wherein each of $R_y$ and $R_z$ is selected from hydrogen atoms, and alkyl groups having from 1 to 6 carbon atoms.

R-18 is selected from hydrogen, a $Ci$-$C_6$ alkyl group which may optionally be substituted with at least one group $R_x$ and a phenyl group which may optionally be substituted with at least one group $R_x$;

R27 is a hydrogen atom or a chlorine atom; and each dotted line represents an optional additional bond, but when a triple bond exists between the C atom to which $R_{25}$ is attached and the C atom to which $R_{26}$ and R27 are attached, then $R_{25}$ and either $R_{26}$ or $R_{27}$ are absent.

A further preferred drug conjugate of formula $[D-(X)_b-(AA)_w-(L)-]_n$-Ab according to the first aspect of the present invention is one wherein L, $(AA)_W$ and X are as defined above and wherein D is a compound of formula (Ia) or (Ib), or a pharmaceutically acceptable salt, ester, solvate, tautomer or stereoisomer thereof, wherein:

R1 is hydrogen or methoxy;
each of $R_2$ and $R_3$ is hydrogen;
$R_3'$ is hydrogen;
each of $R_5$, $R_7$, Rs, R9 and R10 is hydrogen;
each of $R_4$ and $R_6$ is methyl;
each of R11 and R13 is hydrogen;
$R1_2$ is isopropyl, tert-butyl or benzyl;
each of $R1_5$, R16, R17, $R_{i7'}$, $R_{18'}$, $R2_4$, $R2_4'$, R25 and $R_{26}$ is independently selected from the group consisting of hydrogen and $Ci$-$C_6$ alkyl group, preferably hydrogen and methyl;
R18 is selected from hydrogen and phenyl, preferably hydrogen;
$R_{27}$ is a hydrogen atom or a chlorine atom; and
each pair of carbon atoms linked by one or more dotted lines is bonded through double bonds.

A further preferred drug conjugate of formula $[D-(X)_b-(AA)_w-(L)-]_n$-Ab according to the first aspect of the present invention is one wherein L, $(AA)_W$ and X are as defined above and wherein D is a compound of formula (I), (Ia) or (Ib), or a pharmaceutically acceptable salt, ester, solvate, tautomer or stereoisomer thereof selected from:

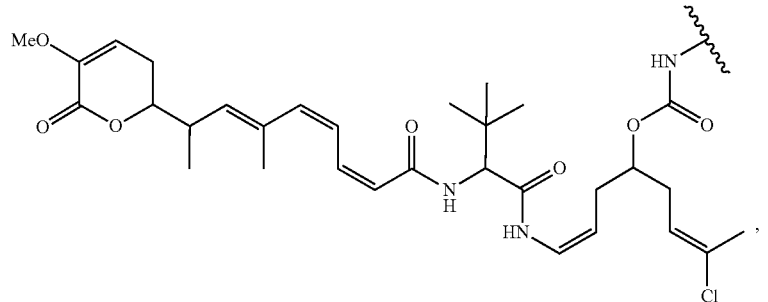

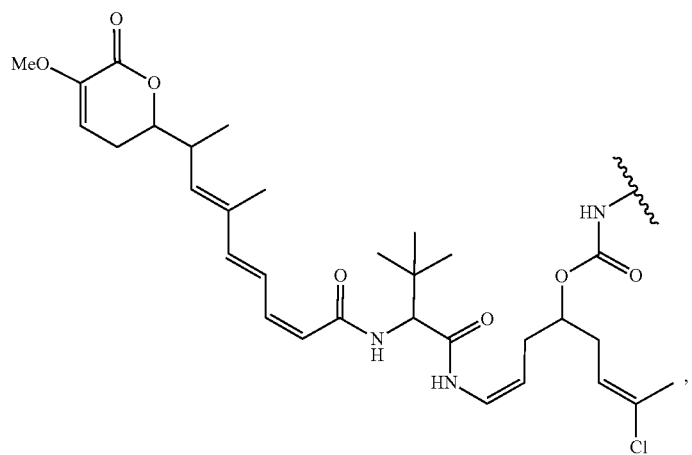

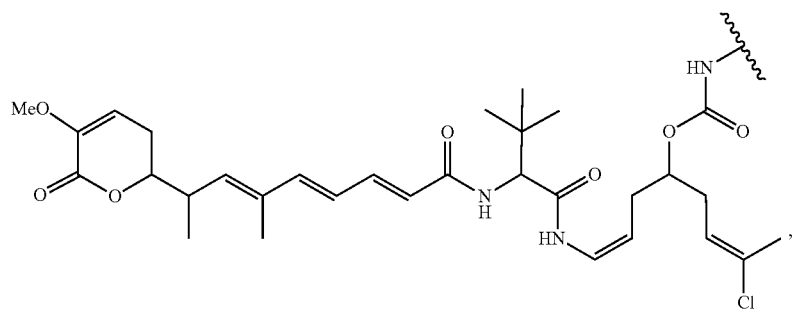

-continued
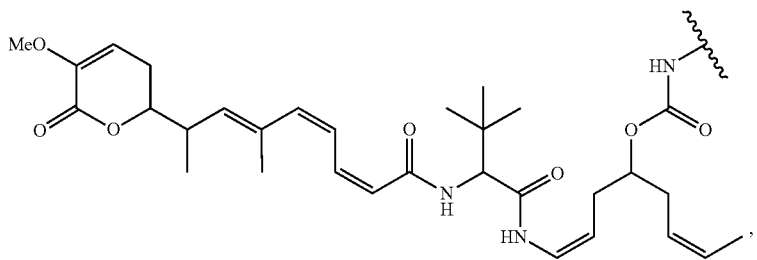
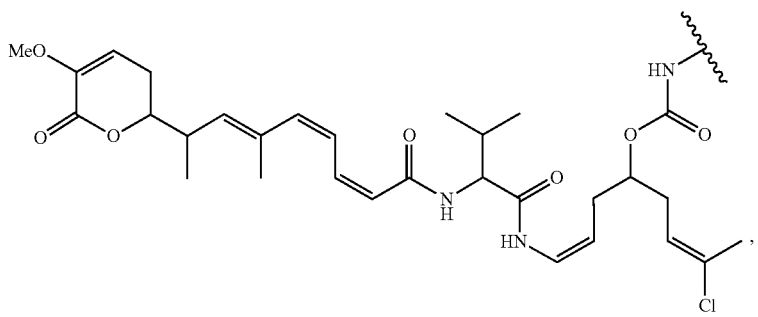
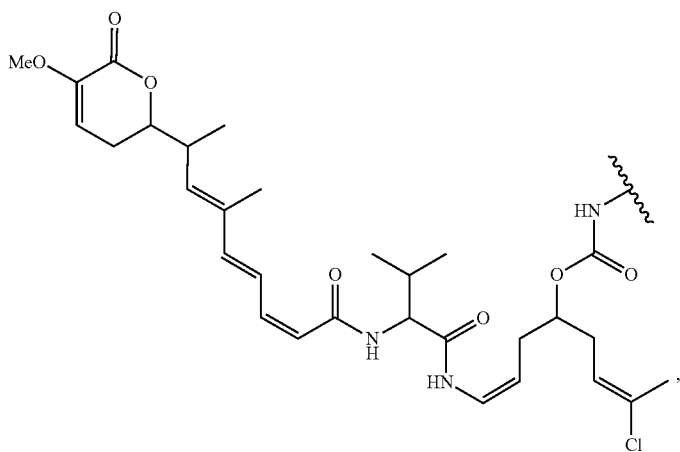
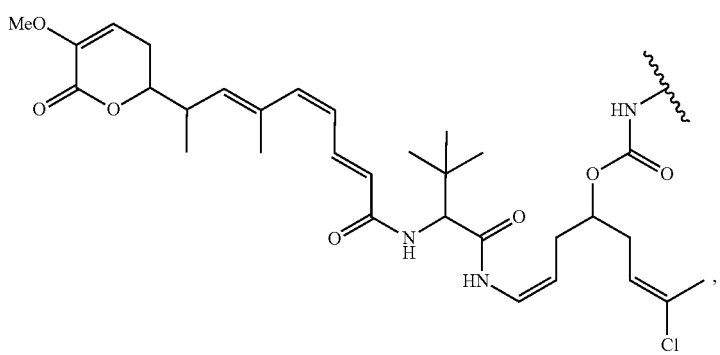
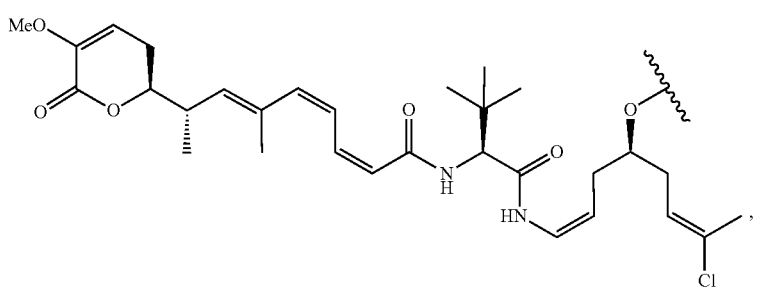

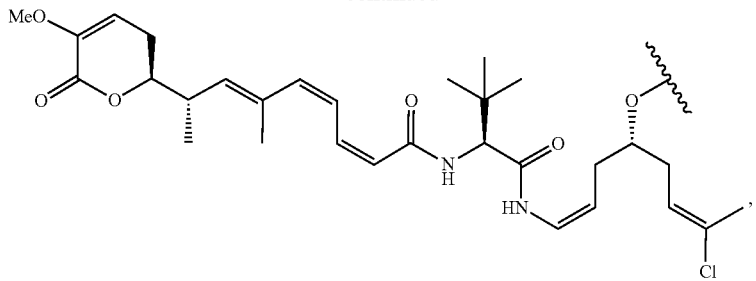
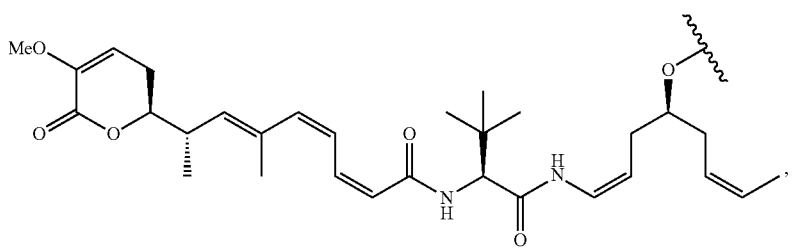
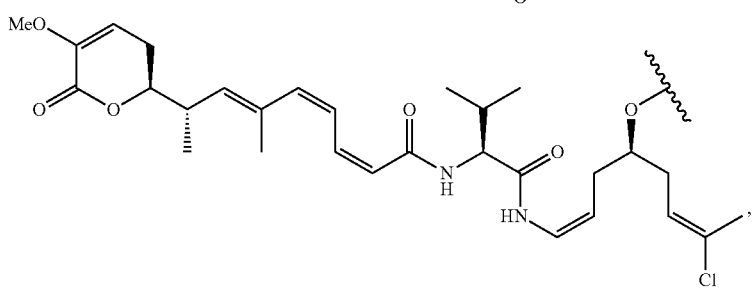
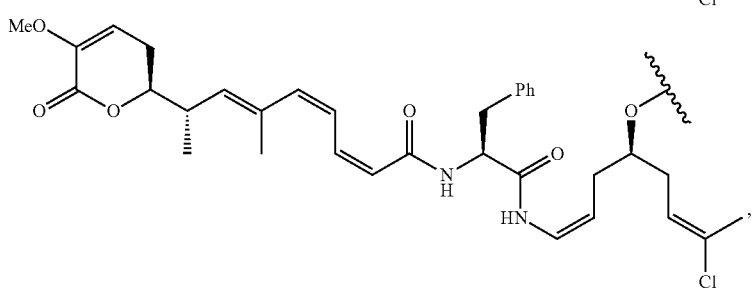
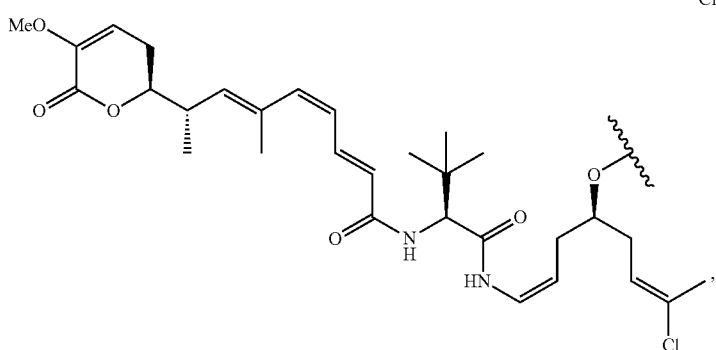
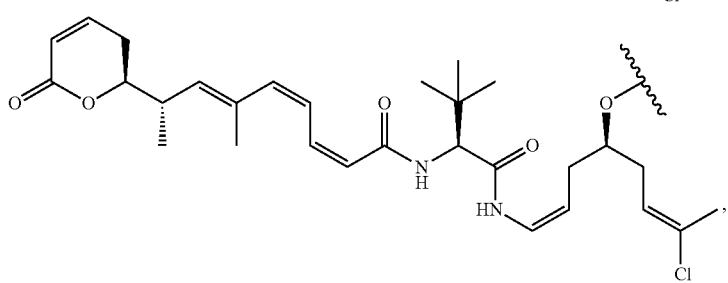

-continued
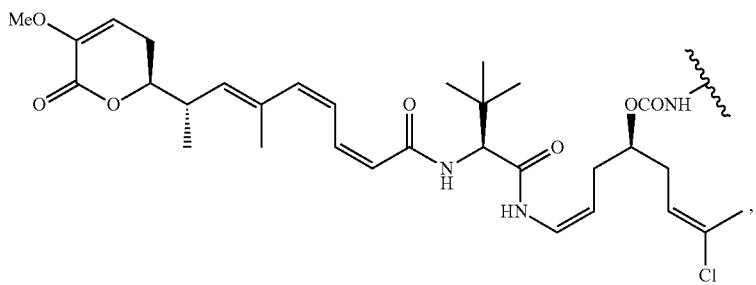
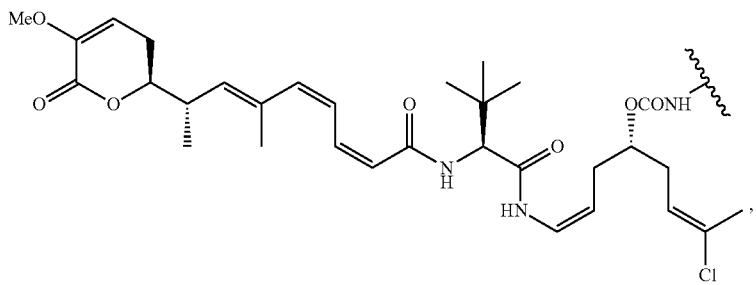
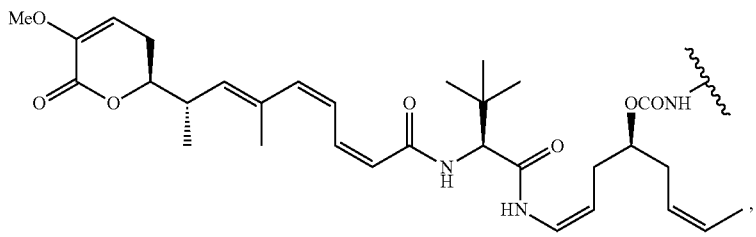
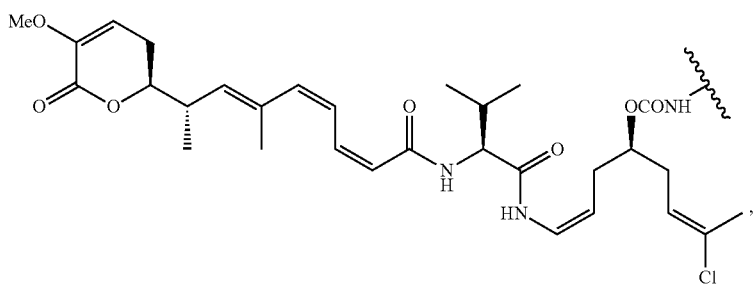
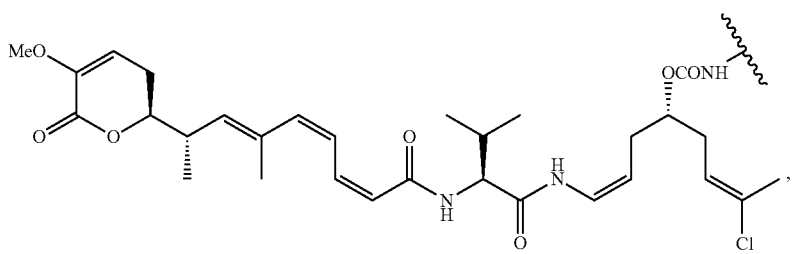
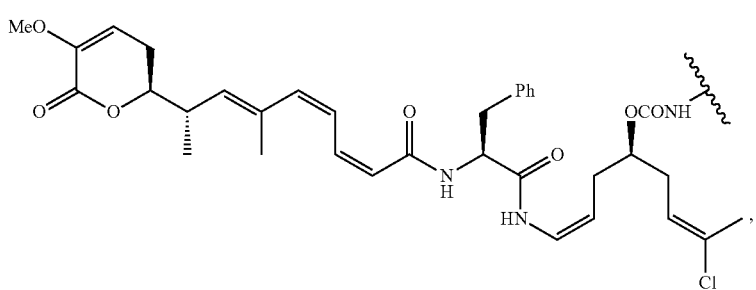

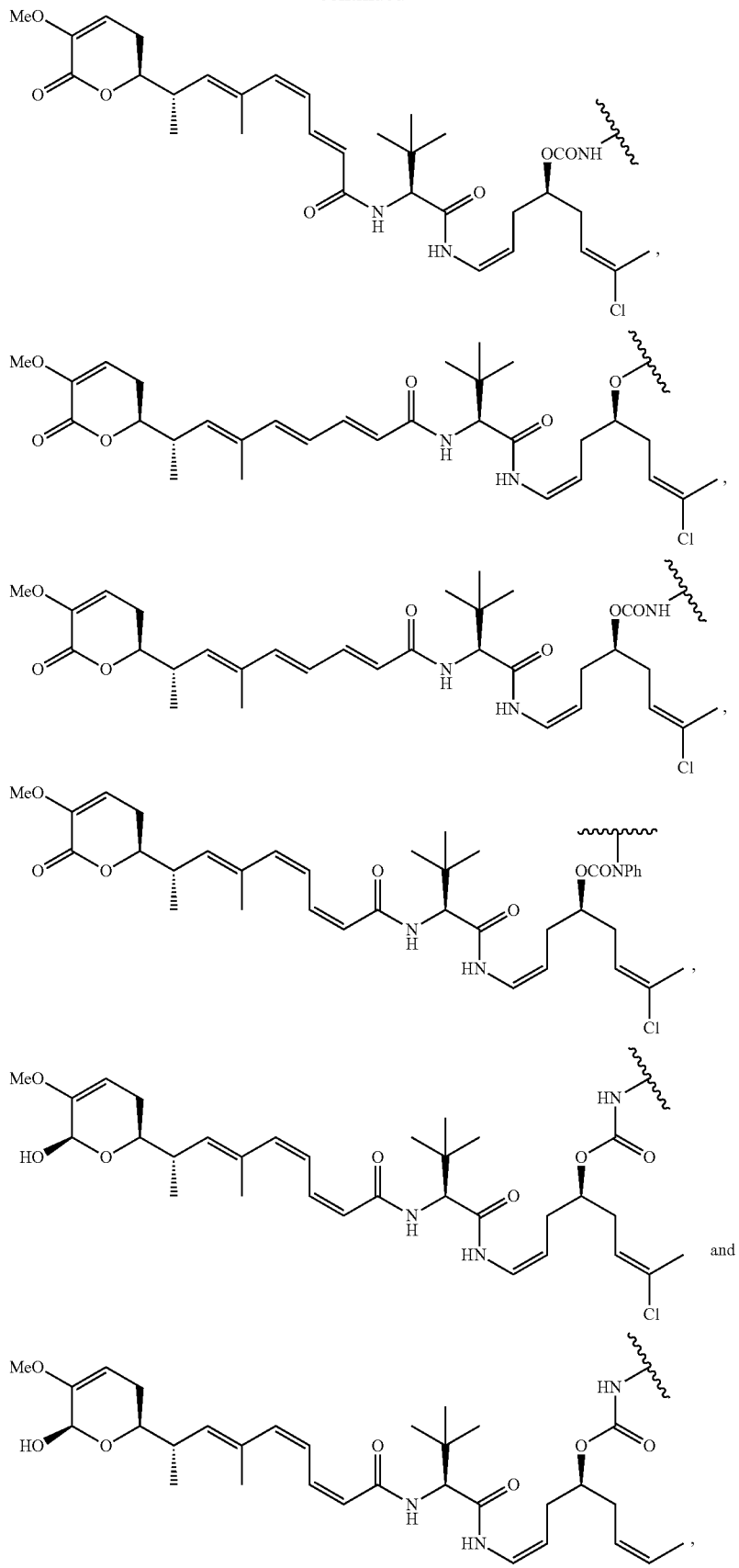

wherein the wavy lines indicate the point of covalent attachment to $(X)_b$ if any, or $(AA)_W$ if any, or the linker group L.

A further preferred drug conjugate of formula $[D-(X)_b-(AA)_w-(L)-]_n-Ab$ according to the first aspect of the present invention is one wherein L, $(AA)_W$ and X are as defined above and wherein D is a compound of formula (I), (Ia) or (Ib), or a pharmaceutically acceptable salt, ester, solvate, tautomer or stereoisomer thereof selected from:

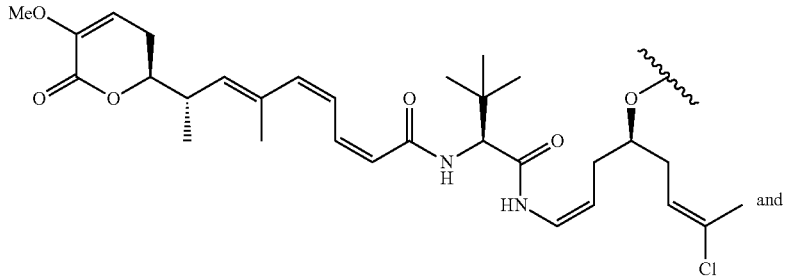

and

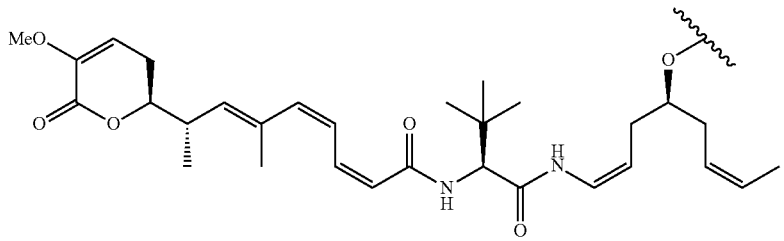

wherein the wavy lines indicate the point of covalent attachment to $(X)_b$ if any, or $(AA)_W$ if any, or the linker group L.

A further preferred drug conjugate of formula $[D-(X)_b-(AA)_w-(L)-]_n-Ab$ according to the first aspect of the present invention is one wherein L, $(AA)_W$ and X are as defined above and wherein D is a compound of formula (I), (Ia) or (Ib), or a pharmaceutically acceptable salt, ester, solvate, tautomer or stereoisomer thereof selected from:

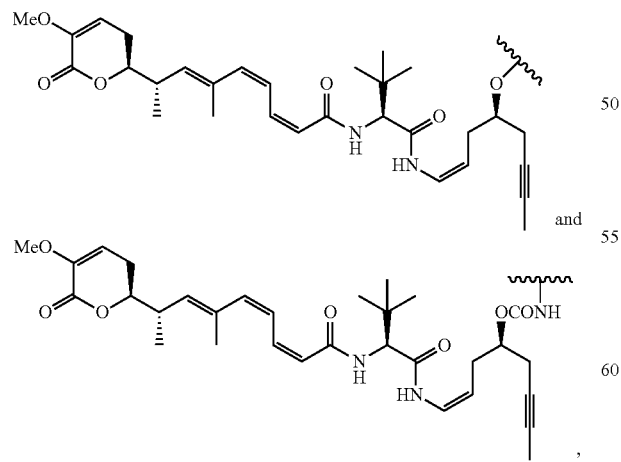

wherein the wavy lines indicate the point of covalent attachment to $(X)_b$ if any, or $(AA)_W$ if any, or the linker group L.

A further preferred drug conjugate of formula $[D-(X)_b-(AA)_w-(L)-]_n-Ab$ according to the first aspect of the present invention is one wherein L, $(AA)_W$ X and D are as defined above and wherein the moiety Ab comprising at least one antigen binding site is an antigen-binding peptide.

A further preferred drug conjugate of formula $[D-(X)_b-(AA)_w-(L)-]_n-Ab$ according to the first aspect of the present invention is one wherein L, $(AA)_W$ X and D are as defined above and the moiety Ab comprising at least one antigen binding site is an antibody, a single domain antibody or an antigen-binding fragment thereof.

A further preferred drug conjugate of formula $[D-(X)_b-(AA)_w-(L)-]_n-Ab$ according to the first aspect of the present invention is one wherein L, $(AA)_W$ X and D are as defined above and the moiety Ab comprising at least one antigen binding site is a monoclonal, polyclonal antibody or bispecific antibody and wherein the antibody or antigen-binding fragment thereof is derived from any species, preferably a human, mouse or rabbit.

A further preferred drug conjugate of formula $[D-(X)_b-(AA)_w-(L)-]_n-Ab$ according to the first aspect of the present invention is one wherein L, $(AA)_W$ X and D are as defined above and the moiety Ab comprising at least one antigen binding site is an antibody or antigen-binding fragment thereof which is selected from the group consisting of a human antibody, an antigen-binding fragment of a human antibody, a humanized antibody, an antigen-binding fragment of a humanized antibody, a chimeric antibody, an antigen-binding fragment of a chimeric antibody, a glycosylated antibody and a glycosylated antigen binding fragment.

A further preferred drug conjugate of formula $[D-(X)_b-(AA)_w-(L)-]_n-Ab$ according to the first aspect of the present invention is one wherein L, $(AA)_W$ X and D are as defined above and the moiety Ab comprising at least one antigen binding site is an antibody or antigen-binding fragment thereof, wherein the antibody or antigen-binding fragment thereof is an antigen-binding fragment selected from the group consisting of an Fab fragment, an Fab' fragment, an F(ab')2 fragment and an Fv fragment.

A further preferred drug conjugate of formula [D-(X)$_b$-(AA)$_w$-(L)-]$_n$-Ab according to the first aspect of the present invention is one wherein L, (AA)$_W$ X and D are as defined above and the moiety Ab comprising at least one antigen binding site is an antibody or antigen-binding fragment thereof, wherein the antibody or antigen-binding fragment thereof is a monoclonal antibody which immunospecifically binds to cancer cell antigens, viral antigens, antigens of cells that produce autoimmune antibodies associated with autoimmune disease, microbial antigens, and preferably a monoclonal antibody which immunospecifically binds to cancer cell antigens.

A further preferred drug conjugate of formula [D-(X)$_b$-(AA)$_w$-(L)-]$_n$-Ab according to the first aspect of the present invention is one wherein L, (AA)$_W$ X and D are as defined above and the moiety Ab comprising at least one antigen binding site is an antibody selected from the group consisting of Abciximab, Alemtuzumab, Basiliximab, Bevacizumab, Cetuximab, Daclizumab, Glembatumumab, Gemtuzumab, Ibritumomab, Inotuzumab, Labetuzumab, Lorvotuzumab, Milatuzumab, Nimotuzumab, Omalizumab, Palivizumab, Panitumumab, Pinatuzumab, Rituximab, Vorsetuzumab, Trastuzumab, an anti-CD4 antibody, an anti-CD5 antibody and an anti-CD13 antibody, or an immunologically active portion thereof, wherein preferably the antibody is selected from Abciximab, Alemtuzumab, Basiliximab, Bevacizumab, Cetuximab, Daclizumab, Glembatumumab, Gemtuzumab, Ibritumomab, Inotuzumab, Labetuzumab, Lorvotuzumab, Milatuzumab, Nimotuzumab, Omalizumab, Palivizumab, Panitumumab, Pinatuzumab, Rituximab, Vorsetuzumab, Trastuzumab and an anti-CD4 antibody, or an immunologically active portion thereof, and yet more preferably Abciximab, Alemtuzumab, Basiliximab, Bevacizumab, Cetuximab, Daclizumab, Gemtuzumab, Ibritumomab, Nimotuzumab, Omalizumab, Palivizumab, Panitumumab, Rituximab and Trastuzumab, or an immunologically active portion thereof. Of these, particularly preferred are Trastuzumab, Rituximab, an anti-CD4 antibody, an anti-CD5 antibody and an anti-CD13 antibody or an immunologically active portion thereof; or the antibody is selected from Trastuzumab, Rituximab and an anti-CD4 antibody or an immunologically active portion thereof, particularly Trastuzumab or an immunologically active portion thereof; or the antibody is selected from an anti-CD5 antibody and an anti-CD13 antibody or an immunologically active portion thereof, particularly an anti-CD13 antibody or an immunologically active portion thereof.

Particularly preferred drug conjugates of formula [D-(X)$_b$-(AA)$_w$-(L)-]$_n$-Ab according to the first aspect of the present invention include the following:

(a) a drug conjugate according to the first aspect of the present invention wherein:
L is selected from the group consisting of:

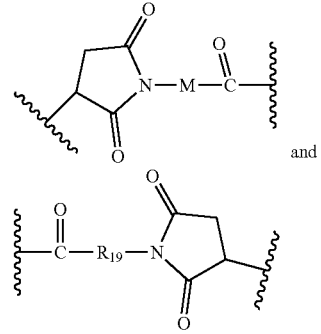

and

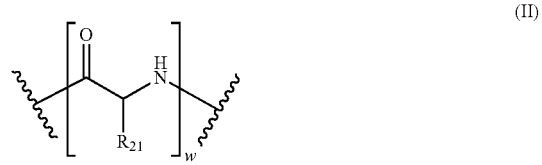

wherein:
the wavy lines indicate the point of covalent attachments to an Ab (the wavy line to the right) and (AA)$_W$ if any, or (X)$_b$ if any, or the drug moiety (the wavy line to the left);
R$_{19}$ is selected from —C1-C12 alkylene-, —0-(Ci-Ci$_2$ alkylene), —C$_6$-Ci$_2$ arylene in one or more rings which may optionally be substituted with one or more substituents R$_x$, —C$_1$-C12 alkylene-C$_6$-Ci2 arylene- wherein the arylene group is in one or more rings which may optionally be substituted with one or more substituents R$_x$, —C$_6$-Ci2 arylene-Ci-C12 alkylene- wherein the arylene group is in one or more rings which may optionally be substituted with one or more substituents R$_x$, —C5-C12 heterocycio- wherein said heterocycio group may be a saturated or unsaturated group having one or more rings and comprising at least one oxygen, nitrogen or sulphur atom in said ring(s), said group optionally being substituted with one or more substituents R$_x$, —C1-C12 alkylene-(C5-C12 heterocycio)- wherein said heterocycio group may be a saturated or unsaturated group having one or more rings and comprising at least one oxygen, nitrogen or sulphur atom in said ring(s), said group optionally being substituted with one or more substituents R$_x$, —(C5-C12 heterocyclo)-CrCi$_2$ alkylene- wherein said heterocycio group may be a saturated or unsaturated group having one or more rings and comprising at least one oxygen, nitrogen or sulphur atom in said ring(s), said group optionally being substituted with one or more substituents R$_x$, —(OCH$_2$CH$_2$)$_r$— and —CH2-(OCH$_2$CH2) r, wherein each of the above alkylene substituents whether alone or attached to another moiety the carbon chain may optionally be substituted by one or more substituents R$_x$;
M is selected from the group consisting of -Ci-C$_6$ alkylene-, -Ci-C$_6$ alkylene-(C$_3$-C$_8$ carbocycio)- and phenylene which may optionally be substituted with one or more substituents R$_x$;
r is an integer ranging from 1-6;
(AA)$_W$ is of formula (II):

(II)

wherein the wavy lines indicate the point of covalent attachments to (X)$_b$ if any, or the drug moiety (the wavy line to the left) and to the linker (the wavy line to the right);

R21 is, at each occurrence, selected from the group consisting of hydrogen, methyl, isopropyl, isobutyl, sec-butyl, benzyl, p-hydroxybenzyl, —CH$_2$OH, —CH(OH)CH$_3$, —CH$_2$CH$_2$SCH$_3$, —CH$_2$CONH$_2$, —CH$_2$OOH, —CH$_2$CH$_2$CONH$_2$, —CH$_2$CH$_2$OOH, —(CH$_2$)$_3$NHC(=NH)NH$_2$, —(CH$_2$)$_3$NH$_2$, —(CH$_2$)$_3$NHCOCH$_3$, —(CH$_2$)$_3$NHCHO, —(CH$_2$)$_4$NHC(=NH)NH$_2$, —(CH$_2$)$_4$NH$_2$, —(CH$_2$)$_4$NHCOCH$_3$, —(CH$_2$)$_4$NHCHO, —(CH$_2$)$_3$NHCONH$_2$, —(CH$_2$)$_4$NHCONH$_2$, —CH$_2$CH$_2$CH(OH)CH$_2$NH$_2$, 2-pyridylmethyl-, 3-pyridylmethyl-, 4-pyridylmethyl-, phenyl, cyclohexyl,

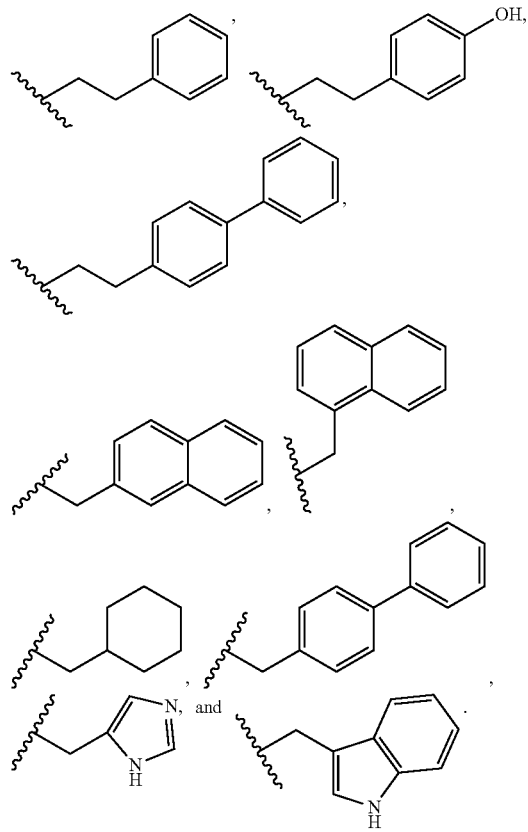

w is an integer ranging from 0 to 12;

wherein X is an extending group selected from —CONH-(Ci-C$_6$ alkylene)NH—, —COO—CH$_2$-(phenylene which may optionally be substituted with one or more substituents R$_x$)—NH—, —CONH-(Ci-C$_6$ alkylene)NH—COO—CH$_2$-(phenylene which may optionally be substituted with one or more substituents R$_x$)—NH—, —CH$_2$-(phenylene which may optionally be substituted with one or more substituents R$_x$)—NH—, —COCH$_2$NH—COCH$_2$—NH—, —COCH$_2$—NH—, —CONH-(Ci-C$_6$ alkylene)S—, —CONH—(C$_1$-C$_6$ alkylene)NHCO(C$_1$-C$_6$ alkylene)S—, —(C$_1$-C$_6$ alkylene)NHCO(C$_1$-C$_6$ alkylene)S—, —(C$_1$-C$_6$ alkylene)S—, —(C$_1$-C$_6$ alkylene)NH— and —(CrC$_6$ alkylene)NH—COO—CH$_2$-(phenylene which may optionally be substituted with one or more substituents R$_x$)—NH—;

D is a drug moiety of formula (Ia) or formula (Ib), or a pharmaceutically acceptable salt, ester, solvate, tautomer or stereoisomer thereof wherein:

R$_1$ is selected from hydrogen, OR$_a$ and OCOR$_a$, wherein R$_a$ is selected from hydrogen and substituted or unsubstituted Ci-C$_6$ alkyl, wherein the optional substituents are one or more substituents R$_x$;

R$_2$ and R$_3$ are each independently selected from hydrogen and substituted or unsubstituted Ci-C$_6$ alkyl, wherein the optional substituents are one or more substituents R$_x$;

R$_3$' is selected from hydrogen, COR$_a$, and substituted or unsubstituted Ci-C$_6$ alkyl, wherein R$_a$ is a substituted or unsubstituted Ci-C$_6$ alkyl, wherein the optional substituents are one or more substituents R$_x$;

each of R$_4$, R$_5$, R6, R7, Rs, R9, R10 and R12 is independently selected from hydrogen and substituted and unsubstituted Ci-C$_6$ alkyl, wherein the optional substituents are one or more substituents R$_x$;

R11 and R-I3 are independently selected from hydrogen and substituted and unsubstituted Ci-C$_6$ alkyl, wherein the optional substituents are one or more substituents R$_x$;

each of R1$_5$, R16, R17, R$_{i7'}$, R$_{18'}$, R24, R24', R25 and R$_2$6 is independently selected from the group consisting of:

hydrogen and substituted or unsubstituted Ci-C$_6$ alkyl groups wherein the optional substituents are selected from the group consisting of alkoxy groups having from 1 to 6 carbon atoms, hydroxyl groups, oxo groups, halogen atoms, OCOR$_y$, OCOOR$_y$, CORy, COOR$_y$, OCON RyR$_z$, CON RyR$_z$, N RyR$_z$ and N R$_y$COR$_z$, wherein each of R$_y$ and Rz is selected from hydrogen atoms and alkyl groups having from 1 to 6 carbon atoms;

R18 is selected from hydrogen, a Ci.C$_6$ alkyl group which may optionally be substituted with at least one group R$_x$, an aryl group having from 6 to 12 carbon atoms in one or more aromatic rings, said aryl groups optionally being substituted with one or more substituents R$_x$ and a 5- to 10-membered unsaturated or saturated heterocyclic group having one or more rings, said heterocyclic group optionally being substituted with one or more substituents R$_x$, wherein the substituents R$_x$ are selected from the group consisting of alkoxy groups having from 1 to 6 carbon atoms, hydroxyl groups, halogen atoms, alkylamino groups having from 1 to 6 carbon atoms and dialkylamino groups having from 1 to 6 carbon atoms;

R$_{27}$ is selected from hydrogen, halogen and substituted and unsubstituted Ci-C$_6$ alkyl, wherein the optional substituents are one or more substituents R$_x$;

each dotted line represents an optional additional bond, but when a triple bond exists between the C atom to which R$_{25}$ is attached and the C atom to which R$_2$6 and R27 are attached, then R$_{25}$ and either R$_2$6 or R$_{27}$ are absent;

the moiety Ab comprising at least one antigen binding site is an antibody or an antigen-binding fragment thereof and it is selected from the group consisting of a human antibody, an antigen-binding fragment of a human antibody, a humanized antibody, an antigen-binding fragment of a humanized antibody, a chimeric antibody, an antigen-binding fragment of a chimeric antibody, a glycosylated antibody and a glycosylated antigen binding fragment; and n is the ratio of the group [D-(X)$_b$-(AA)$_w$-(L)-] to the moiety Ab comprising at least one antigen binding site and is in the range from 1 to 12.

(b) a drug conjugate according to the first aspect of the present invention selected from the formulas (IV) and (V):

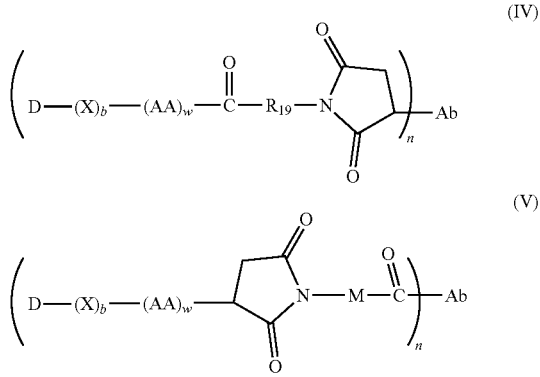

wherein:

Rig is selected from —CrC$_8$ alkylene-, –0-(Ci-C$_8$ alkylene), -Ci-C$_8$ alkylene-C$_6$-Ci$_2$ arylene- wherein the arylene group is in one or more rings which may optionally be substituted with one or more substituents R$_x$ and —C$_6$-Ci$_2$arylene-Ci-C$_8$ alkylene- wherein the arylene group is in one or more rings which may optionally be substituted with one or more substituents R$_x$, wherein each of the above alkylene substituents whether alone or attached to another moiety the carbon chain may optionally be substituted by one or more substituents R$_x$;

M is selected from the group consisting of -Ci-C$_3$ alkylene- and -Ci-C$_3$ alkylene-(C$_5$-C$_7$ carbocyclo)-;

(AA)$_W$ is of formula (II)

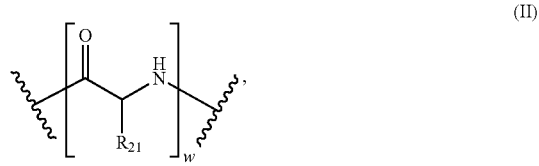

wherein:

the wavy lines indicate the point of covalent attachments to (X)$_b$ if any, or the drug moiety (the wavy line to the left) and to the linker (the wavy line to the right);

R21 is, at each occurrence, selected from the group consisting of hydrogen, methyl, isopropyl, sec-butyl, benzyl, indolylmethyl, —(CH$_2$)$_3$NHCON H2, —(CH$_2$)4N H2, —(CH$_2$)$_3$NHC(=NH)NH$_2$ and —(CH$_2$)$_4$NHC(=NH)NH$_2$;

w is an integer from 0 to 6;

X is an extending group selected from the group consisting of —CONH—(C$_2$-C$_4$ alkylene)NH—, —COO—CH$_2$-phenylene-NH—, wherein said phenylene group may optionally be substituted with from one to four substituents R$_x$ selected from the group consisting of alkyl groups having from 1 to 6 carbon atoms, alkoxy groups having from 1 to 6 carbon atoms, halogen atoms, nitro groups and cyano groups, —CONH—(C$_2$-C$_4$ alkylene)NH—COO—CH$_2$-(phenylene which may optionally be substituted with from one to four substituents R$_x$ selected from the group consisting of alkyl groups having from 1 to 6 carbon atoms, alkoxy groups having from 1 to 6 carbon atoms, halogen atoms, nitro groups and cyano groups)-NH—, —COCH$_2$NH—COCH$_2$—NH—, —CONH—(C$_2$-C$_4$ alkylene)S—, —CONH—(C$_2$-C$_4$ alkylene)NHCO(C$_1$-C$_3$ alkylene)S—, —(C$_2$-C$_4$ alkylene)NHCO(C$_1$-C$_3$ alkylene)S—, —(C$_2$-C$_4$ alkylene)S—, —(C$_2$-C$_4$ alkylene)NH— and —(C$_2$-C$_4$ alkylene)NH—COO—CH$_2$-(phenylene which may optionally be substituted with from one to four substituents R$_x$ selected from the group consisting of alkyl groups having from 1 to 6 carbon atoms, alkoxy groups having from 1 to 6 carbon atoms, halogen atoms, nitro groups and cyano groups)-NH—;

D is a drug moiety of formula (Ia) or formula (Ib), or a pharmaceutically acceptable salt, ester, solvate, tautomer or stereoisomer thereof wherein:

R$_1$ is hydrogen or methoxy;

each of R$_2$ and R$_3$ is hydrogen;

R$_3$' is hydrogen;

each of R$_4$, R5, R6, R7, Rs, R9, R10 and Ri$_2$ is independently selected from hydrogen, substituted and unsubstituted methyl, substituted and unsubstituted isopropyl and substituted and unsubstituted tert-butyl, wherein the optional substituents are one or more substituents R$_x$;

each of R$_{11}$ and R$_{13}$ is hydrogen;

each of R1$_5$, R16, R$_{17}$, R$_{17'}$, R$_{18'}$, R$_{24}$, R24', R25 and R$_2$6 is independently selected from the group consisting of:

hydrogen and substituted or unsubstituted Ci-C$_6$ alkyl groups wherein the optional substituents are selected from the group consisting of alkoxy groups having from 1 to 6 carbon atoms, hydroxyl groups, oxo groups, halogen atoms, OCOR$_y$, OCOOR$_y$, CORy, COOR$_y$, OCONRyR$_z$, CONRyR$_z$, NRyR$_z$, NRyCOR$_z$, wherein each of R$_y$ and R$_z$ is selected from hydrogen atoms and alkyl groups having from 1 to 6 carbon atoms.

R18 is selected from hydrogen, a Ci-C$_6$ alkyl group which may optionally be substituted with at least one group R$_x$, and a phenyl group optionally being substituted with one or more substituents R$_x$;

R27 is a hydrogen atom or a chlorine atom;

each dotted line represents an optional additional bond, but when a triple bond exists between the C atom to which R$_{25}$ is attached and the C atom to which R$_{26}$ and R$_{27}$ are attached, then R$_{25}$ and either R$_{26}$ or R$_{27}$ are absent;

the moiety Ab comprising at least one antigen binding site is an antibody or an antigen-binding fragment thereof, wherein the antibody or antigen-binding fragment is a monoclonal antibody which immunospecifically binds to cancer cell antigens, viral antigens, antigens of cells that produce autoimmune antibodies associated with autoimmune disease, microbial antigens, and preferably a monoclonal antibody which immunospecifically binds to cancer cell antigens; and n is the ratio of the group [D-(X)$_b$-(AA)$_w$-(L)-] wherein L is as defined in formulas (IV) or (V) to the moiety Ab comprising at least one antigen binding site and is in the range from 3 to 8.

(c) a drug conjugate according to the first aspect selected from the formulas (IV) and (V):

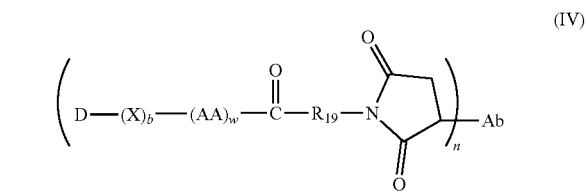

-continued

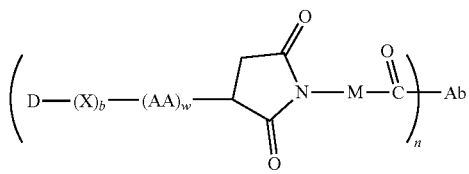

(V)

wherein:
Rig is selected from -Ci-C$_6$ alkylene-, -phenylene-CrC$_6$ alkylene- wherein the phenylene group may optionally be substituted with one or more substituents R$_x$ selected from the group consisting of alkyl groups having from 1 to 6 carbon atoms, alkoxy groups having from 1 to 6 carbon atoms, halogen atoms, nitro groups and cyano groups, wherein each of the above alkylene substituents whether alone or attached to another moiety in the carbon chain may optionally be substituted by one or more substituents R$_x$ selected from the group consisting of alkyl groups having from 1 to 6 carbon atoms, alkoxy groups having from 1 to 6 carbon atoms, aryl groups having from 6 to 12 carbon atoms, halogen atoms, nitro groups and cyano groups, and preferably R$_{19}$ is a Ci-C$_6$ alkylene group;
M is —C1-C3 alkylene-(C$_5$-C$_7$ carbocyclo)-;
w is 0 or 2, and where w is 2, then (AA)$_W$ is of formula (III):

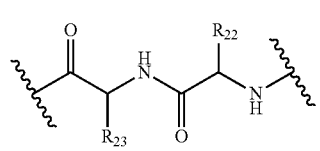

(III)

wherein the wavy lines indicate the point of covalent attachments to (X)$_b$ if any, or the drug moiety (the wavy line to the left) and to the linker (the wavy line to the right);
R$_{22}$ is selected from methyl, benzyl, isopropyl, sec-butyl and indolylmethyl;
R$_{23}$ is selected from methyl, —(CH$_2$)$_4$NH$_2$, —(CH$_2$)$_3$NHCONH$_2$ and —(CH$_2$)$_3$NHC(=NH)NH$_2$;
X is an extending group selected from the group consisting of —CONH—(C$_2$-C$_4$ alkylene)NH—, —COO—CH$_2$-phenylene-NH—, wherein said phenylene group may optionally be substituted with from one to four substituents R$_x$ selected from the group consisting of alkyl groups having from 1 to 6 carbon atoms, alkoxy groups having from 1 to 6 carbon atoms, halogen atoms, nitro groups and cyano groups, —CONH—(C$_2$-C$_4$ alkylene)NH—COO—CH$_2$-(phenylene which may optionally be substituted with from one to four substituents R$_x$ selected from the group consisting of alkyl groups having from 1 to 6 carbon atoms, alkoxy groups having from 1 to 6 carbon atoms, halogen atoms, nitro groups or cyano groups)-NH—, —COCH$_2$NH—COCH$_2$—NH—, —CONH—(C$_2$-C$_4$ alkylene)S—, —CONH—(C$_2$-C$_4$ alkylene)NHCO(C$_1$-C$_3$ alkylene)S—, —(C$_2$-C$_4$ alkylene) NHCO(C$_1$-C$_3$ alkylene)S—, —(C$_2$-C$_4$ alkylene)S—, —(C$_2$-C$_4$ alkylene)NH— and —(C$_2$-C$_4$ alkylene)NH—COO—CH$_2$-(phenylene which may optionally be substituted with from one to four substituents R$_x$ selected from the group consisting of alkyl groups having from 1 to 6 carbon atoms, alkoxy groups having from 1 to 6 carbon atoms, halogen atoms, nitro groups and cyano groups)-NH—;

D is a drug moiety of formula (Ia) or formula (Ib), or a pharmaceutically acceptable salt, ester, solvate, tautomer or stereoisomer thereof wherein:
R1 is hydrogen or methoxy;
each of R$_2$ and R$_3$ is hydrogen;
R$_3$' is hydrogen;
each of R$_5$, R7, Rs, R9 and R10 is hydrogen;
each of R$_4$ and R$_6$ is methyl;
each of R11 and R13 is hydrogen;
R1$_2$ is isopropyl, tert-butyl or benzyl;
each of R1$_5$, R16, R17, R17', R$_{18'}$, R2$_4$, R2$_4$', R25 and R$_{26}$ is independently selected from the group consisting of hydrogen and Ci-C$_6$ alkyl group, preferably hydrogen and methyl;
R18 is selected from hydrogen and phenyl, preferably hydrogen;
R$_{27}$ is a hydrogen atom or a chlorine atom;
each pair of carbons linked by one or more dotted lines is bonded through double bonds;
the moiety Ab comprising at least one antigen binding site is a monoclonal antibody selected from the group consisting of Abciximab, Alemtuzumab, Basiliximab, Bevacizumab, Cetuximab, Daclizumab, Glembatumumab, Gemtuzumab, Ibritumomab, Inotuzumab, Labetuzumab, Lorvotuzumab, Milatuzumab, Nimotuzumab, Omalizumab, Palivizumab, Panitumumab, Pinatuzumab, Rituximab, Vorsetuzumab, Trastuzumab, an anti-CD4 antibody, an anti-CD5 antibody, and an anti-CD13 antibody or an immunologically active portion thereof, preferably it is a monoclonal antibody selected from the group consisting of Abciximab, Alemtuzumab, Basiliximab, Bevacizumab, Cetuximab, Daclizumab, Glembatumumab, Gemtuzumab, Ibritumomab, Inotuzumab, Labetuzumab, Lorvotuzumab, Milatuzumab, Nimotuzumab, Omalizumab, Palivizumab, Panitumumab, Pinatuzumab, Rituximab, Vorsetuzumab, Trastuzumab and an anti-CD4 antibody, or an immunologically active portion thereof, and yet more preferably Abciximab, Alemtuzumab, Basiliximab, Bevacizumab, Cetuximab, Daclizumab, Gemtuzumab, Ibritumomab, Nimotuzumab, Omalizumab, Palivizumab, Panitumumab, Rituximab and Trastuzumab, or an immunologically active portion thereof. Of these, particularly preferred are an antibody selected from Trastuzumab, Rituximab, an anti-CD4 antibody, an anti-CD5 antibody, and an anti-CD13 antibody, or an immunologically active portion thereof, more preferably the antibody is selected from Trastuzumab, an anti-CD13 antibody, and anti-CD4 antibody, an anti-CD5 antibody or an immunologically active portion thereof; or an antibody selected from Trastuzumab, Rituximab and an anti-CD4 antibody, or an immunologically active portion thereof, preferably Trastuzumab or an immunologically active portion thereof; or an antibody selected from an anti-CD5 antibody and an anti-CD13 antibody or an immunologically active portion thereof, particularly an anti-CD13 antibody or an immunologically active portion thereof; and
n is the ratio of the group [D-(X)$_b$-(AA)$_w$-(L)-] wherein L is as defined in formulas (IV) or (V) to the moiety Ab comprising at least one antigen binding site and is in the range from 3 to 5.
(d) A drug conjugate according to the first aspect of the present invention selected from the formulas (IV) and (V):

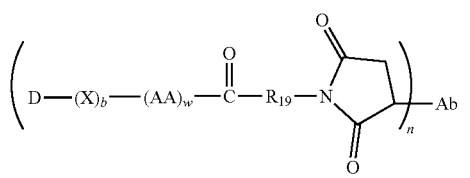

(IV)

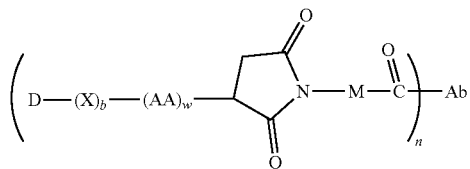

(V)

wherein:
R19 is —C3-C6 alkylene-;
M is —C1-C3 alkylene-(C5-C7carbocyclo)-;
w is 0 or 2, and where w is 2, then (AA)_W is of formula (III):

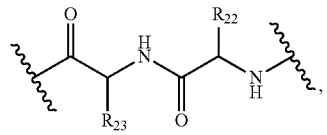

(III)

wherein R22 is isopropyl, R23 is —(CH2)3NHCON H2, wherein the wavy lines indicate the point of covalent attachments to (X)_b if any, or the drug moiety (the wavy line to the left) and to the linker (the wavy line to the right);

X is an extending group selected from the group consisting of —CONH—(C2-C4 alkylene)NH—, —COO—CH2-phenylene-NH—, wherein said phenylene group may optionally be substituted with from one to four substituents R_x selected from the group consisting of alkyl groups having from 1 to 6 carbon atoms, alkoxy groups having from 1 to 6 carbon atoms, halogen atoms, nitro groups and cyano groups, —CONH—(C2-C4 alkylene)NH—COO—CH2-(phenylene which may optionally be substituted with from one to four substituents R_x selected from the group consisting of alkyl groups having from 1 to 6 carbon atoms, alkoxy groups having from 1 to 6 carbon atoms, halogen atoms, nitro groups and cyano groups)-NH—, —COCH2NH—COCH2—NH—, —CONH—(C2-C4 alkylene)S—, —CONH—(C2-C4 alkylene)NHCO(C1-C3 alkylene)S—, —(C2-C4 alkylene)N HCO(C1-C3 alkylene)S—, —(C2-C4 alkylene)S—, —(C2-C4 alkylene)N H— and —(C2-C4 alkylene)N H—COO—CH2-(phenylene which may optionally be substituted with from one to four substituents R_x selected from the group consisting of alkyl groups having from 1 to 6 carbon atoms, alkoxy groups having from 1 to 6 carbon atoms, halogen atoms, nitro groups and cyano groups)-N H—;

D is a drug moiety of formula (Ia) or formula (Ib), or a pharmaceutically acceptable salt, ester, solvate, tautomer or stereoisomer thereof selected from the following group:

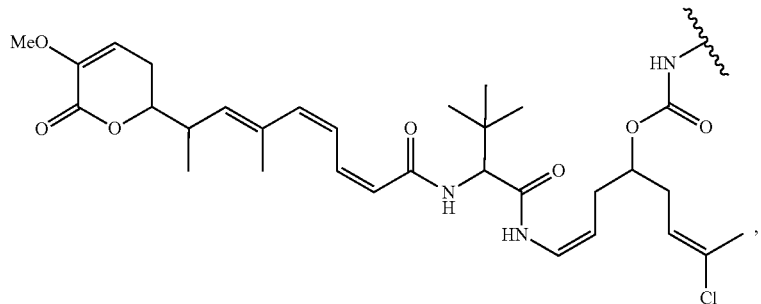

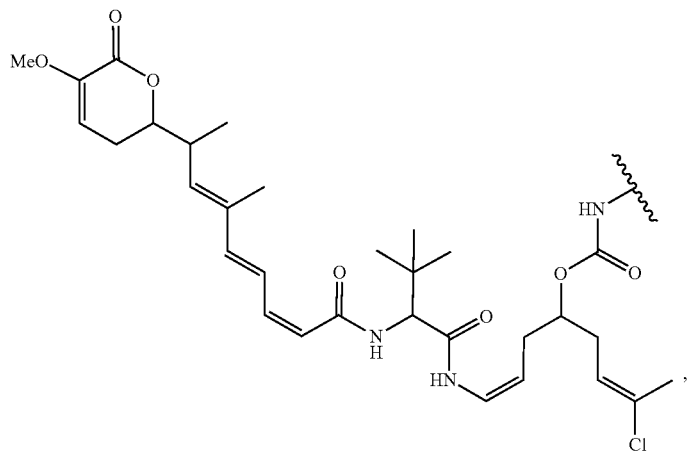

-continued
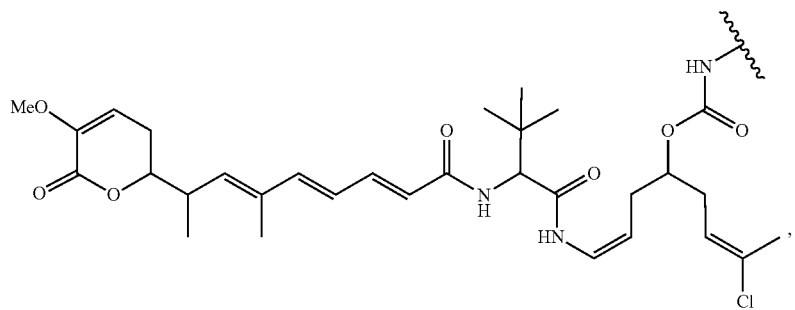
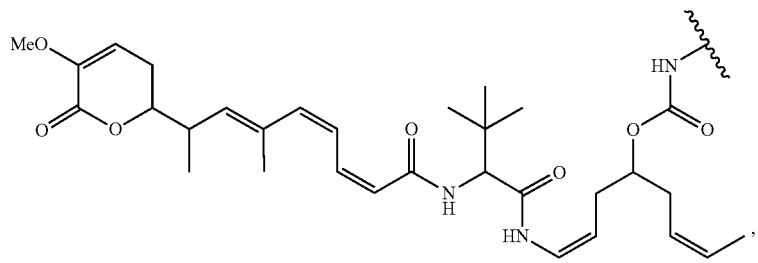
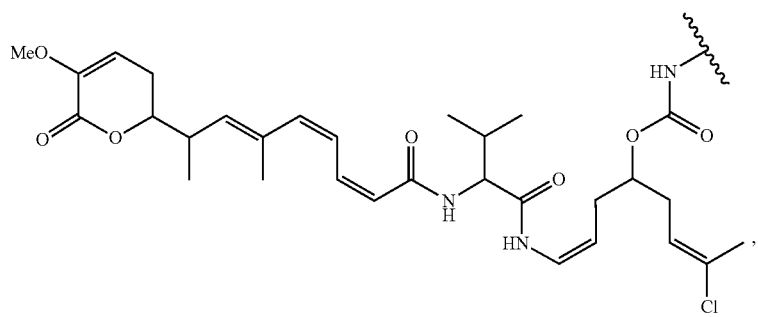
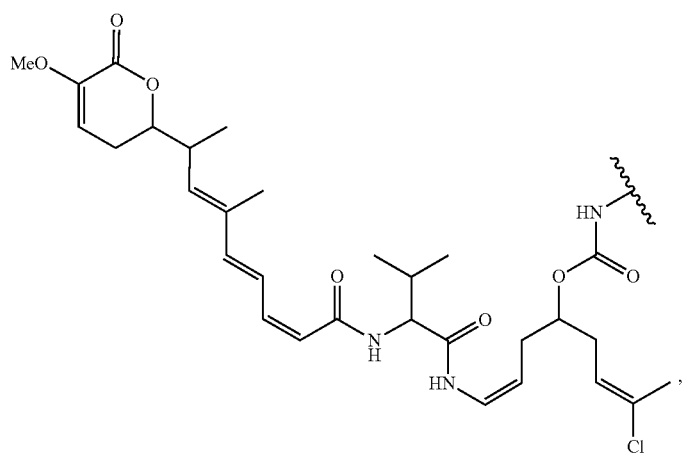
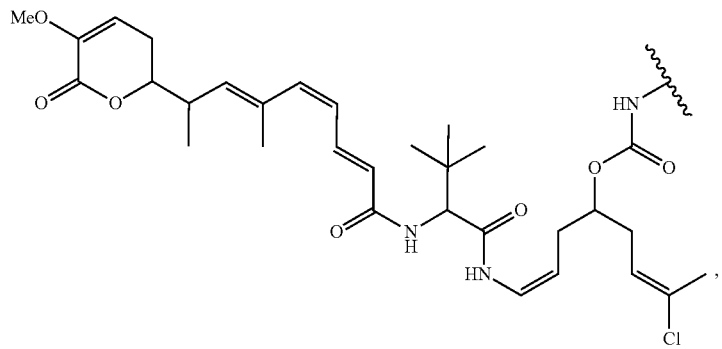

-continued
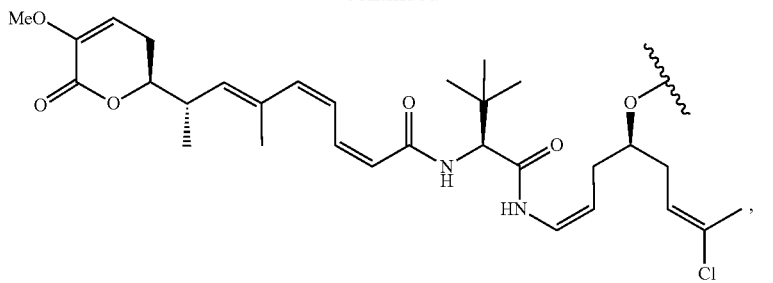
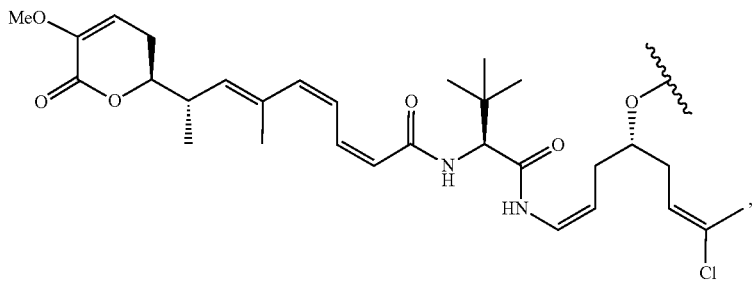
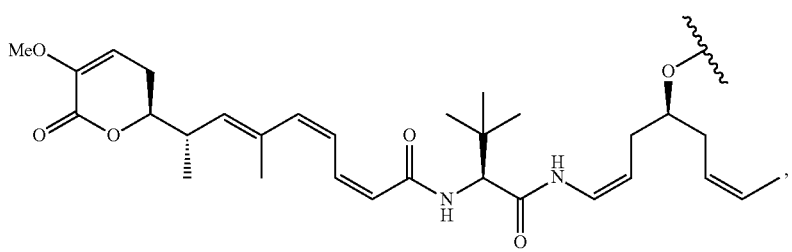
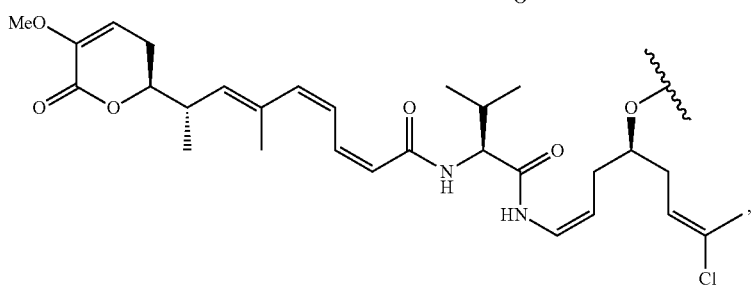
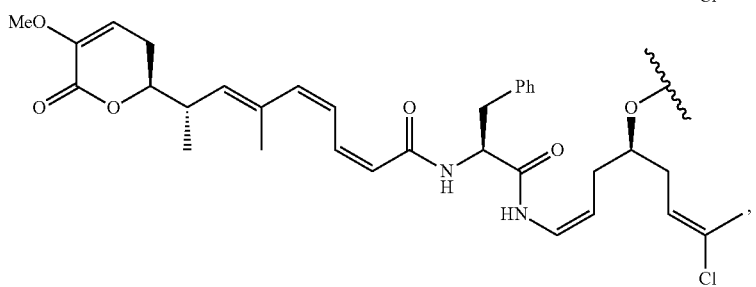
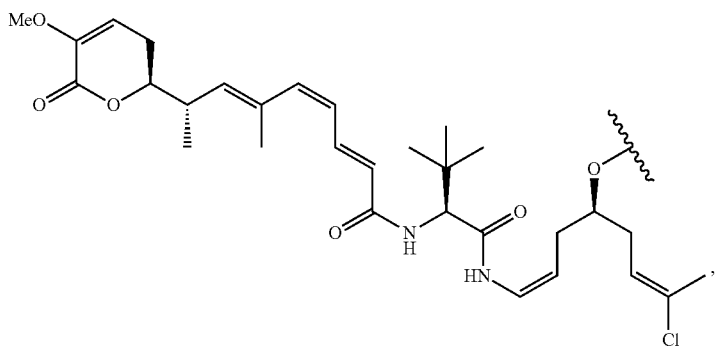

-continued
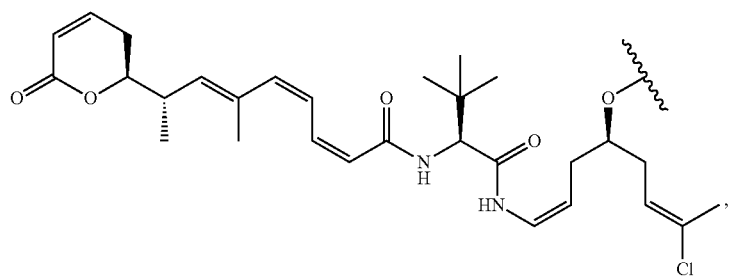
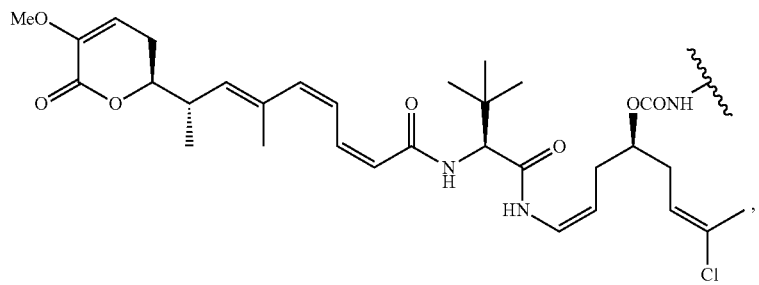
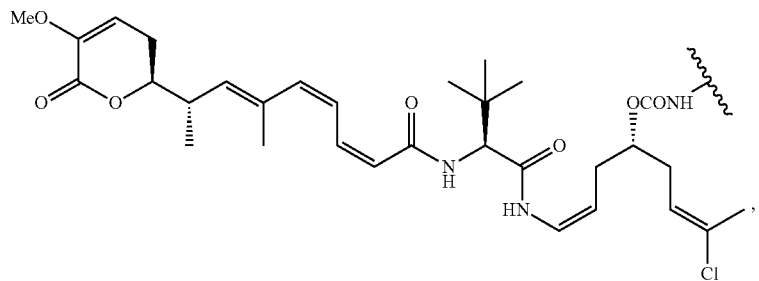
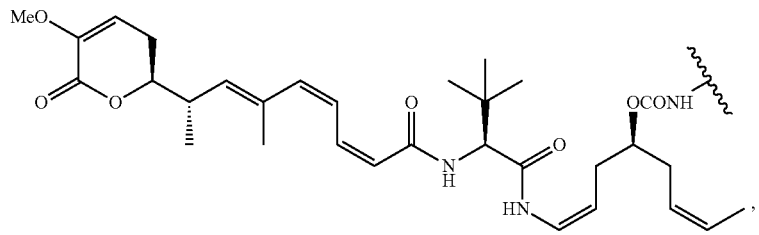
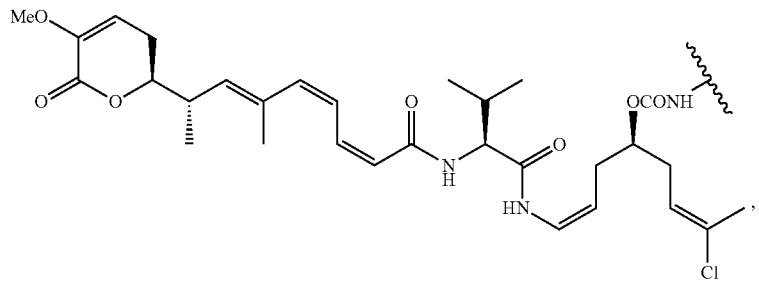
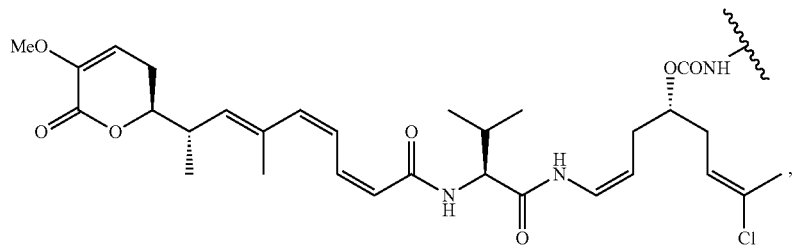

-continued
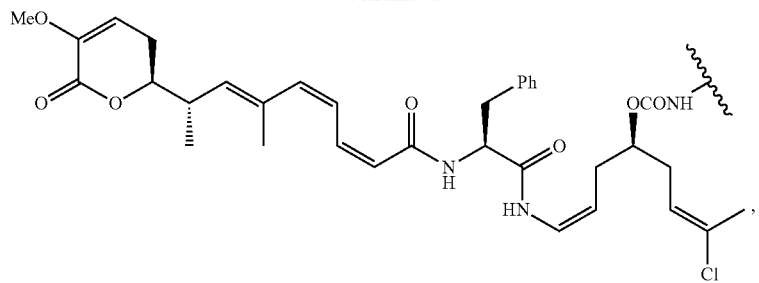
,
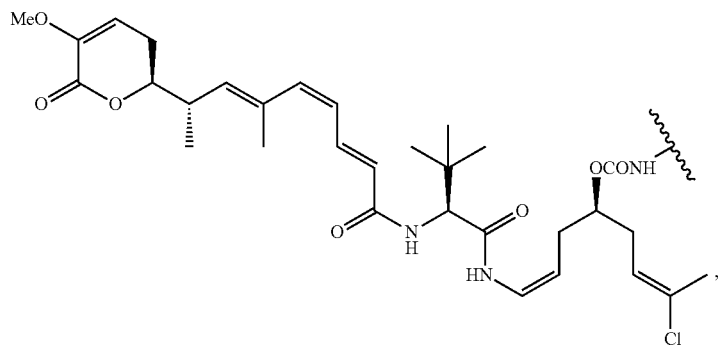
,
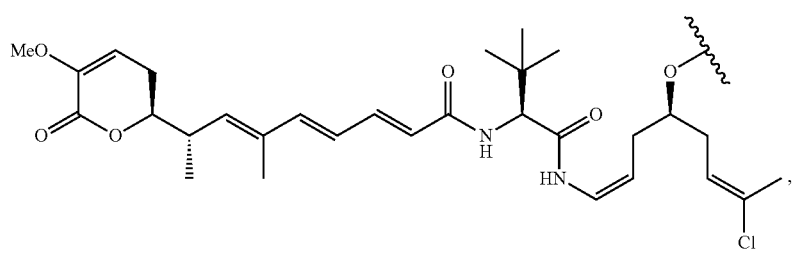
,
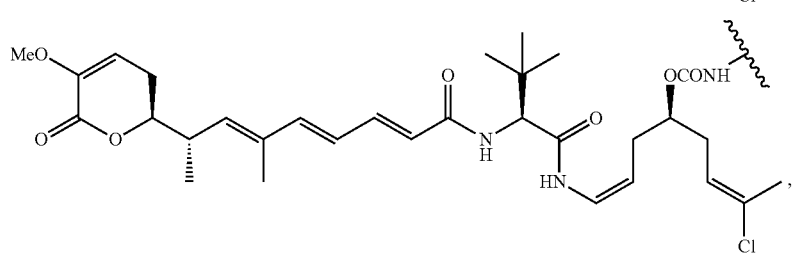
,
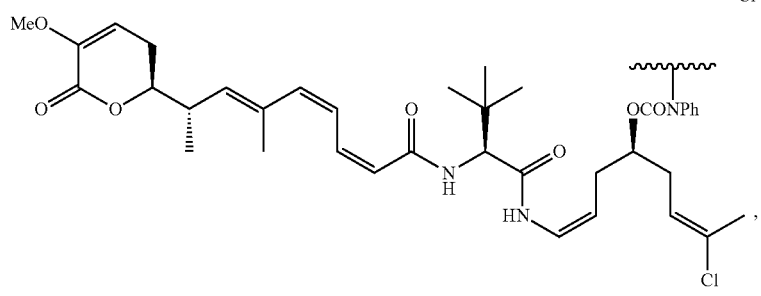
,
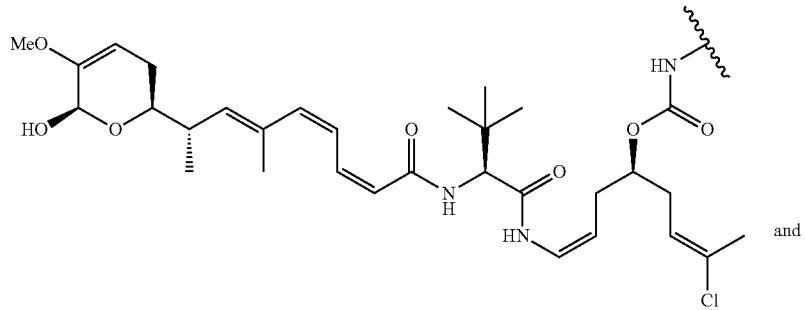
and -continued

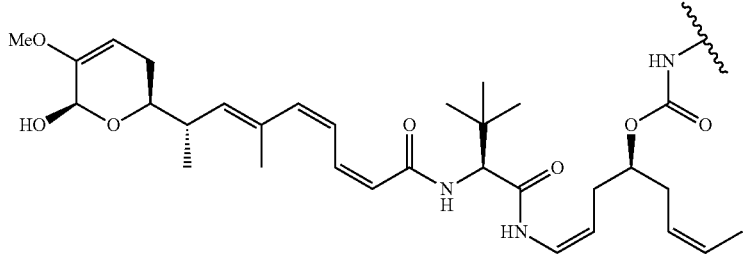

wherein the wavy lines indicate the point of covalent attachment to $(X)_b$ if any, or $(AA)_W$ if any, or the linker group L; the moiety Ab comprising at least one antigen binding site is selected from Trastuzumab, Rituximab, an anti-CD4 antibody, an anti-CD5 antibody, and an anti-CD13 antibody or an immunologically active portion thereof, and more preferably it is selected from Trastuzumab, an anti-CD4 antibody, an anti-CD5 antibody and an anti-CD13 antibody or an immunologically active portion thereof, or it is selected from Trastuzumab, Rituximab and an anti-CD4 antibody or an immunologically active portion thereof, preferably Trastuzumab or an immunologically active portion thereof; or it is selected from an anti-CD5 antibody and an anti-CD13 antibody or an immunologically active portion thereof, particularly an anti-CD13 antibody or an immunologically active portion thereof; and n is the ratio of the group $[D-(X)_b-(AA)_w-(L)-]$ wherein L is as defined in formulas (IV) or (V) to the moiety Ab comprising at least one antigen binding site and is in the range from 3 to 5.

(e) A drug conjugate according to the first aspect of the present invention selected from the formulas (IV) and (V):

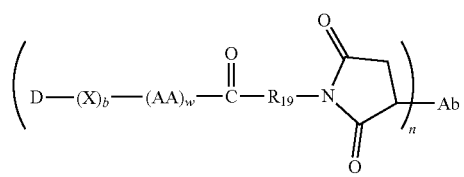
(IV)

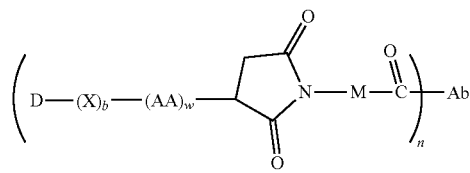
(V)

wherein
Rig is —$C_3$-$C_6$ alkylene-;
M is —C1-C3 alkylene-($C_5$-$C_7$carbocyclo)-;
w is 0 or 2, and where w is 2, then $(AA)_W$ is of formula (III):

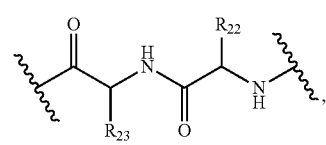
(III)

wherein R22 is isopropyl, R23 is —$(CH_2)3N$ HCON H2, and the wavy lines indicate the point of covalent attachments to $(X)_b$ if any, or the drug moiety (the wavy line to the left) and to the linker (the wavy line to the right);

X is an extending group selected from the group consisting of —CON H—($C_2$-$C_4$ alkylene)N H—, —COO—$CH_2$-phenylene-N H—, wherein said phenylene group may optionally be substituted with from one to four substituents $R_x$ selected from the group consisting of alkyl groups having from 1 to 6 carbon atoms, alkoxy groups having from 1 to 6 carbon atoms, halogen atoms, nitro groups and cyano groups, —CON H—($C_2$-$C_4$ alkylene)N H—COO—$CH_2$-(phenylene which may optionally be substituted with from one to four substituents $R_x$ selected from the group consisting of alkyl groups having from 1 to 6 carbon atoms, alkoxy groups having from 1 to 6 carbon atoms, halogen atoms, nitro groups and cyano groups)-N H—, —$COCH_2NH$—COCH2-N H—, —CON H—($C_2$-$C_4$ alkylene)S—, —CON H—($C_2$-$C_4$ alkylene)N HCO($C_1$-$C_3$ alkylene)S—, —($C_2$-$C_4$ alkylene)N HCO($C_1$-$C_3$ alkylene)S—, —($C_2$-$C_4$ alkylene) S—, —($C_2$-$C_4$ alkylene)N H— and —($C_2$-$C_4$ alkylene)N H—COO—$CH_2$-(phenylene which may optionally be substituted with from one to four substituents $R_x$ selected from the group consisting of alkyl groups having from 1 to 6 carbon atoms, alkoxy groups having from 1 to 6 carbon atoms, halogen atoms, nitro groups and cyano groups)-N H—;

D is a drug moiety of formula (Ia) or formula (Ib), or a pharmaceutically acceptable salt, ester, solvate, tautomer or stereoisomer thereof selected from:

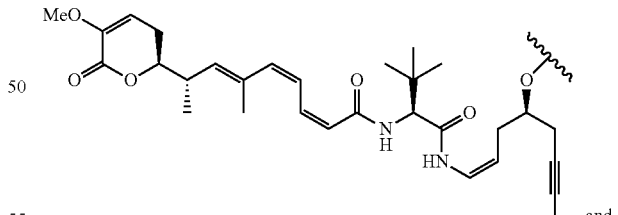

and

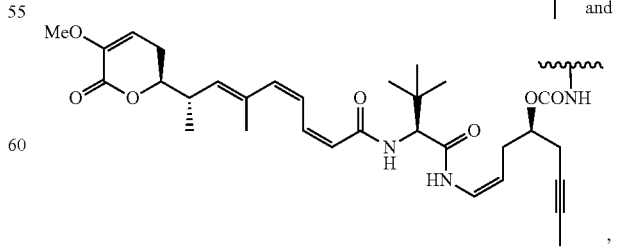

wherein the wavy lines indicate the point of covalent attachment to $(X)_b$ if any, or $(AA)_W$ if any, or the linker group L;

the moiety Ab comprising at least one antigen binding site is selected from Trastuzumab, Rituximab, an anti-CD4 antibody, an anti-CD5 antibody and an anti-CD13 antibody or an immunologically active portion of thereof; more preferably it is selected from Trastuzumab, Rituximab and an anti-CD4 antibody or an immunologically active portion of thereof, and most preferably it is Trastuzumab or an immunologically active portion thereof; and n is the ratio of the group [D-(X)$_b$-(AA)$_w$-(L)-] wherein L is as defined in formulas (IV) or (V) to the moiety comprising at least one antigen binding site and is in the range from 3 to 5.

(f) A drug conjugate according to the first aspect of the present invention of formula (IV):

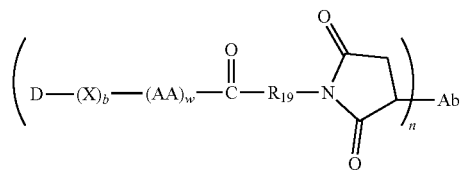

wherein:
R$_{19}$ is C$_5$ alkylene-;
b is 1;
w is 0 or 2, and where w is 2, then (AA)$_W$ is of formula (III):

(III)

wherein R$_{22}$ is isopropyl, R$_{23}$ is —(CH$_2$)$_3$NHCONH2, and the wavy lines indicate the point of covalent attachments to (X)$_b$ if any, or the drug moiety (the wavy line to the left) and to the linker (the wavy line to the right); and X is an extending group selected from —CONH(CH$_2$)$_3$NHCOOCH$_2$-phenylene-NH—, and —CONH(CH$_2$)$_3$NH—;
or of formula (V)

(V)

wherein M is -methyl-cyclohexylene-;
b is 1;
w is 0; and
X is an extending group selected from —CONH(CH$_2$)3S— and —CONH(CH$_2$)$_3$NHCO(CH$_2$)$_2$S—;
D is a drug moiety of formula (Ia), or a pharmaceutically acceptable salt, ester, solvate, tautomer or stereoisomer thereof selected from:

and wherein the wavy lines indicate the point of covalent attachment to (X)$_b$ if any, or (AA)$_W$ if any, or the linker group L;
the moiety Ab comprising at least one antigen binding site is Trastuzumab, Rituximab, an anti-CD4 antibody, an anti-CD5 antibody and an anti-CD13 antibody or an immunologically active portion thereof, more preferably it is selected from Trastuzumab, an anti-CD13 antibody, an anti-CD4 antibody and an anti-CD5 antibody, or an immunologically active portion thereof; or it is selected from Trastuzumab, Rituximab and an anti-CD4 antibody, or an immunologically active portion thereof, and most preferably it is Trastuzumab or an immunologically active portion thereof; or it is selected from an anti-CD5 antibody and an anti-CD13 antibody or an immunologically active portion thereof, and most preferably it is an anti-CD13 antibody or an immunologically active portion thereof; and n is the ratio of the group [D-(X)$_b$-(AA)$_w$-(L)-] wherein L is as defined in formulas (IV) or (V) to the moiety Ab comprising at least one antigen binding site and is in the range from 3 to 5, and preferably 4.

(g) A drug conjugate according to the first aspect of the present invention of formula (IV):

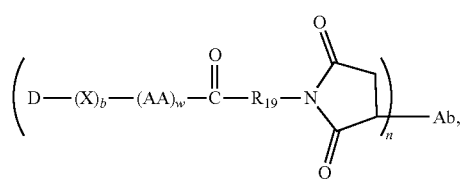

(IV)

wherein R$_{19}$ is —C$_5$ alkylene-;
b is 1;
w is 0 or 2, and where w is 2, then (AA)$_W$ is of formula (III):

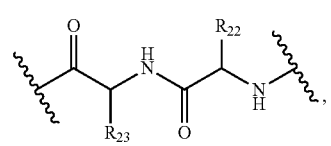

(III)

wherein R$_{22}$ is isopropyl, R$_{23}$ is —(CH$_2$)$_3$NHCON H2, and the wavy lines indicate the point of covalent attachments to (X)$_b$ if any, or the drug moiety (the wavy line to the left) and to the linker (the wavy line to the right); and
X is an extending group selected from —(CH$_2$)$_3$NHCOOCH2-phenylene-NH—, and —(CH$_2$)$_3$NH—;
or of formula (V)

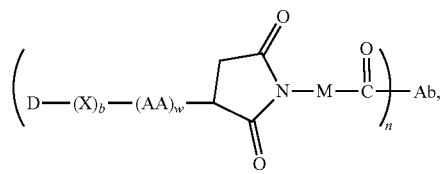

(V)

wherein M is -methyl-cyclohexyl ene-;
b is 1:
w is 0; and
X is an extending group selected from —(CH$_2$)$_3$S— and —(CH$_2$)$_3$NHCO(CH$_2$)$_2$S—;
D is a drug moiety of formula (Ib), or a pharmaceutically acceptable salt, ester, solvate, tautomer or stereoisomer thereof selected from:

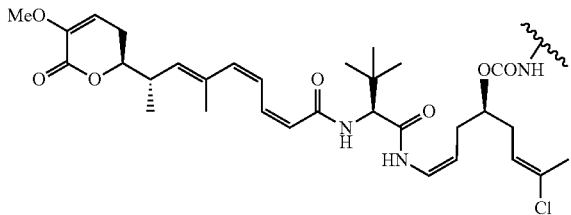

and

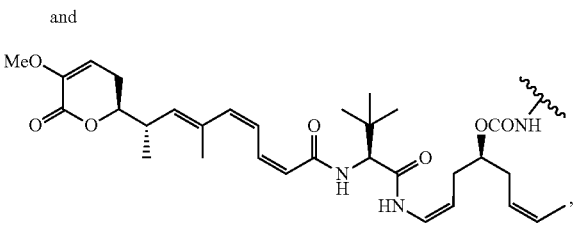

wherein the wavy lines indicate the point of covalent attachment to (X)$_b$ if any, or (AA)$_W$ if any, or the linker group L;
the moiety Ab comprising at least one antigen binding site is selected from Trastuzumab, Rituximab, an anti-CD4 antibody, an anti-CD5 antibody, and an anti-CD13 antibody or an immunologically active portion thereof; and more preferably it is selected from Trastuzumab, an anti-CD13 antibody, an anti-CD4 antibody, and an anti-CD5 antibody or an immunologically active portion thereof; or it is selected from Trastuzumab, Rituximab and an anti-CD4 antibody, or an immunologically active portion thereof; and most preferably it is Trastuzumab or an immunologically active portion thereof; or it is selected from an anti-CD5 antibody and an anti-CD13 antibody or an immunologically active portion thereof, particularly an anti-CD13 antibody or an immunologically active portion thereof; and n is the ratio of the group [D-(X)$_b$-(AA)$_w$-(L)-] wherein L is as defined in formulas (IV) or (V) to the moiety Ab comprising at least one antigen binding site and is in the range from 3 to 5, and preferably 4.

h) A drug conjugate according to the first aspect of the present invention of formula (IV):

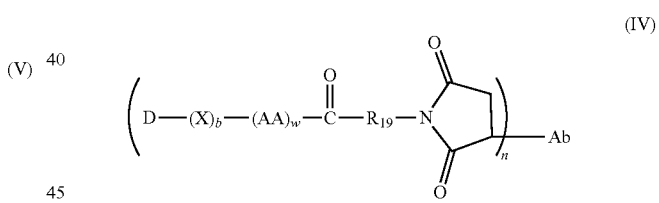

(IV)

wherein R$_{19}$ is —C$_5$alkylene-;
b is 1;
w is 0 or 2, and where w is 2, the (AA)$_W$ is of formula (III):

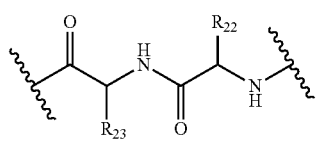

(III)

Wherein R$_{22}$ is isopropyl, R$_2$3 is —(CH$_2$)$_3$NHCON H2, and the wavy lines indicate the point of covalent attachments to (X)$_b$ if any, or the drug moiety (the wavy line to the left) and to the linker (the wavy line to the right); and X is an extending group selected from —(CH$_2$)$_3$NHCOOCH$_2$-phenylene-NH—, and —(CH$_2$)$_3$NH—;
or of formula V)

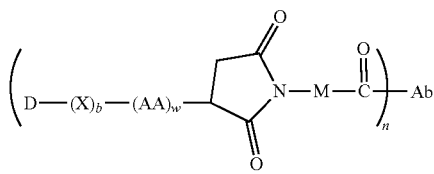

(V)

wherein M is -methyl-cyclohexyl ene-;
b is 1;
w is 0; and
X is an extending group selected from —(CH$_2$)$_3$S— and —(CH$_2$)$_3$NHCO(CH$_2$)$_2$S—:
D is a drug moiety of formula

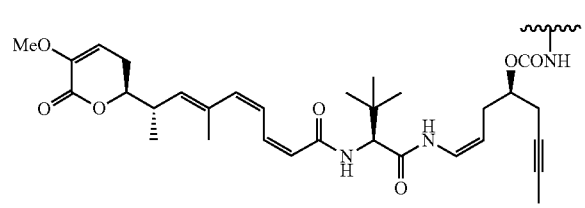

or a pharmaceutically acceptable salt, ester, solvate, tautomer or stereoisomer thereof, wherein the wavy lines indicate the point of covalent attachment to (X)$_b$ f any, or (AA)$_W$ if any, or the linker group L;
the moiety Ab comprising at least one antigen binding site is selected from Trastuzumab, Rituximab, an anti-CD4 antibody, an anti-CD5 antibody, and an anti-CD13 antibody or an immunologically active portion thereof or it is selected from Trastuzumab, Rituximab and an anti-CD4 antibody, or an immunologically active portion thereof; and most preferably it is Trastuzumab or an immunologically active portion thereof; and
n is the ratio of the groups [D-(X)$_b$-(AA)$_w$-(L)-] wherein L is as defined in formulas (IV) or (V) to the moiety Ab comprising at least one antigen binding site and is in the range from 3 to 5, and preferably 4.
i) A drug conjugate according to the first aspect of the present invention of formula (IV):

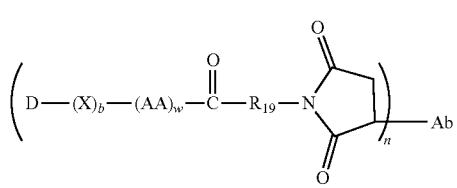

(IV)

wherein R$_{19}$ is —C$_5$alkylene-;
b is 1;
w is 0 or 2, and where w is 2, the (AA)$_W$ is of formula (III):

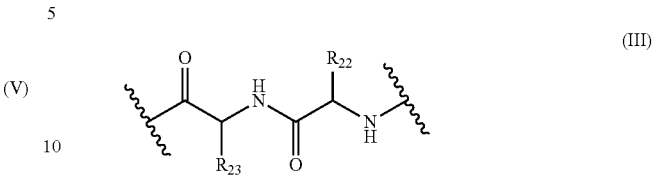

(III)

Wherein R$_{22}$ is isopropyl, R$_{23}$ is —(CH$_2$)$_3$NHCON H2, and the wavy lines indicate the point of covalent attachments to (X)$_b$ if any, or the drug moiety (the wavy line to the left) and to the linker (the wavy line to the right); and
X is an extending group selected from —CONH(CH$_2$)$_3$NHCOOCH$_2$-phenylene-NH—, and —CONH(CH$_2$)$_3$NH—;
or of formula (V)

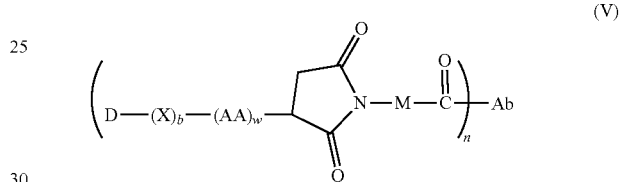

(V)

wherein M is -methyl-cyclohexylene-;
b is 1;
w is 0; and
X is an extending group selected from —CONH(CH$_2$)$_3$S— and —CONH(CH$_2$)$_3$NHCO(CH)$_2$S—:
D is a drug moiety of formula

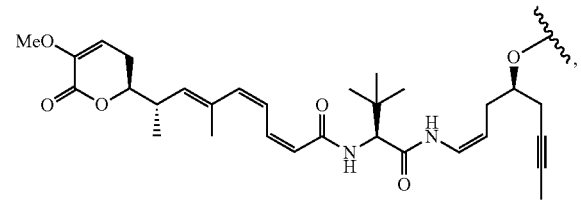 [SMILES: *O[C@@H](CC#CC)C/C=C\NC(=O)[C@@H](NC(=O)\C=C/C=C\C(C)=C\[C@H](C)[C@@H]1CC=C(OC)C(=O)O1)C(C)(C)C]

or a pharmaceutically acceptable salt, ester, solvate, tautomer or stereoisomer thereof,
wherein the wavy lines indicate the point of covalent attachment to (X)$_b$ if any, or (AA)$_W$ if any, or the linker group L;
The moiety Ab comprising at least one antigen binding site is selected from Trastuzumab, Rituximab, an anti-CD4 antibody, an anti-CD5 antibody, and an anti-CD13 antibody or an immunologically active portion thereof or it is selected from Trastuzumab, Rituximab and an anti-CD4 antibody, or an immunologically active portion thereof; and more preferably it is selected from Trastuzumab or an immunologically active portion thereof; and
n is the ratio of the groups [D-(X)$_b$-(AA)$_w$-(L)-] wherein L is as defined in formulas (IV) or (V) to the moiety Ab comprising at least one antigen binding site and is in the range from 3 to 5, and preferably 4.
j) an antibody drug conjugate according to the first aspect of the present invention, selected from the group consisting of:

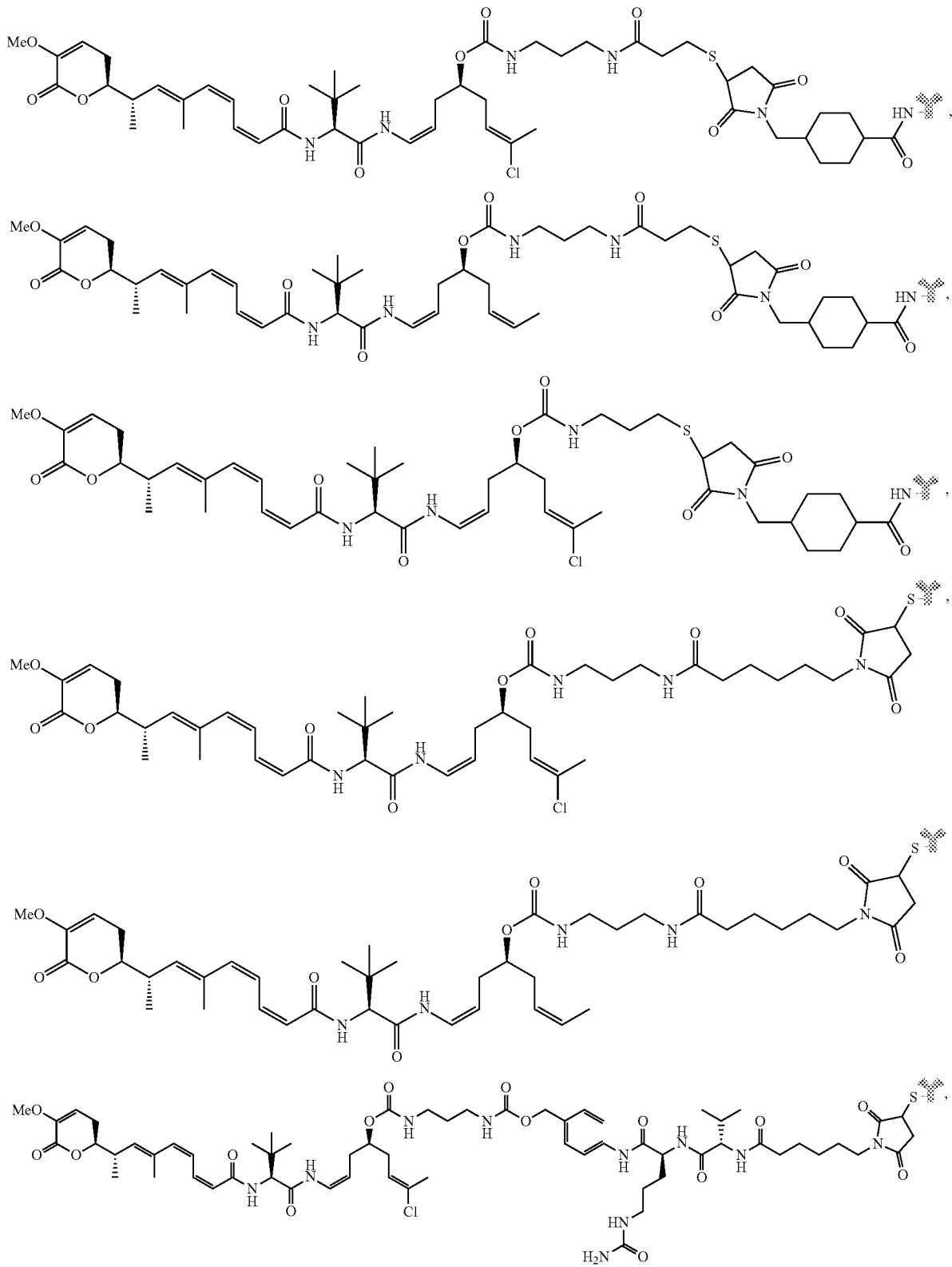

-continued

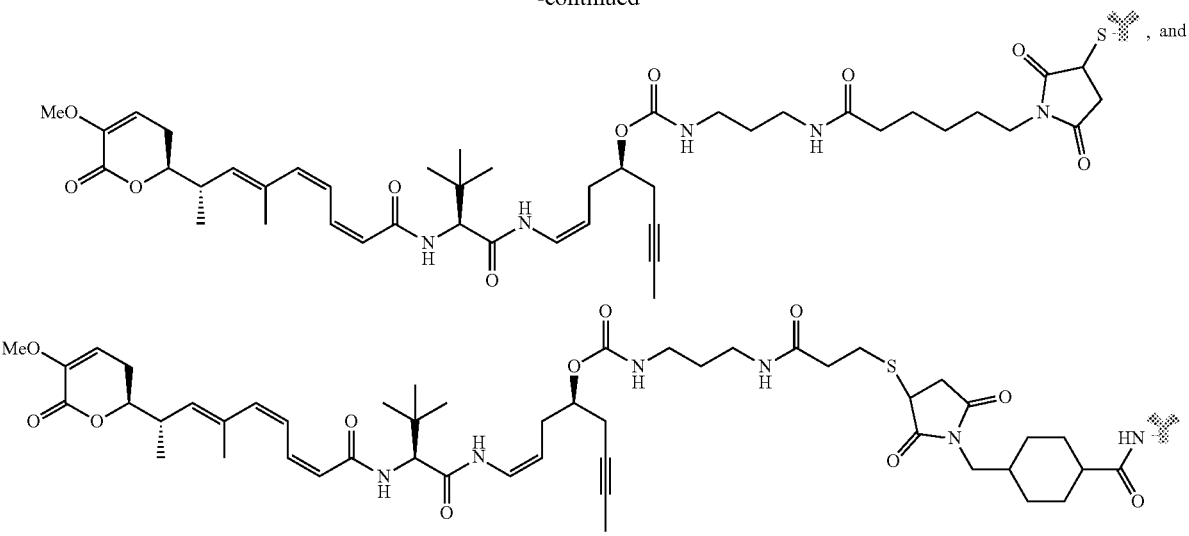

wherein each of

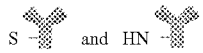

is selected from Trastuzumab, Rituximab, an anti-CD4 antibody, an anti-CD5 antibody and an anti-CD13 antibody or an immunologically active portion thereof, preferably Trastuzumab, Rituximab and an anti-CD4 antibody or an immunologically active portion thereof, and most preferably Trastuzumab or an immunologically active portion thereof; or alternatively an anti-CD5 antibody and an anti-CD13 antibody or an immunologically active portion thereof, and most preferably an anti-CD13 antibody or an immunologically active portion thereof. More preferably the antibody drug conjugate is selected from the group consisting of:

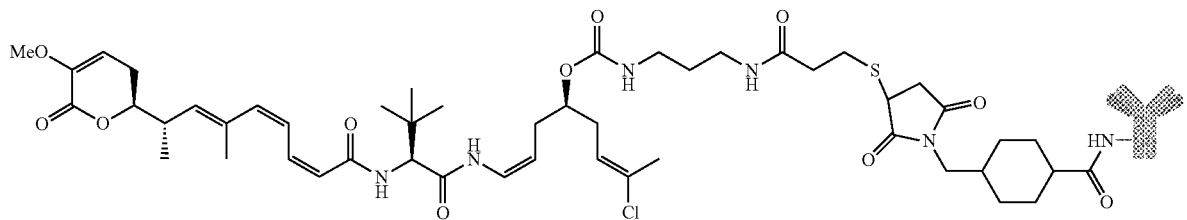 [SMILES: COC1=CC[C@@H]([C@@H](C)/C=C(C)/C=C\C=C/C(=O)N[C@H](C(=O)N/C=C\C[C@H](C/C=C(\C)Cl)OC(=O)NCCCNC(=O)CCSC2CC(=O)N(CC3CCC(C(N)=O)CC3)C2=O)C(C)(C)C)OC1=O]

wherein

is selected from Trastuzumab and an anti-CD13 antibody or an immunologically active portion thereof, preferably Trastuzumab or an immunologically active portion thereof; or preferably an anti-CD13 antibody or an immunologically active portion thereof,

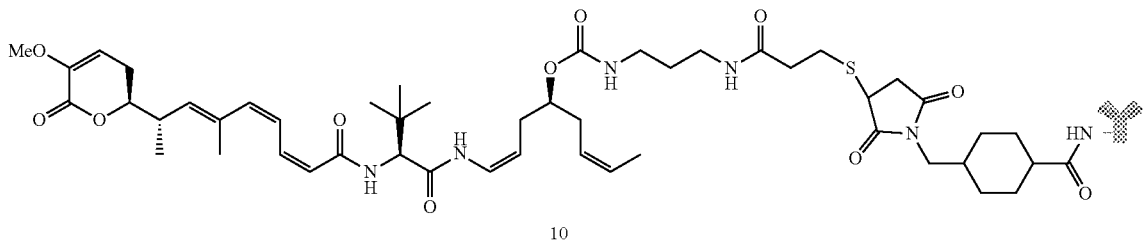

wherein

is Trastuzumab or an immunologically active portion thereof,

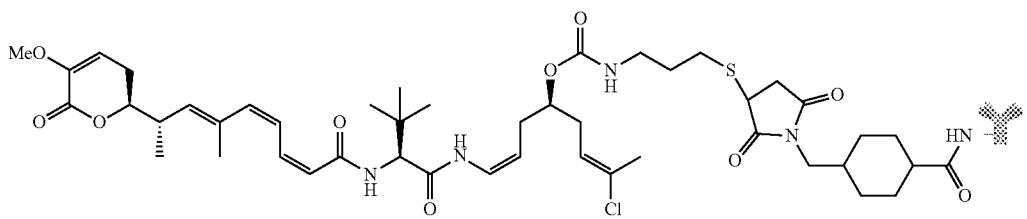 [SMILES: COC1=CC[C@@H]([C@@H](C)/C=C(C)/C=C\C=C/C(=O)N[C@H](C(=O)N/C=C\C[C@H](C/C=C(\C)Cl)OC(=O)NCCCSC2CC(=O)N(CC3CCC(C(N)=O)CC3)C2=O)C(C)(C)C)OC1=O]

wherein

is Trastuzumab or an immunologically active portion thereof,

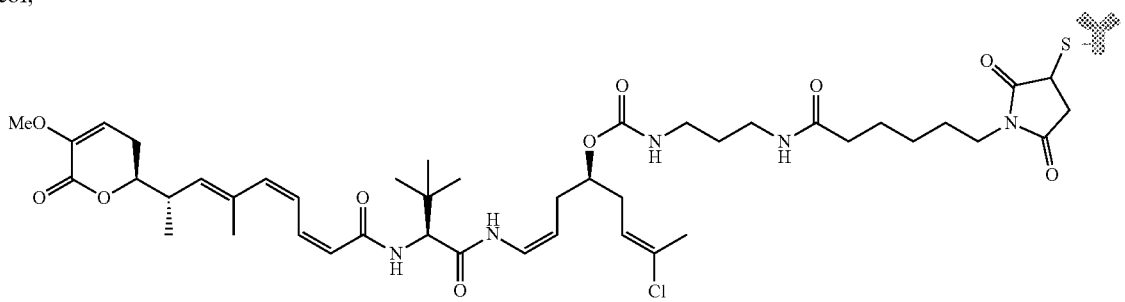

wherein

is selected from Trastuzumab, Rituximab, an anti-CD4 antibody, an anti-CD5 antibody and an anti-CD13 antibody or an immunologically active portion thereof, preferably Trastuzumab, Rituximab and an anti-CD4 antibody or an immunologically active portion thereof, and most preferably Trastuzumab or an immunologically active portion thereof; or alternatively an anti-CD5 antibody and an anti-CD13 antibody, or an immunologically active portion thereof, and most preferably an anti-CD13 antibody or an immunologically active portion thereof,

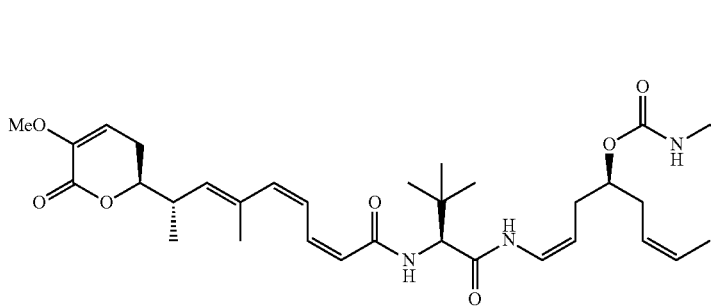

wherein

is Trastuzumab or an immunologically active portion thereof,

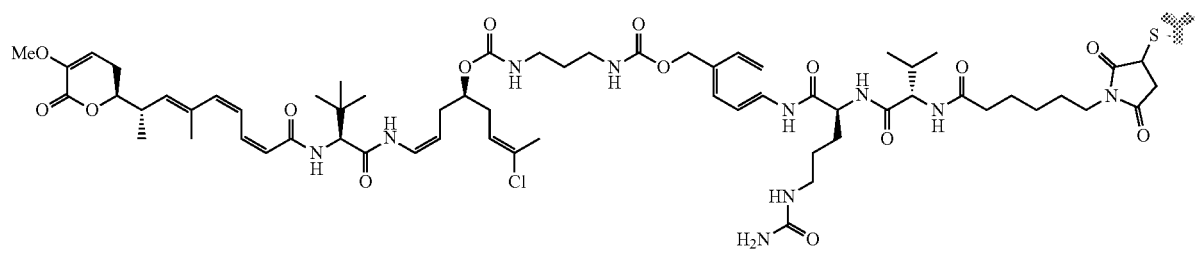 [SMILES: C=C/C(=C\C=C\NC(=O)[C@H](CCCNC(N)=O)NC(=O)[C@@H](NC(=O)CCCCCN1C(=O)CC(S)C1=O)C(C)C)COC(=O)NCCCNC(=O)O[C@H](C/C=C\NC(=O)[C@@H](NC(=O)\C=C/C=C\C(C)=C\[C@H](C)[C@@H]1CC=C(OC)C(=O)O1)C(C)(C)C)C/C=C(\C)Cl]

wherein

is selected from Trastuzumab, Rituximab, an anti-CD4 antibody, an anti-CD5 antibody and an anti-CD13 antibody or an immunologically active portion thereof, preferably Trastuzumab, Rituximab and an anti-CD4 antibody or an immunologically active portion thereof, and most preferably Trastuzumab or an immunologically active portion thereof; or alternatively an anti-CD5 antibody and an anti-CD13 antibody or an immunologically active portion thereof, and most preferably an anti-CD13 antibody or an immunologically active portion thereof,

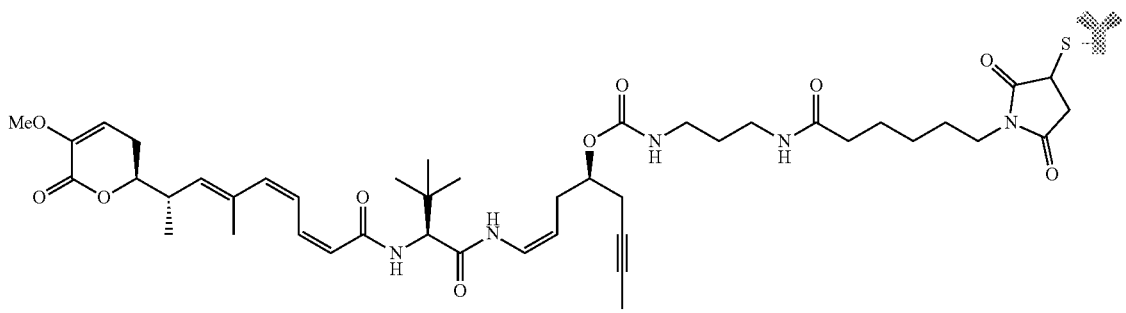 [SMILES: CC#CC[C@@H](C/C=C\NC(=O)[C@@H](NC(=O)\C=C/C=C\C(C)=C\[C@H](C)[C@@H]1CC=C(OC)C(=O)O1)C(C)(C)C)OC(=O)NCCCNC(=O)CCCCCN1C(=O)CC(S)C1=O]

wherein

is Trastuzumab or a immunologically active portion thereof, and

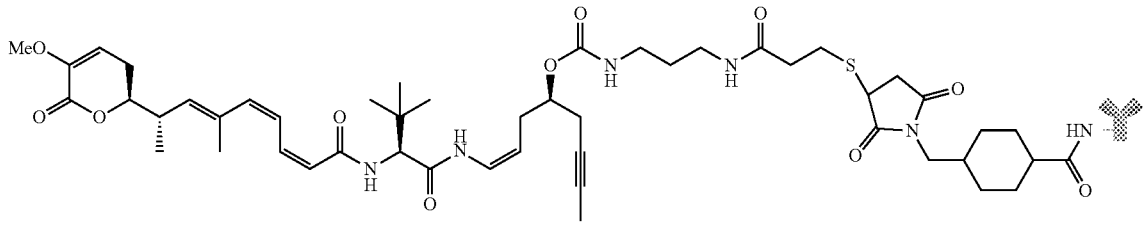 [SMILES: CC#CC[C@@H](C/C=C\NC(=O)[C@@H](NC(=O)\C=C/C=C\C(C)=C\[C@H](C)[C@@H]1CC=C(OC)C(=O)O1)C(C)(C)C)OC(=O)NCCCNC(=O)CCSC1CC(=O)N(CC2CCC(C(N)=O)CC2)C1=O]

wherein

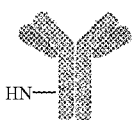

is Trastuzumab or an immunologically active portion thereof.

Particularly preferably, the antibody drug conjugates according to the present invention should be in isolated or purified form.

Preferred compounds of formula D-X-(AA)$_w$-(L$_1$)b according to the second aspect of the present invention include:

a compound of formula D-X-(AA)$_W$-L$_1$ or of formula D-X-(AA)$_W$-H according to the second aspect of the present invention wherein:

L$_1$ is a linker of formula:

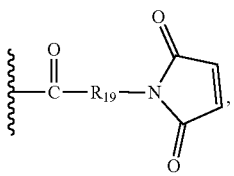

wherein:
the wavy line indicates the point of covalent attachment to a (AA)$_W$ if any, or to X;
Rig is selected from —C1-C12 alkylene-, –0-(Ci-Ci$_2$ alkylene), —C$_6$-Ci$_2$ arylene in one or more rings which may optionally be substituted with one or more substituents R$_x$, —C$_1$-C12 alkylene-C$_6$-Ci2 arylene- wherein the arylene group is in one or more rings which may optionally be substituted with one or more substituents R$_x$, —C$_6$-Ci2 arylene-Ci-C12 alkylene- wherein the arylene group is in one or more rings which may optionally be substituted with one or more substituents R$_x$, —C5-C12 heterocycio- wherein said heterocycio group may be a saturated or unsaturated group having one or more rings and comprising at least one oxygen, nitrogen or sulphur atom in said ring(s), said group optionally being substituted with one or more substituents R$_x$, —C1-C12 alkylene-(C5-C12 heterocycio)- wherein said heterocycio group may be a saturated or unsaturated group having one or more rings and comprising at least one oxygen, nitrogen or sulphur atom in said ring(s), said group optionally being substituted with one or more substituents R$_x$, —(C5-C12 heterocyclo)-CrCi$_2$ alkylene- wherein said heterocycio group may be a saturated or unsaturated group having one or more rings and comprising at least one oxygen, nitrogen or sulphur atom in said ring(s), said group optionally being substituted with one or more substituents R$_x$, —(OCH$_2$CH$_2$)$_r$— and —CH2-(OCH$_2$CH$_2$) r, wherein each of the above alkylene substituents whether alone or attached to another moiety the carbon chain may optionally be substituted by one or more substituents R$_x$;
r is an integer ranging from 1-6; and
each of D, X, AA and w are as defined in the first aspect of the invention.

a compound of formula D-X-(AA)$_W$-L$_1$ or of formula D-X-(AA)$_W$-H according to the second aspect of the present invention wherein:

L$_1$ is linker of formula:

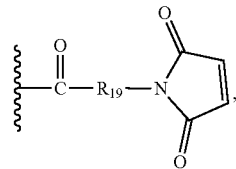

wherein:
the wavy line indicates the point of covalent attachment to a (AA)$_W$ if any, or to X;
Rig is selected from —CrC$_8$ alkylene-, –0-(Ci-C$_8$ alkylene), —CrC$_8$ alkylene-C$_6$-Ci$_2$ arylene- wherein the arylene group is in one or more rings which may optionally be substituted with one or more substituents R$_x$, —C$_6$-Ci$_2$arylene-Ci-C$_8$ alkylene- wherein the arylene group is in one or more rings which may optionally be substituted with one or more substituents R$_x$, wherein each of the above alkylene substituents whether alone or attached to another moiety the carbon chain may optionally be substituted by one or more substituents R$_x$;
(AA)$_W$ is of formula (II):

(II)

wherein the wavy lines indicate the point of covalent attachments to X (the wavy line to the left) and to $L_1$ or to a hydrogen atom (the wavy line to the right);

wherein $R_2i$ is selected, at each occurrence, from the group consisting of hydrogen, methyl, isopropyl, sec-butyl, benzyl, indolylmethyl, —$(CH_2)_3NHCON$ H2, —$(CH_2)_4NH2$, —$(CH_2)_3NHC(=NH)NH_2$ and —$(CH_2)_4NHC—(=NH)NH_2$, and w is an integer from 0 to 6;

X is an extending group selected from the group consisting of —CONH—($C_2$-$C_4$ alkylene)NH—, —COO—$CH_2$-phenylene-NH, wherein said phenylene group may optionally be substituted with from one to four substituents $R_x$ selected from the group consisting of alkyl groups having from 1 to 6 carbon atoms, alkoxy groups having from 1 to 6 carbon atoms, halogen atoms, nitro groups and cyano groups, —CONH—($C_2$-$C_4$ alkylene)NH—COO—$CH_2$-(phenylene which may optionally be substituted with from one to four substituents $R_x$ selected from the group consisting of alkyl groups having from 1 to 6 carbon atoms, alkoxy groups having from 1 to 6 carbon atoms, halogen atoms, nitro groups and cyano groups)-NH—, —$COCH_2NH$—$COCH_2$—NH—, —CONH—($C_2$-$C_4$ alkylene)S—, —CONH—($C_2$-$C_4$ alkylene)-NHCO($C_1$-$C_3$ alkylene)S—, —($C_2$-$C_4$ alkylene)NHCO($C_1$-$C_3$ alkylene)S—, —($C_2$-$C_4$ alkylene)S—, —($C_2$-$C_4$ alkylene)NH— and —($C_2$-$C_4$ alkylene)NH—COO—$CH_2$ (phenylene which may optionally be substituted with from one to four substituents $R_x$ selected from the group consisting of alkyl groups having from 1 to 6 carbon atoms, alkoxy groups having from 1 to 6 carbon atoms, halogen atoms, nitro groups and cyano groups)-NH—; and D is a drug moiety of formula (Ia) or a formula (Ib), or a pharmaceutically acceptable salt, ester, solvate, tautomer or stereoisomer thereof wherein:

(Ia)
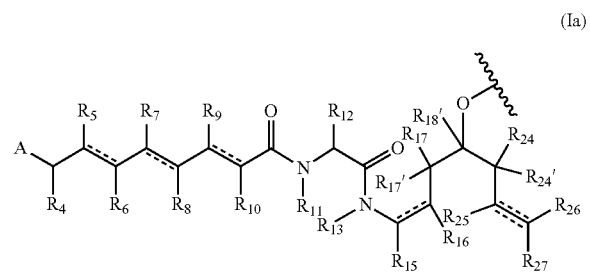

(Ib)
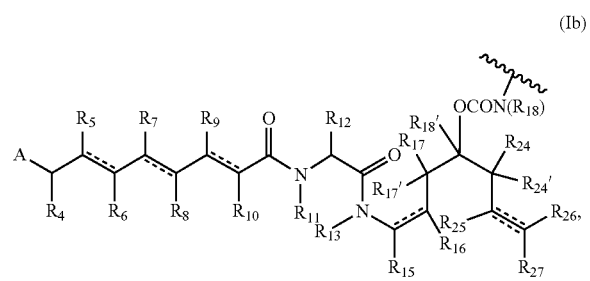

wherein the wavy lines of (Ia) and (Ib) indicate the point of covalent attachment to X;

A is selected from

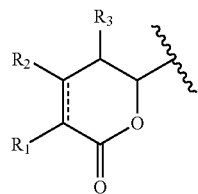 and 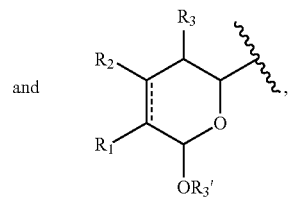

wherein the wavy lines of the moiety A indicate the point of covalent attachment to the rest of the drug moiety;

R1 is selected from hydrogen, $OR_a$ and $OCOR_a$, wherein $R_a$ is selected from hydrogen and substituted or unsubstituted $C_i$-$C_6$ alkyl, wherein the optional substituents are one or more substituents $R_x$;

$R_2$ and $R_3$ are each independently selected from hydrogen and substituted or unsubstituted $C_i$-$C_6$ alkyl, wherein the optional substituents are one or more substituents $R_x$;

$R_3'$ is selected from hydrogen, $COR_a$, and substituted or unsubstituted $C_i$-$C_6$ alkyl, wherein $R_a$ is a substituted or unsubstituted $C_i$-$C_6$ alkyl, wherein the optional substituents are one or more substituents $R_x$;

each of $R_4$, R5, R6, R7, Rs, R9, R10 and R12 is independently selected from hydrogen and substituted and unsubstituted $C_i$-$C_6$ alkyl, wherein the optional substituents are one or more substituents $R_x$;

each of R11 and R13 is independently selected from hydrogen and substituted or unsubstituted $C_i$-$C_6$ alkyl, wherein the optional substituents are one or more substituents $R_x$;

each of $R1_5$, R16, R17, $R_{i7'}$, R18', $R2_4$, $R2_4'$, R25 and $R_26$ is independently selected from the group consisting of:

hydrogen and substituted or unsubstituted $C_i$-$C_6$ alkyl groups wherein the optional substituents are selected from the group consisting of alkoxy groups having from 1 to 6 carbon atoms, hydroxyl groups, oxo groups, halogen atoms, $OCOR_y$, $OCOOR_y$, $COR_y$, $COOR_y$, OCON $RyR_z$, CON $RyR_z$, N $RyR_z$, N $RyCORz$ wherein each of $R_y$ and $R_z$ is selected from hydrogen atoms and alkyl groups having from 1 to 6 carbon atoms.

R-18 is selected from hydrogen, a $C_i$-$C_6$ alkyl group which may optionally be substituted with at least one group $R_x$, and a phenyl group optionally being substituted with one or more substituents $R_x$:

R27 is selected from hydrogen, halogen and substituted or unsubstituted $C_i$-$C_6$ alkyl, wherein the optional substituents are one or more substituents $R_x$;

and each dotted line represents an optional additional bond, but when a triple bond exists between the C atom to which $R_{25}$ is attached and the C atom to which $R_26$ and R27 are attached, then $R_{25}$ and either $R_26$ or $R_2$ are absent.

a compound of formula D-X-$(AA)_w$-$L_1$ or of formula D-X-$(AA)_w$-H according to the second aspect of the present invention wherein:

$L_1$ is a group of formula:

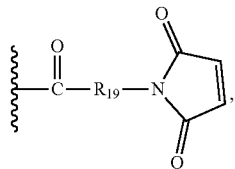

wherein:
the wavy line indicates the point of covalent attachment to $(AA)_W$ if any, or to X;
$R_{1g}$ is selected from —$C_i$-$C_6$ alkylene-, phenylene-$C_rC_6$ alkylene- wherein the phenylene group may optionally be substituted with one or more substituents $R_x$ selected from the group consisting of alkyl groups having from 1 to 6 carbon atoms, alkoxy groups having from 1 to 6 carbon atoms, halogen atoms, nitro groups and cyano groups, wherein each of the above alkylene substituents whether alone or attached to another moiety in the carbon chain may optionally be substituted by one or more substituents $R_x$ selected from the group consisting of alkyl groups having from 1 to 6 carbon atoms, alkoxy groups having from 1 to 6 carbon atoms, aryl groups having from 6 to 12 carbon atoms, halogen atoms, nitro groups and cyano groups, and preferably R19 is a $C_i$-$C_6$ alkylene group;
w is 0 or 2, and where w is 2, then $(AA)_W$ is of formula (III):

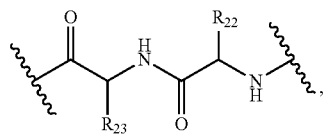
(III)

wherein the wavy lines indicate the point of covalent attachments to X (the wavy line to the left) and to $L_1$ or to a hydrogen atom (the wavy line to the right);
$R_{22}$ is selected from methyl, benzyl, isopropyl, sec-butyl and indolylmethyl;
$R_{23}$ is selected from methyl, —$(CH_2)_4NH_2$, —$(CH_2)_3NHCONH_2$ and —$(CH_2)_3NHC(=NH)NH_2$;
X is an extending group selected from —CONH—($C_2$-$C_4$ alkylene)NH—, —CONH($C_2$-$C_4$ alkylene)NHCOO—$CH_2$-(phenylene which may optionally be substituted with one or more substituents $R_x$ selected from the group consisting of alkyl groups having from 1 to 6 carbon atoms, alkoxy groups having from 1 to 6 carbon atoms, halogen atoms, nitro groups and cyano groups)-NH, —CONH—($C_2$-$C_4$ alkylene)S—, —CONH—($C_2$-$C_4$ alkylene)NHCO—($C_rC_3$ alkylene)S—, —($C_2$-$C_4$ alkylene)NHCO($C_1$-$C_3$ alkylene)S—, —($C_2$-$C_4$ alkylene)S—, —($C_2$-$C_4$ alkylene)NH— and —($C_2$-$C_4$ alkylene)NH—COO—$CH_2$ (phenylene which may optionally be substituted with from one to four substituents $R_x$ selected from the group consisting of alkyl groups having from 1 to 6 carbon atoms, alkoxy groups having from 1 to 6 carbon atoms, halogen atoms, nitro groups and cyano groups)-NH—; and
D is a drug moiety of formula (Ia) or a formula (Ib), or a pharmaceutically acceptable salt, ester, solvate, tautomer or stereoisomer thereof:

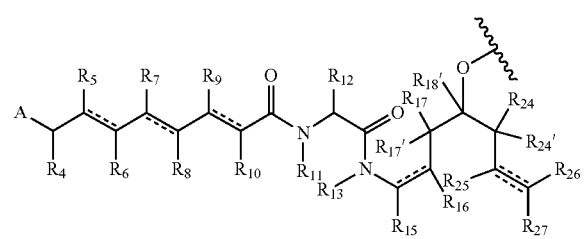
(Ia)

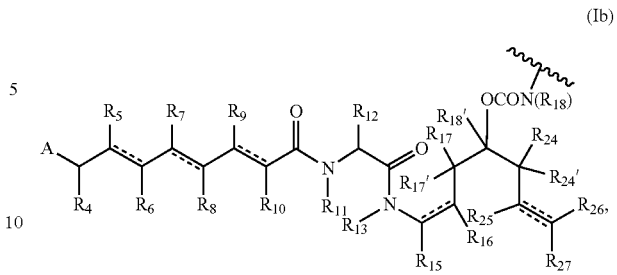
(Ib)

wherein the wavy lines of (Ia) and (Ib) indicate the point of covalent attachment to X;
A is selected from

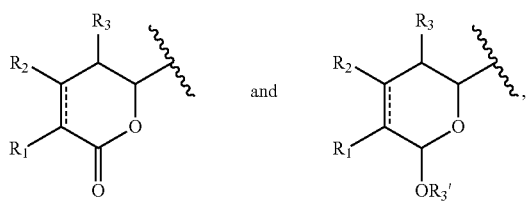

wherein the wavy lines of the moiety A indicate the point of covalent attachment to the rest of the drug moiety;
$R_1$ is hydrogen or methoxy;
each of $R_2$ and $R_3$ is hydrogen;
$R_3'$ is hydrogen;
each of $R_5$, $R_7$, Rs, R9 and R10 is hydrogen;
each of $R_4$ and $R_6$ is methyl;
Ri2 is isopropyl, tert-butyl or benzyl;
each of $R_{11}$ and $R_{13}$ is hydrogen;
each of $R1_5$, R16, R17, $Ri_7$, R18', R24, R24', R25 and $R_26$ is independently selected from the group consisting of hydrogen and $C_i$-$C_6$ alkyl group, preferably hydrogen and methyl;
R18 is selected from hydrogen and phenyl, and preferably hydrogen;
R27 is hydrogen or halogen;
and each dotted line represents an optional additional bond, but when a triple bond exists between the C atom to which $R_{25}$ is attached and the C atom to which $R_26$ and R27 are attached, then $R_{25}$ and either $R_26$ or R27 are absent.
a compound of formula D-X-$(AA)_W$-$L_1$ or of formula D-X-$(AA)_W$-H according to the second aspect of the present invention wherein:
$L_1$ is a linker of formula:

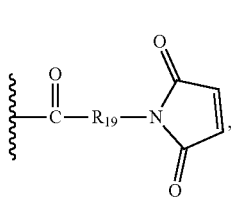

wherein:
the wavy line indicates the point of covalent attachment to a $(AA)_w$ if any, or to X;
Rig is —$C_3$-$C_6$ alkylene-;
w is 0 or 2, and where w is 2, then $(AA)_W$ is of formula (III):

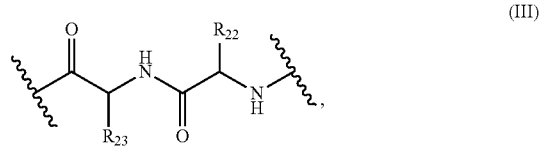

R22 is isopropyl, R23 is —$(CH_2)_3NHCON H2$, wherein the wavy lines indicate the point of covalent attachments to X (the wavy line to the left) and to $L_1$ or to a hydrogen atom (the wavy line to the right);
X is an extending group selected from the group consisting of —CONH—($C_2$-$C_4$ alkylene)NH—, —COO—$CH_2$-phenylene-NH—, wherein said phenylene group may optionally be substituted with from one to four substituents $R_x$ selected from the group consisting of alkyl groups having from 1 to 6 carbon atoms, alkoxy groups having from 1 to 6 carbon atoms, halogen atoms, nitro groups and cyano groups, —CONH—($C_2$-$C_4$ alkylene)NH—COO—$CH_2$-(phenylene which may optionally be substituted with from one to four substituents $R_x$ selected from the group consisting of alkyl groups having from 1 to 6 carbon atoms, alkoxy groups having from 1 to 6 carbon atoms, halogen atoms, nitro groups and cyano groups)-NH—, —CONH—($C_2$-$C_4$ alkylene)S—, —CONH—($C_2$-$C_4$ alkylene)NHCO($C_1$-$C_3$ alkylene)S—, —($C_2$-$C_4$ alkylene)NHCO($C_1$-$C_3$ alkylene)S—, —($C_2$-$C_4$ alkylene)S—, —($C_2$-$C_4$ alkylene)NH— and —($C_2$-$C_4$ alkylene)NH—COO—$CH_2$ (phenylene which may optionally be substituted with from one to four substituents $R_x$ selected from the group consisting of alkyl groups having from 1 to 6 carbon atoms, alkoxy groups having from 1 to 6 carbon atoms, halogen atoms, nitro groups and cyano groups)-NH—; and
D is a drug moiety of formula (Ia) or formula (Ib), or a pharmaceutically acceptable salt, ester, solvate, tautomer or stereoisomer thereof selected from the following group:

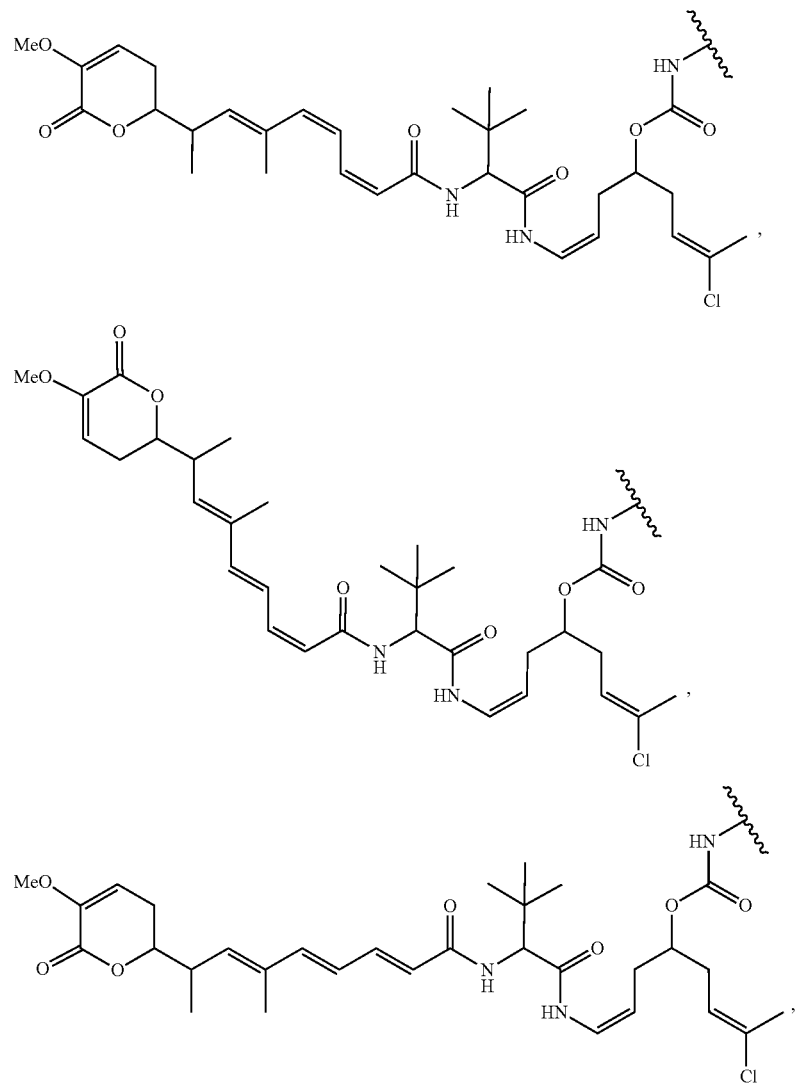

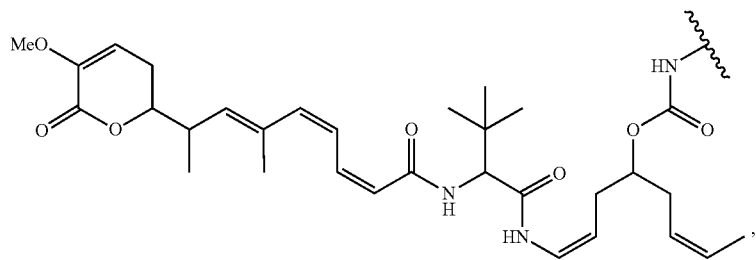
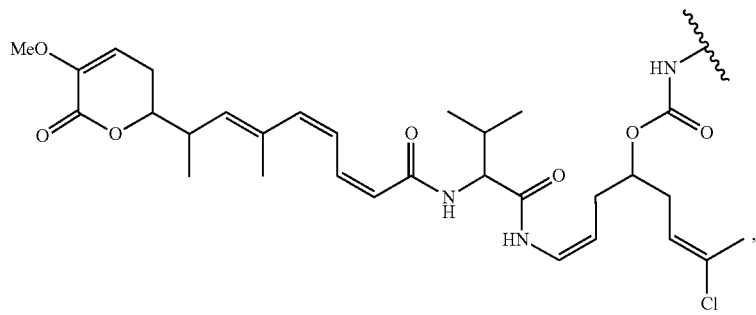
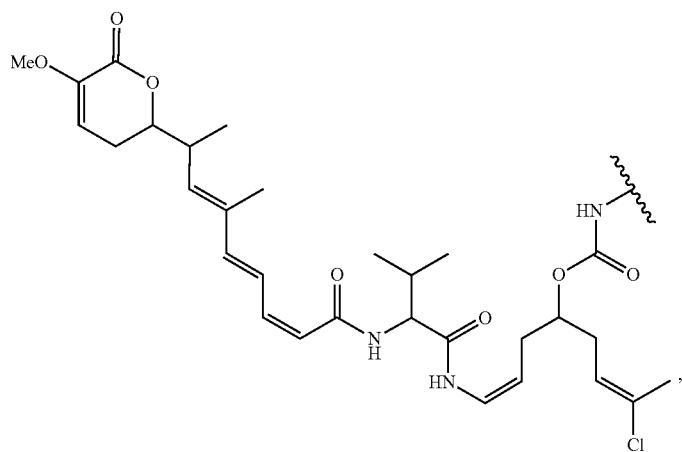
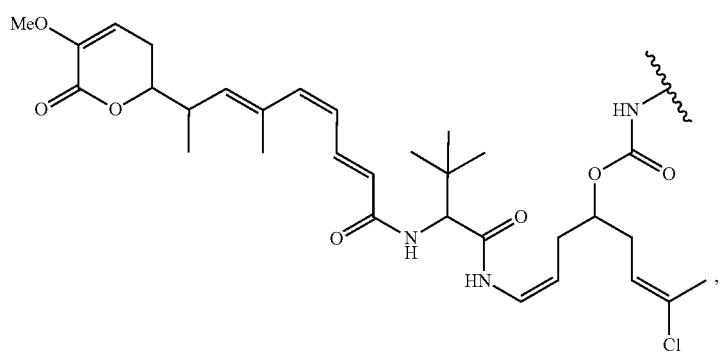
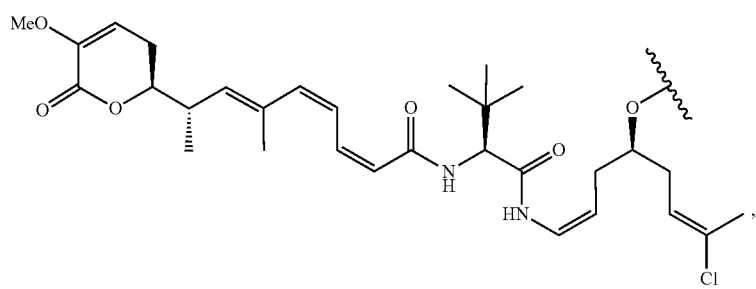

-continued
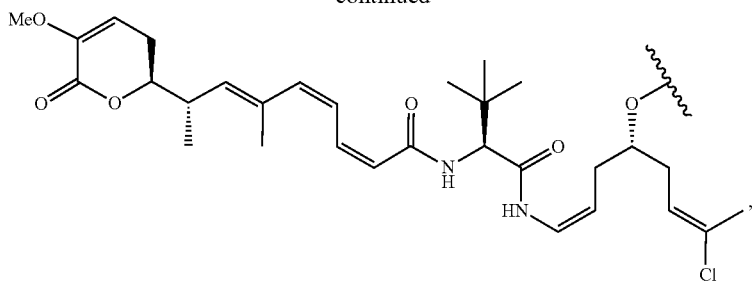
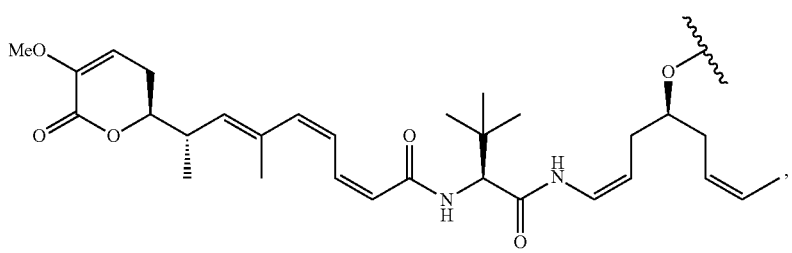
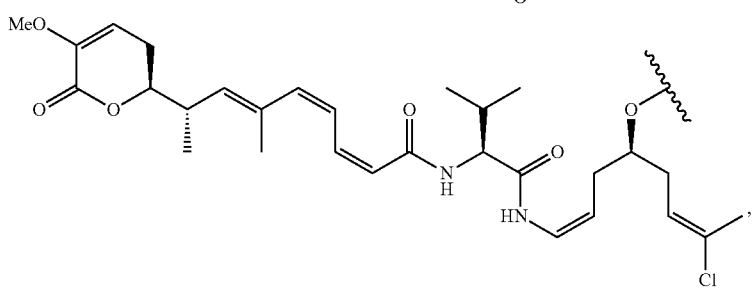
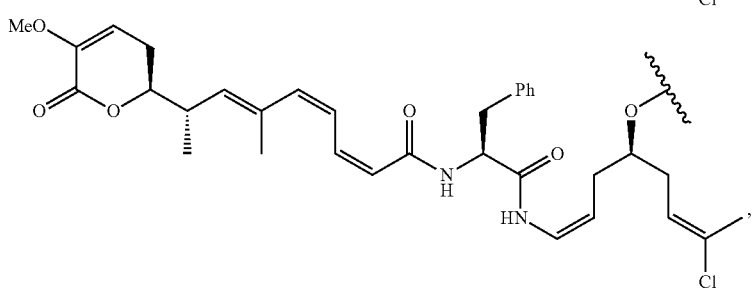
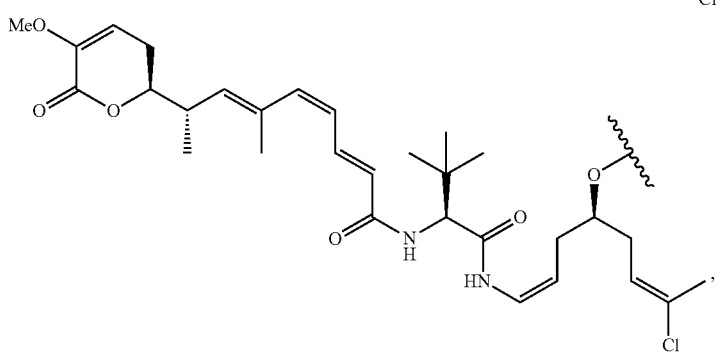
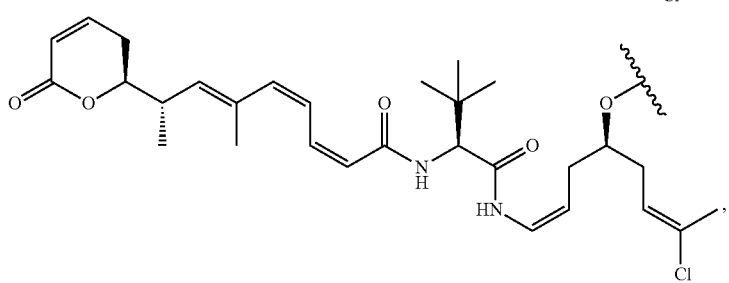

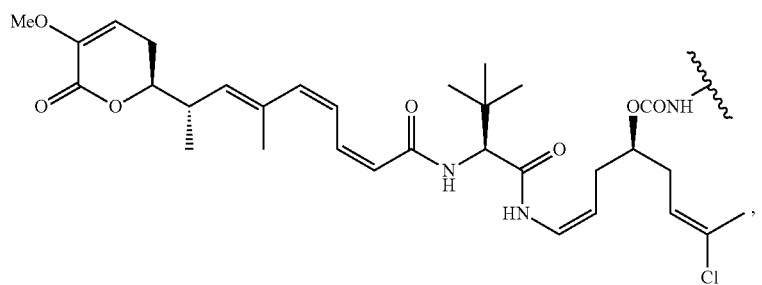
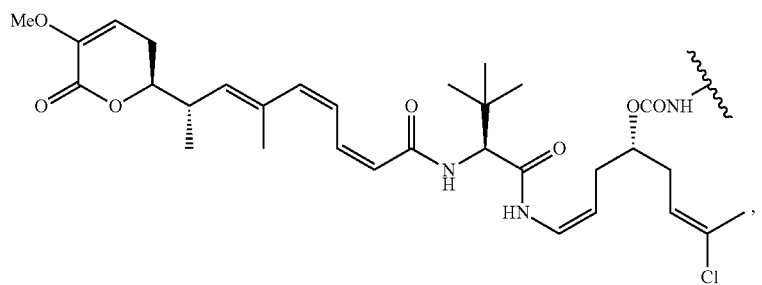
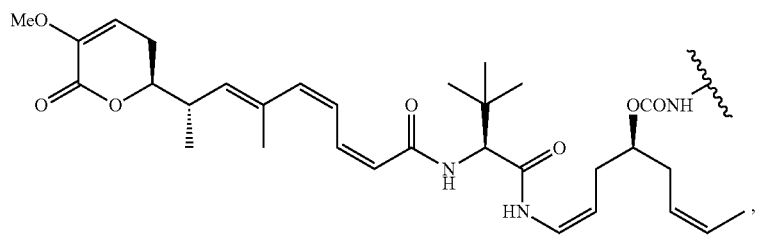
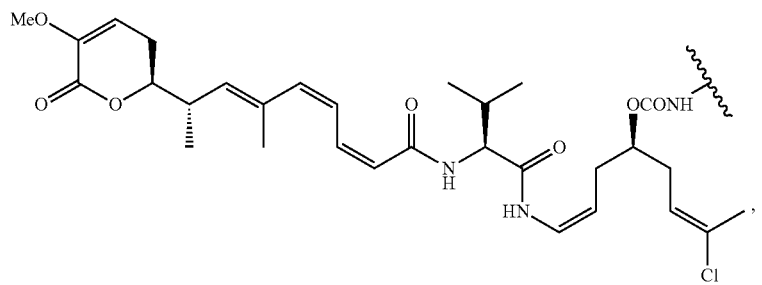
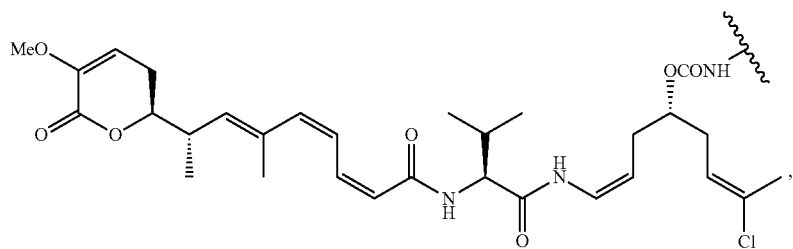
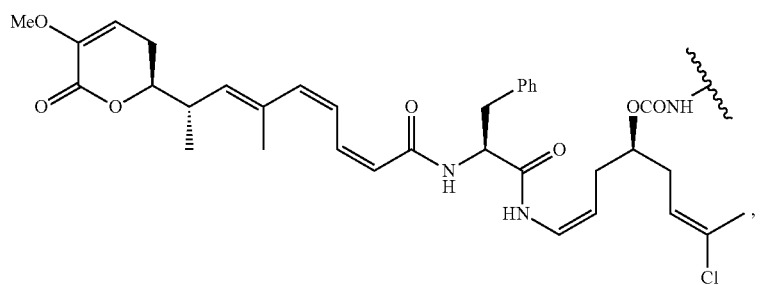

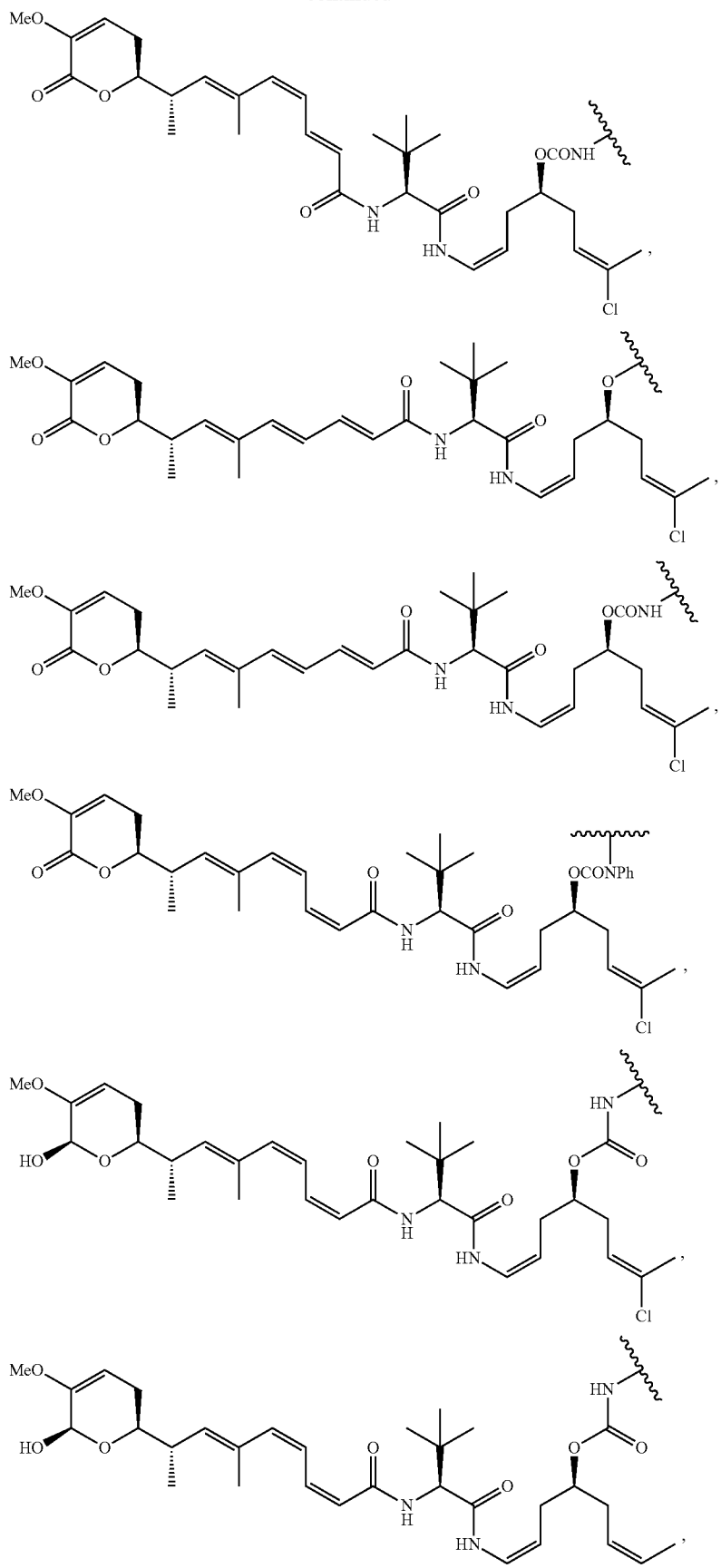

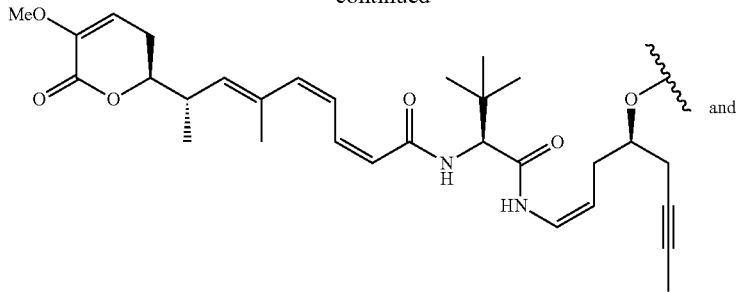

and

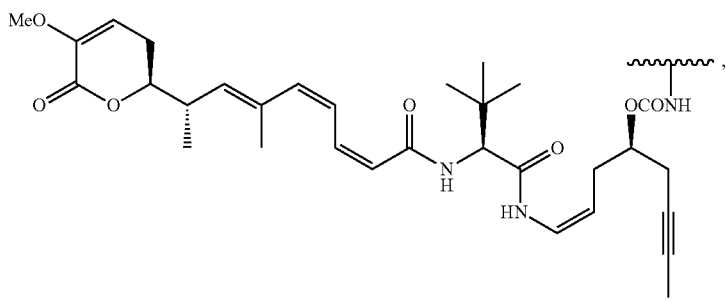

, wherein the wavy line indicates the point of covalent attachment to X.

a compound of formula D-X-(AA)$_W$-L$_1$ or of formula D-X-(AA)$_W$-H according to the second aspect of the present invention wherein:

L$_1$ is a group of formula:

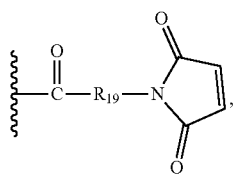

wherein the wavy line indicates the point of covalent attachment to a (AA)$_W$ if any, or to X;

R$_{19}$ is —C5 alkylene-;

w is 0 or 2, and where w is 2, then (AA)$_W$ is of formula (III):

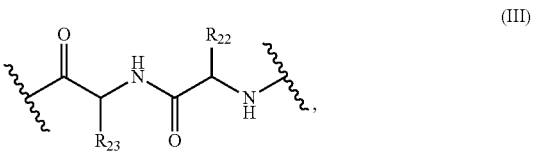

(III)

wherein R$_{22}$ is isopropyl, R$_2$3 is —(CH$_2$)$_3$NHCON H2, wherein the wavy lines indicate the point of covalent attachments to X (the wavy line to the left) and to L$_1$ or to a hydrogen atom (the wavy line to the right);

X is an extending group selected from —CONH(CH$_2$)$_3$NHCOOCH$_2$-phenylene-NH—, and —CONH(CH$_2$)$_3$NH—, —CONH(CH$_2$)$_3$—S— and —CONH(CH$_2$)$_3$NHCO(CH$_2$)$_2$S—; and D is a drug moiety of formula (Ia), or a pharmaceutically acceptable salt, ester, solvate, tautomer or stereoisomer thereof selected from:

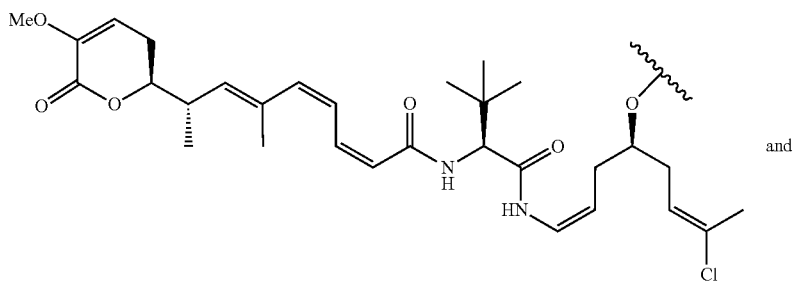

and

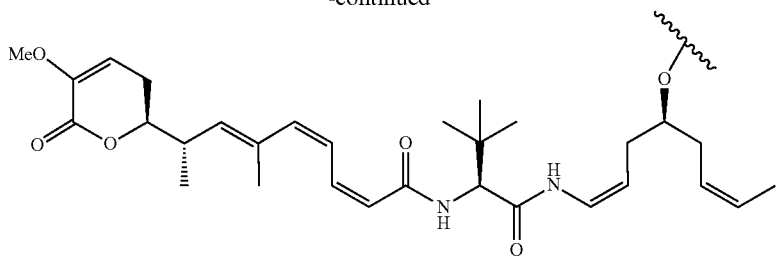
wherein the wavy line indicates the point of covalent attachment to X.
a compound of formula D-X-(AA)$_W$-L$_1$ selected from:
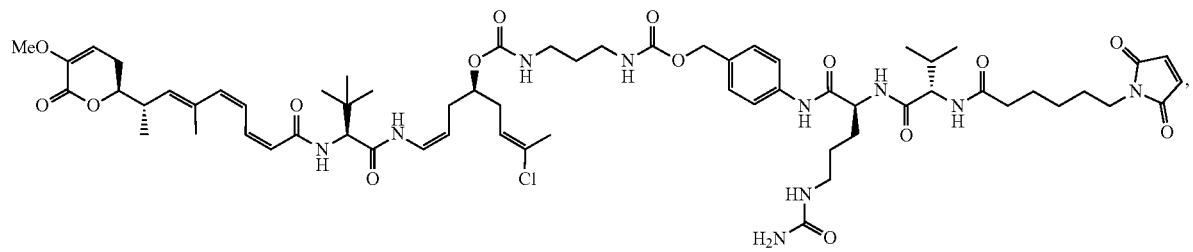
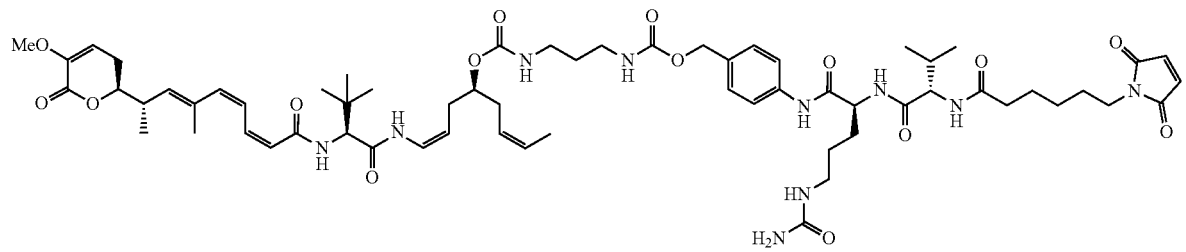
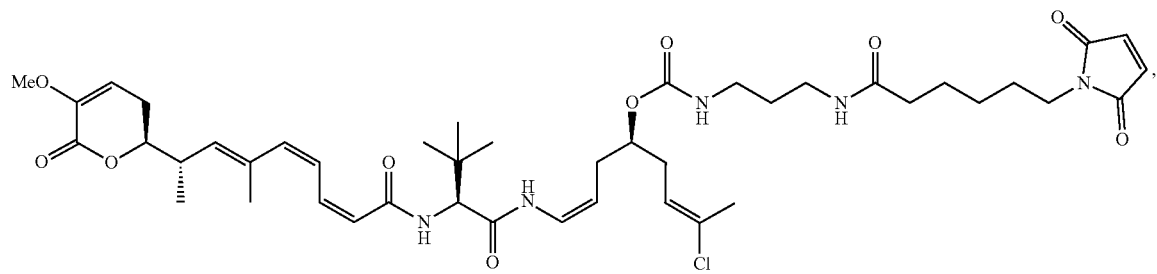
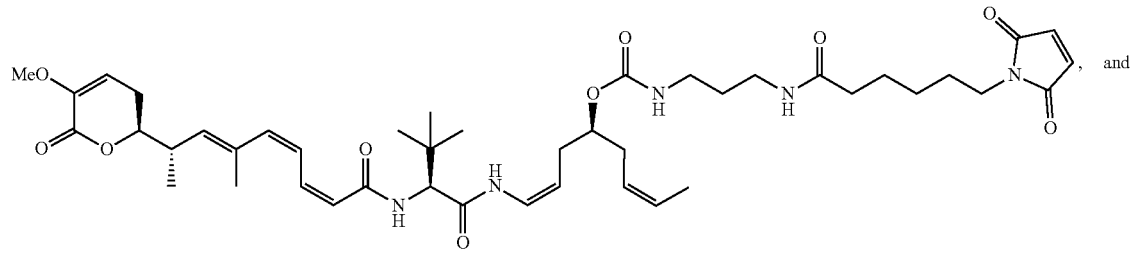
and

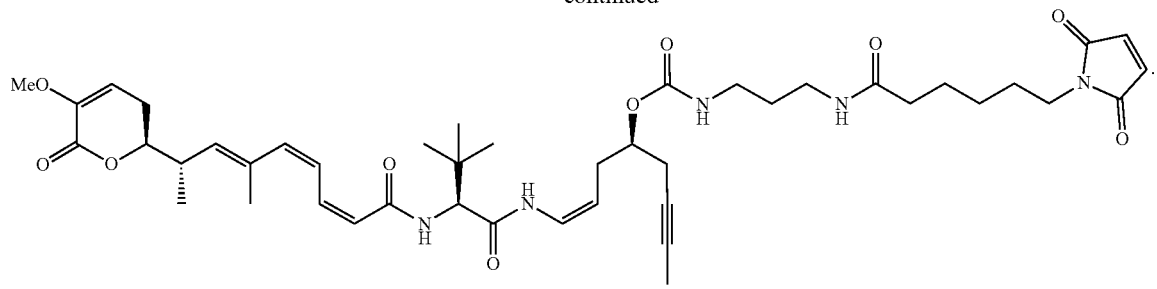
a compound of formula D-X-(AA)$_w$-H selected from:
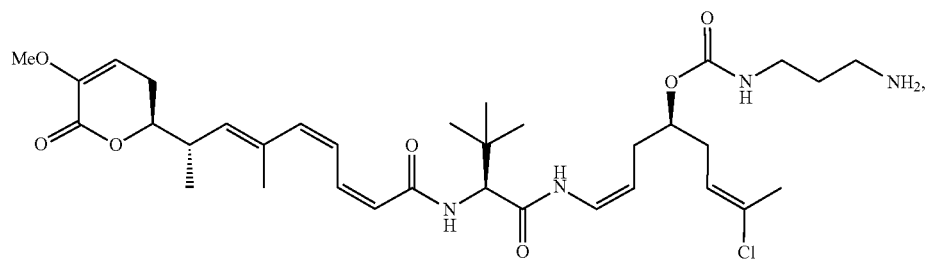
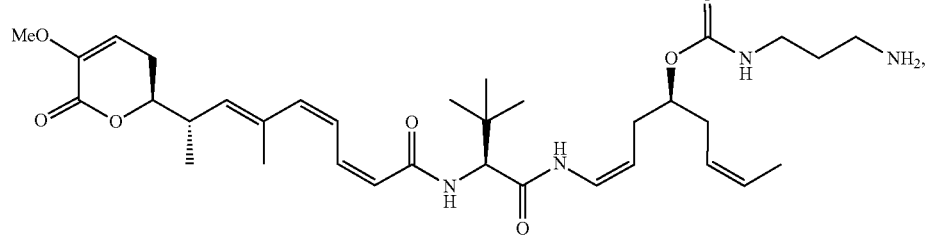
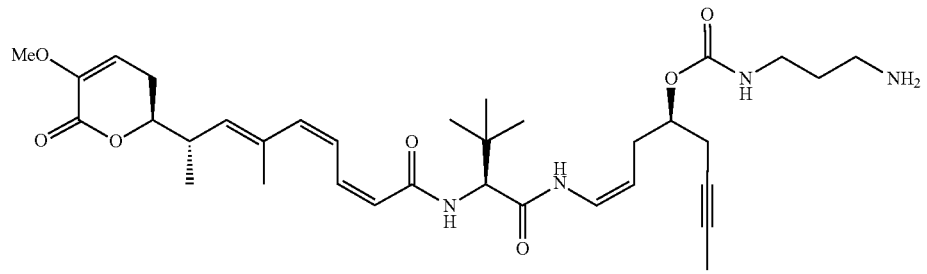
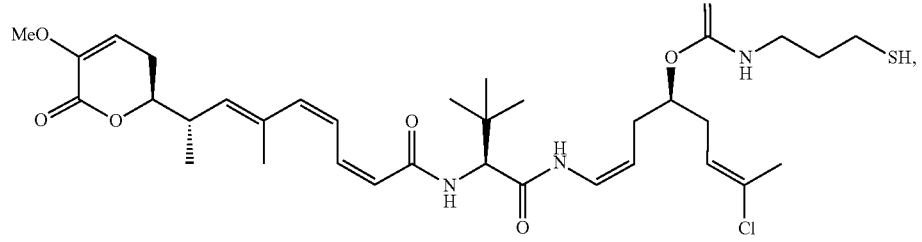
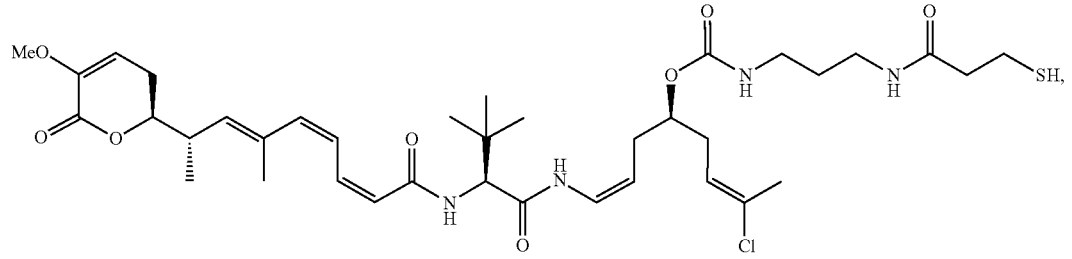

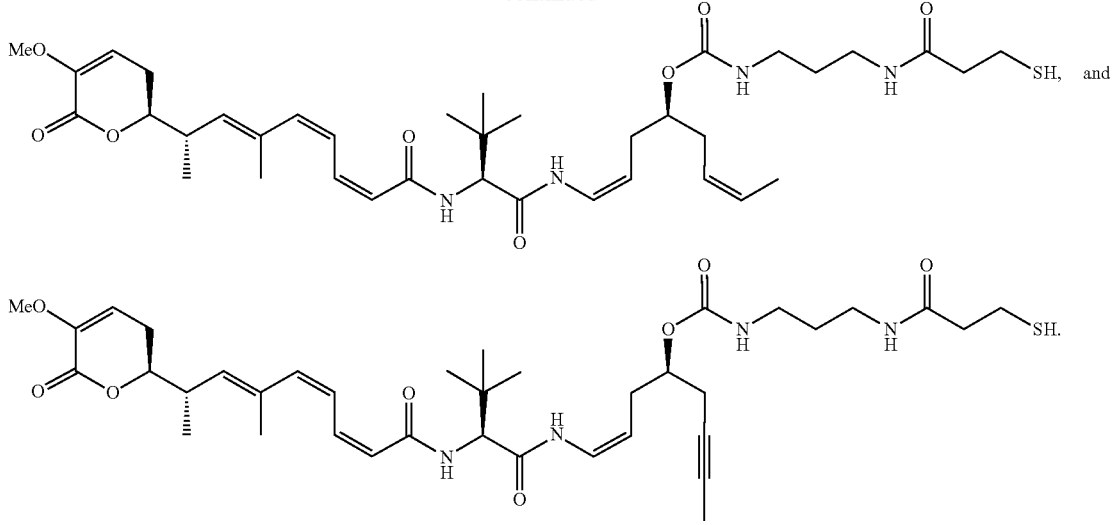

and

The term "pharmaceutically acceptable salts, esters, solvates, tautomers or stereoisomers" in the drug conjugates of the present invention refers to any pharmaceutically acceptable salt, ester, solvate, hydrate or stereosiomeric form or any other compound which, upon administration to the patient is capable of providing a compound as described herein, whether directly or indirectly. However, it will be appreciated that non-pharmaceutically acceptable salts also fall within the scope of the invention since those may be useful in the preparation of pharmaceutically acceptable salts. The preparation of salts, prodrugs and derivatives can be carried out by methods known in the art.

For instance, pharmaceutically acceptable salts of compounds provided herein are synthesized from the parent compound, which contains a basic or acidic moiety, by conventional chemical methods. Generally, such salts are, for example, prepared by reacting the free acid or base forms of these compounds with a stoichiometric amount of the appropriate base or acid in water or in an organic solvent or in a mixture of the two. Generally, nonaqueous media like ether, ethyl acetate, ethanol, isopropanol or acetonitrile are preferred. Examples of the acid addition salts include mineral acid addition salts such as, for example, hydrochloride, hydrobromide, hydroiodide, sulphate, nitrate, phosphate, and organic acid addition salts such as, for example, acetate, trifluoroacetate, maleate, fumarate, citrate, oxalate, succinate, tartrate, malate, mandelate, methanesulphonate and p-toluenesulphonate. Examples of the alkali addition salts include inorganic salts such as, for example, sodium, potassium, calcium and ammonium salts, and organic alkali salts such as, for example, ethylenediamine, ethanolamine, N,N-dialkylenethanolamine, triethanolamine and basic aminoacids salts.

The drug conjugates of the present invention may be in crystalline form either as free compounds or as solvates (e.g. hydrates) and it is intended that both forms are within the scope of the present invention. Methods of solvation are generally known within the art.

Any compound that is a prodrug of the drug conjugate of the present invention is within the scope and spirit of the invention. The term "prodrug" is used in its broadest sense and encompasses those derivatives that are converted in vivo to the compounds of the invention. Such derivatives would readily occur to those skilled in the art, and include, for example, compounds where a free hydroxy group is converted into an ester derivative. Many suitable prodrugs are well-known to the person in the art and can be found, for example, in Burger "Medicinal Chemistry and Drug Discovery 6$^{th}$ ed. (Donald J. Abraham ed., 2001, Wiley) and "Design and Applications of Prodrugs" (H. Bundgaard ed., 1985, Harwood Academic Publishers), the contents of which are incorporated herein by reference.

In relations to the compounds of the present invention, the pharmacologically acceptable esters are not particularly restricted, and can be selected by a person with an ordinary skill in the art. In the case of said esters, it is preferable that such esters can be cleaved by a biological process such as hydrolysis in vivo. The group constituting the said esters (the group shown as R when the esters thereof are expressed as —COOR) can be, for example, a Ci-$C_4$ alkoxy $C_1$-$C_4$ alkyl group such as methoxyethyl, 1-ethoxyethyl, 1-methyl-1-methoxyethyl, 1-(isopropoxy)ethyl, 2-methoxyethyl, 2-ethoxyethyl, 1,1-dimethyl-1-methoxymethyl, ethoxymethyl, propoxymethyl, isopropoxymethyl, butoxymethyl or t-butoxymethyl; a $C_1$-$C_4$ alkoxylated $C_1$-$C_4$ alkoxy $C_1$-$C_4$alkyl group such as 2-methoxyethoxymethyl; a $C_6$-$Ci_0$ aryloxy $C_1$-$C_4$ alkyl group such as phenoxymethyl; a halogenated $C_1$-$C_4$ alkoxy $C_1$-$C_4$ alkyl group such as 2,2,2-trichloroethoxymethyl or bis(2-chloroethoxy)methyl; a $C_1$-$C_4$ alkoxycarbonyl C1-$C_4$ alkyl group such as methoxycarbonylmethyl; a cyano $C_1$-$C_4$ alkyl group such as cyanomethyl or 2-cyanoethyl; a $C_1$-$C_4$ alkylthiomethyl group such as methylthiomethyl or ethylthiomethyl; a $C_6$-$Ci_0$ arylthiomethyl group such as phenylthiomethyl or naphthylthiomethyl; a $C_1$-$C_4$ alkylsulfonyl $C_1$-$C_4$ lower alkyl group, which may be optionally substituted with a halogen atom(s) such as 2-methanesulfonylethyl or 2-trifluoromethanesulfonylethyl; a $C_6$-$Ci_0$ arylsulfonyl $C_1$-$C_4$ alkyl group such as 2-benzenesulfonylethyl or 2-toluenesulfonylethyl; a $CrC_7$ aliphatic acyloxy $C_1$-$C_4$ alkyl group such as formyloxymethyl, acetoxymethyl, propionyloxymethyl, butyryloxymethyl, pivaloyloxymethyl, valeryloxymethyl, isovaleryloxymethyl, hexanoyloxymethyl, 1-formyloxyethyl, 1-acetoxyethyl, 1-propionyloxyethyl, 1-butyryloxyethyl, 1-pivaloyloxyethyl, 1-valeryloxyethyl, 1-isovaleryloxyethyl, 1-hexanoyloxyethyl, 2-formyloxyethyl, 2-acetoxyethyl, 2-propionyloxyethyl, 2-butyryloxyethyl, 2-pivaloyloxyethyl, 2-valeryloxyethyl, 2-isovaleryloxyethyl, 2-hexanoyloxyethyl, 1-formyloxypropyl, 1-acetoxypropyl, 1-propionyloxypropyl, 1-butyryloxypropyl, 1-pivaloyloxypropyl, 1-valeryloxypropyl, 1-isovaleryloxypropyl, 1-hexanoyloxypropyl, 1-acetoxybutyl, 1-propionyloxybutyl, 1-butyryloxybutyl, 1-pivaloyloxybutyl, 1-acetoxypentyl, 1-propionyloxypentyl, 1-butyryloxypentyl, 1-pivaloyloxypentyl or 1-pivaloyloxyhexyl; a $C_5$-$C_6$ cycloalkylcarbonyloxy Ci-$C_4$ alkyl group such as cyclopentylcarbonyloxymethyl, cyclohexylcarbonyloxymethyl, 1-cyclopentylcarbonyloxyethyl, 1-cyclohexylcarbonyloxyethyl, 1-cyclopentylcarbonyloxypropyl, 1-cyclohexylcarbonyloxypropyl, 1-cyclopentylcarbonyloxybutyl or 1-cyclohexylcarbonyloxybutyl; a $C_6$-$Ci_0$ arylcarbonyloxy $C_1$-$C_4$ alkyl group such as benzoyloxymethyl; a Ci-$C_6$ alkoxycarbonyloxy $C_1$-$C_4$ alkyl group such as methoxycarbonyloxymethyl, 1-(methoxycarbonyloxy)ethyl, 1-(methoxycarbonyloxy)propyl, 1-(methoxycarbonyloxy)butyl, 1-(methoxycarbonyloxy)pentyl, 1-(methoxycarbonyloxy)hexyl, ethoxycarbonyloxymethyl, 1-(ethoxycarbonyloxy)ethyl, 1-(ethoxycarbonyloxy)propyl, 1-(ethoxycarbonyloxy)butyl, 1-(ethoxycarbonyloxy)pentyl, 1-(ethoxycarbonyloxy)hexyl, propoxycarbonyloxymethyl, 1-(propoxycarbonyloxy)ethyl, 1-(propoxycarbonyloxy)propyl, 1-(propoxycarbonyloxy)butyl, isopropoxycarbonyloxymethyl, 1-(isopropoxycarbonyloxy)ethyl, 1-(isopropoxycarbonyloxy)butyl, butoxycarbonyloxymethyl, 1-(butoxycarbonyloxy)ethyl, 1-(butoxycarbonyloxy)propyl, 1-(butoxycarbonyloxy)butyl, isobutoxycarbonyloxymethyl, 1-(isobutoxycarbonyloxy)ethyl, 1-(isobutoxycarbonyloxy)propyl, 1-(isobutoxycarbonyloxy)butyl, t-butoxycarbonyloxymethyl, 1-(t-butoxycarbonyloxy)ethyl, pentyloxycarbonyloxymethyl, 1-(pentyloxycarbonyloxy)ethyl, 1-(pentyloxycarbonyloxy)propyl, hexyloxycarbonyloxymethyl, 1-(hexyloxycarbonyloxy)ethyl or 1-(hexyloxycarbonyloxy)propyl; a $C_5$-$C_6$ cycloalkyloxycarbonyloxy $C_1$-$C_4$ alkyl group such as cyclopentyloxycarbonyloxymethyl, 1-(cyclopentyloxycarbonyloxy)ethyl, 1-(cyclopentyloxycarbonyloxy)propyl, 1-(cyclopentyloxycarbonyloxy)butyl, cyclohexyloxycarbonyloxymethyl, 1-(cyclohexyloxycarbonyloxy)ethyl, 1-(cyclohexyloxycarbonyloxy)propyl or 1-(cyclohexyloxycarbonyloxy)butyl; a [5-(Ci-$C_4$ alkyl)-2-oxo-1,3-dioxolen-4-yl]methyl group such as (5-methyl-2-oxo-1,3-dioxolen-4-yl)methyl, (5-ethyl-2-oxo-1,3-dioxolen-4-yl)methyl, (5-propyl-2-oxo-1,3-dioxolen-4-yl)methyl, (5-isopropyl-2-oxo-1,3-dioxolen-4-yl)methyl or (5-butyl-2-oxo-1,3-dioxolen-4-yl)methy; a [5-(phenyl, which may be optionally substituted with a C1-C4 alkyl, C1-C4 alkoxy or halogen atom(s))-2-oxo-1,3-dioxolen-4-yl]methyl group such as (5-phenyl-2-oxo-1,3-dioxolen-4-yl)methyl, [5-(4-methylphenyl)-2-oxo-1,3-dioxolen-4-yl]methyl, [5-(4-methoxyphenyl)-2-oxo-1,3-dioxolen-4-yl]methyl, [5-(4-fluorophenyl)-2-oxo-1,3-dioxolen-4-yl]methyl or [5-(4-chlorophenyl)-2-oxo-1,3-dioxolen-4-yl]methyl; or a phthalidyl group, which may be optionally substituted with a C1-C4 alkyl or C1-C4 alkoxy group(s), such as phthalidyl, dimethylphthalidyl or dimethoxyphthalidyl, and is preferably a pivaloyloxymethyl group, phthalidyl group or (5-methyl-2-oxo-1,3-dioxolen-4-yl)methyl group, and more preferably a (5-methyl-2-oxo-1,3-dioxolen-4-yl)methyl group.

Any compound referred to herein is intended to represent such specific compound as well as certain variations or forms. In particular, compounds referred to herein may have asymmetric centres and therefore exist in different enantiomeric forms. All optical isomers and stereoisomers of the compounds referred to herein, and mixtures thereof, are considered within the scope of the present invention. Thus any given compound referred to herein is intended to represent any one of a racemate, one or more enantiomeric forms, one or more diastereomeric forms, one or more atropisomeric forms, and mixtures thereof. Particularly, the drug conjugates of formula $[D-(X)_b-(AA)_w-(L)]_n$-Ab and compounds of formula D-X-$(AA)_{w'}$-$L_1$ or D-X-$(AA)_{w'}$—H may include enantiomers depending on their asymmetry or diastereoisomers. Stereoisomerism about the double bond is also possible, therefore in some cases the molecule could exist as (E)-isomer or (Z)-isomer. If the molecule contains several double bonds, each double bond will have its own stereoisomerism, that could be the same or different than the stereoisomerism of the other double bonds of the molecule. The single isomers and mixtures of isomers fall within the scope of the present invention.

Furthermore, compounds referred to herein may exist as geometric isomers (i.e., c/s and trans isomers), as tautomers, or as atropisomers. Specifically, the term tautomer refers to one of two or more structural isomers of a compound that exist in equilibrium and are readily converted from one isomeric form to another. Common tautomeric pairs are amine-imine, amide-imide, keto-enol, lactam-lactim, etc. Additionally, any compound referred to herein is intended to represent hydrates, solvates, and polymorphs, and mixtures thereof when such forms exist in the medium. In addition, compounds referred to herein may exist in isotopically-labelled forms. All geometric isomers, tautomers, atropisomers, hydrates, solvates, polymorphs, and isotopically labelled forms of the compounds referred to herein, and mixtures thereof, are considered within the scope of the present invention.

In the compounds of the present invention, Ab is a moiety comprising at least one antigen binding site. In an alternative embodiment, Ab can be any suitable agent that is capable of binding to a target cell, preferably an animal cell and more preferably, a human cell. Examples of such agents include lymphokines, hormones, growth factors and nutrient-transport molecules (e.g. transferrin).

Where Ab is a moiety comprising at least one antigen binding site, the moiety is preferably an antigen-binding peptide or polypeptide. In a preferred embodiment, the moiety is an antibody or an antigen-binding fragment thereof.

The term 'antibody' in the drug conjugates of the present invention refers to any immunoglobulin, preferably a full-length immunoglobulin. Preferably, the term covers monoclonal antibodies, polyclonal antibodies, multispecific antibodies, such as bispecific antibodies, and antibody fragments thereof, so long as they exhibit the desired biological activity. Antibodies may be derived from any species, but preferably are of rodent, for examples rat or mouse, human or rabbit origin. Alternatively, the antibodies, preferably monoclonal antibodies, may be humanised, chimeric or antibody fragments thereof. The term 'chimeric antibodies' may also include "primatised" antibodies comprising variable domain antigen-binding sequences derived from a non-human primate (e.g., Old World Monkey, Ape etc) and human constant region sequences. The immunoglobulins can also be of any type (e.g. IgG, IgE, IgM, IgD, and IgA), class (e.g., IgGI, IgG2, IgG3, IgG4, IgAI and IgA2) or subclass of immunoglobulin molecule.

The term 'monoclonal antibody' refers to a substantially homogenous population of antibody molecules (i.e. the individual antibodies comprising the population are identical except for possible naturally occurring mutations that may be present in minor amounts), produced by a single clone of B lineage cells, often a hybridoma. Importantly, each monoclonal has the same antigenic specificity—i.e. it is directed against a single determinant on the antigen.

The production of monoclonal antibodies can be carried out by methods known in the art. However, as an example, the monoclonal antibodies can be made by the hybridoma method (Kohler et al (1975) Nature 256:495), the human B cell hybridoma technique (Kozbor et al., 1983, Immunology Today 4: 72), or the EBV-hybridoma technique (Cole et al., 1985, Monoclonal Antibodies and Cancer Therapy, Alan R. Liss, Inc., pp. 77-96). Alternatively, the monoclonal antibody can be produced using recombinant DNA methods (see, U.S. Pat. No. 4,816,567) or isolated from phage antibody libraries using the techniques described in Clackson et al (1991) Nature, 352:624-628; Marks et al (1991) J. Mol. Biol., 222:581-597.

Polyclonal antibodies are antibodies directed against different determinants (epitopes). This heterogenous population of antibody can be derived from the sera of immunised animals using various procedures well known in the art.

The term 'bispecific antibody' refers to an artificial antibody composed of two different monoclonal antibodies. They can be designed to bind either to two adjacent epitopes on a single antigen, thereby increasing both avidity and specificity, or bind two different antigens for numerous applications, but particularly for recruitment of cytotoxic T- and natural killer (NK) cells or retargeting of toxins, radionuclides or cytotoxic drugs for cancer treatment (Holliger & Hudson, Nature Biotechnology, 2005, 9, 23). The bispecific antibody may have a hybrid immunoglobulin heavy chain with a first binding specificity in one arm, and a hybrid immunoglobulin heavy chain-light chain pair (providing a second binding specificity) in the other arm. This asymmetric structure facilitates the separation of the desired bispecific compound from unwanted immunoglobulin chain combinations, as the presence of an immunoglobulin light chain in only one half of the bispecific molecule provides for a facile way of separation (WO 94/04690; Suresh et al., Methods in Enzymology, 1986, 121:210; Rodrigues et al., 1993, J. of Immunology 151:6954-6961; Carter et al., 1992, Bio/Technology 10:163-167; Carter et al., 1995, J. of Hematotherapy 4:463-470; Merchant et al., 1998, Nature Biotechnology 16:677-681.

Methods to prepare hybrid or bispecific antibodies are known in the art. In one method, bispecific antibodies can be produced by fusion of two hybridomas into a single 'quadroma' by chemical cross-linking or genetic fusion of two different Fab or scFv modules (Holliger & Hudson, Nature Biotechnology, 2005, 9, 23).

The term 'chimeric' antibody refers to an antibody in which different portions are derived from different animal species. For example, a chimeric antibody may derive the variable region from a mouse and the constant region from a human. In contrast, a 'humanised antibody' comes predominantly from a human, even though it contains non-human portions. Specifically, humanised antibodies are human immunoglobulins (recipient antibody) in which residues from a hypervariable region of the recipient are replaced by residues from hypervariable regions of a non-human species (donor antibody) such as mouse, rat, rabbit or nonhuman primate having the desired specificity, affinity and capacity. In some instances, framework region (FR) residues of the human immunoglobulin are replaced by corresponding non-human residues. Furthermore, humanised antibodies may comprise residues that are not found in the recipient antibody or in the donor antibody. These modifications are made to further refine antibody performance. In general, the humanised antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanised antibody optionally also will comprise at least a portion of an immunoglobulin constant region (Fc), typically that of a human immunoglobulin.

Recombinant antibodies such as chimeric and humanised monoclonal antibodies can be produced by recombinant DNA techniques known in the art. Completely human antibodies can be produced using transgenic mice that are incapable of expressing endogenous immunoglobulin heavy and light chains genes, but which can express human heavy and light chain genes. The transgenic mice are immunized in the normal fashion with a selected antigen. Monoclonal antibodies directed against the antigen can be obtained using conventional hybridoma technology. The human immunoglobulin transgenes harboured by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, Int. Rev. Immunol. 13:65-93). For a detailed discussion of this technology for producing human antibodies and human monoclonal antibodies and protocols for producing such antibodies, see, for example, U.S. Pat. Nos. 5,625,126; 5,633,425; 5,569,825; 5,661,016; 5,545,806; each of which is incorporated herein by reference in its entirety. Other human antibodies can be obtained commercially from, for example, Abgenix, Inc. (Freemont, CA) and Genpharm (San Jose, CA).

The term 'antigen-binding fragment' in the drug conjugates of the present invention refers to a portion of a full length antibody where such antigen-binding fragments of antibodies retain the antigen-binding function of a corresponding full-length antibody. The antigen-binding fragment may comprise a portion of a variable region of an antibody, said portion comprising at least one, two, preferably three CDRs selected from CDR1, CDR2 and CDR3. The antigen-binding fragment may also comprise a portion of an immunoglobulin light and heavy chain. Examples of antibody fragments include Fab, Fab', F(ab')2, scFv, di-scFv, and BiTE (Bi-specific T-cell engagers), Fv fragments including nanobodies, diabodies, diabody-Fc fusions, triabodies and, tetrabodies; minibodies; linear antibodies; fragments produced by a Fab expression library, anti-idiotypic (anti-Id) antibodies, CDR (complementary determining region), and epitope-binding fragments of any of the above that immunospecifically bind to a target antigen such as a cancer cell antigens, viral antigens or microbial antigens, single-chain or single-domain antibody molecules including heavy chain only antibodies, for example, camelid VHH domains and shark V-NAR; and multispecific antibodies formed from antibody fragments. For comparison, a full length antibody, termed 'antibody' is one comprising a VL and VH domains, as well as complete light and heavy chain constant domains.

The antibody may also have one or more effector functions, which refer to the biological activities attributable to the Fc region (a native sequence Fc region or amino acid sequence variant Fc region engineered according to methods in the art to alter receptor binding) of an antibody. Examples of antibody effector functions include C1q binding; complement dependent cytotoxicity; Fc receptor binding; antibody-dependent cell-mediated cytotoxicity (ADCC); phagocytosis; down regulation of cell surface receptors (e.g., B cell receptor; BCR), etc.

The antibody can also be a functionally active fragment, derivative or analog of an antibody that immunospecifically binds to a target antigen such as a cancer cell antigen, viral antigen, or microbial antigen or other antibodies bound to tumour cells. In this regard, functionally active means that the fragment, derivative or analog is able to elicit anti-idiotype antibodies that recognise the same antigen that the antibody from which the fragment, derivative or analog is derived recognised. Specifically, in an exemplary embodiment the antigenicity of the idiotype of the immunoglobulin molecule can be enhanced by deletion of framework and CDR sequences that are C-terminal to the CDR sequence that specifically recognizes the antigen. To determine which CDR sequences bind the antigen, synthetic peptides containing the CDR sequences can be used in binding assays with the antigen by any binding assay method known in the art (e.g., the BIA core assay), see, for example, Kabat et al., 1991, Sequences of Proteins of Immunological Interest, Fifth Edition, National Institute of Health, Bethesda, Md.; Kabat E et al., 1980, J. of Immunology 125(3):961-969).

The term 'antibody' may also include a fusion protein of an antibody, or a functionally active fragment thereof, for example in which the antibody is fused via a covalent bond (e.g., a peptide bond), at either the N-terminus or the C-terminus to an amino acid sequence of another protein (or portion thereof, such as at least 10, 20 or 50 amino acid portion of the protein) that is not the antibody. The antibody or fragment thereof may be covalently linked to the other protein at the N-terminus of the constant domain.

Furthermore, the antibody or antigen-binding fragments of the present invention may include analogs and derivatives of antibodies or antigen-binding fragments thereof that are either modified, such as by the covalent attachment of any type of molecule as long as such covalent attachment permits the antibody to retain its antigen binding immuno-specificity. Examples of modifications include glycosylation, acetylation, pegylation, phosphorylation, amidation, derivatization by known protecting/blocking groups, proteolytic cleavage, linkage to a cellular antibody unit or other protein, etc. Any of numerous chemical modifications can be carried out by known techniques, including, but not limited to specific chemical cleavage, acetylation, formylation, metabolic synthesis in the presence of tunicamycin, etc. Additionally, the analog or derivative can contain one or more unnatural amino acids.

The antibodies or antigen-binding fragments of the present invention may also have modifications (e.g., substitutions, deletions or additions) in the Fc domain of the antibody. Specifically, the modifications may be in the Fc-hinge region and result in an increased binding for the FcRn receptor (WO 97/34631).

In one embodiment, the antibody in the drug conjugate of the present invention may be any antibody or antigen-binding fragment thereof, preferably a monoclonal antibody that is useful in the treatment of a disease, preferably cancer. The cancer may be breast cancer, colorectal cancer, endometrial cancer, kidney cancer melanoma, leukaemias, lung cancer, multiple myeloma, lymphomas (e.g. Hodgkin's disease and non-Hodgkin's Lymphoma), solid tumors such as sarcoma and carcinomas, melanoma, mesothelioma, osteosarcoma, ovarian cancer and renal cancer. In a preferred embodiment the cancer is lung cancer, colorectal cancer, breast cancer, pancreas carcinoma, kidney cancer, leukaemia, multiple myeloma, lymphoma and ovarian cancer. In a more preferred embodiment the cancer is colorectal cancer, breast cancer, leukaemia, lymphoma, and ovarian cancer Antibodies that may be useful in the treatment of cancer include, but are not limited to, antibodies against the following antigens: CA125 (ovarian), CA15-3 (carcinomas), CA19-9 (carcinomas), L6 (carcinomas), Lewis Y (carcinomas), Lewis X (carcinomas), alpha fetoprotein (carcinomas), CA 242 (colorectal), placental alkaline phosphatase (carcinomas), prostate specific antigen (prostate), prostatic acid phosphatase (prostate), epidermal growth factor (carcinomas) for example EGF receptor 2 protein (breast cancer), MAGE-I (carcinomas), MAGE-2 (carcinomas), MAGE-3 (carcinomas), MAGE-4 (carcinomas), anti-transferrin receptor (carcinomas), p97 (melanoma), MUCI-KLH (breast cancer), CEA (colorectal), gplOO (melanoma), MARTI (melanoma), PSA (prostate), IL-2 receptor (T-cell leukemia and lymphomas), CD20 (non-Hodgkin's lymphoma), CD52 (leukemia), CD33 (leukemia), CD22 (lymphoma), human chorionic gonadotropin (carcinoma), CD38 (multiple myeloma), CD40 (lymphoma), mucin (carcinomas), P21 (carcinomas), MPG (melanoma), and Neu oncogene product (carcinomas). Some specific, useful antibodies include, but are not limited to, BR96 mAb (Trail, P. A., et al Science (1993) 261, 212-215), BR64 (Trail, P A, et al Cancer Research (1997) 57, 100-105, mAbs against the CD40 antigen, such as S2C6 mAb (Francisco, J. A., et al Cancer Res. (2000) 60:3225-3231), mAbs against the CD70 antigen, such as 1F6 mAb, and mAbs against the CD30 antigen, such as ACIO (Bowen, M. A., et al (1993) J. Immunol., 151:5896-5906; Wahl et al., 2002 Cancer Res. 62(13):3736-42). Many other internalizing antibodies that bind to tumor associated antigens can be used and have been reviewed (Franke, A. E., et al Cancer Biother Radiopharm. (2000) 15:459-76; Murray, J. L., (2000) Semin Oncol, 27:64-70; Breitling, F., and Dubel, S., Recombinant Antibodies, John Wiley, and Sons, New York, 1998).

Other tumour-associated antigens include, but are not limited to, BMPR1 B, E16, STEAP1, STEAP2, 0772P. MPF, Napi3b, Sema5b, PSCA hIg, ETBR, MSG783, TrpM4, CRIPTO, CD21, CD79b, FcRH2, HER2, NCA, MDP, IL20Ra, Brevican, EphB2R, ASLG659, PSCA, GEDA, BAFF-R, CD79A, CXCR5, HLA-DOB, P2X5, CD72, LY64, FCRH1, IRTA2 and TENB2.

In an alternative embodiment, the antibody in the drug conjugate of the present invention may be an antibody or antigen-binding fragment thereof, preferably a monoclonal antibody, that immunospecifically binds to a viral antigen, microbial antigen or an antigen of a cell that produces autoimmune antibodies associated with autoimmune disease.

The viral antigen may include, but is not limited to, any viral peptide, polypeptide or protein such as HIV gp120, HIV nef, RSV F glycoprotein, influenza virus neuraminidase, influenza virus hemagglutinin, HTLV tax, herpes simplex virus glycoprotein (e.g., Gb, Gc, Gd, and Ge) and hepatitis B surface antigen) that is capable of eliciting an immune response.

The microbial antigen may include, but is not limited to, any microbial peptide, polypeptide, protein, saccharide, polysaccharide, or lipid molecule (e.g., a bacterial, fungi, pathogenic protozoa, or yeast polypeptide including, e.g., LPS and capsular polysaccharide) that is capable of eliciting an immune response.

In another embodiment, the antibody may be any antibody known for the treatment or prevention of viral or microbial infection—i.e. an infectious disease. Examples of such antibodies include, but are not limited to, PR0542

(Progenies) which is a CD4 fusion antibody useful for the treatment of HIV infection; OsTAVIR (Protein Design Labs, Inc., CA) which is a human antibody useful for the treatment of hepatitis B virus; PROTOVIR. (Protein Design Labs, Inc., CA) which is a humanised IgG1 antibody useful for the treatment of cytomegalovirus (CMV); and anti-LPS antibodies.

Other antibodies useful in the treatment of infectious diseases include, but are not limited to, antibodies against the antigens from pathogenic strains of bacteria (*Streptococcus pyogenes, Streptococcus pneumoniae, Neisseria gonorrheae, Neisseria meningitidis, Corynebacterium diphtheriae, Clostridium botulinum, Clostridium perfringens, Clostridium tetani, Hemophilus influenzae, Klebsiella pneumoniae, Klebsiella ozaenas, Klebsiella rhinoscleromotis, Staphylococcus aureus, Vibrio colerae, Escherichia coli, Pseudomonas aeruginosa, Campylobacter* (*Vibrio*) *fetus, Aeromonas hydrophila, Bacillus cereus, Edwardsiella tarda, Yersinia enterocolitica, Yersinia pestis, Yersinia pseudotuberculosis, Shigella dysenteriae, Shigella flexneri, Shigella sonnei, Salmonella typhimurium, Treponema pallidum, Treponema pertenue, Treponema carateneum, Borrelia vincentii, Borrelia burgdorferi, Leptospira icterohernorrhagiae, Mycobacterium tuberculosis, Pneumocystis carinii, Francisella tularensis, Brucella abortus, Brucella suis, Brucella melitensis, Mycoplasma* spp., *Rickettsia prowazeki, Rickettsia tsutsugumushi, Chlamydia* spp.); pathogenic fungi (*Coccidioides immitis, Aspergillus fumigatus, Candida albicans, Blastomyces dermatitidis, Cryptococcus neoformans, Histoplasma capsulatum*); protozoa (*Entomoeba histolytica, Toxoplasma gondii, Trichomonas tenas, Trichomonas hominis, Trichomonas vaginalis, Tryoanosoma gambiense, Trypanosoma rhodesiense, Trypanosoma cruzi, Leishmania donovani, Leishmania tropica, Leishmania braziliensis, Pneumocystis pneumonia, Plasmodium vivax, Plasmodium falciparum, Plasmodium* malaria); or Helminiths (*Enterobius vermicularis, Trichuris trichiura, Ascaris lumbricoides, Trichinella spiralis, Strongyloides stercoralis, Schistosoma japonicum, Schistosoma mansoni, Schistosoma haematobium*, and hookworms).

Other antibodies useful for the treatment of viral disease include, but are not limited to, antibodies against antigens of pathogenic viruses, including as examples and not by limitation: Poxviridae, Herpesviridae, Herpes Simplex virus 1, Herpes Simplex virus 2, Adenoviridae, Papovaviridae, Enteroviridae, Picornaviridae, Parvoviridae, Reoviridae, Retroviridae, influenza viruses, parainfluenza viruses, mumps, measles, respiratory syncytial virus, rubella, Arboviridae, Rhabdoviridae, Arenaviridae, Hepatitis A virus, Hepatitis B virus, Hepatitis C virus, Hepatitis E virus, Non-A/Non-B Hepatitis virus, Rhinoviridae, Coronaviridae, Rotoviridae, and Human Immunodeficiency Virus.

In an alternative embodiment, the antibody of the drug conjugate of the present invention may also be any antibody known for the treatment of prevention of autoimmune disorders, such as, but not limited to, Th2-lymphocyte related disorders (e.g. atopic dermatitis, atopic asthma, rhinoconjunctivitis, allergic rhinitis, Omenn's syndrome, systemic sclerosis, and graft versus host disease); Th1 lymphocyte-related disorders (e.g. rheumatoid arthritis, multiple sclerosis, psoriasis, Sjorgren's syndrome, Hashimoto's thyroiditis, Grave's disease, primary biliary cirrhosis, Wegener's granulomatosis, and tuberculosis); activated B lymphocyte-related disorders (e.g. systemic lupus erythematosus, Goodpasture's syndrome, rheumatoid arthritis, and type I diabetes); and Active Chronic Hepatitis, Addison's Disease, Allergic Alveolitis, Allergic Reaction, Allergic Rhinitis, Alport's Syndrome, Anaphlaxis, Ankylosing Spondylitis, Anti-phosholipid Syndrome, Arthritis, Ascariasis, Aspergillosis, Atopic Allergy, Atropic Dermatitis, Atropic Rhinitis, Behcet's Disease, Bird-Fancier's Lung, Bronchial Asthma, Caplan's Syndrome, Cardiomyopathy, Celiac Disease, Chagas' Disease, Chronic Glomerulonephritis, Cogan's Syndrome, Cold Agglutinin Disease, Congenital Rubella Infection, CREST Syndrome, Crohn's Disease, Cryoglobulinemia, Cushing's Syndrome, Dermatomyositis, Discoid Lupus, Dresser's Syndrome, Eaton-Lambert Syndrome, Echovirus Infection, Encephalomyelitis, Endocrine opthalmopathy, Epstein-Barr Virus Infection, Equine Heaves, Erythematosis, Evan's Syndrome, Felty's Syndrome, Fibromyalgia, Fuch's Cyclitis, Gastric Atrophy, Gastrointestinal Allergy, Giant Cell Arteritis, Glomerulonephritis, Goodpasture's Syndrome, Graft v. Host Disease, Graves' Disease, Guillain-Barre Disease, Hashimoto's Thyroiditis, Hemolytic Anemia, Henoch-Schonlein Purpura, Idiopathic Adrenal Atrophy, Idiopathic Pulmonary Fibrosis, IgA Nephropathy, Inflammatory Bowel Diseases, Insulin-dependent Diabetes Mellitus, Juvenile Arthritis, Juvenile Diabetes Mellitus (Type I), Lambert-Eaton Syndrome, Laminitis, Lichen Planus, Lupoid Hepatitis, Lupus Lymphopenia, Meniere's Disease, Mixed Connective Tissue Disease, Multiple Sclerosis, Myasthenia Gravis, Pernicious Anemia, Polyglandular Syndromes, Presenile Dementia, Primary Agammaglobulinemia, Primary Biliary Cirrhosis, Psoriasis, Psoriatic Arthritis, Raynauds Phenomenon, Recurrent Abortion, Reiter's Syndrome, Rheumatic Fever, Rheumatoid Arthritis, Sampter's Syndrome, Schistosomiasis, Schmidt's Syndrome, Scleroderma, Shulman's Syndrome, Sjorgen's Syndrome, Stiff-Man Syndrome, Sympathetic Ophtahnia, Systemic Lupus Erythematosis, Takayasu's Arteritis, Temporal Arteritis, Thyroiditis, Thrombocytopenia, Thyrotoxicosis, Toxic Epidermal Necrolysis, Type B Insulin Resistance, Type I Diabetes Mellitus, Ulcerative Colitis, Uveitis, Vitiligo, Waldenstrom's Macroglobulemia and Wegener's Granulomatosis.

Antibodies immunospecific for an antigen of a cell that is responsible for producing autoimmune antibodies can be obtained by any method known to one of skill in the art such as, e.g., chemical synthesis or recombinant expression techniques. Examples of autoimmune antibodies include, but are not limited to, Anti-Nuclear Antibody; Anti ds DNA; Anti ss DNA, Anti Cardiolipin Antibody IgM, IgG; Anti Phospholipid Antibody IgM, IgG; Anti SM Antibody; Anti Mitochondrial Antibody; Thyroid Antibody; Microsomal Antibody; Thyroglobulin Antibody; Anti SCL-70; Anti-Jo; Anti-U1 RNP; Anti-La/SSB; Anti SSA; Anti SSB; Anti Perital Cells Antibody; Anti Histones; Anti-RNP; C-ANCA; P-ANCA; Anti centromere; Anti-Fibrillarin, and Anti-GBM Antibody.

In another embodiment, the antibody of the drug conjugate of the present invention can be one that binds to both a receptor or a receptor complex expressed on an activated lymphocyte, such as one associated with an autoimmune disease. The receptor or receptor complex can comprise an immunoglobulin gene superfamily member, a TNF receptor superfamily member, an integrin, an interleukin, a cytokine receptor, a chemokine receptor, a major histocompatibility protein, a lectin, or a complement control protein. Non-limiting examples of suitable immunoglobulin superfamily members are CD2, CD3, CD4, CD5, CD8, CD13, CD19, CD22, CD28, CD79, CD90, CD152/CTLA-4, PD-1, and ICOS. Non-limiting examples of suitable TNF receptor superfamily members are CD27, CD40, CD95/Fas, CD134/OX40, CD137/4-1 BB, TNF-RI, TNFR-2, RANK, TACI, BCMA, osteoprotegerin, Apo2/TRAEL-RI, TRAIL-R2, TRAIL-R3, TRABL-R4, and APO-3. Non-limiting examples of suitable integrins are CDI Ia, CDIIb, CDIIc, CD18, CD29, CD41, CD49a, CD49b, CD49c, CD49d, CD49e, CD49f, CD103, and CD104. Non-limiting examples of suitable lectins are C-type, S-type, and I-type lectin.

An antibody that binds a molecular target or an antigen of interest, e.g., ErbB2 antigen, is one capable of binding that antigen with sufficient affinity such that the antibody is useful in targeting a cell expressing the antigen. Where the antibody is one which binds ErbB2, it will usually preferentially bind ErbB2 as opposed to other ErbB receptors, and may be one which does not significantly cross-react with other proteins such as EGFR, ErbB 3 or ErbB4. In such embodiments, the extent of binding of the antibody to these non-ErbB2 proteins (e.g., cell surface binding to endogenous receptor) will be less than 10% as determined by fluorescence activated cell sorting (FACS) analysis or radioimmunoprecipitation (RIA). Sometimes, the anti-ErbB2 antibody will not significantly cross-react with the rat neu protein, e.g., as described in Schecter et al., Nature 312:513 (1984) and Drebin et al., Nature 312:545-548 (1984).

In another embodiment, the antibody of the drug conjugate or target of the present invention may be selected from an antibody or target in the below table. Such antibodies are immunospecific for a target antigen and can be obtained commercially or produced by any method known in the art such as, e.g., recombinant expression techniques.

TABLE 1

Therapeutic monoclonal antibodies

| Name | Trade name | Target |
|---|---|---|
| 3F8 | | GD2 |
| 8H9 | | B7-H3 |
| Abagovomab | | CA-125 (imitation) |
| Abciximab | ReoPro | CD41 (integrin alpha-IIb) |
| Actoxumab | | *Clostridium difficile* |
| Adalimumab | Humira | TNF-α |
| Adecatumumab | | EpCAM |
| Afelimomab | | TNF-α |
| Afutuzumab | | CD20 |
| Alacizumab pegol | | VEGFR2 |
| ALD518 | | IL-6 |
| Alemtuzumab | Campath, MabCampath | CD52 |
| Alirocumab | | NARP-1 |
| Altumomab | | CEA |
| Amatuximab | | mesothelin |
| Anatumomab | | TAG-72 |
| Anifrolumab | | interferon α/β receptor |
| Anrukinzumab | | IL-13 |
| Apolizumab | | HLA-DR β-chain |
| Arcitumomab | CEA-Scan | CEA |
| Aselizumab | | L-selectin (CD62L) |
| Atinumab | | RTN4 |
| Atlizumab (=tocilizumab) | Actemra, RoActemra | IL-6 receptor |
| Atorolimumab | | Rhesus factor |
| Bapineuzumab | | beta amyloid |
| Basiliximab | Simulect | CD25 (α chain of IL-2 receptor) |
| Bavituximab | | phosphatidylserine |
| Belimumab | Benlysta, LymphoStat-B | BAFF |
| Benralizumab | | CD125 |
| Bertilimumab | | CCL11 (eotaxin-1) |
| Besilesomab | Scintimun | CEA-related antigen |
| Bevacizumab | Avastin | VEGF-A |
| Bezlotoxumab | | *Clostridium difficile* |
| Biciromab | FibriScint | fibrin II, beta chain |
| Bimagrumab | | ACVR2B |
| Bivatuzumab | | CD44 v6 |
| Blinatumomab | | CD19 |

TABLE 1-continued

Therapeutic monoclonal antibodies

| Name | Trade name | Target |
|---|---|---|
| Blosozumab | | SOST |
| Brentuximab | | CD30 (TNFRSF8) |
| Briakinumab | | IL-12, IL-23 |
| Brodalumab | | IL-17 |
| Canakinumab | Ilaris | IL-1beta |
| Cantuzumab | | MUC-1 |
| Caplacizumab | | VWF |
| Capromab | | prostatic carcinoma cells |
| Carlumab | | MCP-1 |
| Catumaxomab | Removab | EpCAM, CD3 |
| CC49 | | TAG-72 |
| Cedelizumab | | CD4 |
| Certolizumab pegol | Cimzia | TNF-α |
| Cetuximab | Erbitux | EGFR |
| Ch.14.18 | | Disialoganglioside (GD2) |
| Citatuzumab | | EpCAM |
| Cixutumumab | | IGF-1 receptor |
| Clazakizumab | | *Otyctolagus cuniculus* |
| Clenoliximab | | CD4 |
| Clivatuzumab | | MUC1 |
| Conatumumab | | TRAIL-R2 |
| Concizumab | | TFPI |
| CR6261 | | Influenza A hemagglutinin |
| Crenezumab | | 1-40-β-amyloid |
| Dacetuzumab | | CD40 |
| Daclizumab | Zenapax | CD25 (a chain of IL-2 receptor) |
| Dalotuzumab | | insulin-like growth factor I receptor |
| Daratumumab | | CD38 (cyclic ADP ribose hydrolase) |
| Demcizumab | | DLL4 |
| Denosumab | Prolia | RANKL |
| Detumomab | | B-lymphoma cell |
| Dorlimomab | | unknown |
| Drozitumab | | DR5 |
| Duligotumab | | HER3 |
| Dupilumab | | IL4 |
| Dusigitumab | | ILGF2 |
| Ecromeximab | | GD3 ganglioside |
| Eculizumab | Soliris | C5 |
| Edobacomab | | endotoxin |
| Edrecolomab | Panorex | EpCAM |
| Efalizumab | Raptiva | LFA-1 (CD1 1a) |
| Efungumab | Mycograb | Hsp90 |
| Eldelumab | | interferon gamma-induced protein |
| Elotuzumab | | SLAMF7 |
| Elsilimomab | | IL-6 |
| Enavatuzumab | | TWEAK receptor |
| Enlimomab pegol | | ICAM-1 (CD54) |
| Enokizumab | | IL9 |
| Enoticumab | | DLL4 |
| Ensituximab | | 5AC |
| Epitumomab | | episialin |
| Epratuzumab | LymphoCide | CD22 |
| Erlizumab | | ITGB2 (CD18) |
| Ertumaxomab | Rexomun | HER2/neu, CD3 |
| Etaracizumab | Abegrin | integrin $\alpha_v \beta_3$ |
| Etrolizumab | | integrin $\alpha_7 \beta_7$ |
| Evolocumab | | PCSK9 |
| Exbivirumab | | hepatitis B surface antigen |
| Faralimomab | | interferon receptor |
| Farletuzumab | | folate receptor 1 |
| Fasinumab | | HNGF |
| FBTA05 | Lymphomun | CD20 |
| Felvizumab | | respiratory syncytial virus |
| Fezakinumab | | IL-22 |
| Ficlatuzumab | | HGF |
| Figitumumab | | IGF-1 receptor |
| Flanvotumab | | glycoprotein 75 |
| Fontolizumab | HuZAF | IFN-Y |
| Foralumab | | CD3 epsilon |
| Foravirumab | | rabies virus glycoprotein |
| Fresolimumab | | TGF-β |
| Fulranumab | | NGF |

TABLE 1-continued

Therapeutic monoclonal antibodies

| Name | Trade name | Target |
|---|---|---|
| Futuximab | | EGFR |
| Galiximab | | CD80 |
| Ganitumab | | IGF-I |
| Gantenerumab | | beta amyloid |
| Gavilimomab | | CD147 (basigin) |
| Gemtuzumab | | CD33 |
| Gevokizumab | | IL-1 β |
| Girentuximab | Rencarex | carbonic anhydrase 9 (CA-IX) |
| Glembatumumab | | GPNMB |
| Golimumab | Simponi | TNF-a |
| Gomiliximab | | CD23 (IgE receptor) |
| GS6624 | | lysyl oxidase like 2 |
| Guselkumab | | IL13 |
| Ibalizumab | | CD4 |
| Ibritumomab | | CD20 |
| Icrucumab | | VEGFR-1 |
| Igovomab | Indimacis-125 | CA-125 |
| Imciromab | Myoscint | cardiac myosin |
| Imgatuzumab | | EGFR |
| Inclacumab | | selectin P |
| Indatuximab | | SDC1 |
| Infliximab | Remicade | TNF-a |
| Inolimomab | | CD25 (a chain of IL-2 receptor) |
| Inotuzumab | | CD22 |
| Intetumumab | | CD51 |
| Ipilimumab | Yervoy | CD152 |
| Iratumumab | | CD30 (TNFRSF8) |
| Itolizumab | | CD6 |
| Ixekizumab | | IL-17A |
| Keliximab | | CD4 |
| Labetuzumab | CEA-Cide | CEA |
| Lambrolizumab | | PDCD1 |
| Lampalizumab | | CFD |
| Lebrikizumab | | IL-13 |
| Lemalesomab | | NCA-90 (granulocyte antigen) |
| Lerdelimumab | | TGF beta 2 |
| Lexatumumab | | TRAIL-R2 |
| Libivirumab | | hepatitis B surface antigen |
| Ligelizumab | | IGHE |
| Lintuzumab | Smart M 195 | CD33 |
| Lirilumab | | KIR2D |
| Lodelcizumab | | PCSK9 |
| Lorvotuzumab | | CD56 |
| Lucatumumab | | CD40 |
| Lumiliximab | | CD23 (IgE receptor) |
| Mapatumumab | | TRAIL-R1 |
| Margetuximab | | ch4D5 |
| Maslimomab | | T-cell receptor |
| Matuzumab | | EGFR |
| Mavrilimumab | | GMCSF receptor a-chain |
| Mepolizumab | Bosatria | IL-5 |
| Metelimumab | | TGF beta 1 |
| Milatuzumab | | CD74 |
| Minretumomab | | TAG-72 |
| Mitumomab | | GD3 ganglioside |
| Mogamulizumab | | CCR4 |
| Morolimumab | | Rhesus factor |
| Motavizumab | Numax | respiratory syncytial virus |
| Moxetumomab | | CD22 |
| Muromonab-CD3 | Orthoclone OKT3 | CD3 |
| Nacolomab | | C242 antigen |
| Namilumab | | CSF2 |
| Naptumomab | | 5T4 |
| Narnatumab | | RON |
| Natalizumab | Tysabri | integrin a₄ |
| Nebacumab | | endotoxin |
| Necitumumab | | EGFR |
| Nerelimomab | | TNF-a |
| Nesvacumab | | angiopoietin 2 |
| Nimotuzumab | Theracim, Theraloc | EGFR |
| Nivolumab | | IgG4 |
| Nofetumomab | | ? |
| Ocaratuzumab | | CD20 |
| Ocrelizumab | | CD20 |
| Odulimomab | | LFA-1 (CD11a) |
| Ofatumumab | Arzerra | CD20 |
| Olaratumab | | PDGF-R a |
| Olokizumab | | IL6 |
| Omalizumab | Xolair | IgE Fc region |
| Onartuzumab | | human scatter factor receptor kinase |
| Oportuzumab | | EpCAM |
| Oregovomab | Ova Rex | CA-125 |
| Orticumab | | oxLDL |
| Otelixizumab | | CD3 |
| Oxelumab | | OX-40 |
| Ozanezumab | | NOGO-A |
| Ozoralizumab | | Lama glama |
| Pagibaximab | | lipoteichoic acid |
| Palivizumab | Synagis, Abbosynagis | F protein of respiratory syncytial virus |
| Panitumumab | Vectibix | EGFR |
| Panobacumab | | Pseudomonas aeruginosa |
| Parsatuzumab | | EGFL7 |
| Pascolizumab | | IL-4 |
| Pateclizumab | | LTA |
| Patritumab | | HER3 |
| Pemtumomab | Theragyn | MUC1 |
| Perakizumab | | IL17A |
| Pertuzumab | Omnitarg | HER2/neu |
| Pexelizumab | | C5 |
| Pidilizumab | | PD-1 |
| Pinatuzumab | | CD22 |
| Pintumomab | | adenocarcinoma antigen |
| Placulumab | | human TNF |
| Polatuzumab | | CD79B |
| Ponezumab | | human beta-amyloid |
| Priliximab | | CD4 |
| Pritoxaximab | | E. coli shiga toxin type-1 |
| Pritumumab | | vimentin |
| PRO 140 | | CCR5 |
| Quilizumab | | IGHE |
| Racotumomab | | N-glycolylneuraminic acid |
| Radretumab | | fibronectin extra domain-B |
| Rafivirumab | | rabies virus glycoprotein |
| Ramucirumab | | VEGFR2 |
| Ranibizumab | Lucentis | VEGF-A |
| Raxibacumab | | anthrax toxin, protective antigen |
| Regavirumab | | cytomegalovirus glycoprotein B |
| Reslizumab | | IL-5 |
| Rilotumumab | | HGF |
| Rituximab | MabThera, Rituxan | CD20 |
| Robatumumab | | IGF-1 receptor |
| Roledumab | | RHD |
| Romosozumab | | scleroscin |
| Rontalizumab | | IFN-a |
| Rovelizumab | | CD11, CD18 |
| Ruplizumab | Antova | CD154 (CD40L) |
| Samalizumab | | CD200 |
| Sarilumab | | IL6 |
| Satumomab | | TAG-72 |
| Secukinumab | | IL-17A |
| Seribantumab | | ERBB3 |
| Setoxaximab | | E. coli Shiga toxin type-1 |
| Sevirumab | | cytomegalovirus |
| Sibrotuzumab | | FAP |
| Sifalimumab | | IFN-a |
| Siltuximab | | IL-6 |
| Simtuzumab | | LOXL2 |
| Siplizumab | | CD2 |
| Sirukumab | | IL-6 |
| Solanezumab | | beta amyloid |
| Solitomab | | EpCAM |
| Sonepcizumab | | sphingosine-1-phosphate |
| Sontuzumab | | episialin |
| Stamulumab | | myostatin |
| Sulesomab | LeukoScan | NCA-90 (granulocyte antigen) |
| Suvizumab | | HIV-1 |
| Tabalumab | | BAFF |
| Tacatuzumab | | alpha-fetoprotein |

TABLE 1-continued

Therapeutic monoclonal antibodies

| Name | Trade name | Target |
|---|---|---|
| Tadocizumab | | integrin $\alpha_{IIb}\beta_3$ |
| Talizumab | | IgE |
| Tanezumab | | NGF |
| Taplitumomab | | CD19 |
| Tefibazumab | Aurexis | clumping factor A |
| Telimomab | | unknown |
| Tenatumomab | | tenascin C |
| Teneliximab | | CD40 |
| Teplizumab | | CD3 |
| Teprotumumab | | CD221 |
| TGN1412 | | CD28 |
| Ticilimumab (=tremelimumab) | | CTLA-4 |
| Tigatuzumab | | TRAIL-R2 |
| Tildrakizumab | | IL23 |
| TNX-650 | | IL-13 |
| Toralizumab | | CD154 (CD40L) |
| Tositumomab | Bexxar | CD20 |
| Tovetumab | | CD140a |
| Tralokinumab | | IL-13 |
| Trastuzumab | Herceptin | HER2/neu |
| TRBS07 | Ektomab | GD2 |
| Tregalizumab | | CD4 |
| Tucotuzumab | | EpCAM |
| Tuvirumab | | hepatitis B virus |
| Ublituximab | | MS4A1 |
| Urelumab | | 4-1 BB |
| Urtoxazumab | | *Escherichia coli* |
| Ustekinumab | Stelara | IL-12, IL-23 |
| Vantictumab | | Frizzled receptor |
| Vapaliximab | | AOC3 (VAP-1) |
| Vatelizumab | | ITGA2 |
| Vedolizumab | | integrin $\alpha_4\beta_7$ |
| Veltuzumab | | CD20 |
| Vepalimomab | | AOC3 (VAP-1) |
| Vesencumab | | NRP1 |
| Visilizumab | Nuvion | CD3 |
| Volociximab | | integrin $\alpha_5\beta_1$ |
| Vorsetuzumab | | CD70 |
| Votumumab | HumaSPECT | tumor antigen CTAA16.88 |
| Zalutumumab | HuMax-EGFr | EGFR |
| Zanolimumab | HuMax-CD4 | CD4 |
| Zatuximab | | HER1 |
| Ziralimumab | | CD147 (basigin) |
| Zolimomab | | CD5 |

In addition to the above, the antibody of the drug antibody conjugate of the present invention may be Vitaxin which is a humanised antibody for the treatment of sarcoma; Smart IDIO which is a humanised anti-HLA-DR antibody for the treatment of non-Hodgkin's lymphoma; Oncolym which is a radiolabeled murine anti-HLA-DrlO antibody for the treatment of non-Hodgkin's lymphoma; and Allomune which is a humanised anti-CD2 mAb for the treatment of Hodgkin's Disease or non-Hodgkin's lymphoma.

The antibody of the drug conjugate of the present invention may also be any antibody-fragment known for the treatment of any disease, preferably cancer. Again, such antibody fragments are immunospecific for a target antigen and can be obtained commercially or produced by any method known in the art such as, e.g., recombinant expression techniques. Examples of such antibodies available include any from the below table.

TABLE 2

Therapeutic monoclonal antibody fragments

| Fragment type/format | Trade name | Target |
|---|---|---|
| Fab/chimeric | ReoPro (abciximab) | GpIIb/gpIIa |
| Fab/ovine | CroFab | Snake venom |
| Fab/ovine | DigiFab | Digoxin |
| Fab/ovine | Digibind | Digoxin |
| Fab/mouse | CEA-scan (arcitumomab) | CEA |
| Fab/humanised | Lucentis (ranibizumab; Rhu-Fab) | VEGF |
| Fab/humanised | Thromboview | D-dimer |
| Fab/PEGylated humanised | CDP791 | VEGF |
| Fab/PEGylated humanised | CDP870 | TNF-α |
| Fab/bispecific humanised | MDX-H210 | Her2/Neu & CD64 (γFcR1) |
| Single-chain Fv (scFv)/humanized | Pexelizumab | Complement C5 |
| (ScFv)$_4$ fused to streptavidin mouse | CC49 | TAG-72 Pancarcinoma antigen |
| ScFv fused to β-lactamase human | SGN-17 | P97 antigen |
| ScFv fused to PEG human | F5 scFv-PEG Immunoliposome | Her2 |
| Diabody $(V_H-V_L)_2$ human | C6.5K-A | Her2/Neu |
| Diabody $(V_H-V_L)_2$ human | L19 L19-γIFN | EDB domain of fibronectin |
| Diabody $(V_H-V_L)_2$ human | T84.66 | CEA |
| Minibody $(scF_v-C_H3)_2$ murine-human chimera (minibody) | T84.66 | CEA |
| Minibody murine-human chimera (minibody) | 10H8 | Her2 |
| S$_c$F$_v$ dimer Fc (S$_c$F$_v$)$_2$-Fc murine-human chimera (minibody) | T84.66 | CEA |
| Bispecific scFv $(V_L-V_H-V_H-V_L)$ mouse | r28M | CD28 and MAP |
| Bispecific scFv $(V_L-V_H-V_H-V_L)$ origin unknown | BITE MT103 | CD19 and CD3 |
| Bispecific scFv (VL-VH-VH-VL) origin unknown | BITE | Ep-CAM and CD3 |
| Bispecific tandem diabody (VH-VL-VH-VL) (mouse) | Tandab | CD19 & CD3 |
| VhH-β-lactamase fusion camelid | Nanobody | CEA |
| Dab/human | Anti-TNFα dAb | TNFα |
| VhH/camelid | Nanobody | TNFα |
| VhH/camelid | Nanobody | Von Willebrand factor |

(Holliger & Hudson, Nature Biotechnology, 2005, 9, 23).

In preferred embodiments, the antibody in the drug conjugates of the present invention may bind to a receptor encoded by the ErbB gene. The antibody may bind specifically to an ErbB receptor selected from EGFR, HER2, HER3 and HER4. Preferably, the antibody in the drug conjugate may specifically bind to the extracellular domain of the HER2 receptor and inhibit the growth of tumour cells which overexpress the HER2 receptor. The antibody of the drug conjugate may be a monoclonal antibody, e.g. a murine monoclonal antibody, a chimeric antibody, or a humanised antibody. Preferably, the humanised antibody may be huMAb4D5-1, huMAb4D5-2, huMAb4D5-3, huMAb4D5-4, huMAb4D5-5, huMAb4D5-6, huMAb4D5-7 or huMAb4D5-8 (Trastuzumab), particularly preferably Trastuzumab. The antibody may also be an antibody fragment, e.g. a Fab fragment.

Other preferred antibodies include:
(i) anti-CD4 antibodies. The antibody of the drug conjugate may be a monoclonal antibody, e.g. a murine monoclonal antibody, a chimeric antibody, or a humanised antibody;
(ii) anti-CD5 antibodies. The antibody of the drug conjugate may be a monoclonal antibody, e.g. a murine monoclonal antibody, a chimeric antibody, or a humanised antibody;
(iii) anti-CD13 antibodies. The antibody of the drug conjugate may be a monoclonal antibody, e.g. a murine monoclonal antibody, a chimeric antibody, or a humanised antibody; and
(iv) anti-CD20 antibodies. The antibody of the drug conjugate may be a monoclonal antibody, e.g. a murine monoclonal antibody, a chimeric antibody, or a humanised antibody. Preferably, the humanised antibody is Rituximab or an antibody fragment thereof, e.g. a Fab fragment Attachment to the moiety such as an antibody is typically by one of three routes: via free thiol groups in cysteines after partial reduction of disulfide groups in the antibody; via free amino groups in lysines in the antibody; and via free hydroxyl groups in serines and/or threonines in the antibody. The attachment method varies depending upon the site of attachment on the moiety such as an antibody. Purification of antibody-drug conjugates by size exclusion chromatography (SEC) has also been described [see, e.g., Liu et al., Proc. Natl. Acad. Set (USA), 93: 8618-8623 (1996), and Chari et al., Cancer Research, 52: 127-131 (1992)].

As previously noted, the drug payloads of the drug conjugates of the present invention are dihydropyran-2-one and tetrahydropyran-2-one derivatives that have been disclosed or fall within the scope of International publications nos. WO-A-2007/144423 and WO-A-2009/080761, the contents of which are incorporated herein by reference thereto. These compounds are synthesised according to the processes described and exemplified in these international applications.

As noted earlier, in the ninth aspect of the present invention there is provided a process for the preparation of a drug conjugate according to the first aspect of the present invention comprising conjugating a moiety Ab comprising at least one antigen binding site and a drug D of formula (I), (Ia) or (Ib), Ab and D being as defined in the first aspect of the present invention.

One example of a process for the preparation of a drug conjugate of the present invention involves the preparation of drug antibody conjugates of formula (G) or (H) of the present invention as follows:

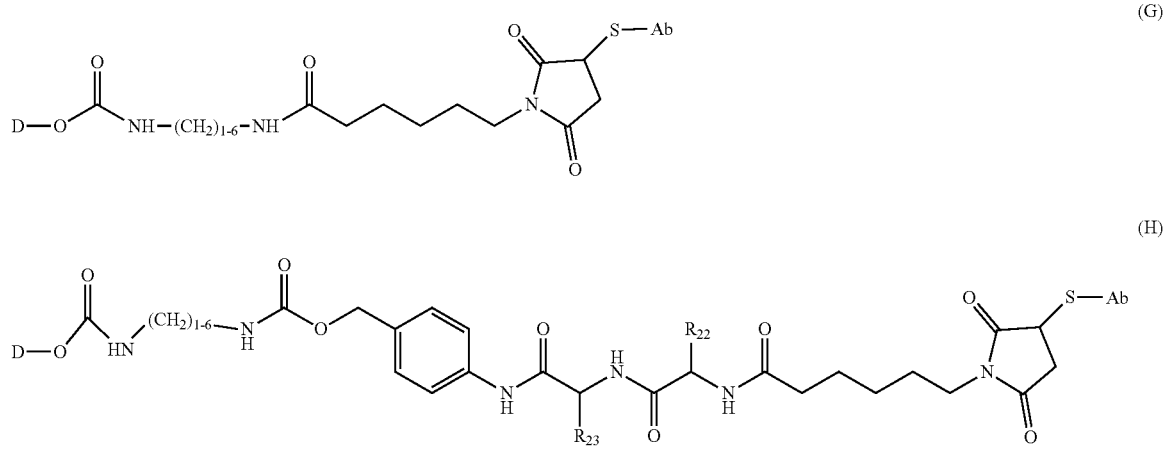

Processes for the Preparation of the Drug Antibody Conjugates

The drug antibody conjugates of the present invention can be prepared according to techniques that are well known in the art. Processes for conjugating moieties comprising at least one antigen binding site antibodies such as antibodies to a number of different drugs using different processes have been described and exemplified previously in, for example, WO-A-2004/0 10957, WO-A-2006/060533 and WO-A-2007/024536, the contents of which are incorporated herein by reference thereto. These involve use of a linker group that derivatises the drug, toxin or radionuclide in such a way that it can then be attached to the moiety such as an antibody.

said process comprising the following steps:
(i) reacting a drug (D) of formula (Ia)-H:

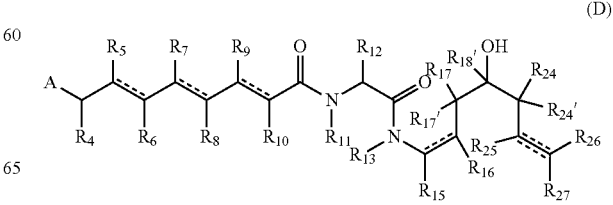

wherein the substituents in the definitions of (Ia) are as defined above, with a compound of formula X$_2$—C(O)-X$_1$ wherein x$_1$ and X$_2$ are leaving groups to give a compound of formula (B):

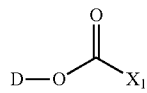
(B)

and the point of attachment of the —(C=O)X$_1$ moiety is the free hydroxyl group attached to the same carbon as R$_{18}$'.

(ii) reacting the compound of formula (B) produced in step (i) with a diamine of formula H$_2$N—(CH2)i-6N H2 to give a compound of formula (C):

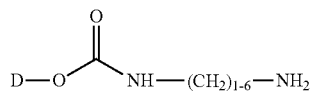
(C)

(iii) either reacting the compound of formula (C) produced in step (ii) with a compound of formula (D'):

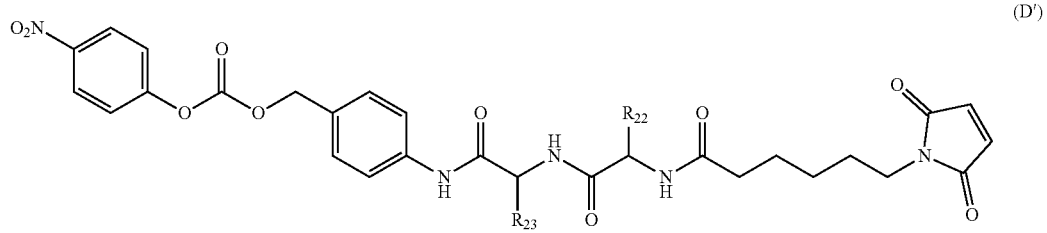
(D')

to give a compound of formula (F):

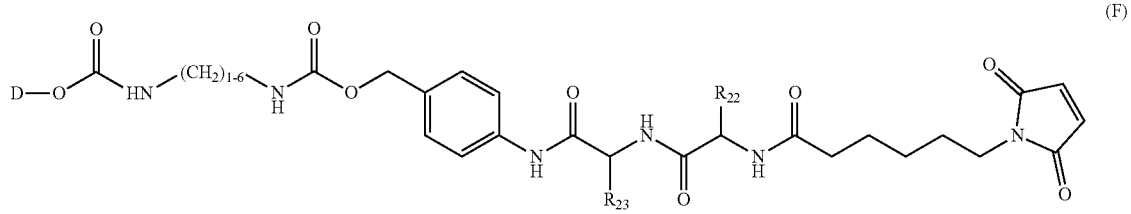
(F)

reacting the compound (C) produced in step (ii) with 6-maleimidohexanoic acid /V-hydroxysuccinimide ester to give (E):

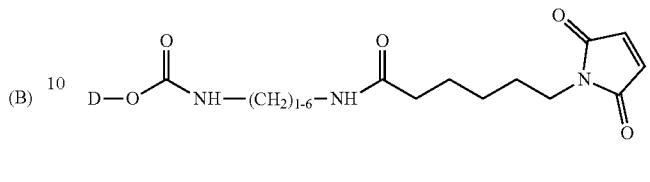
(E)

(iv) partial reduction of one or more disulfide bonds in the antibody to be conjugated to give a reduced antibody Ab-SH having free thiol groups:

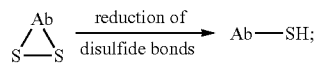

and (v) reaction of the partially reduced antibody Ab-SH having free thiol groups with the compound of formula (E) or (F) produced in step (iv) to give the desired drug antibody conjugate of formula (G) or (H) respectively:

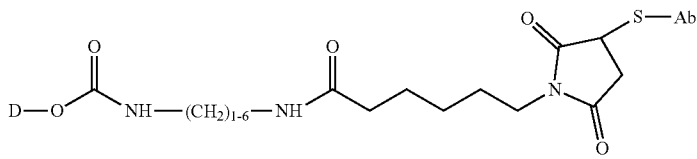

(G)

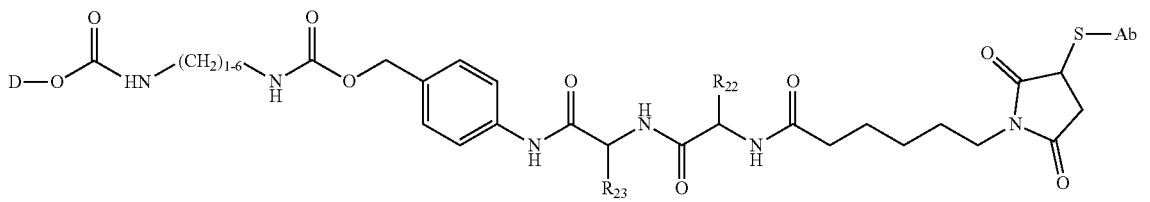

(H)

Preferably, the compound of formula $X_2$—C(0)-Xi reacted with drug (A) in step (i) is 1,1'carbonyldiimidazole.

Preferably, the diamine in step (ii) has the formula N H2-$(CH_2)_{2-4}$-N H2, and more preferably it is propylene-1,3-diamine.

In one preferred embodiment of this process, intermediate (C) is reacted with a compound of formula (D') wherein $R_2$3 is —$(CH_2)_3$-NH—CO—N H2 and R22 is isopropyl.

In another preferred embodiment of this process, the antibody is selected from Trastuzumab, Rituximab, an anti-CD4 antibody, an anti-CD5 antibody and an anti-CD13 antibody or an immunologically active portion thereof, or it is selected from Trastuzumab, Rituximab and an anti-CD4 antibody, or an immunologically active portion thereof, and most preferably it is Trastuzumab or an immunologically active portion thereof; or it is selected from an anti-CD5 antibody and an anti-CD13 antibody, or an immunologically active portion thereof, and most preferably it is an anti-CD13 antibody or an immunologically active portion thereof. Furthermore, the partial reduction of this monoclonal antibody is performed using tris[2-carboxyethyl]phosphine hydrochloride (TCEP).

Another example of a process for the preparation of a drug antibody conjugate of the present invention, involves the preparation of drug antibody conjugates of formula (O) or (P) as follows

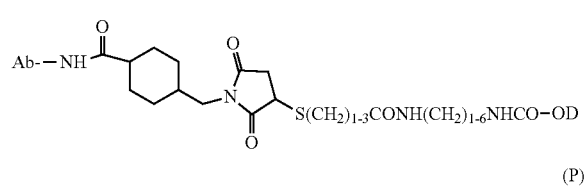

(O)

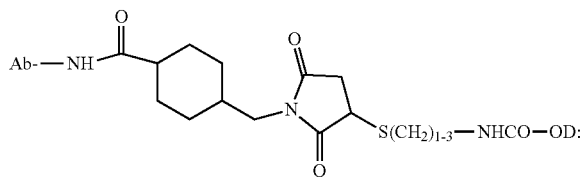

(P)

said process comprising the following steps:
(i) either:
reacting a drug (D) of formula (Ia)-H:

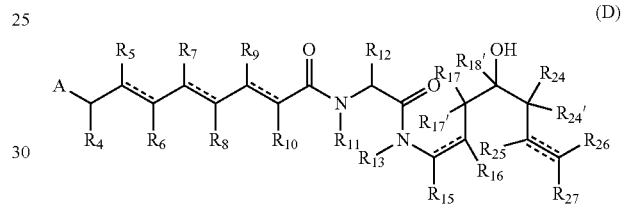

(D)

wherein the substituents in the definitions of (Ia)-H are as defined above, with a compound of formula $X_2$—C(0)-Xi wherein $X_1$ and X2 are leaving groups to give a compound of formula (B):

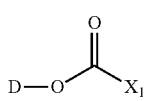

(B)

and the point of attachment of the X-i(CO) moiety is the free hydroxyl group attached to the same carbon atom as $R_{18'}$, or
(b) reacting said drug (A) of formula (Ia)-H as defined above with 4-nitro-phenylchloroformate to give a compound of formula (J):

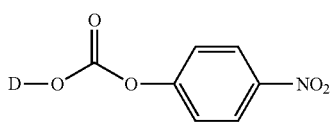

(J)

and the point of attachment of the (4-nitrophenyl)-0-CO— group is the same as that for the Xi(CO) moiety in (a) above;
(ii) either:
(c) reacting the compound of formula (B) produced in step (i) with a diamine of formula $H_2N$—(CH2)i-6N H2 to give a compound of formula (C):

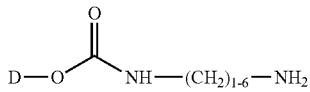

and then reacting the resulting compound of formula (C) with a compound of formula Me-S—S—(CH2)$_{1-3}$-CO$_2$H to give a compound of formula (K)

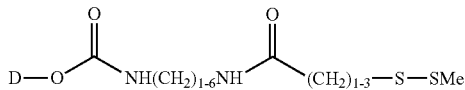

(K)

or (d) reacting the compound (J) produced in step (i) with an aminoalkylthio compound of formula H$_2$N—(CH2)$_{1-3}$SH to give a compound of formula (L):

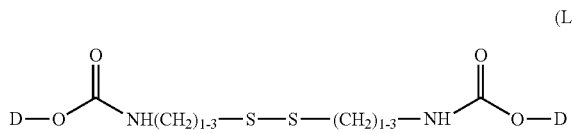

(L)

(iii) reacting (K) or (L) produced in step (ii) with dithiothreitol under disulfide reducing conditions to give compounds of formula (M) and (N) respectively:

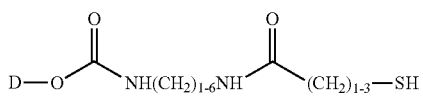

(M)

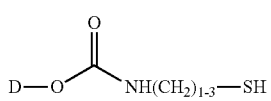

(N)

(iv) reacting the antibody to be conjugated with succininimidyl-4-(/V-maleimidomethyl)cyclohexane-1-carboxylate to derivatise said antibody at one or more lysine groups with a succininimidyl-4-(N-maleimidomethyl)cyclohexane-1-carbonyl group:

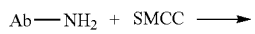

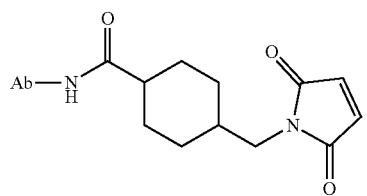

(v) reacting the derivatised antibody produced in step (iv) with either (M) or (N) produced in step (iii) to give the desired drug antibody conjugate of formula (O) or (P):

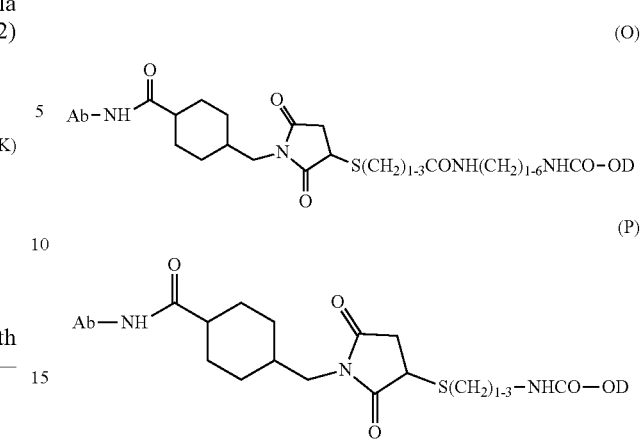

(O)

(P)

As for the earlier process, the compound of formula X$_2$—C(0)-Xi is preferably 1,1'-carbonyldiimidazole. Similarly, the diamine compound of formula (B) is preferably NH2-(CH$_2$)2-4-N H2, and more preferably propylene-1,3-diamine.

In one preferred embodiment of this invention, the compound reacted with the compound of formula (C) to give the compound of formula (K) is 3-(methyldisulfanyl)propanoic acid.

In another preferred embodiment, the aminoalkylthio compound that is reacted with a compound of formula (J) to give a compound of formula (L) is 3-aminopropane-1-thiol.

Where attachment to the drug linker moiety is via free thiol groups in cysteines after partial reduction of disulfide groups in the moiety comprising at least one antigen binding site such as a monoclonal antibody, the partial reduction is typically conducted by first diluting to a suitable concentration and buffering the solution before partial reduction of the disulfide bonds by means of the addition of a suitable reducing agent such as tris[2-carboxyethyl]phosphine hydrochloride (TCEP) or dithiothreitol (DTT). By choosing appropriate ratios of the moiety to be reduced such as a monoclonal antibody and the reducing agent, the reaction conditions and the time of the reduction it is possible to obtain a desired free thiol to moiety ratio, e.g. four free thiol groups per monoclonal antibody.

The partially reduced moiety such as the partially reduced monaoclonal antibody having the free thiol groups, prepared as described above, is then reacted with drug-linker compounds of the invention of formula D-X-(AA)$_W$-L$_1$ (wherein the group L in such compound is a maleimide group which is free to react with the thiol groups). The resulting drug antibody conjugates are purified by any suitable means known in the art, e.g. by size exclusion chromatography (SEC) [see, e.g., Liu et al., Proc. Natl. Acad. Set (USA), 93: 8618-8623 (1996), and Chari et al., Cancer Research, 52: 127-131 (1992)].

In one preferred embodiment of this invention, the partially reduced monoclonal antibody is Trastuzumab or an anti-CD13 antibody or an immunologically active portion thereof, preferably Trastuzumab or an immunologically active portion thereof; or preferably an anti-CD13 antibody or an immunologically active portion thereof.

In an alternative embodiment of the invention, lysines in the moiety comprising at least one antigen binding site such as a monoclonal antibody can first be reacted with succinimidyl-4-(/V-maleimidomethyl)cyclohexane-1-carboxylate.

A free amine group on an antibody can react with the N-hydroxysuccinimide ester to give a maleimide-activated antibody:

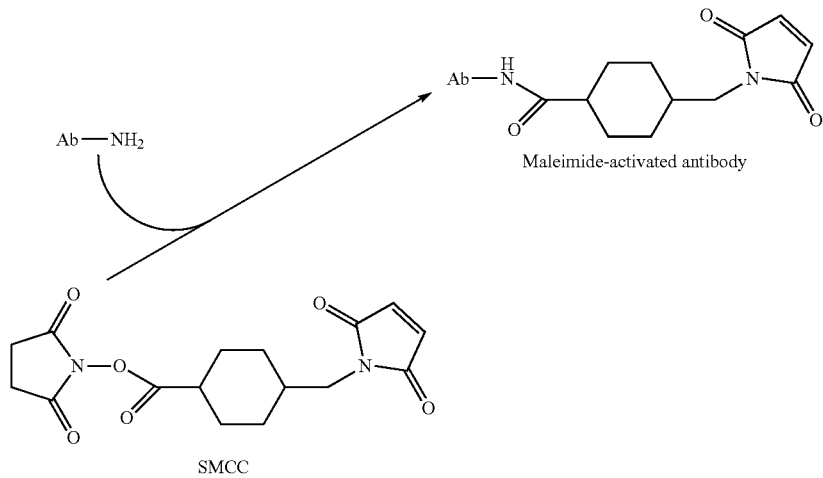

The maleimide-activated antibody can then be reacted with a compound of formula D-X-(AA)$_w$-H having a reactive thiol moiety.

Two specific examples of processes for the preparation of drug antibody conjugates of formula [D-(X)$_b$-(AA)$_w$-(L)-]$_n$-Ab of the present invention by conjugation via free thiol groups in cysteines after partial reduction of disulfide groups in the antibody and via free amino groups in lysines in the antibody following activation with a maleimide group are shown in FIGS. 1 and 2.

Compositions Comprising the Drug Antibody Conjugate of the Invention and Uses Thereof In the fifth aspect of the present invention, there is provided a pharmaceutical composition comprising a drug conjugate according to the present invention and a pharmaceutically acceptable carrier. Examples of the administration form of a drug conjugate having the general formula [D-(X)$_b$-(AAX$_v$-(L)-]$_n$-Ab of the present invention include without limitation oral, topical, parenteral, sublingual, rectal, vaginal, ocular, and intranasal. Parenteral administration includes subcutaneous injections, intravenous, intramuscular, intrasternal injection or infusion techniques. Preferably, the compositions are administered parenterally. Pharmaceutical compositions of the invention can be formulated so as to allow a drug conjugate of the present invention to be bioavailable upon administration of the composition to an animal, preferably human. Compositions can take the form of one or more dosage units, where for example, a tablet can be a single dosage unit, and a container of a drug antibody conjugate of the present invention in aerosol form can hold a plurality of dosage units.

The pharmaceutically acceptable carrier or vehicle can be particulate, so that the compositions are, for example, in tablet or powder form. The carrier(s) can be liquid, with the compositions being, for example, an oral syrup or injectable liquid. In addition, the carrier(s) can be gaseous, so as to provide an aerosol composition useful in, for example, inhalatory administration. The term "carrier" refers to a diluent, adjuvant or excipient, with which a drug antibody conjugate of the present invention is administered. Such pharmaceutical carriers can be liquids, such as water and oils, including those of petroleum, animal, vegetable or synthetic origin, such as peanut oil, soybean oil, mineral oil, sesame oil and the like. The carriers can be saline, gum acacia, gelatin, starch paste, talc, keratin, colloidal silica, urea, and the like. In addition, auxiliary, stabilizing, thickening, lubricating and coloring agents can be used. In one embodiment, when administered to an animal, the drug antibody conjugates of the present invention or compositions and pharmaceutically acceptable carriers are sterile. Water is a preferred carrier when the drug antibody conjugates of the present invention are administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

When intended for oral administration, the composition is preferably in solid or liquid form, where semi-solid, semi-liquid, suspension and gel forms are included within the forms considered herein as either solid or liquid.

As a solid composition for oral administration, the composition can be formulated into a powder, granule, compressed tablet, pill, capsule, chewing gum, wafer or the like form. Such a solid composition typically contains one or more inert diluents. In addition, one or more of the following can be present: binders such as carboxymethylcellulose, ethyl cellulose, microcrystalline cellulose, or gelatin; excipients such as starch, lactose or dextrins, disintegrating agents such as alginic acid, sodium alginate, corn starch and the like; lubricants such as magnesium stearate; glidants such as colloidal silicon dioxide; sweetening agents such as sucrose or saccharin; a flavoring agent such as peppermint, methyl salicylate or orange flavoring; and a coloring agent.

When the composition is in the form of a capsule (e.g. a gelatin capsule), it can contain, in addition to materials of the above type, a liquid carrier such as polyethylene glycol, cyclodextrin or a fatty oil.

The composition can be in the form of a liquid, e.g. an elixir, syrup, solution, emulsion or suspension. The liquid can be useful for oral administration or for delivery by injection. When intended for oral administration, a composition can comprise one or more of a sweetening agent, preservatives, dye/colorant and flavor enhancer. In a composition for administration by injection, one or more of a surfactant, preservative, wetting agent, dispersing agent, suspending agent, buffer, stabilizer and isotonic agent can also be included.

The preferred route of administration is parenteral administration including, but not limited to, intradermal, intramuscular, intraperitoneal, intravenous, subcutaneous, intranasal, epidural, intranasal, intracerebral, intraventricular, intrathecal, intravaginal or transdermal. The preferred mode of administration is left to the discretion of the practitioner, and will depend in part upon the site of the medical condition (such as the site of cancer). In a more preferred embodiment, the present drug antibody conjugates of the present invention are administered intravenously.

The liquid compositions of the invention, whether they are solutions, suspensions or other like form, can also include one or more of the following: sterile diluents such as water for injection, saline solution, preferably physiological saline, Ringer's solution, isotonic sodium chloride, fixed oils such as synthetic mono or digylcerides, polyethylene glycols, glycerin, or other solvents; antibacterial agents such as benzyl alcohol or methyl paraben; and agents for the adjustment of tonicity such as sodium chloride or dextrose. A parenteral composition can be enclosed in an ampoule, a disposable syringe or a multiple-dose vial made of glass, plastic or other material. Physiological saline is a preferred adjuvant.

The amount of the drug conjugate of the present invention that is effective in the treatment of a particular disorder or condition will depend on the nature of the disorder or condition, and can be determined by standard clinical techniques. In addition, in vitro or in vivo assays can optionally be employed to help identify optimal dosage ranges. The precise dose to be employed in the compositions will also depend on the route of administration, and the seriousness of the disease or disorder, and should be decided according to the judgment of the practitioner and each patient's circumstances.

The compositions comprise an effective amount of a drug conjugate of the present invention such that a suitable dosage will be obtained. The correct dosage of the compounds will vary according to the particular formulation, the mode of application, and its particular site, host and the disease being treated, e.g. cancer and, if so, what type of tumor. Other factors like age, body weight, sex, diet, time of administration, rate of excretion, condition of the host, drug combinations, reaction sensitivities and severity of the disease shall be taken into account. Administration can be carried out continuously or periodically within the maximum tolerated dose.

Typically, this amount is at least about 0.01% of a drug conjugate of the present invention by weight of the composition. When intended for oral administration, this amount can be varied to range from about 0.1% to about 80% by weight of the composition. Preferred oral compositions can comprise from about 4% to about 50% of the drug conjugate of the present invention by weight of the composition.

Preferred compositions of the present invention are prepared so that a parenteral dosage unit contains from about 0.01% to about 2% by weight of the drug conjugate of the present invention.

For intravenous administration, the composition can comprise from about typically about 0.1 mg/kg to about 250 mg/kg of the animal's body weight, preferably, between about 0.1 mg/kg and about 20 mg/kg of the animal's body weight, and more preferably about 1 mg/kg to about 10 mg/kg of the animal's body weight.

The drug conjugate of the present invention or compositions can be administered by any convenient route, for example by infusion or bolus injection, by absorption through epithelial or mucocutaneous linings.

In specific embodiments, it can be desirable to administer one or more drug conjugates of the present invention or compositions locally to the area in need of treatment. In one embodiment, administration can be by direct injection at the site (or former site) of a cancer, tumor or neoplastic or pre-neoplastic tissue. In another embodiment, administration can be by direct injection at the site (or former site) of a manifestation of an autoimmune disease.

Pulmonary administration can also be employed, e.g. by use of an inhaler or nebulizer, and formulation with an aerosolizing agent, or via perfusion in a fluorocarbon or synthetic pulmonary surfactant. In certain embodiments, the drug antibody conjugate of the present invention or compositions can be formulated as a suppository, with traditional binders and carriers such as triglycerides.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. Other examples of suitable pharmaceutical carriers are described in "Remington's Pharmaceutical Sciences" by E. W. Martin.

The pharmaceutical compositions can be prepared using methodology well known in the pharmaceutical art. For example, a composition intended to be administered by injection can be prepared by combining a drug conjugate of the present invention with water so as to form a solution. A surfactant can be added to facilitate the formation of a homogeneous solution or suspension.

We have found that the drug conjugates and compositions of the present invention are particularly effective in the treatment of cancer.

Thus, as described earlier, the sixth aspect of the present invention provides a method of treating a patient in need thereof, notably a human, affected by cancer which comprises administering to the affected individual a therapeutically effective amount of a drug conjugate or a composition of the present invention. The fourth aspect of the present invention provides a drug conjugate according to the first aspect of the present invention for use in the treatment of cancer, and more preferably a cancer selected from lung cancer, colorectal cancer, breast cancer, pancreas carcinoma, kidney cancer, leukaemia, multiple myeloma and lymphoma.

The drug conjugates and compositions of the present invention are useful for inhibiting the multiplication of a tumor cell or cancer cell, or for treating cancer in an animal. The drug conjugates and compositions of the present invention can be used accordingly in a variety of settings for the treatment of animal cancers. The conjugates of the invention comprising Drug-Linker-Moiety comprising at least one antigen binding site can be used to deliver a Drug or Drug unit to a tumor cell or cancer cell. Without being bound by theory, in one embodiment, the Moiety comprising at least one antigen binding site of a drug conjugate of the present invention binds to or associates with a cancer-cell or a tumor-cell-associated antigen, and the drug conjugate of the present invention can be taken up inside a tumor cell or cancer cell through receptor-mediated endocytosis. The antigen can be attached to a tumor cell or cancer cell or can be an extracellular matrix protein associated with the tumor cell or cancer cell. Once inside the cell, one or more specific sequences within the Linker unit are hydrolytically cleaved by one or more tumor-cell or cancer-cell-associated proteases or hydrolases, resulting in release of a Drug or a Drug-Linker Compound. The released Drug or Drug-Linker Compound is then free to migrate in the cell and induce cytotoxic activities. In an alternative embodiment, the Drug or Drug unit is cleaved from the drug conjugate of the present invention outside the tumor cell or cancer cell, and the Drug or Drug-Linker Compound subsequently penetrates the cell.

In one embodiment, the Moiety comprising at least one antigen binding site binds to the tumor cell or cancer cell. In another embodiment, the Moiety comprising at least one antigen binding site binds to a tumor cell or cancer cell antigen which is on the surface of the tumor cell or cancer cell. In yet another embodiment, the Moiety comprising at least one antigen binding site binds to a tumor cell or cancer cell antigen which is an extracellular matrix protein associated with the tumor cell or cancer cell.

The specificity of the Moiety comprising at least one antigen binding site for a particular tumor cell or cancer cell can be important for determining those tumors or cancers that are most effectively treated. For example, drug conjugates of the present invention having a Trastuzumab unit can be useful for treating antigen positive carcinomas including leukaemias, lung cancer, colon cancer, lymphomas (e.g. Hodgkin's disease, non-Hodgkin's Lymphoma), solid tumors such as, sarcoma and carcinomas, Multiple myeloma, kidney cancer and melanoma. The cancer may preferably be lung cancer, colorectal cancer, breast cancer, pancreas carcinoma, kidney cancer, leukaemia, multiple myeloma, lymphoma or ovarian cancer. For example, drug conjugates of the present invention having a Rituximab unit can be useful for treating CD-20 expressing tumors such as haematological cancers including leukemias and lymphomas. For example, drug conjugates of the present invention having an anti-CD4 antibody unit can be useful for treating CD-4 expressing tumors such as haematological cancers including lymphomas. For example, drug conjugates of the present invention having an anti-CD5 antibody unit can be useful for treating CD-5 expressing tumors such as haematological cancers including leukemias and lymphomas. For example, drug conjugates of the present invention having an anti-CD13 antibody unit can be useful for treating CD-13 expressing tumors such as haematological cancers including leukemias and lymphomas.

Other particular types of cancers that can be treated with drug conjugates of the present invention include, but are not limited to: blood-borne cancers including all forms of leukemia; lymphomas, such as Hodgkin's disease, non-Hodgkin's Lymphoma and Multiple myeloma.

In particular, the drug conjugates and compositions of the present invention show excellent activity in the treatment of cancers such as lung cancer, colorectal cancer, breast cancer, pancreas carcinoma, kidney cancer, leukaemia, multiple myeloma, lymphoma and ovarian cancer.

Drug conjugates and compositions of the present invention provide conjugation specific tumor or cancer targeting, thus reducing general toxicity of these conjugates. The Linker units stabilize the drug antibody conjugates in blood, yet are cleavable by tumor-specific proteases and hydrolases within the cell, liberating a Drug.

The drug conjugates and compositions of the present invention can be administered to an animal that has also undergone surgery as treatment for the cancer. In one embodiment of the present invention, the additional method of treatment is radiation therapy.

In a specific embodiment of the present invention, the drug conjugate or composition of the present invention is administered concurrently with a chemotherapeutic agent or with radiation therapy. In another specific embodiment, the chemotherapeutic agent or radiation therapy is administered prior or subsequent to administration of a drug conjugate or composition of the present invention, preferably at least an hour, five hours, 12 hours, a day, a week, a month, more preferably several months (e.g. up to three months), prior or subsequent to administration of a drug antibody conjugate or composition of the present invention.

A chemotherapeutic agent can be administered over a series of sessions, any one or a combination of chemotherapeutic agents known in the art can be administered.

With respect to radiation, any radiation therapy protocol can be used depending upon the type of cancer to be treated. For example, but not by way of limitation, x-ray radiation can be administered; in particular, high-energy megavoltage (radiation of greater that 1 MeV energy) can be used for deep tumors, and electron beam and orthovoltage x-ray radiation can be used for skin cancers. Gamma-ray emitting radioisotopes, such as radioactive isotopes of radium, cobalt and other elements, can also be administered.

In the eighth aspect of the present invention, there is provided a kit comprising a therapeutically effective amount of a drug conjugate according to the first aspect of the present invention and a pharmaceutically acceptable carrier.

In one embodiment, the kit according to this aspect is for use in the treatment of cancer, and more preferably a cancer selected from lung cancer, colorectal cancer, breast cancer, pancreas carcinoma, kidney cancer, leukaemia, multiple myeloma, lymphoma and ovarian cancer.

BRIEF DESCRIPTION OF THE DRAWINGS

The invention is diagrammatically illustrated, byway of example, in the accompanying drawings in which.

EXAMPLES

Figure 1:
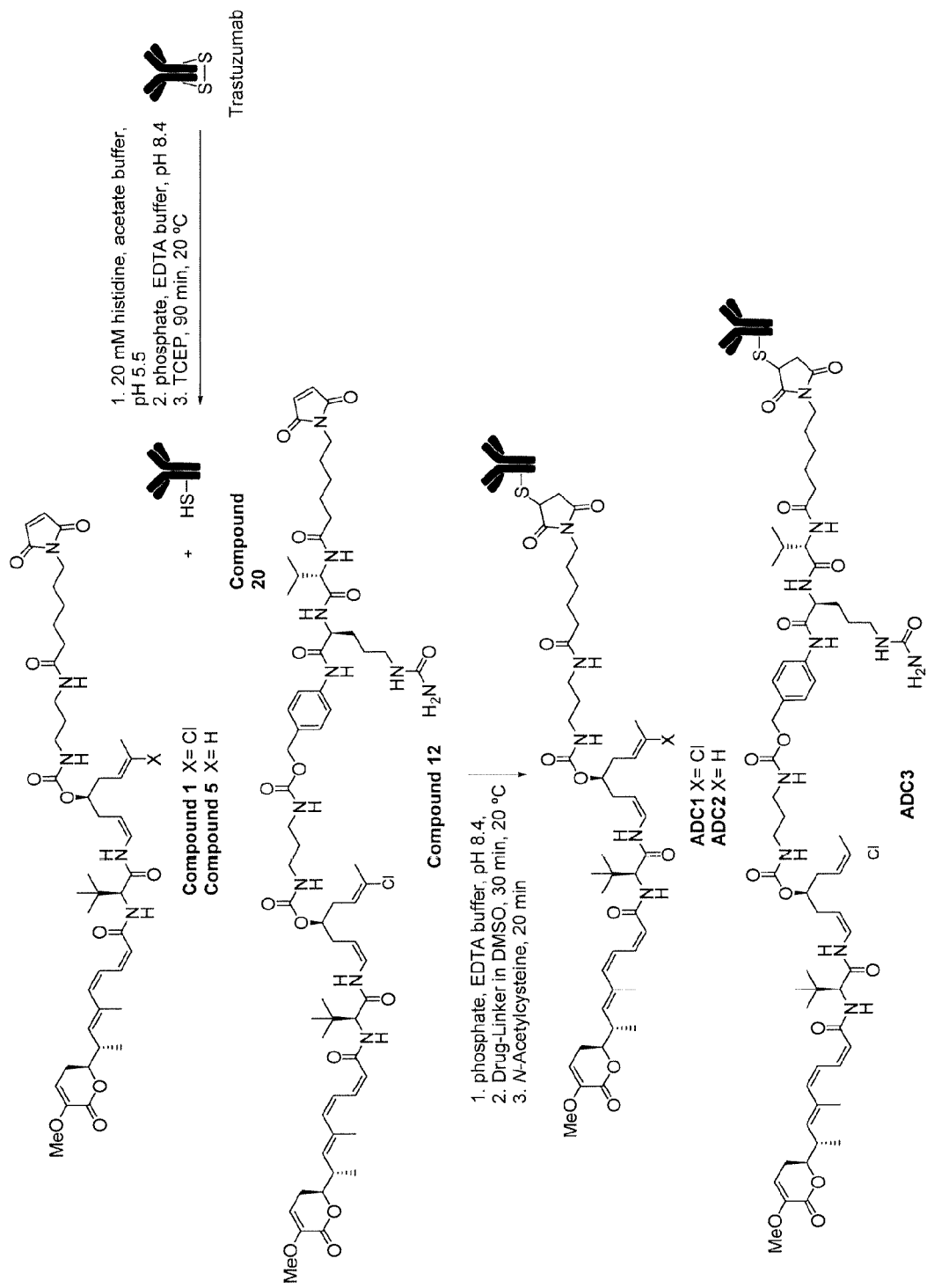
FIG. 1 is a schematic illustration of one process according to the present invention wherein conjugation to the antibody is via free thiol groups.
Figure 2:
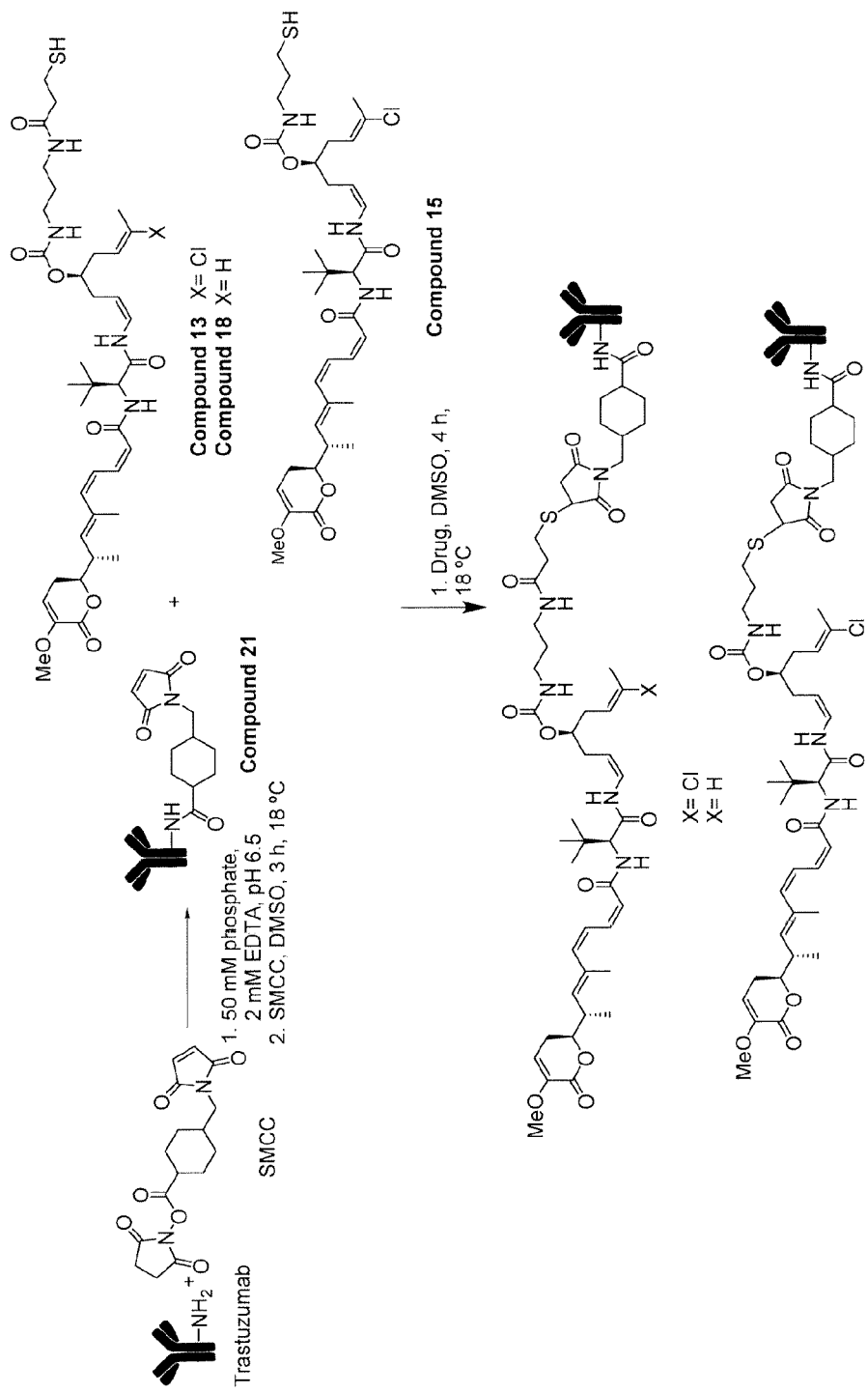
FIG. 2 is a schematic illustration of another process according to the present invention wherein conjugation to the antibody is via free lysine groups.

The present invention is further illustrated by way of the following, non-limiting examples. In the examples, the following abbreviations are used:
CDI, 1,1'-carbonyldiimidazole
DIPEA, diisopropylethylamine
Hex, hexane
EtOAc, ethyl acetate
DCM, dichloromethane
NMP, /V-methyl-2-pyrrolidone
DMF, dimethylformamide
EDC, /V-(3-dimethylaminopropyl)-/V-ethylcarbodiimide hydrochloride
EDTA, ethylenediaminetetraacetic acid
MeOH, methanol
DTT, dithiothreitol
Py, pyridine
THF, tetrahydrofuran
TCEP, Tris[2-carboxyethyl]phosphine hydrochloride
MC, 6-maleimidocaproyl
Fmoc, 9-fluorenylmethoxycarbonyl
Cit, citrulline
Val, valine
DMSO, dimethylsulfoxide
Trt, triphenylmethyl
HOBt, 1-hydroxybenzotriazole
DIPCDI, N,N'-diisopropylcarbodiimide
TFA, trifluoroacetic acid
PABOH, 4-aminobenzyl alcohol
bis-PNP, bis(4-nitrophenyl) carbonate
NAC, /V-Acetylcysteine
SEC, size-exclusion chromatography
HPLC, high performance liquid chromatography
ADC, antibody drug conjugate
ATCC, American Type Culture Collection
DMEM, Dulbecco's Modified Eagle's Medium
RPMI, Rosmell Park Memorial Institute medium
ITS, Insulin-transferrin-sodium selenite media supplement
FCS, Fetal Calf Serum
SRB, sulforhodamine B
PBS, phosphate buffered saline
DR, dose-response
UV, ultraviolet
SMCC, Succinimidyl-4-(/V-maleimidomethyl)cyclohexane-1-carboxylate
LAR, Linker to Antibody Ratio Preparative Example Preparation of Compound 9:
MC-Val-Cit-PABC-PNP

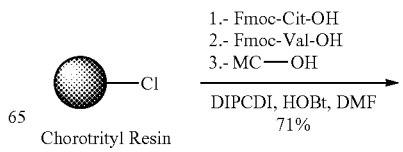

Reaction Scheme

1.- Fmoc-Cit-OH
2.- Fmoc-Val-OH
3.- MC—OH

DIPCDI, HOBt, DMF
71%

Chorotrityl Resin —Cl

-continued

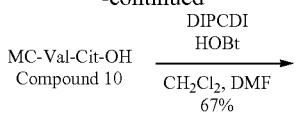

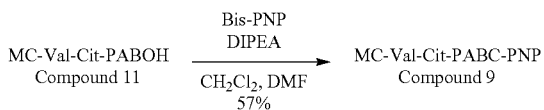

(a) Preparation of Compound 10: MC-Val-Cit-OH

Compound 10

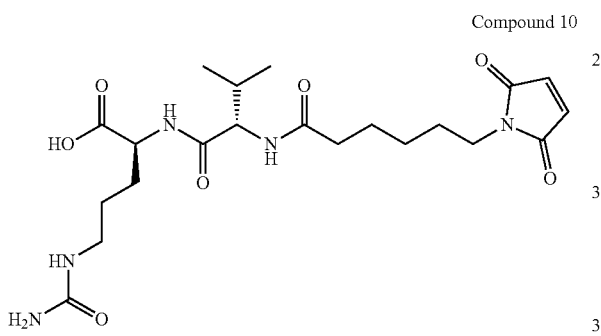

Cl-TrtCl-resin (20 g, 1.49 mmol/g) (Iris Biotech, Ref.: BR-1065, 2-Chlorotrityl chloride resin (200-400 mesh, 1% DVB, 1.0-1.6 mmol/g), CAS 42074-68-0) was placed in a filter plate. 100 mL of DCM was added to the resin and the mixture was stirred for 1 h. The solvent was eliminated by filtration under vacuum. A solution of Fmoc-Cit-OH (11.83 g, 29.78 mmol) and DIPEA (17.15 mL, 98.45 mmol) in DCM (80 mL) was added and the mixture was stirred for 10 min. After that DIPEA (34.82 mmol, 199.98 mmol) was added and the mixture was stirred for 1 h. The reaction was terminated by addition of MeOH (30 mL) after stirring for 15 minutes. The Fmoc-Cit-O-TrtCl-resin produced as a result was subjected to the following washing/treatments: DCM (5×50 mL×0.5 min), DMF (5×50 mL×0.5 min), piperidine:DMF (1:4, 1×1 min, 2×10 min), DMF (5×50 mL×0.5 min), DCM (5×50 mL×0.5 min). The final piperidine wash gave NH$_2$-Cit-O-TrtCl-resin. The loading was calculated: 1.15 mmol/g.

The NH$_2$-Cit-O-TrtCl-resin produced above was washed with DMF (5×50 mL×0.5 min) and a solution of Fmoc-Val-OH (31.22 g, 91.98 mmol), HOBt (11.23 g, 91.98 mmol) in DMF (100 mL) was added to the NH$_2$-Cit-O-TrtCl-resin, stirred and DIPCDI (14.24 mL, 91.98 mmol) was added and the mixture was stirred for 1.5 h. The reaction was terminated by washing with DMF (5×50 mL×0.5 min). The Fmoc-Val-Cit-O-TrtCl-resin thus produced was treated with piperidine:DMF (1:4, 1×1 min, 2×10 min) and washed with DMF (5×50 mL×0.5 min). The final piperidine wash gave NH$_2$-Val-Cit-O-TrtCl-resin.

A solution of 6-maleimidocaproic acid (MC-OH) (9.7 g, 45.92 mmol), HOBt (6.21 g, 45.92 mmol) in DMF (100 mL) was added to the NH$_2$—Val-Cit-0-TrtCl-resin produced above, stirred and DIPCDI (7.12 mL, 45.92 mmol) was added and the mixture was stirred for 1.5 h. The reaction was terminated by washing with DMF (5×50 mL×0.5 min) and DCM (5×50 mL×0.5 min).

The peptide was cleaved from the resin by treatments with TFA:DCM (1:99, 5×100 mL). The resin was washed with DCM (7×50 mL×0.5 min). The combined filtrates were evaporated to dryness under reduced pressure and the solid obtained was triturated with Et$_2$O and filtrated to obtain Compound 10 (7.60 g, 71%) as a white solid.

$^1$H NMR (500 MHz, DMSO-d$_6$): δ 12.47 (s, 1H), 8.13 (d, J=7.3 Hz, 1H), 7.74 (d, J=9.0 Hz, 1H), 6.99 (s, 2H), 5.93 (s, 1H), 5.35 (s, 2H), 4.20 (dd, J=9.0, 6.8 Hz, 1H), 4.15-4.07 (m, 1H), 3.36 (t, J=7.0 Hz, 2H), 3.00-2.88 (m, 2H), 2.21-2.12 (m, 1H), 2.11-2.03 (m, 1H), 1.98-1.86 (m, 1H), 1.74-1.62 (m, 1H), 1.61-1.50 (m, 1H), 1.50-1.31 (m, 6H), 1.21-1.11 (m, 2H), 0.84 (d, J=6.8 Hz, 3H), 0.80 (d, J=6.8 Hz, 3H).

ESI-MS m/z: Calcd. for C$_{21}$H$_{33}$N$_5$O$_7$: 467.2. Found: 468.3 (M+H)$^+$.

(b) Preparation of Compound 11: MC-Val-Cit-PABOH

Compound 11

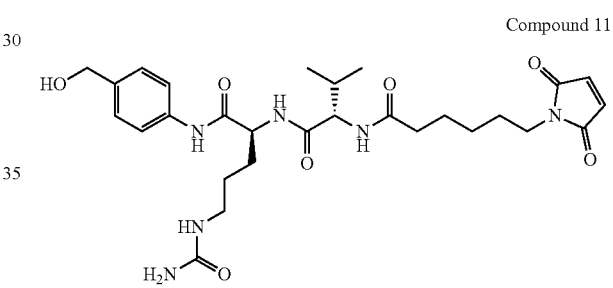

To a solution of Compound 10 (1.6 g, 3.42 mmol) and 4-aminobenzyl alcohol (PABOH) (0.84 g, 6.84 mmol) in DCM (60 mL) was added a solution of HOBt (0.92 g, 6.84 mmol) in DMF (5 mL). DIPCDI (1.05 mL, 6.84 mmol) was added, the reaction mixture was stirred for 2 h at 23° C., Et$_2$O (150 mL) was added, and the solid obtained was filtrated in a filter plate under vacuum to obtain Compound 11 (1.31 g, 67%).

$^1$H NMR (500 MHz, DMSO-d$_6$): δ 9.88 (s, 1H), 8.03 (d, J=7.6 Hz, 1H), 7.77 (dd, J=12.2, 8.5 Hz, 1H), 7.53 (d, J=8.2 Hz, 2H), 7.21 (d, J=8.2 Hz, 2H), 6.99 (s, 3H), 6.01-5.92 (m, 1H), 5.39 (s, 2H), 5.07 (s, 1H), 4.41 (s, 2H), 4.39-4.31 (m, 1H), 4.23-4.12 (m, 1H), 3.36 (t, J=7.0 Hz, 2H), 3.06-2.97 (m, 1H), 2.96-2.90 (m, 1H), 2.22-2.03 (m, 2H), 2.01-1.88 (m, 1H), 1.76-1.62 (m, 1H), 1.63-1.28 (m, 6H), 1.25-1.11 (m, 2H), 0.84 (d, J=6.9 Hz, 3H), 0.81 (d, J=6.8 Hz, 3H).

ESI-MS m/z: Calcd. for C$_{28}$H$_{40}$N$_6$O$_7$: 572.3. Found: 573.3 (M+H)$^+$.

(c) Preparation of Compound 9:
MC-Val-Cit-PAB-PNP

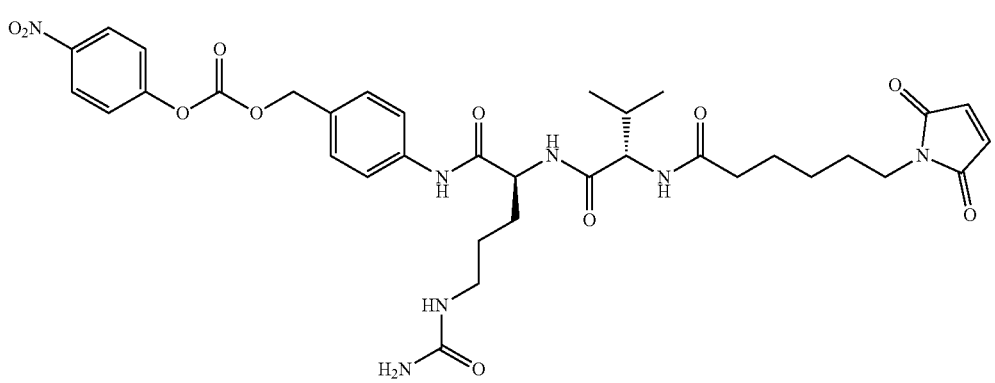

Compound 9

To a solution of Compound 11 (500 mg, 0.87 mmol) and bis(4-nitrophenyl) carbonate (bis-PNP) (2.64 g, 8.72 mmol) in DCM:DMF (8:2, 25 mL) was added DIPEA (0.45 mL, 2.61 mmol). The reaction mixture was stirred for 20 h at 23° C. and poured onto a silica gel column (DCM:CH$_3$OH, from 50:1 to 10:1) to afford pure target Compound 9 (364 mg, 57%).

$R_f$=0.40 (CH$_2$Cl$_2$:CH$_3$OH, 9:1).

$^1$H NMR (400 MHz, CDCl$_3$/CD$_3$OD): δ 9.45 (s, 1H), 8.23 (d, J=8.3 Hz, 2H), 7.59 (d, J=8.5 Hz, 2H), 7.35 (d, J=8.3 Hz, 2H), 7.34 (d, J=8.5 Hz, 2H), 6.65 (s, 2H), 5.20 (s, 2H), 4.56 (dt, J=10.5, 5.4 Hz, 1H), 4.15 (d, J=7.2 Hz, 1H), 3.46 (dd, J=8.0, 6.4 Hz, 2H), 3.16-2.89 (m, 2H), 2.21 (dd, J=8.3, 6.6 Hz, 2H), 2.06-1.97 (m, 1H), 1.90-1.83 (m, 1H), 1.73-1.46 (m, 7H), 1.34-1.20 (m, 2H), 0.91 (d, J=6.7 Hz, 3H), 0.90 (d, J=6.7 Hz, 3H).

$^{13}$C NMR (125 MHz, CDCl$_3$/CD$_3$OD) δ 174.4, 172.4, 171.1, 170.6, 160.5, 155.5, 152.5, 145.3, 138.7, 134.1, 129.9, 129.5, 125.2, 121.8, 120.0, 70.6, 59.0, 53.2, 37.5, 35.8, 30.6, 29.6, 29.3, 28.1, 26.2, 26.2, 25.1, 19.1, 18.1.

ESI-MS m/z: Calcd. for C$_{35}$H$^{\wedge}$N$_7$O$^{\wedge}$: 737.3. Found: 738.3 (M+H)$^+$.

Example 1

Preparation of Compound 1

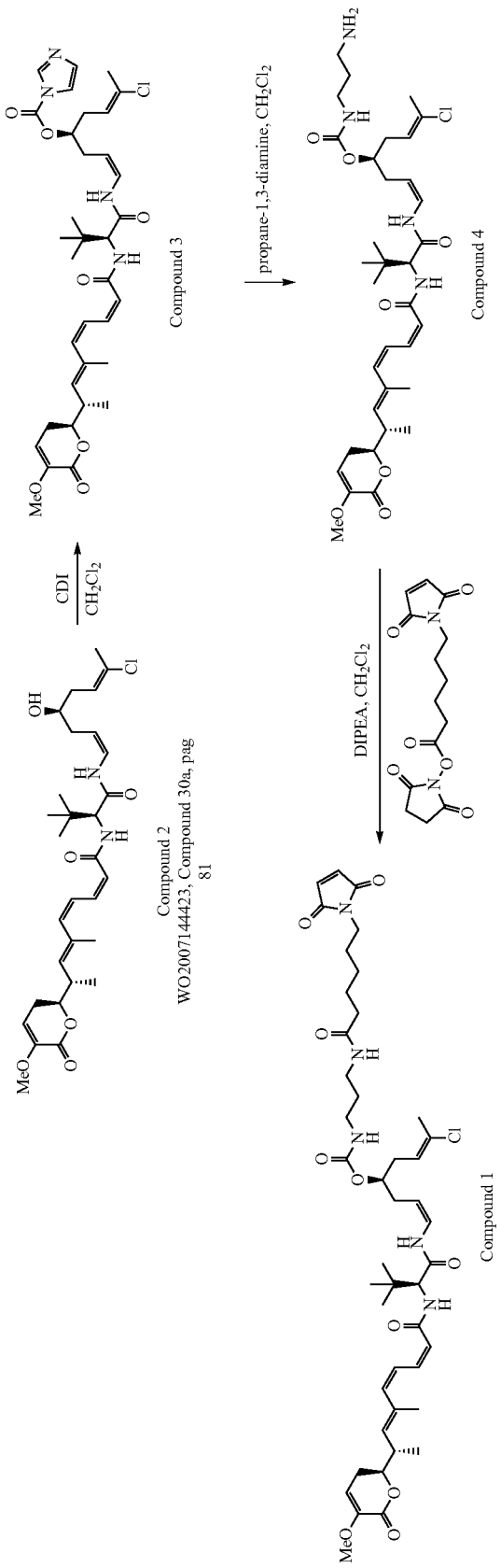

(a) Preparation of Compound 3

To a solution of Compound 2 (Compound 30a, prepared as described in WO 2007144423, the contents of which are incorporated herein by reference) (1.014 g, 1.8 mmol) in DCM (45 mL) was added 1,1'-carbonyldiimidazole (876 mg, 5.4 mmol). After being stirred at 23° C. overnight, the reaction mixture was concentrated under vacuum. The residue obtained was purified in a system for flash chromatography (SiO$_2$, Hex:EtOAc mixtures, from 99:1 to 85:15) to yield pure Compound 3 (1.176 g, 86%).

$^1$H NMR (500 MHz, CDCl$_3$): δ 8.39 (d, J=9.0 Hz, 1H), 8.12 (bs, 1H), 7.40 (bs, 1H), 7.30 (t, J=11.5 Hz, 1H), 7.08 (bs, 1H), 6.91 (t, J=12.0 Hz, 1H), 6.86 (t, J=10.0 Hz, 1H), 6.22 (d, J=9.0 Hz, 1H), 6.18 (d, J=11.0 Hz, 1H), 5.67 (d, J=12.0 Hz, 1H), 5.63-5.61 (m, 2H), 5.28 (d, J=11.5 Hz, 1H), 4.94-4.91 (m, 1H), 4.81-4.76 (m, 1H), 4.42 (d, J=9.0 Hz, 1H), 4.23-4.19 (m, 1H), 3.66 (s, 3H), 2.87-2.82 (m, 1H), 2.58-2.46 (m, 3H), 2.42-2.35 (m, 3H), 2.08 (s, 3H), 1.83 (s, 3H), 1.16 (d, J=6.6 Hz, 3H), 1.06 (s, 9H).

$^{13}$C NMR (125 MHz, CDCl$_3$): δ 168.5, 166.4, 161.5, 148.7, 145.2, 140.4, 137.6, 137.0, 134.4, 133.9, 133.0, 130.9, 124.2, 123.9, 121.0, 120.5, 117.03, 110.0, 108.1, 104.1, 81.7, 77.8, 60.4, 55.4, 37.2, 34.5, 26.6, 26.3, 21.0, 17.1, 16.6.

ESI-MS m/z: Calcd. for C$_3$4H$_4$5ClN4O$_7$: 656.30. Found: 657.3 (M+H)$^+$.

(b) Preparation of Compound 4

To a solution of Compound 3 (1.160 g, 1.78 mmol) in DCM (45 mL), prepared as described in step (a) above, was added propane 1,3-diamine (0.19 mL, 2.22 mmol). The reaction mixture was stirred at 23° C. overnight, and then concentrated under vacuum. The residue obtained was purified in a system for flash chromatography (SiNH$_2$, DCM:CH$_3$OH, from 100:0 to 97:3) to obtain pure Compound 4 (800 mg, 68%).

$^1$H NMR (300 MHz, CDCl$_3$): δ 8.90 (d, J=11.7 Hz, 1H), 7.34-7.26 (m, 1H), 6.99-6.74 (m, 2H), 6.50 (d, J=9.0 Hz, 1H), 6.15 (d, J=12.9 Hz, 1H), 5.83 (t, J=11.5 Hz, 1H), 5.70 (d, J=11.5 Hz, 1H), 5.68-5.57 (m, 2H), 5.27 (d, J=9.4 Hz, 1H), 4.80 (q, J=8.3 Hz, 1H), 4.52-4.44 (m, 2H), 4.24-4.17 (m, 1H), 3.66 (s, 3H), 3.39-3.17 (m, 2H), 2.93-2.82 (m, 1H), 2.78 (t, J=6.5 Hz, 2H), 2.50-2.34 (m, 2H), 2.34-2.24 (m, 2H), 2.19-1.99 (m, 2H), 2.06 (s, 3H), 1.84 (s, 3H), 1.72-1.50 (m, 2H), 1.16 (d, J=6.6 Hz, 3H), 1.04 (s, 9H).

$^{13}$C NMR (125 MHz, CDCl$_3$): δ 168.4, 166.1, 161.5, 156.7, 145.2, 139.9, 137.1, 134.0, 133.9, 131.8, 124.3, 124.2, 122.5, 120.9, 108.1, 105.5, 81.8, 74.3, 60.6, 55.4, 39.81, 39.30 37.2, 34.7, 33.1, 31.5, 29.6, 26.7, 26.2, 21.0, 17.1, 16.6.

ESI-MS m/z: Calcd. for C$_{34}$H$_{51}$ClN$_4$O$_7$: 662.30. Found: 663.3 (M+H)$^+$.

(c) Preparation of Compound 1

To a solution of Compound 4 (52 mg, 0.078 mmol), prepared as described in step (b) above, and 6-maleimidohexanoic acid /V-hydroxysuccinimide ester (27.1 mg, 0.088 mmol) in DCM (2 mL) was added DIPEA (15 μL, 0.086 mmol). The reaction mixture was stirred at 23° C. overnight and concentrated under vacuum. The residue obtained was purified in a system for flash chromatography (SiO$_2$, Hex:EtOAc mixtures) to afford pure target Compound 1 (29.7 mg, 44%).

$^1$H NMR (500 MHz, CDCl$_3$): δ 8.86 (d, J=10.8 Hz, 1H), 7.30 (t, J=11.6 Hz, 1H), 6.90 (td, J=11.5, 1.2 Hz, 1H), 6.78 (t, J=9.7 Hz, 1H), 6.68 (bs, 2H), 6.63 (d, J=9.4 Hz, 1H), 6.51 (t, J=6.4 Hz, 1H), 6.16 (d, J=11.8 Hz, 1H), 5.76 (t, J=6.4 Hz, 1H), 5.72 (d, J=11.6 Hz, 1H), 5.65 (dd, J=6.4, 2.9 Hz, 1H), 5.62-5.57 (m, 1H), 5.29 (d, J=11.1 Hz, 1H), 4.81 (q, J=8.3 Hz, 1H), 4.52-4.48 (m, 2H), 4.24 (ddd, J=11.4, 7.3, 4.3 Hz, 1H), 3.66 (s, 3H), 3.50 (t, J=7.3 Hz, 2H), 3.33-3.10 (m, 4H), 2.93-2.81 (m, 1H), 2.45-2.31 (m, 5H), 2.17 (t, J=7.6 Hz, 2H), 2.10-1.98 (m, 1H), 2.07 (s, 3H), 1.84 (s, 3H), 1.72-1.54 (m, 8H), 1.16 (d, J=6.6 Hz, 3H), 1.05 (s, 9H).

$^{13}$C NMR (125 MHz, CDCl$_3$): δ 173.8, 170.8, 168.3, 166.5, 161.6, 157.1, 145.1, 140.4, 137.5, 134.2, 134.1, 134.0, 131.9, 124.2, 124.0, 122.5, 120.6, 108.3, 106.0, 81.8, 74.5, 60.6, 55.4, 37.7, 37.6, 37.2, 36.3, 36.1, 34.7, 33.4, 31.0, 29.8, 28.3, 26.7, 26.3, 26.2, 25.6, 21.0, 17.2, 16.6.

ESI-MS m/z: Calcd. for C$_4$4H$_{62}$ClN$_5$O$_{10}$: 855.42. Found: 856.5 (M+H)$^+$.

Example 2

Preparation of Compound 5

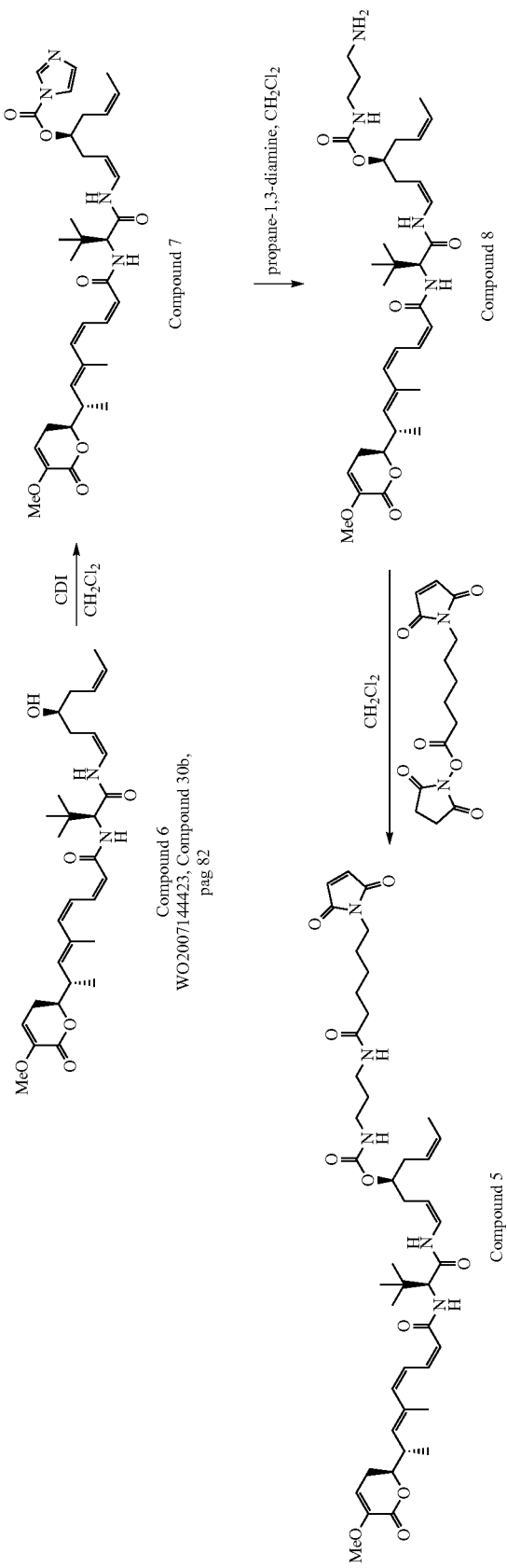

(a) Preparation of Compound 7

To a solution of Compound 6 (Compound 30b, prepared as described in WO 2007144423, the contents of which are incorporated herein by reference) (750 mg, 1.42 mmol) in DCM (35.5 mL) was added 1,1'-carbonyldiimidazole (691 mg, 4.26 mmol). After being stirred at 23° C. overnight, the reaction mixture was concentrated under vacuum. The residue obtained was purified in a system for flash chromatography (SiO$_2$, Hex:EtOAc mixtures) to afford pure Compound 7 (717 mg, 81%).

$^1$H NMR (300 MHz, CDCl$_3$): δ 8.24 (d, J=11.0 Hz, 1H), 8.09 (s, 1H), 7.40 (s, 1H), 7.36-7.23 (m, 1H), 7.05 (s, 1H), 6.95-6.83 (m, 2H), 6.34 (d, J=9.2 Hz, 1H), 6.14 (d, J=11.8 Hz, 1H), 5.74-5.57 (m, 3H), 5.43-5.34 (m, 1H), 5.28 (d, J=10.2 Hz, 1H), 4.98-4.88 (m, 1H), 4.78 (q, J=7.8 Hz, 1H), 4.47 (d, J=9.2 Hz, 1H), 4.25-4.16 (m, 1H), 3.64 (s, 3H), 2.92-2.76 (m, 1H), 2.59-2.37 (m, 6H), 1.83 (s, 3H), 1.64 (d, J=6.7 Hz, 3H), 1.14 (d, J=6.7 Hz, 3H), 1.03 (s, 9H).

(b) Preparation of Compound 8

To a solution of Compound 7 (1.68 g, 2.7 mmol), prepared as described in step (a) above, in DCM (80 mL) was added propane 1,3-diamine (0.27 mL, 3.24 mmol). The reaction mixture was stirred at 23° C. overnight and concentrated under vacuum. The residue obtained was purified in a system for flash chromatography (SiO$_2$, DCM:CH$_3$OH, from 100:0 to 97:3) to obtain Compound 8 (854 mg, 50%).

$^1$H NMR (300 MHz, CDCl$_3$): δ 8.90 (d, J=11.7 Hz, 1H), 7.39-7.18 (m, 1H), 6.92-6.84 (m, 2H), 6.50 (d, J=9.0 Hz, 1H), 6.15 (d, J=12.9 Hz, 1H), 5.75-5.67 (m, 2H), 5.66-5.54 (m, 2H), 5.46-5.33 (m, 1H), 5.26 (d, J=10.3 Hz, 1H), 4.83 (q, J=8.3 Hz, 1H), 4.50-4.48 (m, 2H), 4.30-4.04 (m, 1H), 3.66 (s, 3H), 3.39-3.17 (m, 2H), 2.93-2.82 (m, 1H), 2.78 (t, J=6.5 Hz, 2H), 2.50-2.34 (m, 3H), 2.34-2.24 (m, 2H), 2.19-1.99 (m, 1H), 1.83 (s, 3H), 1.72-1.50 (m, 2H), 1.62 (d, J=6.7 Hz, 3H), 1.16 (d, J=6.6 Hz, 3H), 1.04 (s, 9H).

$^{13}$C NMR (125 MHz, CDCl$_3$): δ 168.3, 166.2, 161.6, 157.1, 145.1, 139.9, 137.1, 134.0, 133.9, 126.9, 124.9, 124.2, 123.9, 120.9, 108.2, 106.3, 81.8, 75.0, 60.6, 55.4, 39.6, 37.2, 34.7, 32.8, 31.5, 31.1, 29.6, 26.7, 26.2, 17.1, 16.6, 12.9.

ESI-MS m/z: Calcd. for C$_{34}$H$_{52}$N$_4$O$_7$: 628.4. Found: 629.5 (M+H)$^+$.

(c) Preparation of Compound 5

To a solution of Compound 8 (150 mg, 0.24 mmol), prepared as described in step (b) above, in DCM (8 mL) at 23° C. was added 6-maleimidohexanoic acid N-hydroxysuccinimide ester (88.3 mg, 0.28 mmol). The reaction mixture was stirred at 23° C. for 18 h, and concentrated under vacuum. The residue obtained was purified in a system for flash chromatography (SiO$_2$, Hex:EtOAc mixtures) to afford pure target Compound 5 (75 mg, 38%).

$^1$H NMR (500 MHz, CDCl$_3$): δ 8.87 (d, J=10.7 Hz, 1H), 7.32-7.22 (m, 1H), 6.89 (t, J=11.6 Hz, 1H), 6.78 (t, J=9.7 Hz, 1H), 6.68 (s, 2H), 6.61 (d, J=9.4 Hz, 1H), 6.54 (t, J=6.0 Hz, 1H), 6.15 (d, J=11.6 Hz, 1H), 5.77-5.51 (m, 2H), 5.64 (dd, J=6.4, 3.0 Hz, 1H), 5.60-5.55 (m, 1H), 5.38 (ddd, J=13.0, 8.8, 6.6 Hz, 1H), 5.28 (d, J=10.0 Hz, 1H), 4.83 (q, J=8.3 Hz, 1H), 4.59-4.44 (m, 2H), 4.23 (ddd, J=11.5, 7.2, 4.4 Hz, 1H), 3.65 (s, 3H), 3.49 (t, J=7.2 Hz, 2H), 3.29-3.12 (m, 4H), 2.87-2.81 (m, 1H), 2.48-2.32 (m, 5H), 2.18-2.09 (m, 3H), 1.88-1.82 (m, 1H), 1.83 (s, 3H), 1.67-1.55 (m, 7H), 1.62 (d, J=6.8 Hz, 3H), 1.15 (d, J=6.7 Hz, 3H), 1.04 (s, 9H).

$^{13}$C NMR (125 MHz, CDCl$_3$): δ 173.6, 170.8, 168.2, 166.4, 161.6, 157.4, 145.2, 140.2, 137.4, 134.2, 134.1, 134.0, 127.0, 124.9, 123.9, 120.7, 108.3, 106.5, 81.8, 75.3, 60.6, 55.4, 37.7, 37.6, 37.2, 36.3, 36.0, 34.7, 31.8, 31.6, 31.1, 29.9, 28.3, 26.7, 26.4, 26.2, 25.2, 22.6, 17.2, 16.6.

ESI-MS m/z: Calcd. for C$_4$$^4$H$_{63}$N$_5$O$_{10}$: 821.5. Found: 822.4 (M+H)$^+$.

Example 3

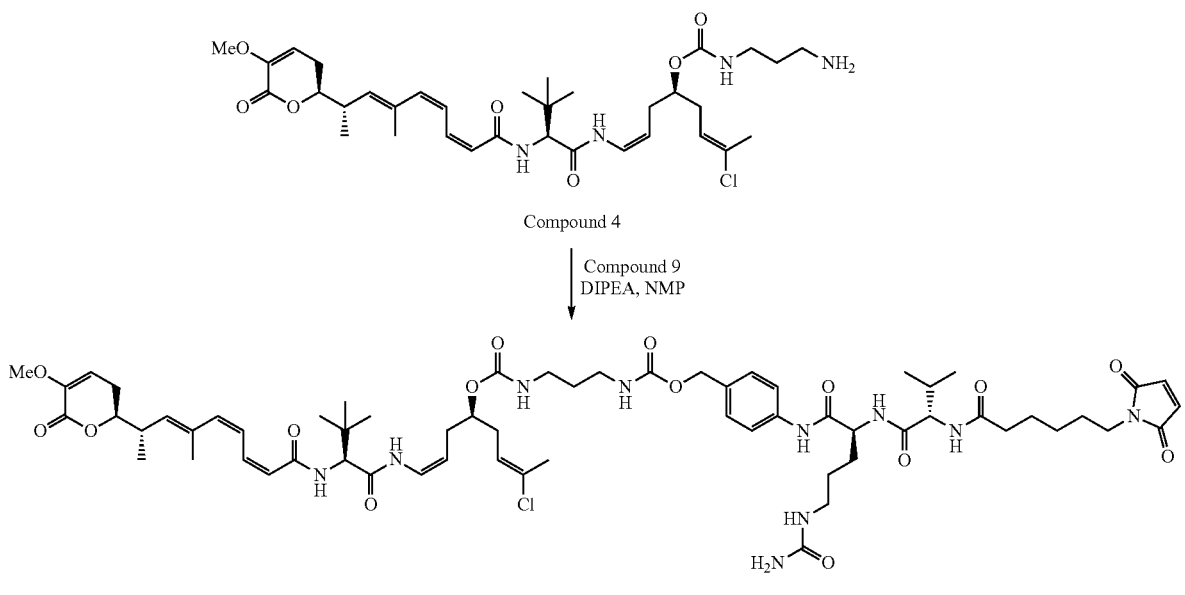

Compound 4

Compound 9
DIPEA, NMP

Compound 12

(a) Preparation of Compound 12

DIPEA (25 μL, 0.14 mmol) was added to a solution of Compound 9 (94.5 mg, 0.13 mmol), prepared as shown in the Preparative Example above, and Compound 4 (85 mg, 0.13 mmol), prepared as described in Example 1(b) above, in NMP (6.5 mL) at 23° C. After 9 h the reaction mixture was diluted with H$_2$0 and extracted with EtOAc. The combined organic layers were dried over anhydrous Na$_2$SO$_4$, filtered, and concentrated under vacuum. The residue obtained was purified in a system for flash chromatography (SiO$_2$, DCM:CH$_3$OH, from 100:0 to 90:10). Finally, purification of target Compound 12 (35.7 mg, 22%) was achieved by semipreparative HPLC (Symmetry C18, 7 μm, 19×150 mm, gradient H$_2$0+CH$_3$CN, flow 15 mL/min, UV detection).

$^1$H NMR (500 MHz, CDCl$_3$/CD$_3$OD): δ 7.49 (d, J=8.1 Hz, 2H), 7.22 (d, J=8.1 Hz, 2H), 7.19 (t, J=11.8 Hz, 1H), 6.96 (dd, J=23.5, 8.9 Hz, 1H), 6.84 (t, J=11.5 Hz, 1H), 6.70-6.64 (m, 1H), 6.64 (s, 2H), 6.10 (d, J=11.6 Hz, 1H), 5.93 (t, J=6.2 Hz, 1H), 5.82 (t, J=6.2 Hz, 1H), 5.69 (d, J=11.4 Hz, 1H), 5.61 (dd, J=6.3, 3.1 Hz, 1H), 5.54 (t, J=7.8 Hz, 1H), 5.22 (d, J=9.7 Hz, 1H), 4.96 (s, 2H), 4.75 (q, J=8.1 Hz, 1H), 4.55-4.49 (m, 2H), 4.43-4.36 (m, 1H), 4.23-4.10 (m, 2H), 3.59 (s, 3H), 3.44 (t, J=7.2 Hz, 2H), 3.18-3.04 (m, 8H), 2.82-2.72 (m, 1H), 2.49-2.34 (m, 3H), 2.27 (t, J=7.1 Hz, 2H), 2.18 (t, J=7.2 Hz, 2H), 2.16-2.06 (m, 1H), 2.01-1.95 (m, 1H), 2.00 (s, 3H), 1.87-1.79 (m, 1H), 1.78 (s, 3H), 1.73-1.40 (m, 11H), 1.35-1.20 (m, 2H), 1.09 (d, J=10.0 Hz, 3H), 0.96 (s, 9H), 0.87 (dd, J=6.8, 4.3 Hz, 6H).

$^{13}$C NMR (125 MHz, CDCl$_3$): δ 174.1, 172.2, 171.0, 170.3, 168.8, 166.8, 162.1, 160.2, 157.0, 156.9, 144.9, 140.2, 137.7, 137.5, 134.0, 132.4, 131.7, 128.7, 124.0, 123.4, 122.4, 120.4, 119.8, 111.5, 108.6, 107.0, 81.9, 73.8, 68.6, 66.2, 60.3, 58.8, 55.4, 53.0, 37.6, 37.5, 37.1, 35.9, 34.6, 33.2, 30.6, 29.9, 29.2, 28.0, 26.5, 26.2, 26.0, 25.0, 22.6, 20.8, 19.1, 18.2, 17.04, 16.4.

ESI-MS m/z: Calcd. for C$_{63}$H$_{89}$ClN$_{10}$O$_{15}$: 1260.6. Found: 1261.6 (M+H)$^+$.

Example 4

Preparation of Compound 13

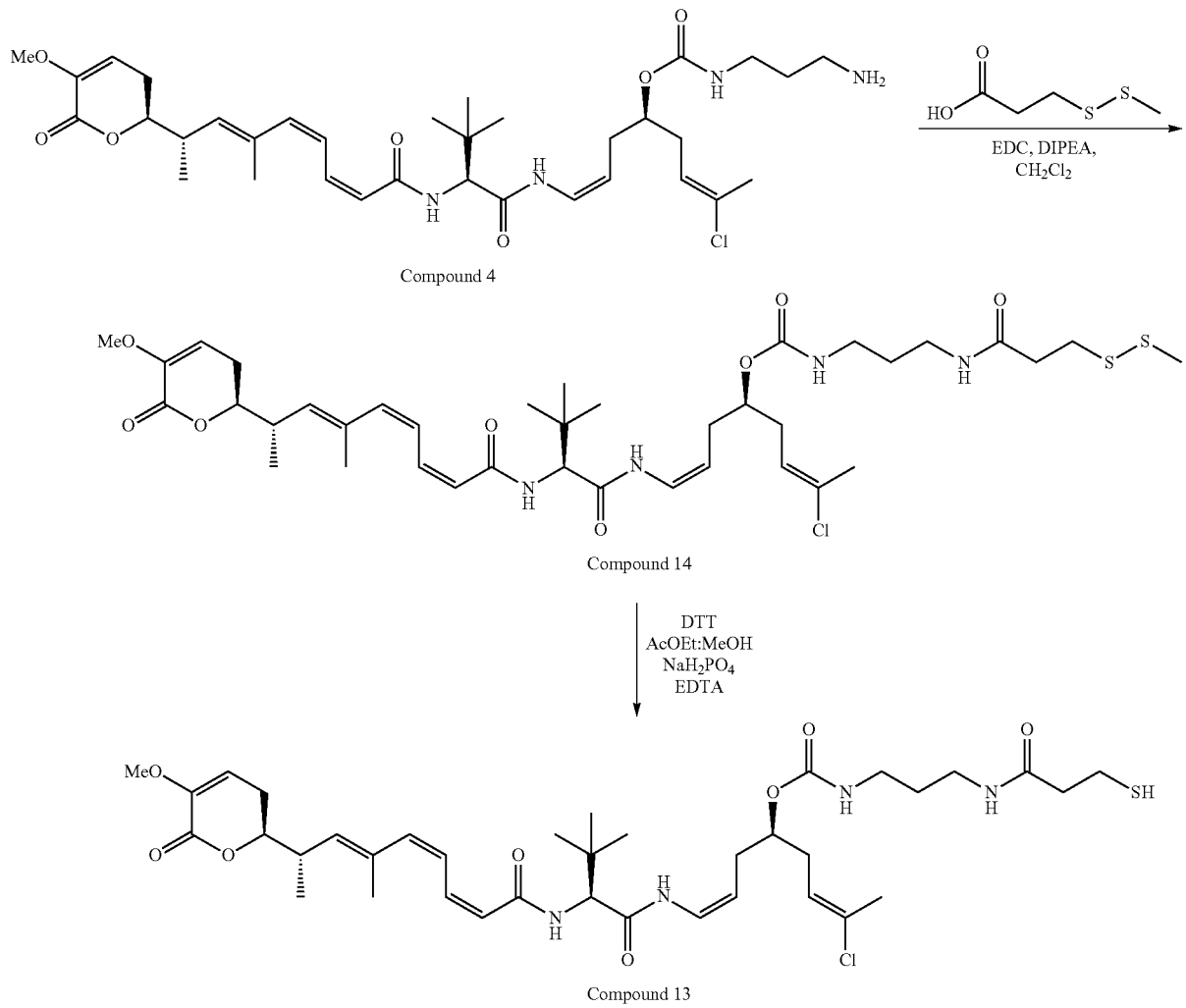

(a) Preparation of Compound 14

To a solution of Compound 4 (110 mg, 0.17 mmol), prepared as described in Example 1(b) above, and 3-(methyldisulfanyl)propanoic acid (34 mg, 0.22 mmol) in DCM (5 ml) were added /V-(3-dimethylaminopropyl)-A/'-ethylcarbodiimide hydrochloride (EDC) (47.8 mg, 0.22 mmol) and N,N'-diisopropylethylamine (3.8 μl, 0.22 mmol). The reaction mixture was stirred at 23° C. for 6 h, diluted with H$_2$0 and extracted with DCM. The combined organic layers were dried over anhydrous Na$_2$S0$_4$, filtered and concentrated under vacuum. The residue obtained was purified in a system for flash chromatography (Si0$_2$, Hex:EtOAc mixtures) to afford pure Compound 14 (123 mg, 93%).

$^1$H NMR (500 MHz, CDCl$_3$): δ 8.88 (d, J=10.8 Hz, 1H), 7.29-7.24 (m, 1H), 6.90 (t, J=11.5 Hz, 1H), 6.82 (t, J=9.1 Hz, 1H), 6.63 (t, J=6.1 Hz, 1H), 6.49 (d, J=9.4 Hz, 1H), 6.16 (dd, J=11.5, 1.5 Hz, 1H), 5.70 (d, J=11.5 Hz, 1H), 5.68-5.51 (m, 3H), 5.29 (d, J=9.7 Hz, 1H), 4.81 (q, J=8.2 Hz, 1H), 4.52 (d, J=9.5 Hz, 1H), 4.52-4.43 (m, 1H), 4.24 (ddd, J=11.5, 7.3, 4.3 Hz, 1H), 3.66 (s, 3H), 3.37-3.21 (m, 3H), 3.21-3.12 (m, 1H), 2.97 (t, J=7.2 Hz, 2H), 2.90-2.81 (m, 1H), 2.60 (t, J=7.2 Hz, 2H), 2.49-2.35 (m, 3H), 2.39 (s, 3H), 2.33 (t, J=7.0 Hz, 2H), 2.14-2.07 (m, 1H), 2.07 (s, 3H), 1.84 (s, 3H), 1.73-1.64 (m, 2H), 1.16 (d, J=6.7 Hz, 3H), 1.05 (s, 9H).

$^{13}$C NMR (125 MHz, CDCl$_3$): δ 171.6, 168.2, 166.4, 161.6, 157.2, 145.2, 140.3, 137.4, 134.2, 134.0, 131.9, 124.4, 124.1, 122.4, 120.7, 108.3, 105.6, 81.8, 74.8, 60.6, 60.4, 55.5, 37.8, 37.2, 36.2, 35.6, 34.7, 33.1, 31.0, 29.8, 26.7, 26.2, 23.0, 21.0, 17.2, 16.6.

(b) Preparation of Compound 13

A solution of Compound 14 (100 mg, 0.125 mmol), prepared as described in step (a) above, in a mixture of EtOAc (4.3 mL) and CH$_3$OH (4.3 mL) was treated with a solution of dithiothreitol (154.8 mg, 1.0 mmol) in 0.05 M potassium phosphate buffer (4.3 mL) at pH 7.5 containing 2 mM ethylenediaminetetraacetic acid (EDTA). The mixture was stirred at 23° C. for 4 h. The reaction was treated with a solution of 0.2 M potassium phosphate buffer (13 mL) at pH 6.0 containing 2 mM EDTA and then extracted with EtOAc. The combined organic layers were dried over anhydrous Na$_2$S0$_4$, filtered and concentrated under vacuum. The crude obtained was purified in a system for flash chromatography (SiO$_2$, Hex: EtOAc mixtures) to yield pure target Compound 13 (35 mg, 37%).

$^1$H NMR (300 MHz, CDCl$_3$): δ 8.91 (d, J=10.8 Hz, 1H), 7.27-7.24 (m, 1H), 6.91 (t, J=11.5 Hz, 1H), 6.82 (t, J=9.7 Hz, 1H), 6.67 (t, J=6.1 Hz, 1H), 6.49 (d, J=9.4 Hz, 1H), 6.16 (d, J=11.6 Hz, 1H), 5.71 (d, J=11.6 Hz, 1H), 5.66-5.57 (m, 3H), 5.29 (d, J=9.9 Hz, 1H), 4.84 (q, J=8.3 Hz, 1H), 4.51 (d, J=9.5 Hz, 1H), 4.50-4.45 (m, 1H), 4.24-4.20 (m, 1H), 3.66 (s, 3H), 3.36-3.12 (m, 4H), 2.90-2.71 (m, 3H), 2.64-2.24 (m, 7H), 2.14-2.04 (m, 1H), 2.06 (s, 3H), 1.83 (s, 3H), 1.73-1.68 (m, 2H), 1.15 (d, J=6.7 Hz, 3H), 1.05 (s, 9H).

ESI-MS m/z: Calcd. for C$_{37}$H$_{55}$ClN$_4$O$_8$S: 750.3. Found: 773.2 (M+Na)$^+$.

Example 5

Preparation of Compound 15

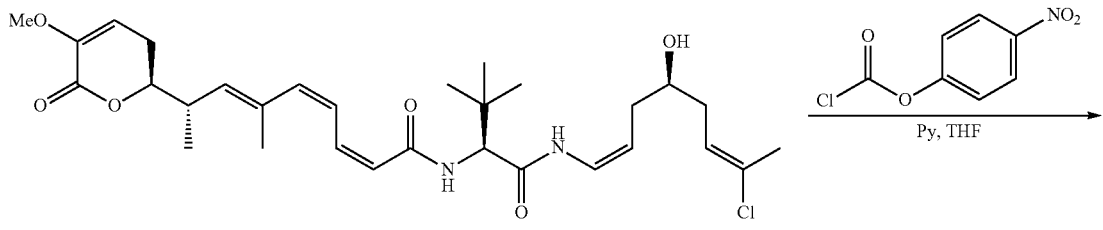

Compound 2
WO2007144423, Compound 30a, pag 81

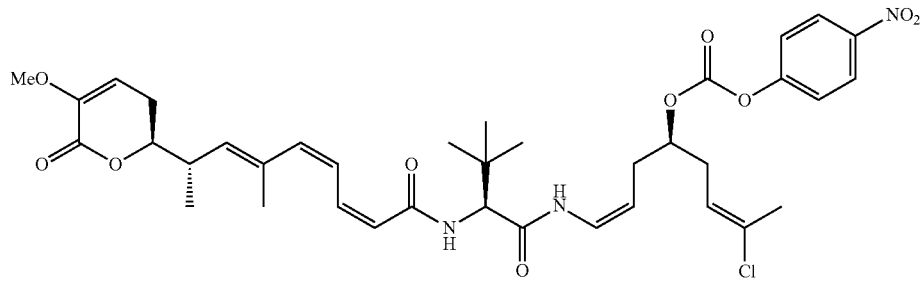

Compound 16

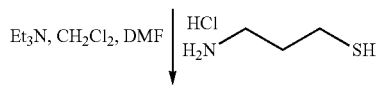

-continued

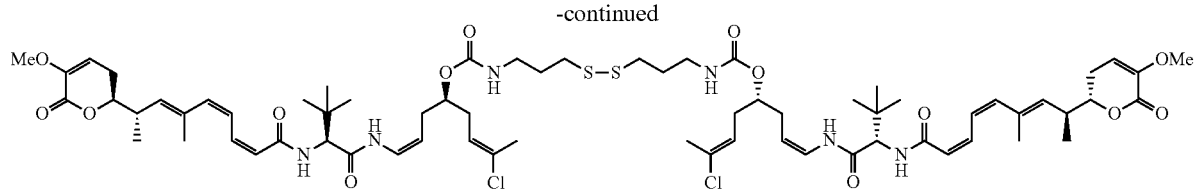

Compound 17

DTT
AcOEt:MeOH
NaH₂PO₄
EDTA

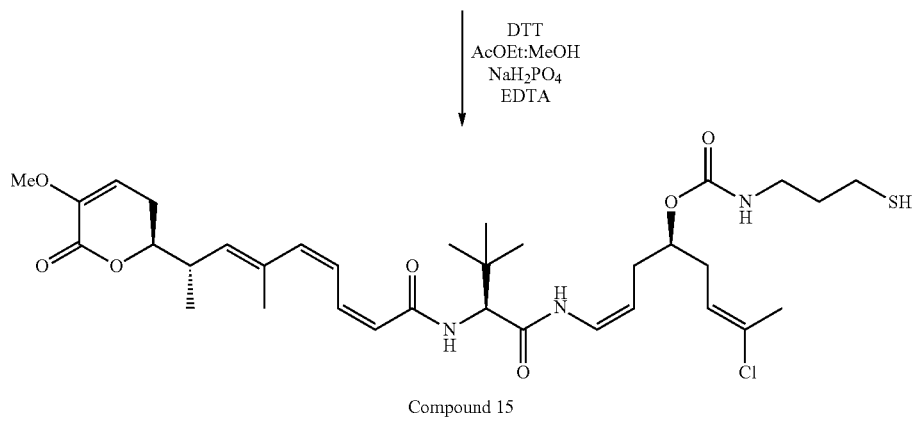

Compound 15

(a) Preparation of Compound 16

To a solution of Compound 2 (Compound 30a, prepared as described in WO 2007144423, the contents of which are incorporated herein by reference) (300 mg, 0.53 mmol) in DCM (5 mL) were added pyridine (85 µl, 1.06 mmol) and 4-nitrophenyl chloroformate (214.7 mg, 1.06 mmol) at 0° C. The reaction mixture was stirred at 23° C. for 1.5 h, diluted with citric acid 10% and extracted with DCM. The combined organic layers were dried over anhydrous $Na_2SO_4$, filtered and concentrated under vacuum. The residue obtained was purified in a system for flash chromatography ($SiO_2$, Hex:EtOAc mixtures) to yield pure Compound 16 (307 mg, 80%).

$^1$H NMR (500 MHz, CDCl₃): δ 8.29 (d, J=9.2 Hz, 2H), 8.08 (d, J=10.9 Hz, 1H), 7.44 (d, J=9.1 Hz, 2H), 7.27-7.22 (m, 1H), 6.92-6.83 (m, 2H), 6.20 (d, J=9.2 Hz, 1H), 6.17 (dd, J=11.6, 1.4 Hz, 1H), 5.67-5.58 (m, 3H), 5.29 (d, J=10.0 Hz, 1H), 4.84 (q, J=8.2 Hz, 1H), 4.77-4.72 (m, 1H), 4.41 (d, J=9.3 Hz, 1H), 4.22 (ddd, J=11.5, 7.5, 4.4 Hz, 1H), 3.67 (s, 3H), 2.89-2.82 (m, 1H), 2.54-2.33 (m, 6H), 2.10 (d, J=1.2 Hz, 3H), 1.85 (d, J=1.3 Hz, 3H), 1.17 (d, J=6.7 Hz, 3H), 1.02 (s, 9H).

$^{13}$C NMR (125 MHz, CDCl₃): δ 168.4, 166.1, 161.5, 155.3, 152.5, 145.5, 145.2, 140.4, 137.6, 134.3, 134.0, 133.2, 125.3, 124.4, 124.1, 121.8, 121.2, 120.4, 108.1, 104.6, 81.8, 79.1, 60.4, 55.5, 37.3, 34.7, 32.7, 30.1, 26.6, 26.3, 21.1, 17.2, 16.6.

(b) Preparation of Compound 17

To a solution of Compound 16 (156.3 mg, 0.21 mmol) in DCM (2.5 ml.) were added a suspension of 3-aminopropane-1-thiol hydrochloride (44.8 mg, 0.26 mmol) in DCM (2.5 mL), triethylamine (58 µL, 0.34 mmol) and DMF (0.1 mL) at 23° C. The reaction mixture was stirred at 23° C. for 3 h, diluted with H₂O and extracted with DCM. The combined organic layers were dried over anhydrous $Na_2SO_4$, filtered and concentrated under vacuum. The residue obtained was purified in a system for flash chromatography ($SiO_2$, Hex:EtOAc mixtures) to afford pure Compound 17 (80 mg, 95%).

$^1$H NMR (300 MHz, CDCl₃): δ 8.68 (d, J=10.6 Hz, 1H), 7.28 (t, J=11.6 Hz, 1H), 6.89 (t, J=11.5 Hz, 1H), 6.76 (t, J=9.6 Hz, 1H), 6.65 (d, J=9.1 Hz, 1H), 6.13 (d, J=11.7 Hz, 1H), 5.87-5.51 (m, 4H), 5.28 (d, J=5.0 Hz, 1H), 4.77 (q, J=8.2 Hz, 1H), 4.61-4.39 (m, 2H), 4.29-4.00 (m, 1H), 3.65 (s, 3H), 3.31-3.18 (m, 2H), 2.98-2.77 (m, 1H), 2.68 (t, J=7.4 Hz, 2H), 2.55-2.22 (m, 6H), 2.04 (s, 3H), 2.00-1.80 (m, 2H), 1.83 (s, 3H), 1.15 (d, J=6.6 Hz, 3H), 1.05 (s, 9H).

ESI-MS m/z: Calcd. for $C_{68}H_{98}Cl_2N_6O_{14}S_2$: 1356.6. Found: 1357.3 (M+H)⁺.

(c) Preparation of Compound 15

A solution of Compound 17 (59.4 mg, 0.044 mmol) in a mixture of EtOAc (1.5 mL) and CH₃OH (1.5 mL) was treated with a solution dithiothreitol (0.35 mL, 0.35 mmol) in 0.05 M potassium phosphate buffer (1.5 mL) at pH 7.5 containing 2 mM ethylenediaminetetraacetic acid (EDTA). The mixture was stirred at 23° C. for 4 h. The reaction was treated with a solution of 0.2 M potassium phosphate buffer at pH 6.0 containing 2 mM EDTA and the extracted with EtOAc (×3). The combined organic layers were dried over anhydrous $Na_2SO_4$, filtered and concentrated under vacuum. The residue obtained was purified in a system for flash chromatography ($SiO_2$, Hex:EtOAc mixtures) to yield pure target Compound 15 (31 mg, 59%).

$^1$H NMR (500 MHz, CDCl₃): δ 8.66 (d, J=10.7 Hz, 1H), 7.29 (t, J=11.2 Hz, 1H), 6.91 (t, J=11.5 Hz, 1H), 6.83 (t, J=9.7 Hz, 1H), 6.38 (d, J=9.4 Hz, 1H), 6.17 (d, J=11.8 Hz, 1H), 5.70 (d, J=11.4 Hz, 1H), 5.65-5.51 (m, 2H), 5.34 (t, J=6.3 Hz, 1H), 5.29 (d, J=10.0 Hz, 1H), 4.82 (q, J=8.3 Hz, 1H), 4.56-4.48 (m, 1H), 4.45 (d, J=9.3 Hz, 1H), 4.22 (ddd, J=11.4, 7.5, 4.3 Hz, 1H), 3.67 (s, 3H), 3.31 (q, J=6.4 Hz, 2H), 2.88-2.83 (m, 1H), 2.55 (q, J=7.7 Hz, 2H), 2.47-2.30

(m, 5H), 2.12-2.07 (m, 1H), 2.08 (s, 3H), 1.88-1.76 (m, 5H), 1.17 (d, J=6.6 Hz, 3H), 1.06 (s, 9H).
$^{13}$C NMR (125 MHz, CDCl$_3$): δ 168.2, 166.2, 161.5, 156.7, 145.2, 140.2, 137.3, 134.2, 134.0, 132.0, 124.4, 124.2, 122.3, 120.8, 108.1, 105.5, 81.8, 74.5, 60.6, 55.4, 39.6, 37.3, 34.6, 33.9, 33.3, 30.8, 26.7, 26.3, 21.8, 21.1, 17.2, 16.7.
ESI-MS m/z: Calcd. for C$_{34}$H$_{50}$ClN$_3$O$_7$S: 679.3. Found: 702.4 (M+Na)$^+$.

Example 6

Preparation of Compound 18 and extracted with DCM. The combined organic layers were dried over anhydrous Na$_2$SO$_4$, filtered and concentrated under vacuum. The residue obtained was purified in a system for flash chromatography (SiO$_2$, Hex:EtOAc mixtures) to afford pure Compound 19 (240 mg, 71%).

$^1$H NMR (500 MHz, CDCl$_3$): δ 8.91 (d, J=10.8 Hz, 1H), 7.34-7.20 (m, 1H), 6.89 (t, J=11.4 Hz, 1H), 6.83-6.72 (m, 2H), 6.51 (d, J=9.5 Hz, 1H), 6.16 (d, J=11.3 Hz, 1H), 5.70 (d, J=11.5 Hz, 1H), 5.64 (dd, J=6.1, 3.3 Hz, 1H), 5.61-5.55 (m, 2H), 5.47-5.33 (m, 1H), 5.28 (d, J=9.3 Hz, 1H), 4.84 (q, J=8.3 Hz, 1H), 4.51 (d, J=9.6 Hz, 1H), 4.52-4.47 (m, 1H), 4.27-4.19 (m, 1H), 3.66 (s, 3H), 3.37-3.21 (m, 3H), 3.21-3.12 (m, 1H), 2.96 (t, J=7.2 Hz, 2H), 2.90-2.81 (m, 1H), 2.60

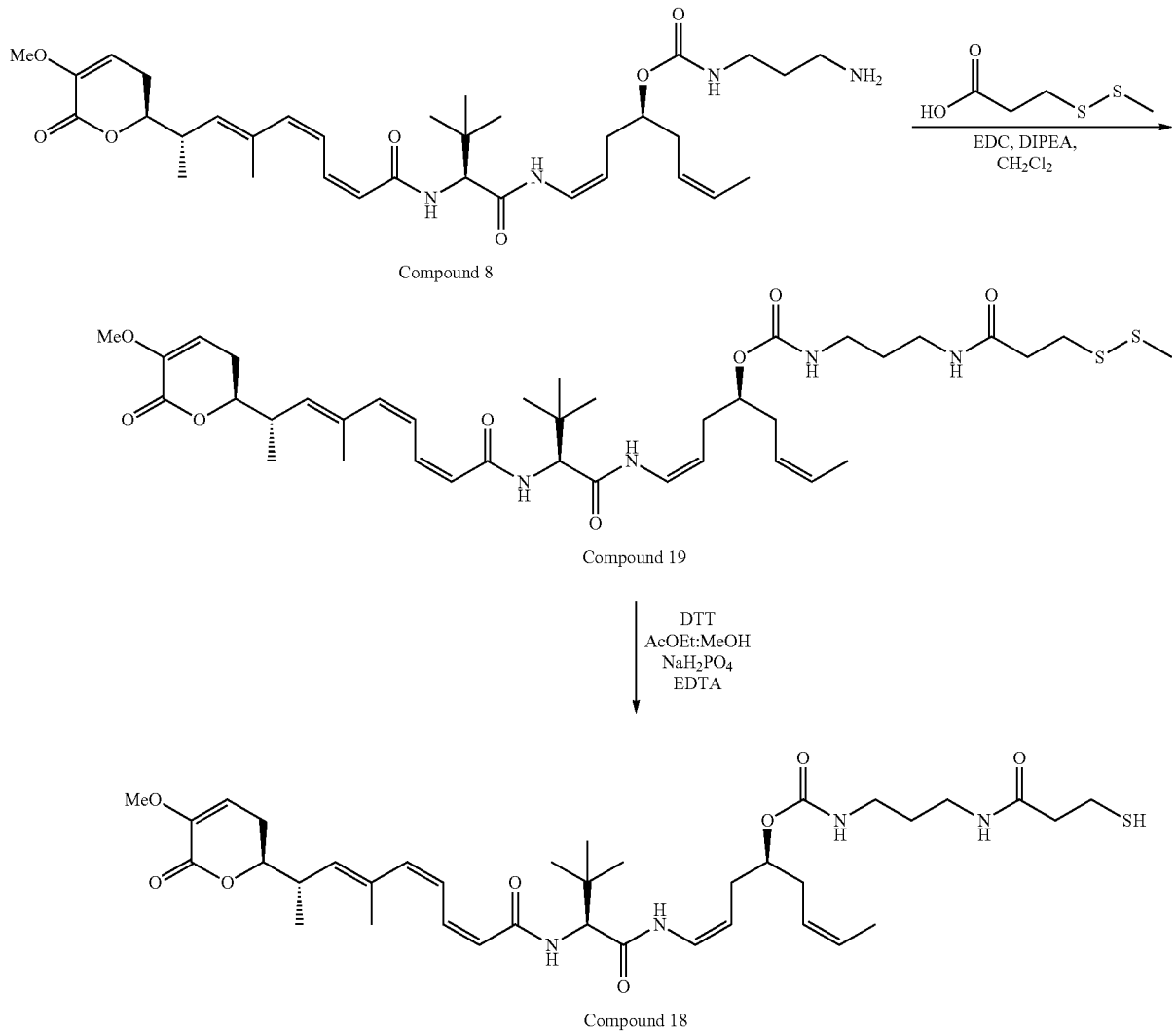

(a) Preparation of Compound 19

To a solution of Compound 8 (280 mg, 0.45 mmol), prepared as described in Example 2(b) above, and 3-(methyldisulfanyl)propanoic acid (88 mg, 0.58 mmol) in DCM (7.5 mL) were added N-(3-dimethylaminopropyl)-N'-ethylcarbodiimide hydrochloride (EDC) (126 mg, 0.58 mmol) and N,N-diisopropylethylamine (0.1 mL, 0.58 mmol). The reaction mixture was stirred at 23° C. for 3 h, diluted with H$_2$O (t, J=7.2 Hz, 2H), 2.43-2.35 (m, 5H), 2.39 (s, 3H), 2.16-2.04 (m, 1H), 1.84 (s, 3H), 1.70-1.61 (m, 5H), 1.16 (d, J=6.7 Hz, 3H), 1.05 (s, 9H).
$^{13}$C NMR (125 MHz, CDCl$_3$) δ 171.5, 168.1, 166.3, 157.4, 145.2, 140.3, 137.4, 134.2, 134.0, 127.0, 124.9, 124.0, 120.8, 108.3, 106.3, 81.8, 75.5, 60.6, 55.4, 53.4, 37.8, 37.2, 36.2, 35.9, 34.7, 33.1, 31.8, 31.2, 29.8, 26.7, 26.2, 23.0, 17.2, 16.6, 13.0.
ESI-MS m/z: Calcd. for C$_{38}$H$_{58}$N$_4$O$_8$S$_2$: 763.4. Found: 762.4 (M+H)$^+$.

(b) Preparation of Compound 18

A solution of Compound 19 (240 mg, 0.31 mmol), prepared as described in step (a) above, in a mixture of EtOAc (15 mL) and CH$_3$OH (22 mL) was treated with a solution dithiothreitol (0.79 mL of 1.0 M solution, 0.79 mmol) in 0.05 M potassium phosphate buffer (17.4 mL) at pH 7.5 containing 2 mM ethylenediaminetetraacetic acid (EDTA). The mixture was stirred at 23° C. for 4 h. The reaction was treated with a solution of 0.2 M potassium phosphate buffer (21 mL) at pH 6.0 containing 2 mM EDTA and the extracted with ethyl acetate. The combined organic layers were dried over anhydrous Na$_2$SO$_4$, filtered and concentrated under vacuum. The crude obtained was purified in a system for flash chromatography (SiO$_2$, Hex:EtOAc mixtures) to yield pure target Compound 18 (105 mg, 47%)

$^1$H NMR (300 MHz, CDCl$_3$): δ 8.93 (d, J=10.6 Hz, 1H), 7.30-7.22 (m, 1H), 6.90 (t, J=11.6 Hz, 1H) 6.86-6.72 (m, 2H), 6.48 (d, J=9.4 Hz, 1H), 6.16 (d, J=11.6 Hz, 1H), 5.70 (d, J=11.4 Hz, 1H), 5.65-5.55 (m, 3H), 5.48-5.34 (m, 1H), 5.29 (d, J=9.9 Hz, 1H), 4.84 (q, J=9.4, 8.7 Hz, 1H), 4.52 (d, J=9.5 Hz, 1H), 4.57-4.44 (m, 1H), 4.32-4.17 (m, 1H), 3.66 (s, 3H), 3.39-3.20 (m, 3H), 3.22-3.09 (m, 1H), 2.90-2.75 (m, 3H), 2.50 (t, J=6.9, 2H), 2.45-2.28 (m, 5H), 2.16-2.08 (m, 1H), 1.83 (s, 3H), 1.72-1.65 (m 2H), 1.64 (d, J=6.6 Hz, 3H) 1.16 (d, J=6.7 Hz, 3H), 1.05 (s, 9H).

ESI-MS m/z: Calcd. for C$_{37}$H$_{56}$N$_4$O$_8$S: 716.4. Found: 717.3 (M+H)$^+$.

Example 7

Preparation of Compound 25

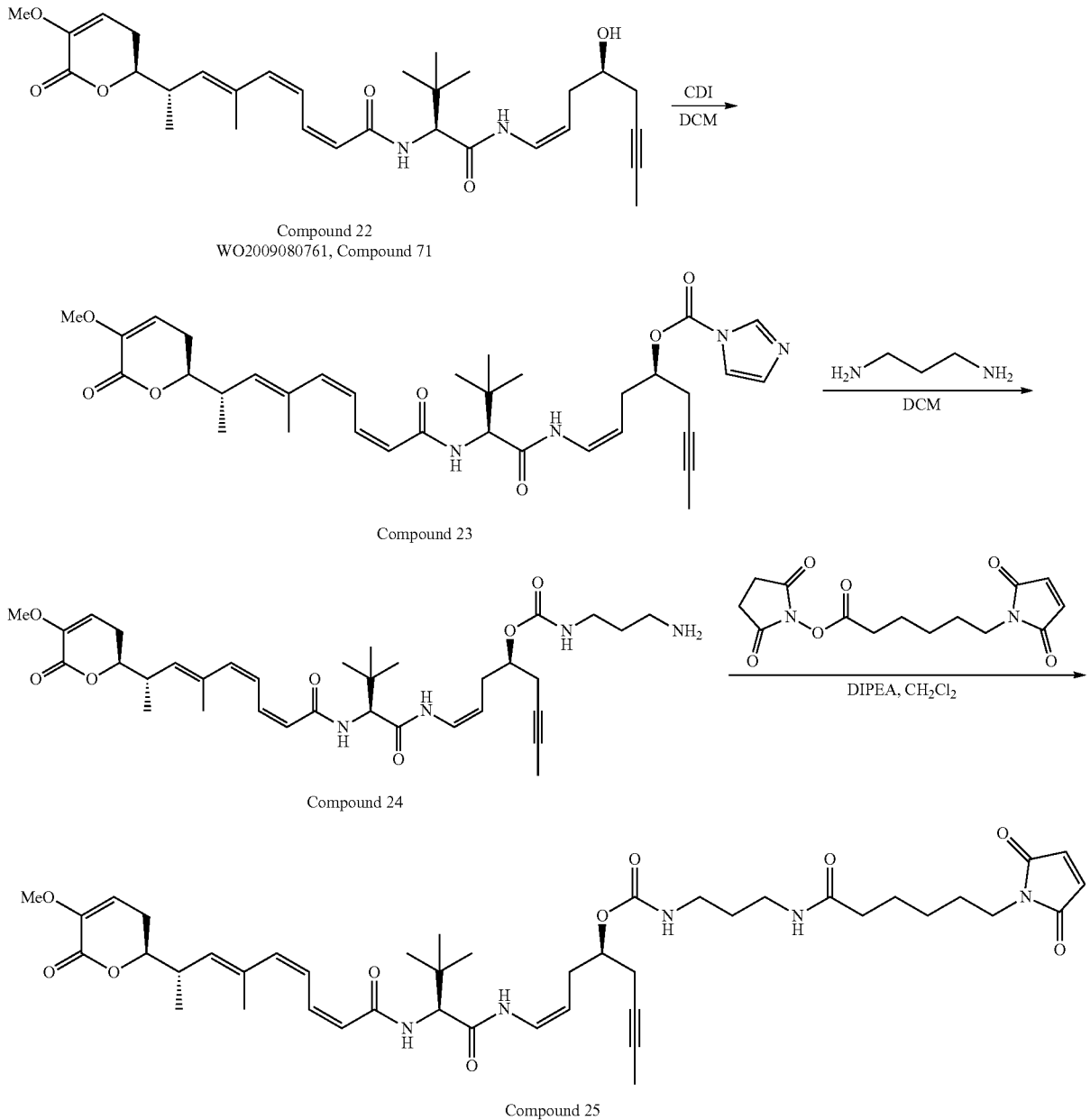

Compound 22
WO2009080761, Compound 71

Compound 23

Compound 24

Compound 25

(a) Preparation of Compound 23

To a solution of Compound 22 (333 mg, 0.63 mmol) (Compound 71, prepared as described in WO 2009080761, the contents of which are incorporated herein by reference) in CH$_2$Cl$_2$ (12.5 mL) was added 1,1'-carbonyldiimidazole (308 mg, 1.90 mmol). After being stirred at 23° C. overnight, the reaction mixture was concentrated under vacuum. The residue obtained was purified in a system for flash chromatography (SiO$_2$, Hex:EtOAc mixtures) to yield pure Compound 23 (344 mg, 88%).

$^1$H NMR (300 MHz, CDCl$_3$): δ 8.14 (s, 1H), 8.11 (d, J=10.8 Hz, 1H), 7.43 (s, 1H), 7.28 (t, J=11.6 Hz, 1H), 7.08 (dd, J=1.7, 0.9 Hz, 1H), 6.96-6.81 (m, 2H), 6.26 (d, J=9.3 Hz, 1H), 6.17 (d, J=11.6 Hz, 1H), 5.66 (dt, J=11.4, 1.4 Hz, 1H), 5.62 (dd, J=5.9, 3.5 Hz, 1H), 5.28 (d, J=10.0 Hz, 1H), 5.04-4.89 (m, 1H), 4.80 (q, J=8.3 Hz, 1H), 4.40 (d, J=9.3 Hz, 1H), 4.21 (ddd, J=10.3, 7.5, 5.3 Hz, 1H), 3.65 (s, 3H), 2.91-2.78 (m, 1H), 2.68-2.49 (m, 3H), 2.45-2.31 (m, 2H), 1.89 (t, J=2.5 Hz, 3H), 1.84 (s, 3H), 1.15 (d, J=6.7 Hz, 3H), 1.05 (s, 9H).

ESI-MS m/z: Calcd. for C$_{34}$H44N4O$_7$: 620.32. Found: 621.3 (M+H)$^+$.

(b) Preparation of Compound 24

To a solution of Compound 23 (0.130 g, 0.21 mmol)), prepared as described in step (a) above, in CH$_2$Cl$_2$ (3.5 ml.) was added propane 1,3-diamine (0.022 ml, 0.26 mmol). The reaction mixture was stirred at 23° C. for 6 hours and concentrated under vacuum. The residue obtained was purified in a system for flash chromatography (SiO$_2$, DCM:CH$_3$OH, from 100:0 to 97:3) to obtain Compound 24 (120 mg, 91%).

$^1$H NMR (300 MHz, CDCl$_3$): δ 8.71 (d, J=10.7 Hz, 1H), 7.28 (t, J=11.6 Hz, 1H), 6.91-6.77 (m, 2H), 6.44 (d, J=9.4 Hz, 1H), 6.14 (d, J=11.6 Hz, 1H), 5.77-5.57 (m, 3H), 5.27 (d, J=10.0 Hz, 1H), 4.83 (q, J=8.3 Hz, 1H), 4.57-4.53 (m, 1H), 4.46 (d, J=12.4 Hz, 1H), 4.31-4.11 (m, 1H), 3.65 (s, 3H), 3.31-3.24 (m, 2H), 2.93-2.67 (m, 3H), 2.56-2.24 (m, 6H), 2.16 (s, 3H), 1.83 (s, 3H), 1.63 (dd, J=9.6, 3.5 Hz, 2H), 1.15 (d, J=6.6 Hz, 3H), 1.04 (s, 9H).

$^{13}$C NMR (125 MHz, CDCl$_3$): δ 168.3, 166.1, 161.6, 156.5, 145.2, 140.0, 137.2, 134.1, 134.0, 124.3, 124.2, 120.9, 108.1, 106.0, 81.8, 78.4, 74.5, 73.2, 60.6, 55.4, 39.8, 39.2, 37.3, 34.8, 33.0, 30.9, 30.2, 26.7, 26.3, 17.2, 16.7, 3.6.

ESI-MS m/z: Calcd. for C$_3$$_4$H$_5$$_0$N$_4$O$_7$: 626.37. Found: 627.3 (M+H)$^+$.

(c) Preparation of Compound 25

To a solution of Compound 24 (40 mg, 0.064 mmol)), prepared as described in step (b) above, in CH$_2$Cl$_2$ (2 ml.) was added 6-maleimidohexanoic acid N-hydroxysuccinimide ester (21.6 mg, 0.07 mmol). The reaction mixture was stirred at 23° C. overnight and concentrated under vacuum. The residue obtained was purified in a system for flash chromatography (SiO$_2$, Hex:EtOAc mixtures) to afford pure Compound 25 (33.5 mg, 64%).

$^1$H NMR (400 MHz, CDCl$_3$): δ 8.67 (d, J=10.7 Hz, 1H), 7.29-7.23 (m, 1H), 6.90 (t, J=11.5 Hz, 1H), 6.80 (t, J=9.6 Hz, 1H), 6.68 (s, 2H), 6.46 (d, J=9.4 Hz, 1H), 6.42 (bs, 1H), 6.16 (d, J=11.6 Hz, 1H), 5.73-5.67 (m, 2H), 5.64 (dd, J=6.2, 3.1 Hz, 1H), 5.30 (d, J=9.6 Hz, 1H), 4.86 (q, J=8.4 Hz, 1H), 4.63-4.54 (m, 1H), 4.44 (d, J=9.4 Hz, 1H), 4.30-4.18 (m, 1H), 3.66 (s, 3H), 3.50 (t, J=7.2 Hz, 2H), 3.34-3.10 (m, 3H), 2.85 (dt, J=9.9, 6.9 Hz, 1H), 2.54-2.37 (m, 4H), 2.36-2.28 (m, 1H), 2.16 (t, J=7.6 Hz, 2H), 1.84 (d, J=1.3 Hz, 3H), 1.83-1.81 (m, 3H), 1.70-1.51 (m, 8H), 1.34-1.23 (m, 2H), 1.16 (d, J=6.6 Hz, 3H), 1.05 (s, 9H).

$^{13}$C NMR (100 MHz, CDCl$_3$): δ 173.4, 170.8, 168.1, 166.4, 161.6, 157.0, 145.2, 140.3, 137.5, 134.3, 134.1, 133.9, 124.2, 120.7, 108.2, 106.2, 81.8, 78.4, 74.3, 73.5, 60.7, 55.4, 37.7, 37.6, 37.3, 36.4, 35.9, 34.6, 32.8, 30.3, 29.9, 28.3, 26.7, 26.4, 26.2, 25.4, 25.2, 24.4, 17.2, 16.6, 3.6.

ESI-MS m/r. Calcd. for C$_{4}$$_{4H}$6$_1$ClN$_5$O$_{10}$: 819.44. Found: 820.4 (M+H)$^+$.

Example 8

Preparation of Compound 27

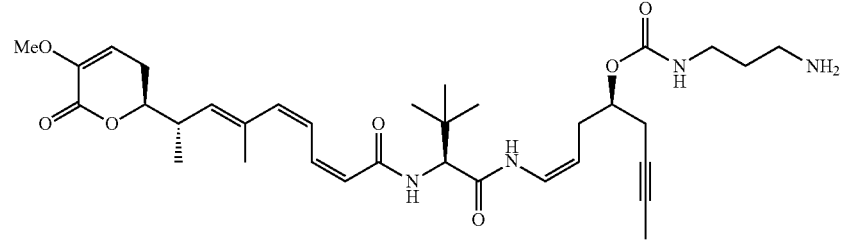

Compound 24

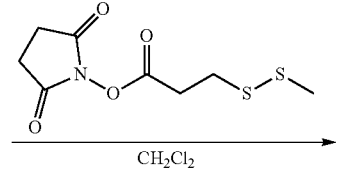

CH$_2$Cl$_2$

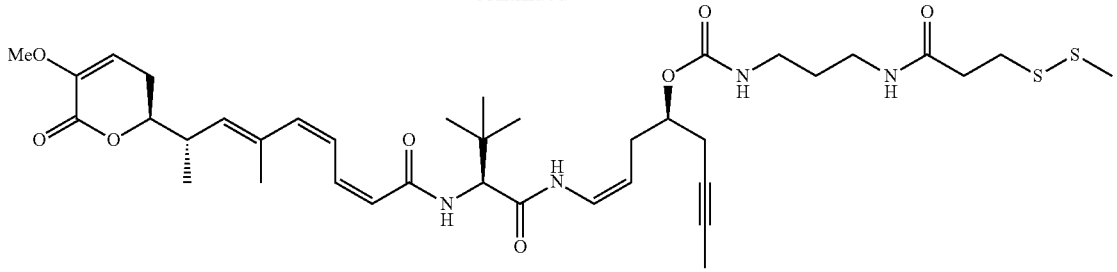

Compound 26

DTT
AcOEt:MeOH
NaH₂PO₄
EDTA

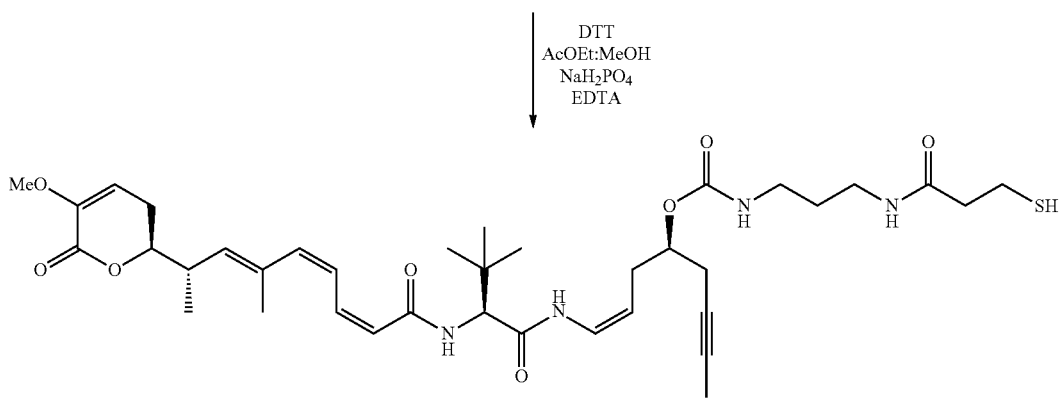

Compound 27

(a) Preparation of Compound 26

To a solution of Compound 24 (70 mg, 0.11 mmol), prepared as described in Example 7(b) above, in $CH_2Cl_2$ (2 mL) was added 3-(methyldisulfanyl)propanoic acid /V-hydroxysuccinimide ester (36.2 mg, 0.12 mmol). The reaction mixture was stirred at 23° C. for 16 h and concentrated under vacuum. The residue obtained was purified in a system for flash chromatography ($SiO_2$, Hex:EtOAc mixtures) to afford pure Compound 26 (46.3 mg, 61%) as a solid white.

¹H NMR (400 MHz, $CDCl_3$): δ 8.72 (d, J=10.8 Hz, 1H), 7.29-7.19 (m, 1H), 6.90 (t, J=11.3 Hz, 1H), 6.80 (t, J=9.7 Hz, 1H), 6.69 (t, J=6.1 Hz, 1H), 6.47 (d, J=9.4 Hz, 1H), 6.16 (d, J=11.0 Hz, 1H), 5.69 (d, J=11.5 Hz, 1H), 5.64 (dd, J=6.3, 3.1 Hz, 1H), 5.30 (d, J=0.5 Hz, 1H), 4.86 (q, J=8.4 Hz, 1H), 4.60-4.54 (m, 1H), 4.46 (d, J=9.4 Hz, 1H), 4.23 (ddd, J=11.5, 7.4, 4.8 Hz, 1H), 3.66 (s, 3H), 3.33-3.22 (m, 3H), 3.19-3.14 (m, 1H), 2.96 (t, J=7.2 Hz, 2H), 2.66-2.54 (m, 1H), 2.59 (t, J=7.2 Hz, 2H), 2.48-2.42 (m, 5H), 2.40 (s, 3H), 2.38-2.28 (m, 1H) 1.83 (s, 3H), 1.82 (s, 3H), 1.73-1.64 (m, 2H), 1.16 (d, J=6.7 Hz, 3H), 1.05 (s, 9H).

¹³C NMR (100 MHz, $CDCl_3$): δ 171.5, 168.1, 166.4, 165.2, 157.0, 145.1, 140.4, 137.5, 134.3, 134.0, 124.20, 124.0, 120.7, 108.2, 106.2, 81.8, 78.4, 74.2, 73.6, 60.7, 55.4, 37.8, 37.3, 35.9, 34.6, 33.1, 30.3, 29.8, 26.7, 26.2, 24.4, 23.0, 17.2, 16.6, 3.6.

(b) Preparation of Compound 27

A solution of Compound 26 (44.3 mg, 0.064 mmol), prepared as described in step (a) above, in a mixture of EtOAc (3.6 mL) and $CH_3OH$ (3.6 mL) was treated with a solution of dithiothreitol (0.19 mL of 1.0 M solution, 0.19 mmol) in 0.05 M potassium phosphate buffer (3.6 mL) at pH 7.5 containing 2 mM ethylenediaminetetraacetic acid (EDTA). The mixture was stirred at 23° C. for 4 h. The reaction was treated with a solution of 0.2 M potassium phosphate buffer (21 mL) at pH 6.0 containing 2 mM EDTA and then extracted with ethyl acetate. The combined organic layers were dried over anhydrous $Na_2SO_4$, filtered and concentrated under vacuum. The crude obtained was purified in a system for flash chromatography ($SiO_2$, Hex:EtOAc mixtures) to yield pure target Compound 27 (33.6 mg, 74%) as a solid white.

¹H NMR (500 MHz, $CDCl_3$): δ 8.73 (d, J=10.7 Hz, 1H), 7.27 (t, J=11.5 Hz, 1H), 6.91 (td, J=11.5, 1.1 Hz, 1H), 6.94-6.86 (m, 1H), 6.85-6.77 (m, 1H), 6.43 (d, J=9.4 Hz, 1H), 6.17 (dd, J=12.0, 1.6 Hz, 1H), 5.71 (d, J=11.4 Hz, 1H), 5.65 (dd, J=6.5, 2.9 Hz, 1H), 5.54 (t, J=6.3 Hz, 1H), 5.30 (d, J=10.5 Hz, 1H), 4.84 (q, J=8.3 Hz, 1H), 4.53 (d, J=9.5 Hz, 1H), 4.48-4.44 (m, 1H), 4.24 (ddd, J=11.5, 7.3, 4.2 Hz, 1H), 3.67 (s, 3H), 3.336-3.22 (m, 3H), 3.21-3.10 (m, 1H), 2.89-2.84 (m, 1H), 2.80 (dt, J=8.2, 6.8 Hz, 2H), 2.49 (t, J=7.2 Hz, 2H), 2.45-2.36 (m, 5H), 2.31-2.28 (m, 1H), 1.84 (s, 3H), 1.83 (s, 3H), 1.72-1.69 (m, 2H), 1.16 (d, J=6.7 Hz, 3H), 1.05 (s, 9H).

ESI-MS m/z: Calcd. for $C_{37}H_{54}N_4O_8S$: 714.37. Found: 737.3 (M+Na)⁺.

Example 9

Preparation of Antibody-Drug Conjugate ADC1 with Trastuzumab and Compound 1

(a) Partial Reduction of Trastuzumab to Give Partially Reduced Trastuzumab (Compound 20)

A Trastuzumab (Trastuzumab purchased from Roche as a white lyophilised powder for the preparation of a concentrated solution for infusion) solution (9.52 ml, 200 mg, 1.38μηηοl) was diluted to a concentration of 5 mg/mL with 20 mM histidine/acetate buffer (pH 5.5, 30.5 mL) followed by a pH adjustment with phosphate/EDTA buffer (pH 8.4, 13 mL). Partial reduction of the disulfide bonds in the antibody was performed by the addition of a 5.17 mM tris[2-carboxyethyl]phosphine hydrochloride (TCEP) solution (689 μl, 3.562μηηοl, 2.6 eq.) The reduction reaction was left to stir for 90 min at 20° C. Immediately after the reduction, an Ellman assay was performed to give a Free Thiol to Antibody ratio (FTAR) of 4.1, very close to the value of 4.0, as planned.

(b) Preparation of ADC1

To the solution of partially reduced Trastuzumab Compound 20 (24.98 mL, 93.0 mg, 0.64μηιοl), prepared as described in Example 7(a) above, in DMSO was added (1.25 mL) followed by addition of a freshly prepared solution of Compound 1, prepared as described in Example 1, (10 mM in DMSO, 366 μL, 3.66μηιοl, 5.7 eq.).

Upon addition of Compound 1, the solution turned very turbid, hence DMSO (1 mL) was additionally added. The conjugation reaction was stirred for 30 min at 20° C. and the turbidity vanished during the conjugation reaction. The excess of drug was quenched by addition of /V-acetylcysteine (NAC) (10 mM, 366 μL, 3.66μηιοl) followed by stirring the solution for 20 min. The quenched conjugation reaction was purified by Vivaspin centrifugation and the buffer was exchanged with the final PBS formulation buffer. The final target product ADC1 was concentrated to a final concentration of 8.56 mg/mL as determined by UV and 7.4 mL (63.3 mg, 0.43μηηοl, 68.0%) ADC solution was obtained. SEC HPLC runs were performed to determine the purity of the product (61.4%).

ADC1 was further purified by preparative gel filtration chromatography on an Akta purifier system using a HiLoad 16/600 superdex 200 column due to the presence of high amounts of aggregates. After pooling, the final concentration (1.6 mg/mL) was determined by UV and the purity (90.9%) of the final drug products was determined by SEC HPLC to yield 8.65 mL (13.7 mg, 0.09μηιοl, 14.7%) of the ADC solution (ADC1).

Example 10

Preparation of Antibody-Drug Conjugate ADC2 with Trastuzumab and Compound 5

(a) Partial Reduction of Trastuzumab to Give Partially Reduced Trastuzumab (Compound 20)

A Trastuzumab solution (14.29 mL, 300 mg, 2.06μηιοl) was diluted to a concentration of 5 mg/mL with 20 mM histidine/acetate buffer (pH, 5.5, 45.74 mL) followed by a pH adjustment with phosphate/EDTA buffer (pH 8.4, 14.4 mL). Partial reduction of the disulfide bonds in the antibody was performed by addition of a 5 mM tris[2-carboxyethyl] phosphine hydrochloride (TCEP) solution (1.07 mL, 5.36μηιοl, 2.6 eq.). The reduction reaction was left to stir for 90 min at 20° C. Immediately after the reduction, an Ellman assay was performed to give a Free Thiol to Antibody ratio (FTAR) of 4.1, very close to the value of 4.0, as planned.

(b) Preparation of ADC2

To the solution of partially reduced Trastuzumab Compound 20 (23.6 mL, 93.8 mg, 0.645μηιοl), prepared as described in Example 8(a) above, DMSO was added (1.18 mL) followed by the addition of freshly prepared solution of Compound 5, prepared as described in Example 2, (10 mM in DMSO, 368 μL, 3.68 ηηιοl, 5.7 eq.). The drug-linker was carefully added in 10 portions. After the sixth portion, the solution turned slightly turbid and the turbidity did not vanish during the conjugation reaction and quench. The conjugation reaction was stirred for 30 min at 20° C. The excess of drug was quenched by addition of /V-acetylcysteine (NAC) (10 mM, 368 μL, 3.68μηιοl) by stirring the solution for 46 min. The solution was filtered over a 0.2μηι syringe filter. The quenched conjugation reaction was concentrated to 16.5 mg/mL by Vivaspin centrifugation and was purified over NAP-25 columns. SEC HPLC runs were performed to determine the purity of the product (36.1%).

ADC2 was further purified by preparative gel filtration chromatography on an Akta purifier system using a HiLoad 16/600 superdex 200 column due to the presence of high amounts of aggregates. After pooling, the final concentration (3.7 mg/mL) was determined by UV and the purity (78.3%) of the final target ADC was determined by SEC HPLC to yield 5.3 mL (19.4 mg, 19.4%) of the ADC solution (ADC2).

Example 11

Preparation of Antibody-Drug Conjugate ADC3 with Trastuzumab and Compound 12

(a) Preparation of ADC3

To the solution of partially reduced Trastuzumab Compound 20 (23.6 mL, 93.8 mg, 0.645μηιοl), prepared as described in Example 10(a) above, DMSO was added (1.18 mL), followed by the addition of freshly prepared solution of Compound 12, prepared as described in Example 3, (10 mM in DMSO, 369 μL, 3.69 ηηιοl, 5.7 eq.). The drug-linker was carefully added in 10 portions, nevertheless the solution started to turn turbid after the third portion. High turbidity was observed during addition of the last two portions. The solution did not clear until the filtration step. The conjugation reaction was stirred for 31 min at 20° C. The excess of drug was quenched by addition of /V-acetylcysteine (NAC) (10 mM, 369 μL, 3.69μηιοl) by stirring the reaction mixture for 50 min. The quenched conjugation reaction solution was filtered over a 0.2μηι syringe filter and concentrated to 14.2 mg/mL by Vivaspin centrifugation. Then it was purified over NAP-25 columns. SEC HPLC runs were performed to determine the purity of the product (34.2%).

ADC3 was further purified by preparative gel filtration chromatography on an Akta purifier system using a HiLoad 16/600 superdex 200 column due to the presence of high amounts of aggregates. After pooling, the final concentration (2.3 mg/mL) was determined by UV and the purity (78.6%) of the final drug products was determined by SEC HPLC to yield 7.3 mL (16.6 mg, 16.6%) of the ADC solution (ADC3).

Example 12

Preparation of Antibody-Drug Conjugates ADCs 4, 5 and 6 with Trastuzumab and Compounds 13, 15 and 18 Respectively (a) SMCC Conjugation to Trastuzumab (Compound 21)

The buffer of the Trastuzumab solution (262 mg, 1.8μηιοl) was exchanged by phosphate buffer (50 mM phosphate, 2 mM EDTA, pH 6.5) using NAP-25 columns. To the pooled Trastuzumab solution in glass reactors (16-17

µg/L) DMSO was added (5%). The linker conjugation was started by adding SMCC (20.0 mM, 8.0 eq.) to the Trastuzumab solution. The reaction was stirred at 18° C. for 3 hours. The reaction mixture was then purified over NAP-25 columns to give Compound 21. A reversed Ellman assay was performed to determine a LAR of 3.7.

(b) Conjugation of Compounds 13, 15 and 18 to Trastuzumab-MCC: Preparation of ADC4, ADC5 and ADC6.

For the conjugation reaction, in a first step the antibody conjugate solution Compound 21, was diluted with phosphate buffer (50 mM phosphate, 2 mM EDTA, pH 6.5) to a concentration of 10 µg/L. Then DMSO (5%) was added to the Compound 21 solution. The conjugation reactions with compounds 13, 15 and 18 were carried out by slowly adding the drug (10 mM, 6.3-6.6 eq.) to the Compound 21 solution and stirring for four hours at 18° C. After the conjugation reaction was complete, the reaction mixtures were 0.2µ η] filtered and again purified over NAP-25 columns with a buffer exchange into 1×PBS buffer. SEC HPLC runs were performed to determine the purity of the product and the concentration of the final product was measured by UV.

ADC from sample preparation with compound 15 was isolated with good purity (74.5%) and a yield of 56% (49 mg) was obtained and did not require further purification. The final concentration (5.7 mg/mL) of the ADC5 solution (87 mL) was determined by UV.

However in the two sample preparations with compound 13 and 18, low molecular species were present. These species had a very similar retention time to the product peak and were not well separated on the SEC column. In order to remove possible remainders of drugs still present in the solution, the solutions were passed again over NAP-25 columns. The chromatograms after the first and second NAP-25 purification were identical, therefore species did not arise from free drugs still present in the solution and must be of larger origin. The samples were then further purified by gel filtration chromatography on a size exclusion column.

After pooling, the final concentrations (2.8 and 3.9 mg/mL) were determined by UV and the purity (62.3% and 50.9%) of the final drug products was determined by SEC HPLC to yield 6.7 mL (19.3 mg, 22.0%) of the ADC4 solution and 6.8 mL (26.7 mg, 30.5%) of the ADC6 solution, respectively.

Example 13

Preparation of Antibody-Drug Conjugates ADCs 7 and 8 with Trastuzumab and Compounds 25 and 27

(a) General Procedures

The antibody concentration was checked spectrophotometrically by monitoring its absorbance at 280 nm using a molar extinction coefficient of $2.18E5$ $M^{-1}$ $cm^{-1}$ and a molecular weight of 150 kDa. Buffers used in these processes were either buffer A (50 mM sodium phosphate pH 6.5 with 2 mM EDTA) or buffer B (50 mM sodium phosphate pH 8.0) or phosphate saline buffer ("PBS"). Drug to antibody ratio ("DAR") was deduced from the linker to antibody ratio ("LAR") in the case of conjugation via Lys, or from the free Cys per mol of antibody ratio in the case of Cys-targeted conjugation, assuming that the conjugation reaction of the drug-linker to either the maleimide connector or to free Cys was quantitative. Both determinations were based on the colorimetric reaction of 5,5'-dithiobis(2-nitrobenzoic acid) ("DTNB") with free thiol groups to form a colored thionitrobenzoate adduct. For LAR determination, the adduct was preformed by mixing equal volumes of a 200 µM solution of DTNB in buffer B with a 200 µM solution of /V-acetyl-cysteine in the same buffer. 75 µL of this mixture were then mixed with 75 µL of the test sample and after a 1 h incubation the absorbance at 412 nm was determined spectrophotometrically and the resulting value was compared to those obtained from a standard curve using known concentrations of 4-(/V-maleimidomethyl)cyclohexanecarboxylic acid N-hydroxysuccinimide ester ("SMCC") to obtain the concentration of maleimides in the sample. This concentration is then referred to the antibody concentration to calculate the LAR. Likewise, free Cys were determined by mixing 50 µL of the test sample with 150 µL of 133 µM DTNB in buffer B, monitoring absorbance at 412 nm and comparing the resulting value with those obtained from a standard curve using known concentrations of Cys: the deduced concentration of free Cys in the test sample is then referred to the antibody concentration to calculate the ratio.

(b) Preparation of the Antibody-Drug Conjugates

When the cytotoxic payload was conjugated to Cys residues (as with Compound 25 for the preparation of ADC7) the antibody was previously reduced with Tris(2-carboxyethyl)phosphine hydrochloride ("TCEP"). Briefly, a 70 µM (10.5 mg/mL) solution of the antibody in buffer B was mixed with the appropriate amount of a 5 mM solution of TCEP in water to keep the reducing agent in a 2.5-fold excess over the antibody. The mixture was incubated and stirred for 60 min at 20° C. and afterwards a small aliquot of the resulting reduced antibody was removed to calculate the free Cys to antibody ratio, while the remaining sample was mixed with the appropriate volume of a 10 mM solution of Compound 25 in DMSO to reach a 6-fold excess of the compound over the antibody: considering that the reduced antibody usually presents less than 6 free Cys per protein molecule, the molar ratio of the compound to the accessible free Cys is never below 1. DMSO was added if needed to keep its concentration at 5% (v/v) and the mixture was incubated for 30 min at 20° C. Afterwards /V-Acetyl-cysteine was added to quench the reaction, using the appropriate volume of a 10 mM solution in water to match the concentration of the drug-linker. The resulting conjugate was finally purified from the rest of the reagents by gel filtration in Sephadex G-25 using PD-10 columns from GE Healthcare. The presence of aggregates was checked by analytical size exclusion chromatography using an Akta FPLC system equipped with a Superdex-100 10/300 column running an isocratic method with PBS at 1 ml/min: if the area of the peak corresponding to aggregates exceeded 10% of the total peak area, monomers were purified using the same chromatography system with a Superdex 200 16/600 preparative column running the same method described above. Final ADC concentration was determined spectrophotometrically by monitoring its absorbance at 280 nm using the same molar extinction coefficient than that of the parental antibody: if the ADC concentration was below 2 mg/mL it was concentrated using Vivaspin devices from GE Healthcare and the new concentration was again determined as above.

When the cytotoxic payload was conjugated to Lys residues (as with Compound 27 for the preparation of ADC8), the antibody was previously activated with SMCC. Briefly, a 70 µM (10.5 mg/mL) solution of the antibody in buffer A was mixed with the appropriate amount of a 20 mM solution of SMCC in DMSO to keep the activating reagent in a 8-fold excess over the antibody. DMSO was added if necessary to reach a final DMSO concentration of 5% (v/v). The mixture was incubated and stirred for 3 h at 18° C. and the excess of SMCC was then removed by gel filtration chromatography on Sephadex G-25 using PD-10 columns from GE Healthcare. A small aliquot of the resulting activated antibody was removed to calculate the LAR and the remaining sample was mixed with the appropriate volume of a 10 mM solution of Compound 27 in DMSO to reach a 8-fold excess of the compound over the antibody: considering that LAR value never exceeds 8, this ensures that the molar ratio of the compound to the accessible reacting sites is never below 1. DMSO was added if needed to keep its concentration at 5% (v/v). The mixture was incubated for 4 h at 18° C. and the resulting conjugate was purified from the rest of the reagents by gel filtration in Sephadex G-25 using PD-10 columns from GE Healthcare. The presence of aggregates was checked by analytical size exclusion chromatography using an Akta FPLC system equipped with a Superdex-100 10/300 column running an isocratic method with PBS at 1 ml/min: if the area of the peak corresponding to aggregates exceeded 10% of the total peak area, monomers were purified using the same chromatography system with a Superdex 200 16/600 preparative column running the same method described above. Final ADC concentration was determined spectrophotometrically by monitoring its absorbance at 280 nm using the same molar extinction coefficient than that of the parental antibody: if the ADC concentration was below 2 mg/mL it was concentrated using Vivaspin devices from GE Healthcare and the new concentration was again determined as above.

Example 14

Preparation of Anti-CD4, Anti-CD5 and Anti-CD13 Monoclonal Antibodies

Anti-CD4, anti-CD5 and anti-CD13 monoclonal antibodies were obtained following well known procedures commonly used in the art. Briefly BALB/c mice were immunized with HPB-ALL cells (for the ultimate production of anti-CD4 antibody) or with human T-cells activated with a mixture of phorbol 12-myristate 13-acetate and commercially available anti-CD3 monoclonal antibody as described by Cebrian et al. (1988, J. Exp. Med. 168:1621-1637) (for the ultimate production of anti-CD5 antibody) or with human endothelial cells isolated from umbilical cord (for the ultimate production of anti-CD13 antibody). To that end, 1.5E7 of the corresponding cells were injected to the mice intraperitoneally on days −45 and −30 and intravenously on day −3. On day 0 spleen from these animals were removed and spleen cells were fused with SP2 mouse myeloma cells at a ratio of 4:1 according to standard techniques to produce the corresponding hybridomas and distributed on 96-well tissue culture plates (Costar Corp., Cambridge, MA). After 2 weeks hybridoma culture supernatants were harvested and their reactivity against the cell line used in the immunization step was tested by flow cytometry. Positive supernatants were assayed by immunofluorescence staining the corresponding cells used as antigens. Hybridomas showing a specific staining, immunoprecipitation pattern and cell distribution were selected and cloned and subcloned by limiting dilution.

Once the clones were selected, cells were cultured in RPMI-1640 medium supplemented with 10% (v/v) fetal calf serum, 2 mM glutamine, 100 U/mL penicillin and 100 µg/mL streptomycin at 37° C. during 3-4 days until the medium turned pale yellow. At that point, two thirds of the medium volume were removed, centrifuged at 1,000×g for 10 min to pellet the cells and the supernatant was either centrifuged again for further cleaning at 3,000×g for 10 min or filtered through 22µη pore size membranes. The clarified supernatant was subjected to precipitation with 55% saturation ammonium sulphate and the resulting pellet was resuspended in 100 mM Tris-HCl pH 7.8 (1 mL per 100 mL of the original clarified supernatant) and dialyzed at 4° C. for 16-24 h against 5 L of 100 mM Tris-HCl pH 7.8 with 150 mM NaCl, changing the dialyzing solution at least three times. The dialyzed material was finally loaded onto a Protein A-Sepharose column and the corresponding monoclonal antibody was eluted with 100 mM sodium citrate pH 3.0 or alternatively with 1M glycine pH 3.0. Those fractions containing the antibody were neutralized with 2M Tris-HCl pH 9.0 and finally dialyzed against PBS and stored at −80° C. until its use.

Example 15

Preparation of Antibody-Drug Conjugates ADCs 9, 10 and 11 with Anti-CD13 and Compounds 1, 12 and 13

(a) General Procedures

In all the methods reported herein the antibody concentration was checked spectrophotometrically by monitoring its absorbance at 280 nm using a molar extinction coefficient of 2.25E5 $M^{-1}$ $cm^{-1}$ and a molecular weight of 150 kDa. Buffers used in these processes were either buffer A (50 mM sodium phosphate pH 6.5 with 2 mM EDTA) or buffer B (50 mM sodium phosphate pH 8.0) or phosphate saline buffer ("PBS"). Drug to antibody ratio ("DAR") was deduced from the linker to antibody ratio ("LAR") in the case of conjugation via Lys, or from the free Cys per mol of antibody ratio in the case of Cys-targeted conjugation, assuming that the conjugation reaction of the drug-linker to either the maleimide connector or to free Cys was quantitative. Both determinations were based on the colorimetric reaction of 5,5'-dithiobis(2-nitrobenzoic acid) ("DTNB") with free thiol groups to form a colored thionitrobenzoate adduct. For LAR determination, the adduct was preformed by mixing equal volumes of a 200 µM solution of DTNB in buffer B with a 200 µM solution of N-acetyl-cysteine in the same buffer. 75 µl of this mixture were then mixed with 75 µl of the test sample and after a 1 h incubation the absorbance at 412 nm was determined spectrophotometrically and the resulting value was compared to those obtained from a standard curve using known concentrations of 4-(/V-maleimidomethyl)cyclohexanecarboxylic acid N-hydroxysuccinimide ester ("SMCC") to obtain the concentration of maleimides in the sample. This concentration is then referred to the antibody concentration to calculate the LAR. Likewise, free Cys were determined by mixing 50 µl of the test sample with 150 µl of 133 µM DTNB in buffer B, monitoring absorbance at 412 nm and comparing the resulting value with those obtained from a standard curve using known concentrations of Cys: the deduced concentration of free Cys in the test sample is then referred to the antibody concentration to calculate the ratio.

(b) Preparation of the Antibody-Drug Conjugates

When the cytotoxic payload was conjugated to Cys residues (as with Compound 1 for the preparation of ADC9 or Compound 12 for the preparation of ADC10) the antibody was previously reduced with Tris(2-carboxyethyl)phosphine hydrochloride ("TCEP"). Briefly, a 70 µM (10.5 mg/mL) solution of the antibody in buffer B was mixed with the appropriate amount of a 5 mM solution of TCEP in water to keep the reducing agent in a 2.5-fold excess over the antibody. The mixture was incubated and stirred for 60 min at 20° C. and afterwards a small aliquot of the resulting reduced antibody was removed to calculate the free Cys to antibody ratio, while the remaining sample was mixed with the appropriate volume of a 10 mM solution of the drug linker (Compound 1 for ADC9 or Compound 12 for ADC10) in DMSO to reach a 6-fold excess of the compound over the antibody: considering that the reduced antibody usually presents less than 6 free Cys per protein molecule, the molar ratio of the compound to the accessible free Cys is never below 1. DMSO was added if needed to keep its concentration at 5% (v/v) and the mixture was incubated for 30 min at 20° C. Afterwards N-Acetyl-cysteine was added to quench the reaction, using the appropriate volume of a 10 mM solution in water to match the concentration of the drug-linker. The resulting conjugate was finally purified from the rest of the reagents by gel filtration in Sephadex G-25 using PD-10 columns from GE Healthcare. The presence of aggregates was checked by analytical size exclusion chromatography using an Akta FPLC system equipped with a Superdex-100 10/300 column running an isocratic method with PBS at 1 ml/min: if the area of the peak corresponding to aggregates exceeded 10% of the total peak area, monomers were purified using the same chromatography system with a Superdex 200 16/600 preparative column running the same method described above. Final ADC concentration was determined spectrophotometncally by monitoring its absorbance at 280 nm using the same molar extinction coefficient than that of the parental antibody: if the ADC concentration was below 2 mg/mL it was concentrated using Vivaspin devices from GE Healthcare and the new concentration was again determined as above.

When the cytotoxic payload was conjugated to Lys residues (as with Compound 13 for the preparation of ADC11), the antibody was previously activated with SMCC. Briefly, a 70 µM (10.5 mg/mL) solution of the antibody in buffer A was mixed with the appropriate amount of a 20 mM solution of SMCC in DMSO to keep the activating reagent in a 8-fold excess over the antibody. DMSO was added if necessary to reach a final DMSO concentration of 5% (v/v). The mixture was incubated and stirred for 3 h at 18° C. and the excess of SMCC was then removed by gel filtration chromatography on Sephadex G-25 using PD-1 0 columns from GE Healthcare. A small aliquot of the resulting activated antibody was removed to calculate the LAR and the remaining sample was mixed with the appropriate volume of a 10 mM solution of Compound 13 in DMSO to reach a 8-fold excess of the compound over the antibody: considering that LAR value never exceeds 8, this ensures that the molar ratio of the compound to the accessible reacting sites is never below 1. DMSO was added if needed to keep its concentration at 5% (v/v). The mixture was incubated for 4 h at 18° C. and the resulting conjugate was purified from the rest of the reagents by gel filtration in Sephadex G-25 using PD-10 columns from GE Healthcare. The presence of aggregates was checked by analytical size exclusion chromatography using an Akta FPLC system equipped with a Superdex-100 10/300 column running an isocratic method with PBS at 1 ml/min: if the area of the peak corresponding to aggregates exceeded 10% of the total peak area, monomers were purified using the same chromatography system with a Superdex 200 16/600 preparative column running the same method described above. Final ADC concentration was determined spectrophotometrically by monitoring its absorbance at 280 nm using the same molar extinction coefficient than that of the parental antibody: if the ADC concentration was below 2 mg/mL it was concentrated using Vivaspin devices from GE Healthcare and the new concentration was again determined as above.

Example 16

Preparation of Antibody-Drug Conjugates ADCs 12 and 13 with Rituximab and Compounds 1 and 12

(a) General Procedures

The antibody concentration was checked spectrophotometrically by monitoring its absorbance at 280 nm using a molar extinction coefficient of 2.45E5 $M^{-1}$ $cm^{-1}$ and a molecular weight of 150 kDa. Buffers used in these processes were either buffer B (50 mM sodium phosphate pH 8.0) or phosphate saline buffer ("PBS"). Drug to antibody ratio ("DAR") was deduced from the free Cys per mol of antibody ratio, assuming that the conjugation reaction of the drug-linker to free Cys was quantitative. The determination was based on the colorimetric reaction of 5,5'-dithiobis(2-nitrobenzoic acid) ("DTNB") with free thiol groups to form a colored thionitrobenzoate adduct. 50 µl of the test sample were mixed with 150 µl of 133 µM DTNB in buffer B, absorbance at 412 nm was then measured and the resulting value compared with those obtained from a standard curve using known concentrations of Cys. The deduced concentration of free Cys in the test sample is then referred to the antibody concentration to calculate the ratio.

(b) Preparation of the Antibody-Drug Conjugates

Prior to conjugation to the drug-linkers via Cys, the antibody was reduced with Tris(2-carboxyethyl)phosphine hydrochloride ("TCEP"). Briefly, a 70 µM (10.5 mg/mL) solution of the antibody in buffer B was mixed with the appropriate amount of a 5 mM solution of TCEP in water to keep the reducing agent in a 2.5-fold excess over the antibody. The mixture was incubated and stirred for 60 min at 20° C. and afterwards a small aliquot of the resulting reduced antibody was removed to calculate the free Cys to antibody ratio, while the remaining sample was mixed with the appropriate volume of a 10 mM solution of the drug linker (Compound 1 for ADC12 or Compound 12 for ADC13) in DMSO to reach a 6-fold excess of the compound over the antibody: considering that the reduced antibody usually presents less than 6 free Cys per protein molecule, the molar ratio of the compound to the accessible free Cys is never below 1. DMSO was added if needed to keep its concentration at 5% (v/v) and the mixture was incubated for 30 min at 20° C. Afterwards /V-Acetyl-cysteine was added to quench the reaction, using the appropriate volume of a 10 mM solution in water to match the concentration of the drug-linker. The resulting conjugate was finally purified from the rest of the reagents by gel filtration in Sephadex G-25 using PD-10 columns from GE Healthcare. The presence of aggregates was checked by analytical size exclusion chromatography using an Akta FPLC system equipped with a Superdex-100 10/300 column running an isocratic method with PBS at 1 ml/min: if the area of the peak corresponding to aggregates exceeded 10% of the total peak area, monomers were purified using the same chromatography system with a Superdex 200 16/600 preparative column running the same method described above. Final ADC concentration was determined spectrophotometrically by monitoring its absorbance at 280 nm using the same molar extinction coefficient than that of the parental antibody: if the ADC concentration was below 1 mg/mL it was concentrated using Vivaspin devices from GE Healthcare and the new concentration was again determined as above.

Example 17

Preparation of Antibody-Drug Conjugates ADCs 14 and 15 with Anti-CD5 and Compounds 1 and 12

(a) General Procedures

The antibody concentration was checked spectrophotometrically by monitoring its absorbance at 280 nm using a molar extinction coefficient of 2.25E5 $M^{-1}$ $cm^{-1}$ and a molecular weight of 150 kDa. Buffers used in these processes were either buffer B (50 mM sodium phosphate pH 8.0) or phosphate saline buffer ("PBS"). Drug to antibody ratio ("DAR") was deduced from the free Cys per mol of antibody ratio, assuming that the conjugation reaction of the drug-linker to free Cys was quantitative. The determination was based on the colorimetric reaction of 5,5'-dithiobis(2-nitrobenzoic acid) ("DTNB") with free thiol groups to form a colored thionitrobenzoate adduct. 50 µl of the test sample were mixed with 150 µl of 133 µM DTNB in buffer B, absorbance at 412 nm was then measured and the resulting value compared with those obtained from a standard curve using known concentrations of Cys. The deduced concentration of free Cys in the test sample is then referred to the antibody concentration to calculate the ratio.

(b) Preparation of the Antibody-Drug Conjugates

Prior to conjugation to the drug-linkers via Cys, the antibody was reduced with Tris(2-carboxyethyl)phosphine hydrochloride ("TCEP"). Briefly, a 70 µM (10.5 mg/mL) solution of the antibody in buffer B was mixed with the appropriate amount of a 5 mM solution of TCEP in water to keep the reducing agent in a 2.5-fold excess over the antibody. The mixture was incubated and stirred for 60 min at 20° C. and afterwards a small aliquot of the resulting reduced antibody was removed to calculate the free Cys to antibody ratio, while the remaining sample was mixed with the appropriate volume of a 10 mM solution of the drug linker (Compound 1 for ADC14 or Compound 12 for ADC15) in DMSO to reach a 6-fold excess of the compound over the antibody: considering that the reduced antibody usually presents less than 6 free Cys per protein molecule, the molar ratio of the compound to the accessible free Cys is never below 1. DMSO was added if needed to keep its concentration at 5% (v/v) and the mixture was incubated for 30 min at 20° C. Afterwards /V-Acetyl-cysteine was added to quench the reaction, using the appropriate volume of a 10 mM solution in water to match the concentration of the drug-linker. The resulting conjugate was finally purified from the rest of the reagents by gel filtration in Sephadex G-25 using PD-10 columns from GE Healthcare. The presence of aggregates was checked by analytical size exclusion chromatography using an Akta FPLC system equipped with a Superdex-100 10/300 column running an isocratic method with PBS at 1 ml/min: if the area of the peak corresponding to aggregates exceeded 10% of the total peak area, monomers were purified using the same chromatography system with a Superdex 200 16/600 preparative column running the same method described above. Final ADC concentration was determined spectrophotometrically by monitoring its absorbance at 280 nm using the same molar extinction coefficient than that of the parental antibody: if the ADC concentration was below 1 mg/mL it was concentrated using Vivaspin devices from GE Healthcare and the new concentration was again determined as above.

Example 18

Preparation of Antibody-Drug Conjugates ADCs 16 and 17 with Anti-CD4 and Compounds 1 and 12

(a) General Procedures

The antibody concentration was checked spectrophotometrically by monitoring its absorbance at 280 nm using a molar extinction coefficient of 2.25E5 $M^{-1}$ $cm^{-1}$ and a molecular weight of 150 kDa. Buffers used in these processes were either buffer B (50 mM sodium phosphate pH 8.0) or phosphate saline buffer ("PBS"). Drug to antibody ratio ("DAR") was deduced from the free Cys per mol of antibody ratio, assuming that the conjugation reaction of the drug-linker to free Cys was quantitative. The determination was based on the colorimetric reaction of 5,5'-dithiobis(2-nitrobenzoic acid) ("DTNB") with free thiol groups to form a colored thionitrobenzoate adduct. 50 µl of the test sample were mixed with 150 µl of 133 µM DTNB in buffer B, absorbance at 412 nm was then measured and the resulting value compared with those obtained from a standard curve using known concentrations of Cys. The deduced concentration of free Cys in the test sample is then referred to the antibody concentration to calculate the ratio.

(b) Preparation of the Antibody-Drug Conjugates

Prior to conjugation to the drug-linkers via Cys, the antibody was reduced with Tris(2-carboxyethyl)phosphine hydrochloride ("TCEP"). Briefly, a 70 µM (10.5 mg/mL) solution of the antibody in buffer B was mixed with the appropriate amount of a 5 mM solution of TCEP in water to keep the reducing agent in a 2.5-fold excess over the antibody. The mixture was incubated and stirred for 60 min at 20° C. and afterwards a small aliquot of the resulting reduced antibody was removed to calculate the free Cys to antibody ratio, while the remaining sample was mixed with the appropriate volume of a 10 mM solution of the drug linker (Compound 1 for ADC16 or Compound 12 for ADC17) in DMSO to reach a 6-fold excess of the compound over the antibody: considering that the reduced antibody usually presents less than 6 free Cys per protein molecule, the molar ratio of the compound to the accessible free Cys is never below 1. DMSO was added if needed to keep its concentration at 5% (v/v) and the mixture was incubated for 30 min at 20° C. Afterwards /V-Acetyl-cysteine was added to quench the reaction, using the appropriate volume of a 10 mM solution in water to match the concentration of the drug-linker. The resulting conjugate was finally purified from the rest of the reagents by gel filtration in Sephadex G-25 using PD-10 columns from GE Healthcare. The presence of aggregates was checked by analytical size exclusion chromatography using an Akta FPLC system equipped with a Superdex-100 10/300 column running an isocratic method with PBS at 1 ml/min: if the area of the peak corresponding to aggregates exceeded 10% of the total peak area, monomers were purified using the same chromatography system with a Superdex 200 16/600 preparative column running the same method described above. Final ADC concentration was determined spectrophotometrically by monitoring its absorbance at 280 nm using the same molar extinction coefficient than that of the parental antibody: if the ADC concentration was below 1 mg/mL it was concentrated using Vivaspin devices from GE Healthcare and the new concentration was again determined as above.

Example 19 Synthesis of a Compound of Formula
D-X-(AA)$_W$-L$_1$

Preparation of Compound 28

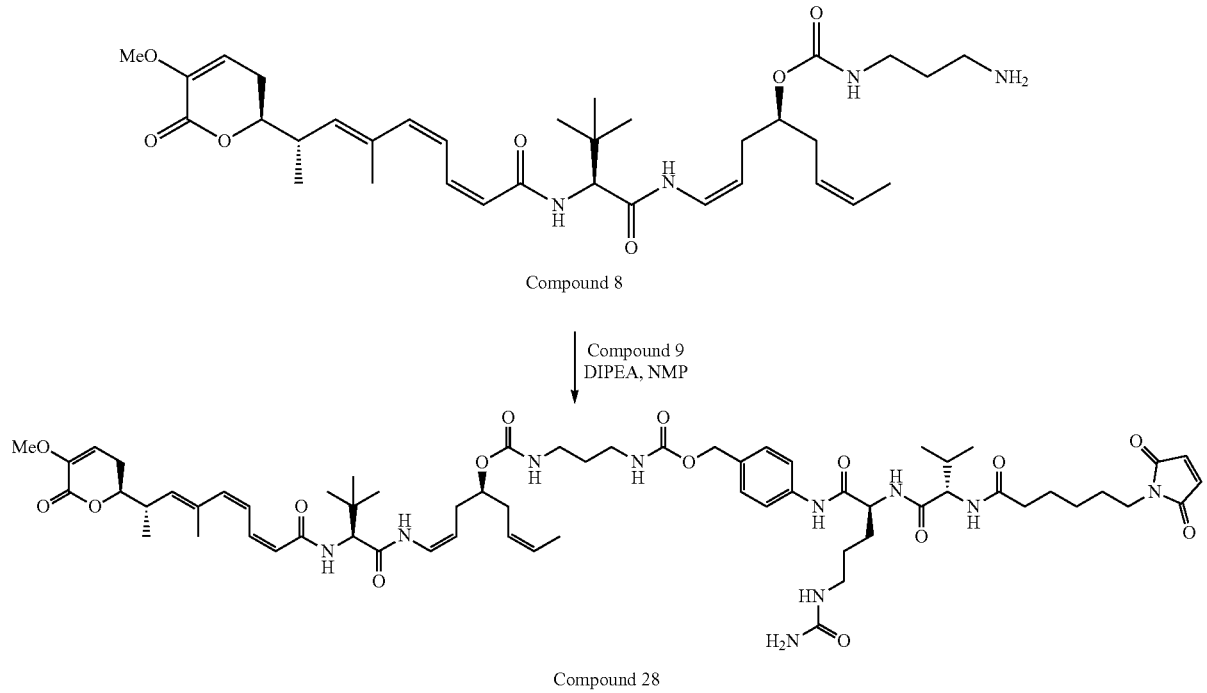

(a) Preparation of Compound 28

DIPEA (10 μL, 0.06 mmol) was added to a solution of Compound 9 (13 mg, 0.02 mmol), prepared as shown in the Preparative Example above, and Compound 8 (20 mg, 0.02 mmol), prepared as described in Example 2 above, in NMP (6.5 mL) at 23° C. After 9 h the reaction mixture was diluted with H$_2$O and extracted with EtOAc. The combined organic layers were dried over anhydrous Na$_2$SO$_4$, filtered, and concentrated under vacuum. The residue obtained was purified in a system for flash chromatography (SiO$_2$, DCM:CH$_3$OH, from 100:0 to 90:10) to afford pure target Compound 28 (9 mg, 38%).

$^1$H NMR (400 MHz, CDCl$_3$/CD$_3$OD): δ 9.40 (s, 1H), 8.92 (d, J=10.6 Hz, 1H), 7.67 (d, J=7.7 Hz, 1H), 7.47 (d, J=8.0 Hz, 2H), 7.21 (d, J=7.9 Hz, 2H), 7.16 (t, J=11.9 Hz, 1H), 6.97 (t, J=9.6 Hz, 2H), 6.82 (t, J=11.4 Hz, 1H), 6.67-6.64 (m, 1H), 6.64 (s, 2H), 6.08 (d, J=11.7 Hz, 1H), 5.68 (d, J=11.4 Hz, 1H), 5.62-5.58 (m, 1H), 5.54-5.47 (m, 1H), 5.35-5.29 (m, 1H), 5.20 (d, J=9.9 Hz, 1H), 4.94 (s, 2H), 4.77 (q, J=8.1 Hz, 1H), 4.54-4.45 (m, 2H), 4.37 (d, J=9.2 Hz, 1H), 4.20-4.12 (m, 1H), 4.08 (t, J=7.8 Hz, 1H), 3.58 (s, 3H), 3.42 (t, J=7.2 Hz, 2H), 3.18-3.00 (m, 7H), 2.81-2.75 (m, 1H), 2.35-2.30 (m, 3H), 2.29-2.25 (m, 3H), 2.17 (t, J=7.2 Hz, 2H), 2.14-2.06 (m, 1H), 2.04-1.92 (m, 1H), 1.86-1.74 (m, 1H), 1.76 (s, 3H), 1.61-1.42 (m, 10H), 1.54 (d, J=6.3 Hz, 3H), 1.30-1.14 (m, 4H), 1.08 (d, J=6.4 Hz, 3H), 0.94 (s, 9H), 0.86 (dd, J=6.8, 4.3 Hz, 6H).

$^{13}$C NMR (100 MHz, CDCl$_3$): δ 173.0, 172.1, 171.0, 170.2, 168.5, 167.1, 162.0, 161.3, 157.2, 157.0, 145.0, 140.2, 137.7, 137.5, 137.1, 134.0, 132.4, 128.8, 126.9, 124.9, 124.4, 124.3, 124.0, 120.5, 119.8, 108.6, 107.3, 81.9, 74.8, 66.1, 60.4, 58.8, 55.4, 37.6, 37.2, 36.0, 34.8, 31.9, 31.6, 30.9, 30.7, 30.0, 29.7, 29.3, 28.1, 26.5, 26.2, 26.1, 25.1, 19.2, 18.3, 17.1, 16.5, 12.9.

ESI-MS m/z: Calcd. for C$_{63}$H$_{90}$N$_{10}$O$_{15}$: 1226.7. Found: 1267.4 (M+H)$^+$.

Example 20 Synthesis of a Compound of Formula
D-X-(AA)$_W$-H

Preparation of Compound 36

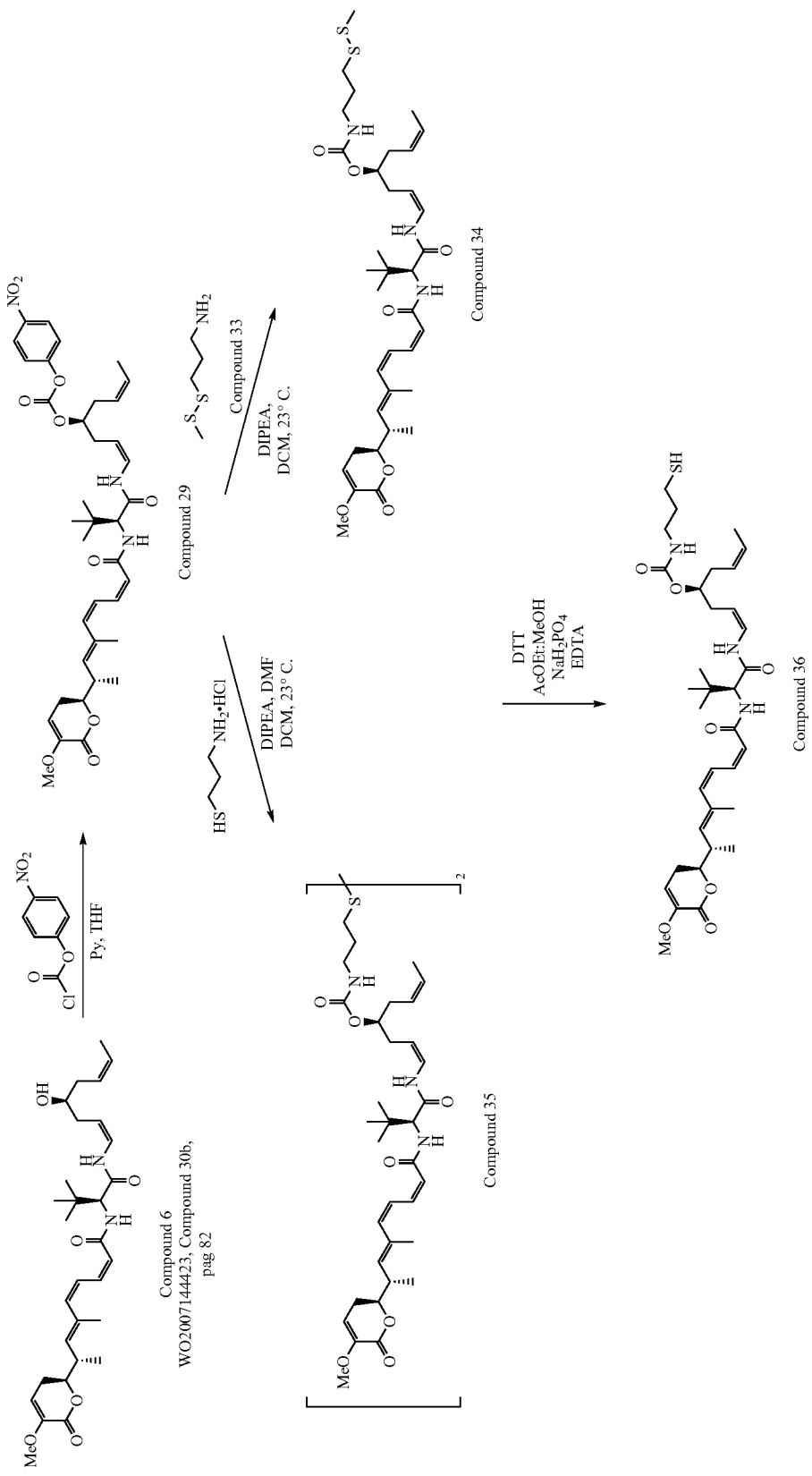

(a) Preparation of Compound 29

To a solution of Compound 6 (1.01 g, 1.91 mmol) (Compound 30b, prepared as described in WO 2007144423, the contents of which are incorporated herein by reference) in DCM (40 mL) were added pyridine (0.31 mL, 3.82 mmol) and 4-nitrophenyl chloroformate (769.7 mg, 3.82 mmol) at 0° C. The reaction mixture was stirred at 23° C. for 1.5 h, diluted with citric acid 10% and extracted with DCM. The combined organic layers were dried over anhydrous $Na_2SO_4$, filtered and concentrated under vacuum. The residue obtained was purified in a system for flash chromatography ($SiO_2$, Hex:EtOAc mixtures) to yield pure Compound 29 (783 mg, 59%).

$^1$H NMR (400 MHz, $CDCl_3$): δ 8.26 (d, J=9.2 Hz, 2H), 8.02 (d, J=10.9 Hz, 1H), 7.43 (d, J=9.2 Hz, 2H), 7.22 (t, J=9.2 Hz, 1H), 6.92-6.76 (m, 2H), 6.21 (d, J=9.3 Hz, 1H), 6.17-6.12 (m, 1H), 5.73-5.64 (m, 1H), 5.65-5.56 (m, 2H), 5.46-5.38 (m, 1H), 5.27 (d, J=9.9 Hz, 1H), 4.86 (q, J=8.2 Hz, 1H), 4.76 (p, J=6.2 Hz, 1H), 4.40 (d, J=9.3 Hz, 1H), 4.21 (ddd, J=10.7, 7.6, 4.9 Hz, 1H), 3.66 (s, 3H), 2.89-2.79 (m, 1H), 2.59-2.29 (m, 6H), 1.83 (d, J=1.3 Hz, 3H), 1.61 (s, 3H), 1.16 (d, J=6.7 Hz, 3H), 1.00 (s, 9H).

(b) Preparation of Compound 33

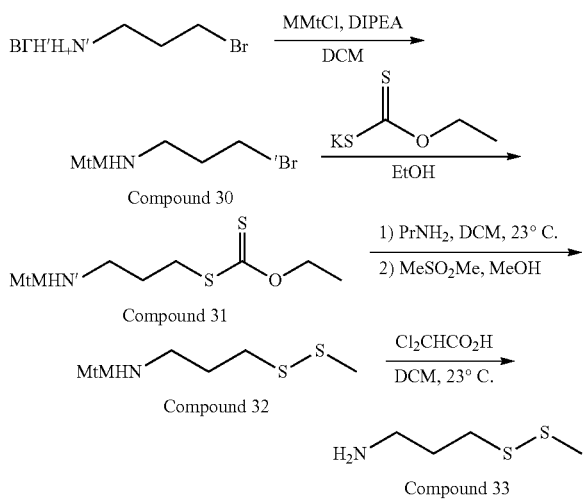

Preparation of Compound 30

To a solution of 3-bromopropylamine hydrobromide (1.22 g, 2.98 mmol) in $CH_2Cl_2$ (30 mL) was added 4-methoxytriphenylmethyl chloride (5.89 g, 19.1 mmol) and DIPEA (6.3, mL, 36.38 mmol). The reaction mixture was stirred at 23° C. overnight, diluted with $H_2O$ and extracted with $CH_2Cl_2$. The combined organic layers were dried over anhydrous $Na_2SO_4$, filtered and concentrated under vacuum. The residue obtained was purified in a system for flash chromatography ($SiO_2$, Hex:EtOAc mixtures) to afford pure Compound 30 (8.16 g, 100%) as a solid white.

$^1$H NMR (400 MHz, $CDCl_3$): δ 7.50-7.42 (m, 4H), 7.39-7.33 (m, 2H), 7.29-7.22 (m, 4H), 7.22-7.15 (m, 2H), 6.81 (d, J=8.9 Hz, 2H), 3.78 (s, 3H), 3.56 (t, J=6.8 Hz, 2H), 2.26 (t, J=6.7 Hz, 2H), 2.07-1.96 (m, 2H).

Preparation of Compound 31

To a solution of Compound 30 (1.49 g, 3.63 mmol) in ethanol (36 mL) was added potassium ethylxanthogenate (1.46 g, 9.08 mmol). The reaction mixture was stirred at 23° C. overnight and the precipitated potassium bromide was then filtered from the solution. After the filtrate was evaporated under reduced pressure, and the solid residue was triturated with Hexane. The resulting solid was eliminated by filtration and the filtrate was evaporated and purified by flash chromatography ($SiO_2$, Hex/EtOAc mixtures) to give Compound 31 (1.31 g, 80%).

$^1$H NMR (400 MHz, $CDCl_3$): δ 7.50-7.42 (m, 4H), 7.39-7.33 (m, 2H), 7.29-7.22 (m, 4H), 7.22-7.15 (m, 2H), 6.81 (d, J=8.9 Hz, 2H), 4.62 (q, J=7.1 Hz, 2H), 3.78 (s, 3H), 3.32-3.20 (dd, J=7.7, 6.9 Hz, 2H), 2.23 (t, J=6.7 Hz, 2H), 1.91-1.80 (m, 2H), 1.41 (t, J=7.1 Hz, 3H).

Preparation of Compound 32

To a solution of Compound 31 (3 g, 6.64 mmol) in DCM (10 mL) was added 1-propylamine (4.4 mL, 66.4 mmol). The reaction mixture was stirred at 23° C. for 10 min and concentrated under vacuum. The residue obtained was used in the next step without further purification. It was dissolved in dry methanol (50 mL) and cooled to 0° C. Methyl methanethiosulfonate (9.7 mL, 7.97 mmol) was added and the solution was stirred for 16 h at 23° C. The solvent was removed in vacuum, the residual oil was dissolved in dichloromethane, washed with pH 7 buffer and brine, dried and evaporated. The residue obtained was purified in a system for flash chromatography ($SiO_2$, Hex:EtOAc mixtures) to yield Compound 32 (1, 6 g, 59%).

$^1$H NMR (400 MHz, $CDCl_3$): δ 7.52-7.44 (m, 4H), 7.38 (d, J=8.9 Hz, 2H), 7.32-7.22 (m, 4H), 7.19 (d, J=7.3 Hz, 2H), 6.82 (d, J=8.9 Hz, 2H), 3.79 (s, 3H), 2.90-2.72 (m, 2H), 2.39 (s, 3H), 2.24 (t, J=6.7 Hz, 2H), 1.88 (p, J=6.9 Hz, 2H).

Preparation of Compound 33

To a solution of Compound 32 (1.22 g, 2.98 mmol) in $CH_2Cl_2$ (30 mL) was added dichloroacetic acid (0.9 mL, 10.9 mmol). The reaction mixture was stirred at 23° C. for 20 min and diluted with water. The organic layer was extracted and the aqueous phase was basificated with KOH 10%. Then it was extracted thoroughly with dichloromethane (3×), and the combined organic extracts were dried over $Na_2SO_4$, filtered and concentrated to give Compound 33 (409 mg, 100%).

$^1$H NMR (400 MHz, $CDCl_3$): δ 2.83-2.75 (m, 2H), 2.41 (s, 3H), 1.88-1.81 (m, 2H).

(c) Preparation of Compound 34

To a solution of Compound 29 (230.2 mg, 0.33 mmol), prepared as described in step (a) above, in $CH_2Cl_2$ (10 mL) was added Compound 33 (50 mg, 0.36 mmol) and DIPEA (0.06 mL, 0.36 mmol). The reaction mixture was stirred at 23° C. for 3 h, diluted with $H_2O$ and extracted with $CH_2Cl_2$. The combined organic layers were dried over anhydrous $Na_2SO_4$, filtered and concentrated under vacuum. The residue obtained was purified in a system for flash chromatography ($SiO_2$, Hex:EtOAc mixtures) to afford pure Compound 34 (150 mg, 66%).

$^1$H NMR (400 MHz, $CDCl_3$): δ 8.68 (d, J=10.7 Hz, 1H), 7.31 (t, J=6.0 Hz, 1H), 6.90 (dd, J=12.7, 10.2 Hz, 1H), 6.81 (dd, J=10.9, 8.5 Hz, 1H), 6.38 (d, J=9.4 Hz, 1H), 6.16 (d,

J=11.7 Hz, 1H), 5.69 (d, J=11.5 Hz, 1H), 5.65-5.52 (m, 3H), 5.41-5.37 (m, 1H), 5.29-5.56 (d, J=8.9 Hz, 1H), 4.83 (q, J=8.3 Hz, 1H), 4.54-4.50 (m, 1H), 4.46 (d, J=9.4 Hz, 1H), 4.24-4.19 (m, 1H), 3.65 (s, 3H), 3.36-3.16 (m, 2H), 2.86-2.82 (m, 1H), 2.70 (t, J=7.2 Hz, 2H), 2.44-2.35 (m, 5H), 2.40 (s, 3H), 2.19-2.04 (m, 1H), 1.98-1.83 (m, 2H), 1.84 (s, 3H), 1.63 (d, J=6.6 Hz, 3H), 1.16 (d, J=6.6 Hz, 3H), 1.05 (s, 9H).

ESI-MS m/z: Calcd. for $C_{35}H_{53}N_3O_7S_2$: 691.33. Found: 692.4 (M+H)$^+$.

(d) Preparation of Compound 35

To a solution of Compound 29 (121.3 mg, 0.17 mmol), prepared as described in step (a) above, in DCM (2.5 mL) were added a suspension of 3-aminopropane-1-thiol hydrochloride (37.2 mg, 0.29 mmol) in DCM (2.5 mL), DIPEA (59 μL, 0.34 mmol) and DMF (0.1 mL) at 23° C. The reaction mixture that was stirred at 23° C. for 7 h, diluted with H$_2$O and extracted with EtOAc. The combined organic layers were dried over anhydrous Na$_2$SO$_4$, filtered and concentrated under vacuum. The residue obtained was purified in a system for flash chromatography (SiO$_2$, Hex:EtOAc mixtures) to afford pure Compound 35 (40.5 mg, 37%).

$^1$H NMR (300 MHz, CDCl$_3$): δ 8.63 (d, J=10.6 Hz, 1H), 7.34-7.21 (m, 1H), 6.88 (t, J=11.4 Hz, 1H), 6.76 (t, J=9.6 Hz, 1H), 6.68 (d, J=9.3 Hz, 1H), 6.13 (d, J=11.6 Hz, 1H), 5.7-5.67 (m, 3H), 5.66-5.48 (m, 3H), 4.81 (q, J=8.1 Hz, 1H), 4.66-4.50 (m, 1H), 4.46 (d, J=9.2 Hz, 1H), 4.25-4.18 (m, 1H), 3.64 (s, 3H), 3.27-3.34 (m, 1H), 2.88-2.77 (m, 1H), 2.66 (t, J=7.2 Hz, 2H), 2.42-2.30 (m, 5H), 2.22-2.06 (m, 2H), 1.89-1.74 (m, 5H), 1.62 (d, J=6.6 Hz, 3H), 1.15 (d, J=6.7 Hz, 3H), 1.05 (s, 9H).

ESI-MS m/z: Calcd. for $C_{68}H_{100}ON_6O_{14}S_2$: 1288.67. Found: 1289.4 (M+H)$^+$.

(e) Preparation of Compound 36

A solution of Compound 35 (40.5 mg, 0.03 mmol) in a mixture of EtOAc (1.5 mL) and CH$_3$OH (1.5 mL) was treated with a solution dithiothreitol (0.36 mL, 0.36 mmol) in 0.05 M potassium phosphate buffer (1.2 mL) at pH 7.5 containing 2 mM ethylenediaminetetraacetic acid (EDTA). The mixture was stirred at 23° C. for 4 h. The reaction was treated with a solution of 0.2 M potassium phosphate buffer at pH 6.0 containing 2 mM EDTA and the extracted with EtOAc (×3). The combined organic layers were dried over anhydrous Na$_2$SO$_4$, filtered and concentrated under vacuum. The residue obtained was purified in a system for HPLC (SiO$_2$, Hex:EtOAc mixtures) to yield Compound 36 (15 mg, 38%).

$^1$H NMR (300 MHz, CDCl$_3$): δ 8.70 (d, J=10.7 Hz, 1H), 7.35-7.21 (m, 1H), 6.89 (t, J=11.4 Hz, 1H), 6.80 (t, J=9.8 Hz, 1H), 6.42 (d, J=9.4 Hz, 1H), 6.16 (d, J=11.3 Hz, 1H), 5.75-5.48 (m, 3H), 5.52-5.13 (m, 3H), 4.83 (q, J=8.3 Hz, 1H), 4.65-4.38 (m, 2H), 4.32-4.16 (m, 1H), 3.65 (s, 3H), 3.29 (q, J=6.6 Hz, 2H), 2.85 (dt, J=9.8, 6.9 Hz, 1H), 2.54 (q, J=7.3 Hz, 2H), 2.48-2.26 (m, 5H), 2.19-2.01 (m, 1H), 1.89-1.74 (m, 5H), 1.63 (dd, J=6.8, 1.7 Hz, 3H), 1.16 (d, J=6.6 Hz, 3H), 1.05 (s, 9H).

ESI-MS m/z: Calcd. for $C_{34}H_{51}N_3O_7S$: 645.85. Found: 668.4 (M+Na)$^+$.

Example 21. Alternative Synthesis of Compound 14

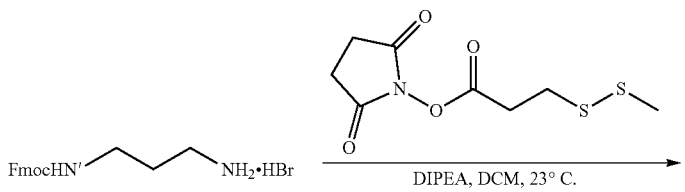

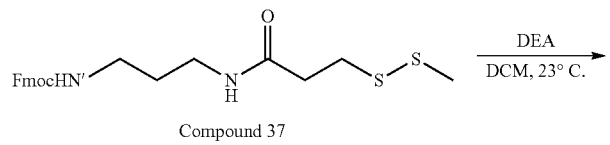

Compound 37

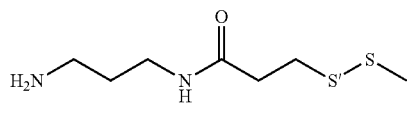

Compound 38

+

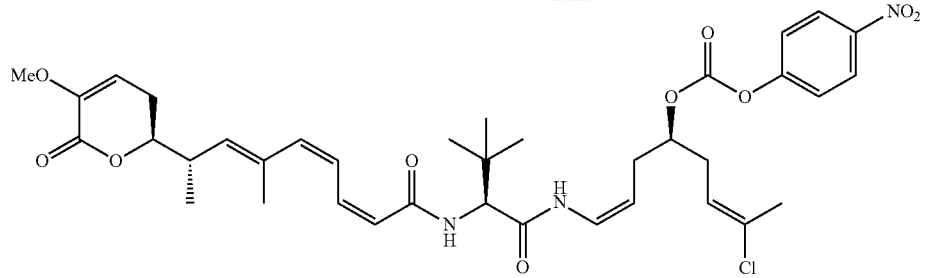

Compound 16

DIPEA,
DCM, 23° C.

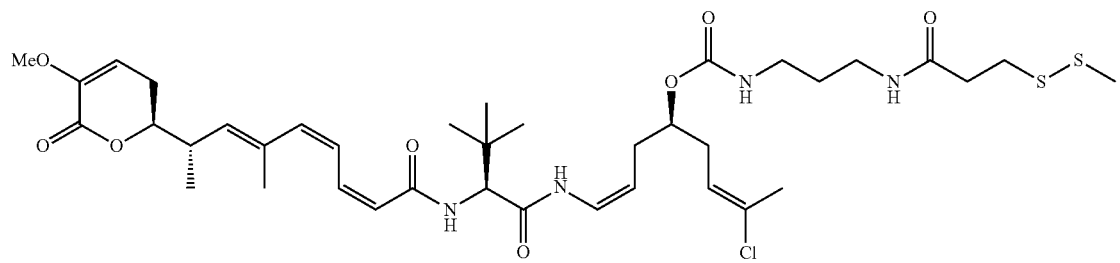

Compound 14

(a) Preparation of Compound 37

To a solution of *N*-Fmoc-1,3-propanediamine hydrobromide (377 mg, 1 mmol) in CH$_2$Cl$_2$ (15 mL) was added DIPEA (0.52 mL, 3 mmol) and 6-Maleimidohexanoic acid *N*-hydroxysuccinimide ester (323.7 mg, 1.1 mmol). The reaction mixture was stirred at 23° C. overnight and concentrated under vacuum. The residue obtained was purified in a system for flash chromatography (SiO$_2$, Hex:EtOAc mixtures) to afford pure Compound 37 (430 mg, 100%) as a white solid.

$^1$H NMR (400 MHz, CDCl$_3$): δ 7.76 (dd, J=7.6, 1.0 Hz, 2H), 7.64-7.55 (m, 2H), 7.45-7.37 (m, 2H), 7.31 (td, J=7.5, 1.2 Hz, 2H), 6.16 (bs, 1H), 5.24 (bs, 1H), 4.42 (d, J=6.9 Hz, 2H), 4.21 (t, J=6.8 Hz, 1H), 3.27 (dq, J=18.3, 6.3 Hz, 4H), 2.99 (t, J=7.0 Hz, 2H), 2.62 (t, J=7.0 Hz, 2H), 2.41 (s, 3H), 1.71-1.59 (m, 2H).

(b) Preparation of Compound 38

To a solution of 37 (430 mg, 1 mmol), prepared as described in step (a) above, in CH$_2$Cl$_2$ (8 mL) was added diethylamine (1.4 ml, 13.5 mmol). The reaction mixture was stirred at 23° C. for 6 h and concentrated under vacuum. The residue obtained was triturated with Et$_2$O and filtrated to obtain Compound 38 (148 mg, 71%) as a white solid.

$^1$H NMR (400 MHz, CDCl$_3$): δ 3.29 (td, J=6.5, 2.3 Hz, 2H), 3.01-2.86 (m, 2H), 2.78 (t, J=6.6 Hz, 2H), 2.57 (t, J=7.1 Hz, 2H), 2.37 (s, 3H), 1.69 (p, J=6.6 Hz, 2H).

(c) Preparation of Compound 14

To a solution of Compound 16 (60 mg, 0.08 mmol), prepared as described in Example 5(a) above, in CH$_2$Cl$_2$ (2 mL) was added a solution of Compound 38 (58 mg, 0.28 mmol), prepared as described in step (b) above, and DIPEA (0.1 mL, 0.56 mmol) in CH$_2$Cl$_2$ (2 mL). The reaction mixture was stirred at 23° C. for 3 h, diluted with H$_2$O and extracted with CH$_2$Cl$_2$. The combined organic layers were dried over anhydrous Na$_2$SO$_4$, filtered and concentrated under vacuum. The residue obtained was purified in a system for flash chromatography (SiO$_2$, Hex:EtOAc mixtures) to afford pure Compound 14 (60.5 mg, 95%).

$^1$H NMR (500 MHz, CDCl$_3$): δ 8.88 (d, J=10.8 Hz, 1H), 7.29-7.24 (m, 1H), 6.90 (t, J=11.5 Hz, 1H), 6.82 (t J=9.1 Hz, 1H), 6.63 (t, J=6.1 Hz, 1H), 6.49 (d, J=9.4 Hz, 1H), 6.16 (dd, J=11.5, 1.5 Hz, 1H), 5.70 (d, J=11.5 Hz, 1H), 5.68-5.51 (m, 3H), 5.29 (d, J=9.7 Hz, 1H), 4.81 (q, J=8.2 Hz, 1H), 4.52 (d, J=9.5 Hz, 1H), 4.52-4.43 (m, 1H), 4.24 (ddd, J=11.5, 7.3, 4.3 Hz, 1H), 3.66 (s, 3H), 3.37-3.21 (m, 3H), 3.21-3.12 (m, 1H), 2.97 (t, J=7.2 Hz, 2H), 2.90-2.81 (m, 1H), 2.60 (t, J=7.2 Hz, 2H), 2.49-2.35 (m, 3H), 2.39 (s, 3H), 2.33 (t, J=7.0 Hz, 2H), 2.14-2.07 (m, 1H), 2.07 (s, 3H), 1.84 (s, 3H), 1.73-1.64 (m, 2H), 1.16 (d, J=6.7 Hz, 3H), 1.05 (s, 9H).

$^{13}$C NMR (125 MHz, CDCl$_3$): δ 171.6, 168.2, 166.4, 161.6, 157.2, 145.2, 140.3, 137.4, 134.2, 134.0, 131.9, 124.4, 124.1, 122.4, 120.7, 108.3, 105.6, 81.8, 74.8, 60.6, 60.4, 55.5, 37.8, 37.2, 36.2, 35.6, 34.7, 33.1, 31.0, 29.8, 26.7, 26.2, 23.0, 21.0, 17.2, 16.6.

Example 22. Alternative Synthesis of Compound 15

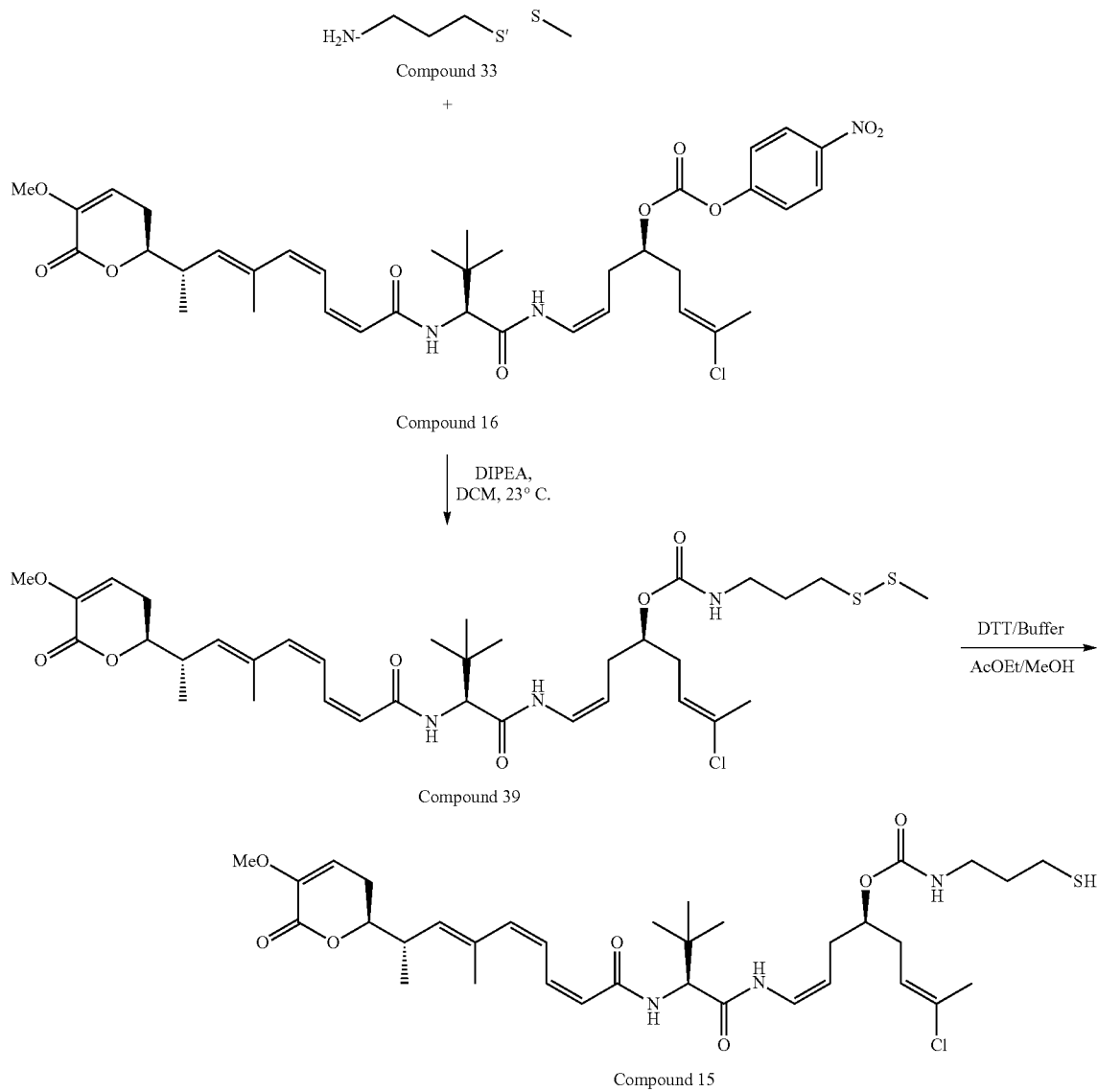

(a) Preparation of Compound 39

To a solution of Compound 16 (178.7 mg, 0.25 mmol), prepared as described in Example 5(a) above, in CH$_2$Cl$_2$ (2.5 mL) was added Compound 33 (120 mg, 0.88 mmol), prepared as described in Example 20(b) above, and DIPEA (0.05 mL, 0.25 mmol). The reaction mixture was stirred at 23° C. for 2 h, diluted with H$_2$O and extracted with CH$_2$Cl$_2$. The combined organic layers were dried over anhydrous Na$_2$SO$_4$, filtered and concentrated under vacuum. The residue obtained was purified in a system for flash chromatography (SiO$_2$, Hex:EtOAc mixtures) to afford pure Compound 39 (100 mg, 56%).

$^1$H NMR (400 MHz, CDCl$_3$): δ 8.65 (d, J=10.7 Hz, 1H), 7.28 (t, J=11.6 Hz, 1H), 6.90 (t, J=11.5 Hz, 1H), 6.82 (t, J=9.6 Hz, 1H), 6.37 (d, J=9.4 Hz, 1H), 6.17 (d, J=11.7 Hz, 1H), 5.69 (d, J=11.4 Hz, 1H), 5.64-5.57 (m, 2H), 5.34 (t, J=6.2 Hz, 1H), 5.29 (d, J=10.0 Hz, 1H), 4.81 (q, J=8.3 Hz, 1H), 4.54-4.49 (m, 1H), 4.45 (d, J=9.4 Hz, 1H), 4.28-4.17 (m, 1H), 3.66 (s, 3H), 3.37-3.21 (m, 2H), 2.85 (dt, J=9.7, 6.9 Hz, 1H), 2.71 (t, J=7.2 Hz, 2H), 2.44-2.30 (m, 5H), 2.38 (s, 3H) 2.13-2.06 (m, 1H), 2.07 (s, 3H), 1.93 (p, J=6.9 Hz, 2H), 1.84 (s, 3H), 1.16 (d, J=6.6 Hz, 3H), 1.06 (s, 9H).

ESI-MS m/z: Calcd. for C$_{35}$H$_{52}$ClN$_3$O$_7$S$_2$: 725.9. Found: 748.3 (M+Na)$^+$.

(b) Preparation of Compound 15

A solution of Compound 39 (90 mg, 0.12 mmol), prepared as described in Example 5(a) above, in a mixture of EtOAc (6.7 mL) and CH$_3$OH (6.7 mL) was treated with a dithiothreitol solution (0.36 mL, 0.36 mmol) in 0.05 M potassium phosphate buffer (6.7 mL) at pH 7.5 containing 2 mM ethylenediaminetetraacetic acid (EDTA). The mixture was stirred at 23° C. for 4 h. The reaction was treated with a solution of 0.2 M potassium phosphate buffer at pH 6.0 containing 2 mM EDTA and the extracted with EtOAc (×3). The combined organic layers were dried over anhydrous $Na_2SO_4$, filtered and concentrated under vacuum. The residue obtained was purified in a system for flash chromatography ($SiO_2$, Hex: EtOAc mixtures) to yield pure target Compound 15 (40.2 mg, 46%).

$^1$H NMR (500 MHz, $CDCl_3$): δ 8.66 (d, J=10.7 Hz, 1H), 7.29 (t, J=11.2 Hz, 1H), 6.91 (t, J=11.5 Hz, 1H), 6.83 (t, J=9.7 Hz, 1H), 6.38 (d, J=9.4 Hz, 1H), 6.17 (d, J=11.8 Hz, 1H), 5.70 (d, J=11.4 Hz, 1H), 5.65-5.51 (m, 2H), 5.34 (t, J=6.3 Hz, 1H), 5.29 (d, J=10.0 Hz, 1H), 4.82 (q, J=8.3 Hz, 1H), 4.56-4.48 (m, 1H), 4.45 (d, J=9.3 Hz, 1H), 4.22 (ddd, J=11.4, 7.5, 4.3 Hz, 1H), 3.67 (s, 3H), 3.31 (q, J=6.4 Hz, 2H), 2.88-2.83 (m, 1H), 2.55 (q, J=7.7 Hz, 2H), 2.47-2.30 (m, 5H), 2.12-2.07 (m, 1H), 2.08 (s, 3H), 1.88-1.76 (m, 5H), 1.17 (d, J=6.6 Hz, 3H), 1.06 (s, 9H).

$^{13}$C NMR (125 MHz, $CDCl_3$): δ 168.2, 166.2, 161.5, 156.7, 145.2, 140.2, 137.3, 134.2, 134.0, 132.0, 124.4, 124.2, 122.3, 120.8, 108.1, 105.5, 81.8, 74.5, 60.6, 55.4, 39.6, 37.3, 34.6, 33.9, 33.3, 30.8, 26.7, 26.3, 21.8, 21.1, 17.2, 16.7.

ESI-MS m/z: Calcd. for $C_{34}H_{50}ClN_3O_7S$: 679.3. Found: 702.4 (M+Na)$^+$.

Examples Demonstrating the Cytotoxicity of the Antibody-Drug Conjugates of the Present Invention Bioassays for the Detection of Antitumor Activity The aim of the assay was to evaluate the in vitro cytostatic (ability to delay or arrest tumor cell growth) or cytotoxic (ability to kill tumor cells) activity of the samples being tested.

Cell Lines and Cell Culture

All tumor cell lines used in this study were obtained from the American Type Culture Collection (ATCC), unless otherwise indicated; BT-474 (ATCC HTB-20, Breast Ductal Carcinoma), SK-BR-3 (ATCC HTB-30, Breast Adenocarcinoma) and HCC-1954 (ATCC CRL-2338, Breast Ductal Carcinoma), all HER2+; MDA-MB-231 (ATCC HTB-26, Breast Adenocarcinoma) and MCF-7 (ATCC HTB-22 Breast Adenocarcinoma, pleural effusion), all HER2-; SK-OV-3 (ATCC HTB-77, Ovary Adenocarcinoma), HER2+; NB-4 (Acute Promyelocytic Leukemia, APL, CD13+, M. Lanotte et al. (1991) *NB4, a maturation inducible cell line with t(15;17) marker isolated from a human acute promyelocytic leukemia (M3). Blood* 77, 1080-1086), (CD13+) and U937 (ATCC CRL-1 593.2, Histiocytic Lymphoma, CD13+ and CD4+); Raji (ATCC CCL-86, Burkitt's Lymphoma) (CD13-, CD20+, CD5-, and CD4-); RPMI-8226 (ATCC CRM-CCL-155, Multiple Myeloma) (CD13-, CD20-, CD5- and CD4-); Karpas-299 (DSMZ ACC-31, Non-Hodgkin's Lymphoma) (CD20-, CD5+, and CD4+); MOLT-4 (ATCC CRL-1 582, Acute Lymphoblastic Leukemia, CD5+). In addition, the two Raji cell (ATCC CCL-86, Burkitt's Lymphoma) clones used in this study Raji-clone #10 (high CD5 expression) and Raji-clone18 (null CD5 expression), were provided by Dr. Juan M. Zapata (Instituto de Investigaciones Biomedicas "Alberto Sols", CSIC-UAM, Madrid, Spain). Cells were maintained at 37° C., 5% CO 2 and 95% humidity in Dulbecco's Modified Eagle's Medium (DMEM) (for MCF and MDA-MB-231 cells), RPMI-1640 (for SK-BR-3, HCC-1954, NB-4, U937, Raji, RPMI-8226, Karpas-299, MOLT-4, Raji-clone #10 and Raji-clone #18 cells), RPMI-1640+1% ITS (for BT-474 cells) or McCOyS (for SK-OV-3 cells), all media supplemented with 10% Fetal Calf Serum (FCS) and 100 units/mL penicillin and streptomycin.

Cytotoxicity Assay

For adherent cells: A colorimetric assay using sulforhodamine B (SRB) was adapted for quantitative measurement of cell growth and cytotoxicity, as described in V. Vichai and K. Kirtikara (2006) Sulforhodamine B colorimetric assay for cytotoxicity screening. *Nature Protocols,* 1, 1112-1 116. Briefly, cells were seeded in 96-well microtiter plates and allowed to stand for 24 hours in drug-free medium before treatment with vehicle alone or the indicated compounds for 72 hours. For quantification, cells were washed twice with phosphate buffered saline (PBS), fixed for 15 min in 1% glutaraldehyde solution, rinsed twice with PBS, stained in 0.4% SRB-1% acetic acid solution for 30 min, rinsed several times with 1% acetic acid solution and air-dried. SRB was then extracted in 10 mM trizma base solution and the optical density measured at 490 nm in a microplate spectrophotometer. Cell survival was expressed as percentage of control, untreated cell survival.

For suspension cells: A standard metabolic assay using MTT (3-(4,5-Dimethylthiazol-2-yl)-2,5-diphenyltetrazolium bromide) was adapted for quantitative measurement of cell growth and cytotoxicity, as described in T. Mosmann (1983) *Rapid colorimetric assay for cellular growth and survival: Application to proliferation and cytotoxicity assays. J. Immunol. Meth.,* 65, 55-63. Briefly, MTT solution was added to the cell cultures at a final concentration of 0.5 mg/mL, and incubated for 1 to 4 hours at 37° C. until formazan crystals are formed. Culture medium is carefully removed from the cell cultures and formazan crystals resuspended in 100 µl DMSO. After mixing to assure solubilization, the quantity of formazan (presumably directly proportional to the number of viable cells) is measured by recording changes in absorbance at 570 nm using a plate reading spectrophotometer. Cell survival was expressed as percentage of control, untreated cell survival.

The $IC_{50}$ value refers to the concentration of compound inducing a 50% of cell death as compared to the control cell survival.

Bioactivity Example 1—Cytotoxicity of ADC1 and Related Reagents Against HER2 Positive and Negative Breast Cancer Cells The in vitro cytotoxicity of ADC1 along with the parent cytotoxic Compounds 1 and 4 and Trastuzumab was evaluated against different human breast cancer cell lines overexpressing or not the HER2 receptor, including BT-474, HCC-1954 and SK-BR-3 (HER2 positive cells) and MDA-MB-231 and MCF-7 (HER negative cells). SK-OV-3, a HER2+ ovarian cancer cell line, was also included in the study as a non-breast tissue cell model. Standard dose-response (DR) curves for 72 hours were performed.

Cytotoxicity of Trastuzumab

First of all, the in vitro cytotoxicty of Trastuzumab was assayed against the different tumor cell lines. In triplicate DR curves ranging from 5.0E01 to 2.6E-03 µg/mL (3.4E-07-1.8E-1 1 M), in two independent experiments, Trastuzumab was completely inactive, not reaching the $IC_{50}$ in any of the cell lines tested, independently of their HER2 status (see Table 3).

TABLE 3

Summary of the in vitro cytotoxicity of Trastuzumab

| | Trastuzumab | | | | | |
|---|---|---|---|---|---|---|
| | Breast cells | | | | | Ovary cells |
| | HER2+ | | | HER2− | | HER2+ |
| | BT-474 | HCC1954 | SK-BR3 | MCF7 | MDA-MB-231 | SK-OV-3 |
| IC50 (ug/mL) | >5.0E+01 | >5.0E+01 | >5.0E+01 | >5.0E+01 | >5.0E+01 | >5.0E+01 |
| IC50 (Molar) | >3.44E−07 | >3.44E−07 | >3.44E−07 | >3.44E−07 | >3.44E−07 | >3.44E−07 |

Cytotoxicity of Compound 4

The cytotoxicity of the intermediate Compound 4 was assayed in DR curves using ten serial dilutions (1/2.5 ratio) from 1E-01 to 2.6E-05 µg/mL (1.5E-07 to 3.9E-1 1 M).

The cytotoxicity of this compound, in two independent experiments, was relatively homogenous along the different cell lines tested, with $IC_{50}$ values in the low nanomolar range, from 8.9E-05 to 1.7E-03 µg/mL (1.34E-1 0 to 2.6E-09 M), with the mean $IC_{50}$ value across the whole cell panel being 5.69E-04 µg/mL (8.57E-10 M). In addition, the cytotoxicity of Compound 4 was independent of the HER2 status of the tumor cell lines (see Table 4).

Cytotoxicity of ADC1

The cytotoxicity of ADC1 was assayed against the different cell lines. To ensure the appropriate range of concentrations, the conjugate was assayed in six different, triplicate DR curves (ten serial dilutions, 1/2.5 ratio) starting from 50, 10, 1, 0.1, 0.01 and 0.001 µg/mL (equivalent to 3.3E-07, 6.6E-08, 6.6E-09, 6.6E-10, 6.6E-1 1 and 6.6E-12 molar concentration), in two independent experiments.

Figure 3:
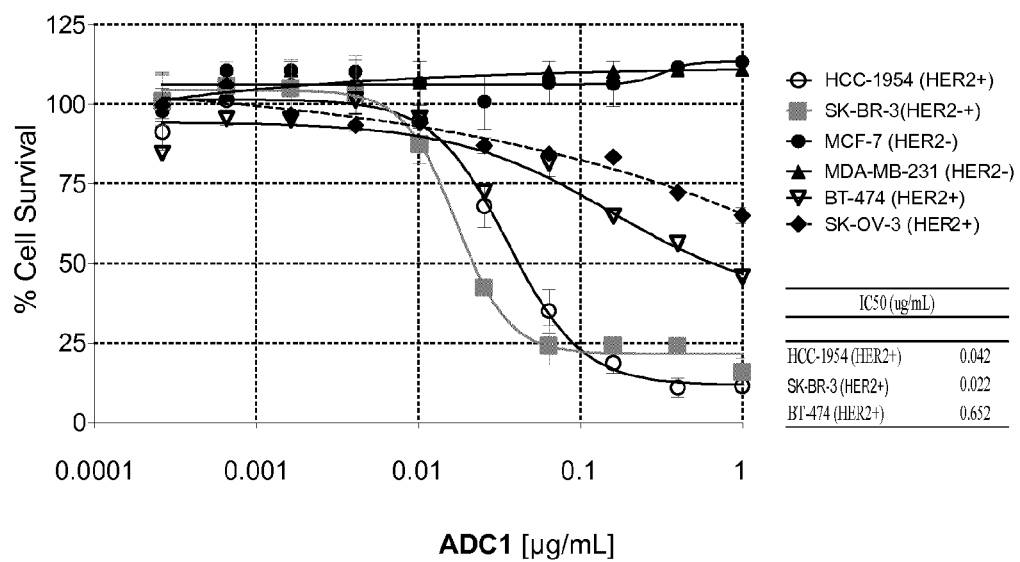
FIG. 3 is a representative dose response curves for ADC1 against various cancer cell lines.

A representative DR curve is shown in FIG. 3.

After adjusting the different DR curves, the mean $IC_{50}$ value calculated for the ADC1 against the different cell lines is shown in Table 6 below. ADC1 showed a cytotoxicity

TABLE 4

Summary of the in vitro cytotoxicity of Compound 4

| | Compound 4 | | | | | |
|---|---|---|---|---|---|---|
| | Breast cells | | | | | Ovary cells |
| | HER2+ | | | HER2− | | HER2+ |
| | BT-474 | HCC1954 | SK-BR3 | MCF7 | MDA-MB-231 | SK-OV-3 |
| IC50 (ug/mL) | 1.74E−03 | 1.30E−04 | 8.90E−05 | 4.15E−04 | 3.10E−04 | 7.30E−04 |
| IC50 (Molar) | 2.62E−09 | 1.96E−10 | 1.34E−10 | 6.26E−10 | 4.68E−10 | 1.10E−09 |

Cytotoxicity of Compound 1

The activity of parent Compound 1 was assayed using the same conditions as above, from 1E-01 to 2.6E-05 µg/mL (1.1E-07 to 3.0E-1 1 M). The cytotoxicity of this compound, in two independent experiments, was also relatively homogenous along the different cell lines tested, with $IC_{50}$ values in the low nanomolar range, from 8.9E-04 to 6.4E-03 µg/mL (1.04E-09 to 7.47E-09 M), with the mean $IC_{50}$ value across the whole cell panel being 3.41 E-03 µg/mL (3.98E-09 M). The maleimide linker seemed to slightly decrease the cytotoxic effect of the compound. Again, the cytotoxicity of Compound 1 was independent of the HER2 status of the tumor cell lines (see Table 5).

relatively similar to that of the parent compound Compound 1 alone and, importantly, a clear specificity against HER2+ expressing cells. We assume, therefore, that the conjugate was actually acting through the interaction of the mAb with the membrane associated HER2 receptor on the tumor cells, and subsequent intracellular delivery of the cytotoxic drug into the target tissue. Among the HER2 positive cell lines, there were significant differences in sensitivity against ADC1. The most sensitive cell lines were HCC-1954 and SK-BR-3, showing $IC_{50}$s of 3.88E-02 and 2.45E-02 µg/mL (equivalent to 2.581 E-10 and 1.63E-10 M), followed by BT-474 cells, which showed a significantly higher $IC_{50}$ value of 7.4E-01 µg/mL (equivalent to 4.93E-09 M). The

TABLE 5

Summary of the in vitro cytotoxicity of Compound 1

| | Compound 1 | | | | | |
|---|---|---|---|---|---|---|
| | Breast cells | | | | | Ovary cells |
| | HER2+ | | | HER2− | | HER2+ |
| | BT-474 | HCC1954 | SK-BR3 | MCF7 | MDA-MB-231 | SK-OV-3 |
| IC50 (ug/mL) | 6.40E−03 | 9.60E−04 | 8.90E−04 | 3.70E−03 | 2.80E−03 | 5.70E−03 |
| IC50 (Molar) | 7.47E−09 | 1.12E−09 | 1.04E−09 | 4.32E−09 | 3.27E−09 | 6.66E−09 | ovarian cell line SK-OV-3 showed an even higher $IC_{50}$ value of 7.0E+00 μg/mL (equivalent to 4.67E-08 M). The two HER negative cells showed a similar sensitivity in the order of 2.0E+01 μg/mL (equivalent to around 1.OE-07 M) (see Table 6).

The cytotoxicity of this compound, in two independent experiments, was relatively homogenous along the different cell lines tested, with $IC_{50}$ values in the nanomolar range, from 3.40E-03 to 6.75E-03 μg/m L (5.4E-09 to 1.OE-08 M), with the mean $IC_{50}$ value across the whole cell panel being 5.53E-03 μg/mL (equivalent to 8.79E-09 M). In addition, the cytotoxicity of Compound 8 was independent of the HER2 status of the tumor cell lines (Table 7).

TABLE 6

Summary of the in vitro cytotoxicity of ADC1 Compound ADC1

| Cell line | Breast cells | | | | | Ovary cells |
|---|---|---|---|---|---|---|
| | HER2+ | | | HER2- | | HER2+ |
| HER2 status | BT-474 | HCC1954 | SK-BR3 | MCF7 | MDA-MB-231 | SK-OV-3 |
| IC50 (ug/mL) | 7.40E-01 | 3.88E-02 | 2.45E-02 | 1.20E+01 | 2.00E+01 | 7.00E+00 |
| Mean IC50 (ug/mL) HER2 (breast) positive cells | | | | | | 2.68E-01 |
| Mean IC50 (ug/mL) HER2 (breast) negative cells | | | | | | 1.60E+01 |
| IC50 (M) | 4.93E-09 | 2.58E-10 | 1.63E-10 | 7.97E-08 | 1.33E-07 | 4.67E-08 |
| Mean IC50 (M) HER2 (breast) positive cells | | | | | | 1.79E-09 |
| Mean IC50 (M) HER2 (breast) negative cells | | | | | | 1.07E-07 |

Thus, the most responsive HER2 positive cell lines were around 300-800 times more sensitive that the HER2 negative cell lines, indicating the specificity of the conjugate against the HER2 expressing cells.

Figure 4:
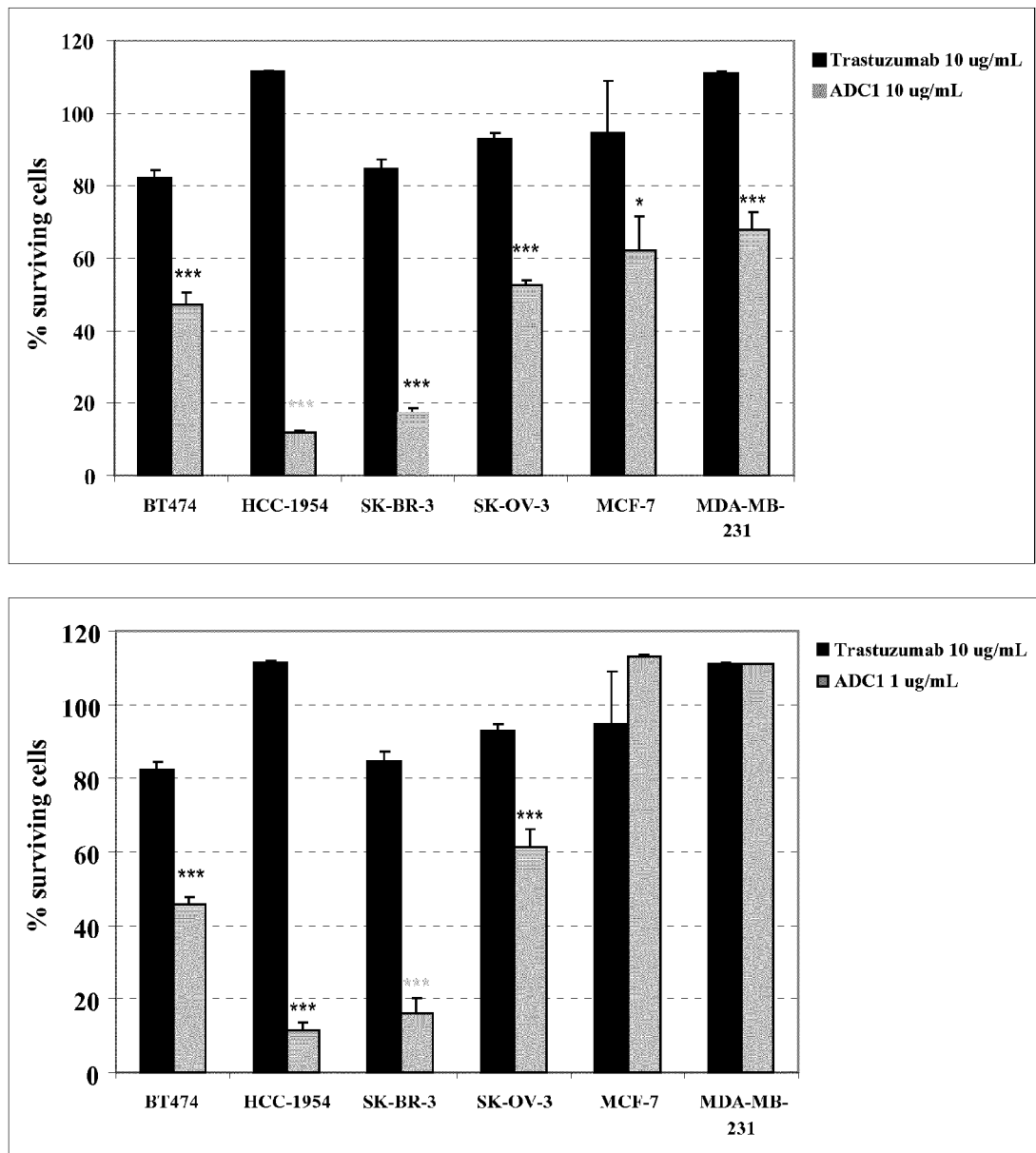
FIG. 4 shows histograms showing the percentages of cell survival after treatment of the different cell lines with the mAb alone (10 µg/mL) or ADC1 at 10 or 1 µg/mL.

To graphically compare the cytotoxicity of the mAb Trastuzumab alone with that of the conjugate ADC1, histograms showing the percentages of cell survival after treatment of the different cell lines with the mAb alone (10 μg/mL) or ADC at 10 or 1 g/mL, are shown in FIG. 4. As can be seen from FIG. 4, at an equal concentration of 10 μg/mL, the mAb Trastuzumab alone showed little or no cytotoxicity (<20% max) against any of the cell lines tested, independently of their HER2 status. In contrast, ADC1 showed a potent cytotoxicity against the HER2 expressing cells, HCC-1954 and SK-BR-3 and, to a lesser extent, BT-474 and SK-OV-3, inducing a mean inhibition of the cell survival of 88%, 82%, 52% and 47% respectively, as compared to the control cells. At this concentration, ADC1 displayed some cytotoxicity against the HER negative cells MCF-7 and MDA-MB-231, with mean percentages of cell survival inhibition of 38% and 32%, respectively. At a concentration of 1 μg/mL, ADC1 conjugate showed a somewhat similar cytotoxicity against the HER2 positive cells to that observed at 10 μg/mL, but in this case without detectable effects on HER2 negative cells (FIG. 4).

These results clearly demonstrated the remarkable cytotoxicity and specificity of ADC1 conjugate against HER2 expressing human tumor cells in vitro.

Bioactivity Example 2—Cytotoxicity of ADC2 and Related Reagents Against HER2 Positive and Negative Breast Cancer Cells The in vitro cytotoxicity of ADC2, a Trastuzumab-Compound 5 ADC, along with the parent cytotoxic Compounds 5 and 8 and the mAb Trastuzumab was evaluated against different human breast cancer cell lines expressing or not the HER2 receptor, including HCC-1954 and SK-BR-3 (HER2 positive cells) and MDA-MB-231 and MCF-7 (HER negative cells). Standard dose-response (DR) curves for 72 hours were performed.

Cytotoxicity of Compound 8

The cytotoxicity of the intermediate Compound 8 was assayed in DR curves using ten serial dilutions (1/2.5 ratio) from 01 E+00 to 2.6E-04 μg/mL (1.6E-06 to 4.0E-10 M).

TABLE 7

Summary data of the in vitro cytotoxicity of Compound 8

| | Compound 8 Breast cells | | | |
|---|---|---|---|---|
| | HER2+ | | HER2- | |
| | HCC1954 | SK-BR3 | MCF7 | MDA-MB-231 |
| IC50 (ug/mL) | 5.40E-03 | 3.40E-03 | 6.75E-03 | 6.55E-03 |
| IC50 (Molar) | 8.59E-09 | 5.41E-09 | 1.07E-08 | 1.04E-08 |

Cytotoxicity of Compound 5

The activity of Compound 5, the modified Compound 8 carrying the maleimide linker, was assayed in the same conditions as above, from 01E+00 to 2.6E-04 Mg/mL (1.2E-06 to 3.1 E-10 M).

The cytotoxicity of this compound, in two independent experiments, was also relatively homogenous along the different cell lines tested, with $IC_{50}$ values in the nanomolar range, from 1.9E-02 to 7.7E-02 μg/mL (2.32E-08 to 9.41 E-08 M), being the mean $IC_{50}$ value across the whole cell panel 4.33E-02 μg/mL (5.26E-08 M). The presence of the maleimide linker in Compound 5 slightly decreased the cytotoxicity of the compound as compared to Compound 8. Also, the cytotoxicity of Compound 5 seemed to be independent of the HER2 status of the tumor cell lines (Table 8).

TABLE 8

Summary data of the in vitro cytotoxicity of Compound 5

| | Compound 5 Breast cells | | | |
|---|---|---|---|---|
| | HER2+ | | HER2- | |
| | HCC1954 | SK-BR3 | MCF7 | MDA-MB-231 |
| IC50 (ug/mL) | 1.95E-02 | 1.90E-02 | 7.75E-02 | 5.70E-02 |
| IC50 (Molar) | 2.38E-08 | 2.32E-08 | 9.41E-08 | 6.94E-08 |

Cytotoxicity of ADC2

Figure 5:
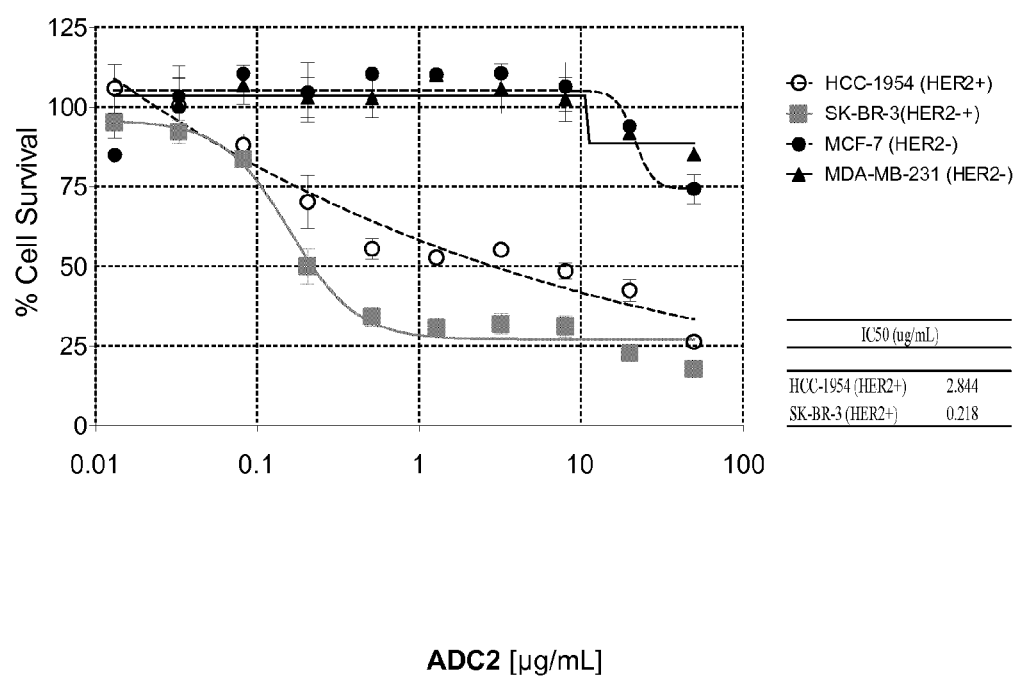
FIG. 5 is a representative dose response curves for ADC2 against various cancer cell lines.

The cytotoxic activity of the ADC2 was assayed against the different cell lines. Just to assure the appropriate range of concentrations, the conjugate was assayed in five different concentration ranges, each in triplicate DR curves (ten serial dilutions, 1/2.5 ratio) starting from 50, 10, 1, 0.1, and 0.01 µg/mL, in two independent experiments. A representative DR curve is shown in FIG. 5. After adjusting all the different DR curves, the mean $IC_{50}$ values calculated for the ADC2 against the different cell lines are shown in Table 9. The conjugate ADC2 showed specificity against the HER2+ expressing cells, HCC-1954 and SK-BR-3, in which the compound demonstrated a cytotoxicity similar to that of the parent Compound 5, with mean $IC_{50}$ values of 5.8E+00 and 2.2E-01 µg/mL (equivalent to 4.0E-08 and 1.5E-09 M), respectively. The two HER-cell lines, MCF-7 and MDA-MB-231, were virtually unresponsive to ADC2 in the range of concentrations tested, not reaching an $IC_{50}$ value (>5.0E+01 µg/mL) (see FIG. 5 and Table 9).

We assume, therefore, that the conjugate was actually acting through the interaction of the mAb with the membrane associated HER2 receptor on tumor cells, and subsequent intracellular delivery of the cytotoxic drug into the target tissue.

TABLE 9

Summary data of the in vitro cytotoxicity of ADC2 (Trastuzumab-Compound 5 ADC)

ADC2 (Trastuzumab-Compound 5 ADC)

| Cell line | Breast cells | | | |
|---|---|---|---|---|
| | HER2+ | | HER2− | |
| HER2 status | HCC1954 | SK-BR3 | MCF7 | MDA-MB-231 |
| IC50 (ug/mL) | 5.80E+00 | 2.20E−01 | >5.0E+01 | >5.0E+01 |
| Mean IC50 (ug/mL) HER2 positive cells | | | 3.01E+00 | |
| Mean IC50 (ug/mL) HER2 negative cells | | | | >5.0E+01 |
| IC50 (M) | 4.00E−08 | 1.52E−09 | >3.4E−07 | >3.4E−07 |
| Mean IC50 (M) HER2 positive cells | | | 2.08E−08 | |
| Mean IC50 (M) HER2 negative cells | | | | >3.4E−07 |

Figure 6:
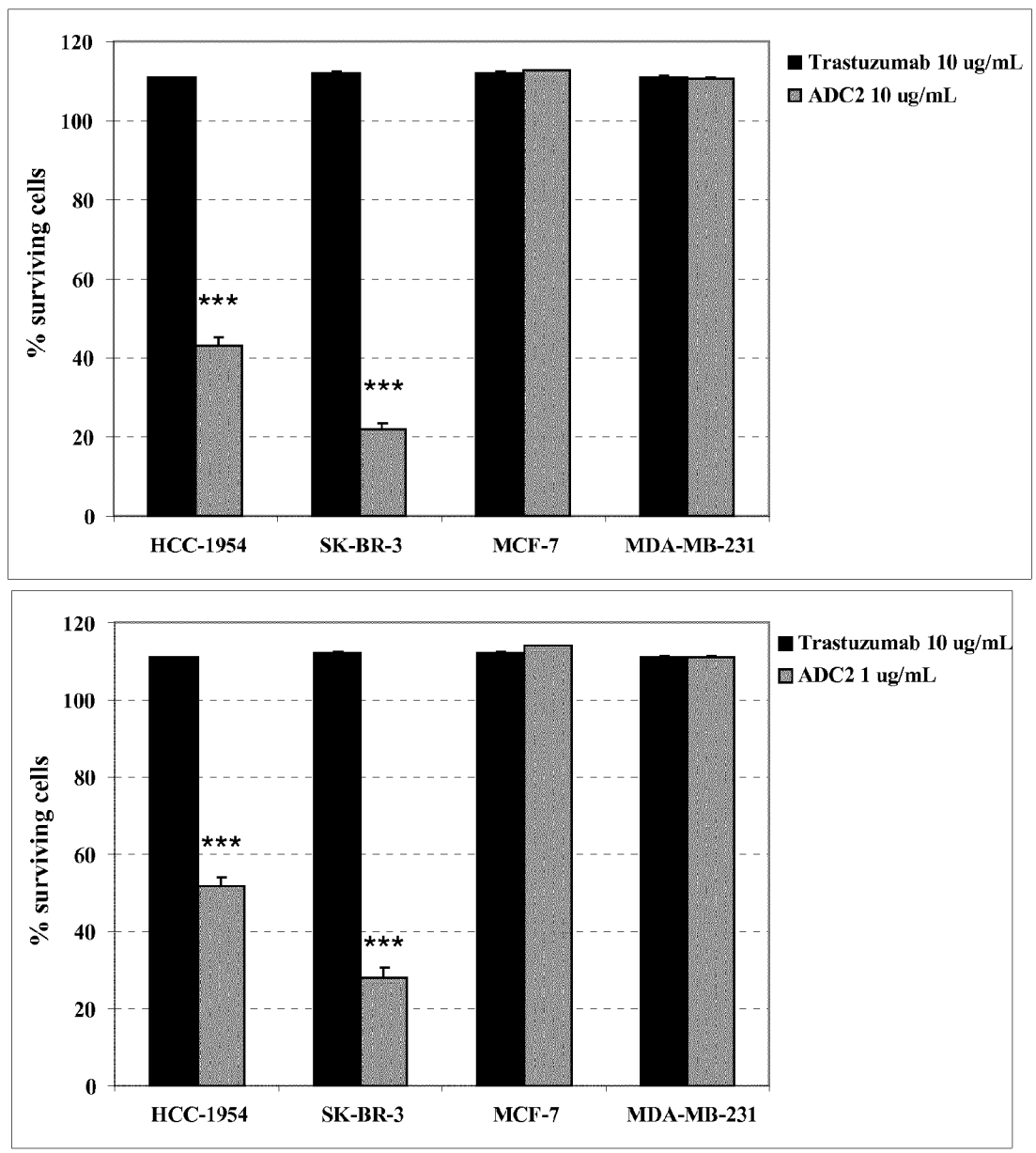
FIG. 6 shows histograms showing the percentages of cell survival after treatment of the different cell lines with the mAb alone (10 µg/mL) or ADC2 at 10 or 1 µg/mL.

To graphically compare the cytotoxicity of the Trastuzumab alone with that of the conjugate ADC2, histograms showing the percentages of cell survival after treatment of the different cell lines with Trastuzumab alone (10 µg/mL) or the ADC at 10 or 1 ug/mL, are shown in FIG. 6. At a concentration of 10 µg/mL, the mAb Trastuzumab alone showed no cytotoxicity against any of the cell lines tested, independently of their HER2 status. In contrast, ADC2 conjugate presented a significant and specific cytotoxicity against HER2 expressing cells HCC-1954 and SK-BR-3, inducing a mean inhibition of the cell survival of 57% and 78%, respectively, as compared to the control cells.

At a concentration of 1 µg/mL, ADC2 conjugate showed a somewhat similar cytotoxicity against the HER2 positive cells to that observed at 10 µg/mL, again, without detectable effects on HER2 negative cells (FIG. 6).

These results clearly demonstrated the remarkable cytotoxicity and specificity of ADC2 conjugate against HER2 expressing human tumor cells in vitro.

Bioactivity Example 3—Cytotoxicity of ADC3 and Related Reagents Against HER2 Positive and Negative Breast Cancer Cells The in vitro cytotoxicity of ADC3, along with the parent cytotoxic Compounds 12 and 4 and the mAb Trastuzumab was evaluated against different human breast cancer cell lines expressing or not the HER2 receptor, including HCC-1954 and SK-BR-3 (HER2 positive cells) and MDA-MB-231 and MCF-7 (HER negative cells). Standard dose-response (DR) curves for 72 hours were performed.

Cytotoxicity of Compound 4

The cytotoxicity of the parent Compound 4 was assayed in DR curves using ten serial dilutions (1/2.5 ratio) from 01E-02 to 2.6E-06 µg/mL (1.5E-07 to 3.9E-12 M).

The cytotoxicity of Compound 4, in two independent experiments, was homogenous along the different cell lines tested, with $IC_{50}$ values in the picomolar range, from 1.16E-04 to 2.80E-04 µg/mL (1.75E-10 to 4.23E-10 M), with the mean $IC_{50}$ value across the whole cell panel being 1.97E-04 µg/mL (equivalent to 2.96E-10 M). In addition, the cytotoxicity of Compound 4 was independent of the HER2 status of the tumor cell lines (Table 10).

TABLE 10

Summary data of the in vitro cytotoxicity of Compound 4

| | Compound 4 Breast cells | | | |
|---|---|---|---|---|
| | HER2+ | | HER2− | |
| | HCC1954 | SK-BR3 | MCF7 | MDA-MB-231 |
| IC50 (ug/mL) | 1.20E−04 | 1.16E−04 | 2.80E−04 | 2.70E−04 |
| IC50 (Molar) | 1.81E−10 | 1.75E−10 | 4.23E−10 | 4.07E−10 |

Cytotoxicity of Compound 12

The activity of Compound 12, the modified Compound 4 carrying the cleavable peptidic linker, was assayed in the same experimental conditions than above, in the range of concentrations from 01E+01 to 2.6E-03 µg/mL (7.9E-06 to 2.0E-09 M).

The cytotoxicity of Compound 12, in two independent experiments, was also relatively homogenous along the different cell lines tested, with $IC_{50}$ values in the low nanomolar range, from 7.60E-03 to 3.05E-02 µg/mL (6.02E-09 to 2.42E-08 M), with the mean $IC_{50}$ value across the whole cell panel being 1.63E-02 µg/mL (1.29E-08 M) (Table 11). The presence of the peptidic linker in Compound 12 had a negative effect on the cytotoxicity of the compound, as compared to Compound 4. The cytotoxicity of Compound 12 was rather independent of the HER2 status of the tumor cell lines.

TABLE 11

Summary data of the in vitro cytotoxicity of Compound 12

| | Compound 12 Breast cells | | | |
|---|---|---|---|---|
| | HER2+ | | HER2− | |
| | HCC1954 | SK-BR3 | MCF7 | MDA-MB-231 |
| IC50 (ug/mL) | 7.60E−03 | 9.05E−03 | 3.05E−02 | 1.80E−02 |
| IC50 (Molar) | 6.02E−09 | 7.18E−09 | 2.42E−08 | 1.43E−08 |

Cytotoxicity of ADC 3

Figure 7:
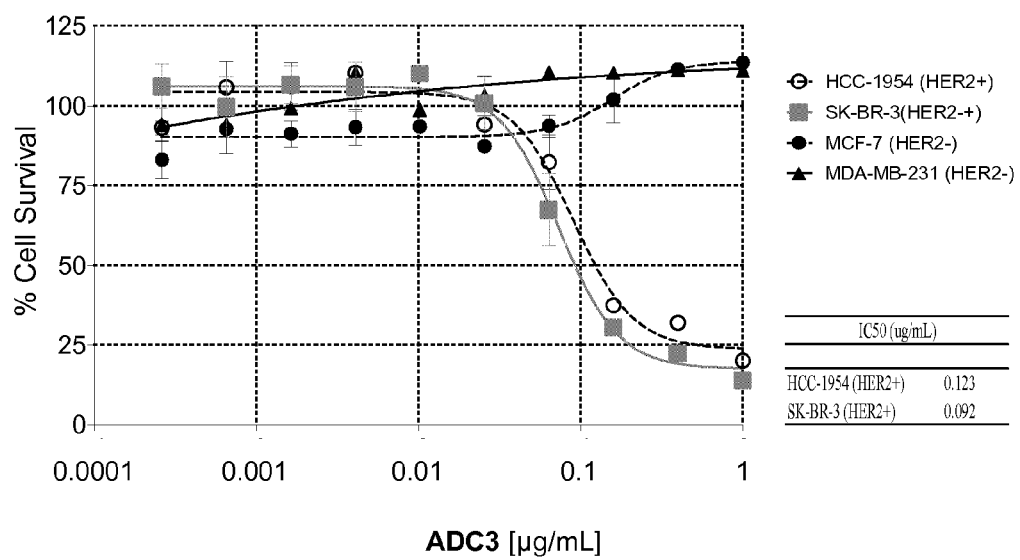
FIG. 7 is a representative dose response curves for ADC3 against various cancer cell lines.

Finally, the cytotoxicity of the ADC3 was assayed against the different cell lines. To ensure the appropriate range of concentrations, the conjugate was assayed in six different concentration ranges, each in triplicate DR curves (ten serial dilutions, 1/2.5 ratio) starting from 50, 10, 1, 0.1, 0.01 and 0.001 µg/mL (equivalent to 3.33E-07, 6.64E-08, 6.64E-09, 6.64E-10, 6.64E-11 and 6.64E-12 molar concentration), in two independent experiments. A representative DR curve is shown in FIG. 7. The mean $IC_{50}$ values calculated for ADC3 against the different cell lines tested are shown in Table 12.

The conjugate ADC3 clearly showed a significant specificity against HER2+ expressing cells, in which the compound demonstrated a potent cytotoxicity, similar to that of the parent Compound 4 (about 1 log more active than the intermediate Compound 12 carrying the peptidic linker). Both HER2+ cell lines, HCC-1954 and SK-BR-3, showed a comparable sensitivity against ADC3, with mean $IC_{50}$ values of 8.83E-02 and 6.77 E-02 µg/mL (equivalent to 5.86E-10 and 4.49E-10 M), respectively. The two HER negative cell lines, MCF-7 and MDA-MB-231, showed a significantly lower sensitivity against ADC3, with mean $IC_{50}$ values of 9.40E+00 and >5.0E+01 µg/mL (equivalent to around 6.24E-08 M and >3.32E-07 M), respectively.

Figure 8:
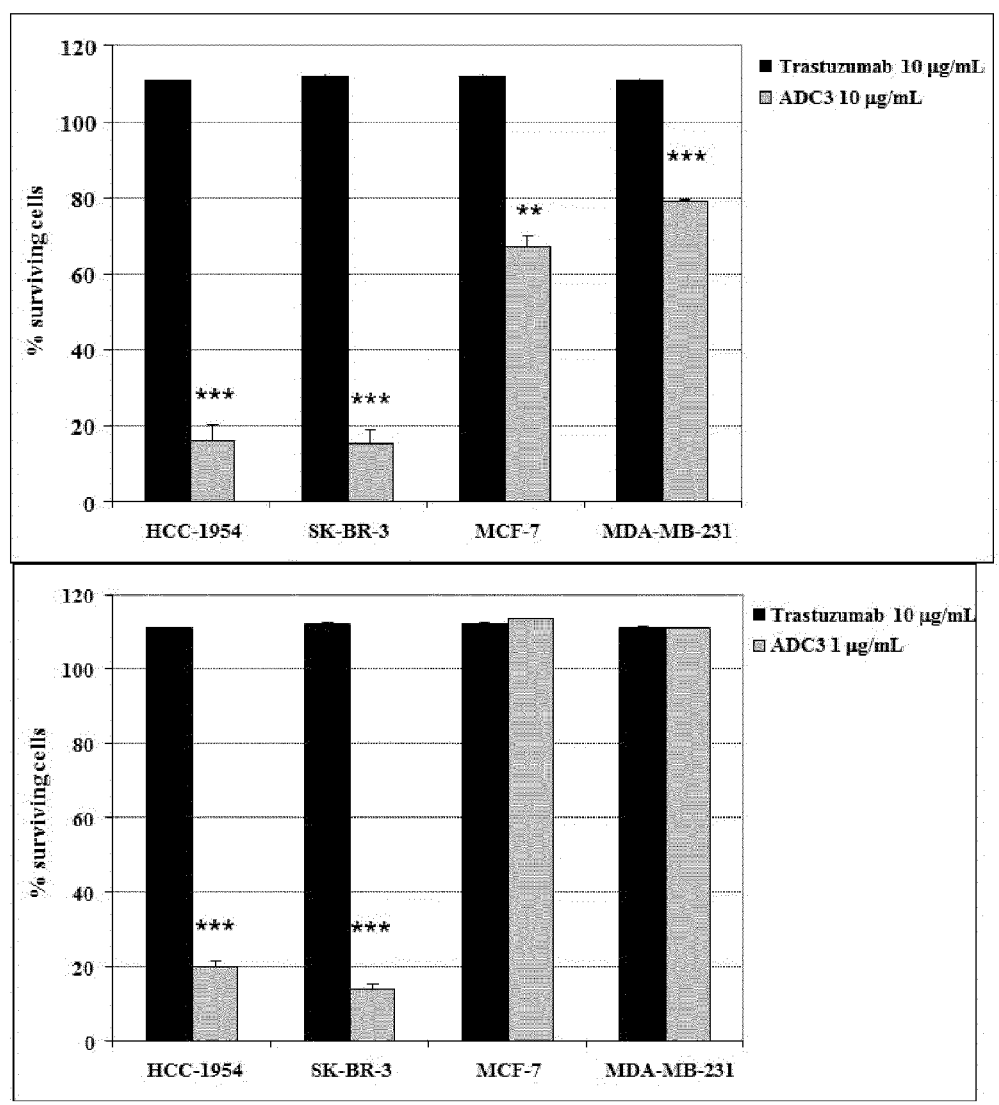
FIG. 8 shows histograms showing the percentages of cell survival after treatment of the different cell lines with the mAb alone (10 µg/mL) or ADC3 at 10 or 1 µg/mL.

FIG. 8 is a plot of the cytotoxicity of ADC3 against HER2 positive and negative breast cancer cells. It was found that HER2+ cell lines (mean $IC_{50}$ 7.80E-02 µg/mL) were at least >120 times more sensitive to ADC3 than the HER2 negative MCF-7 cells (mean $IC_{50}$ 9.40E+00 µg/mL), and far more sensitive than the MDA-MB-231 cells, clearly showing the specificity of ADC3 against the HER2 expressing cells (FIG. 7 and Table 12). We assume, therefore, that the conjugate was actually acting through the interaction of the mAb with the membrane associated HER2 receptor on tumor cells, and subsequent intracellular delivery of the cytotoxic drug into the target tissue.

TABLE 12

Summary data of the in vitro cytotoxicity of ADC3 (Trastuzumab-Compound 12).
ADC3 (Trastuzumab-Compound 12 ADC)

| Cell line | Breast cells | | | |
|---|---|---|---|---|
| | HER2+ | | HER2− | |
| HER2 status | HCC1954 | SK-BR3 | MCF7 | MDA-MB-231 |
| IC50 (ug/mL) | 8.83E−02 | 6.77E−02 | 9.40E+00 | >5.0E+01 |
| Mean IC50 (ug/mL) HER2 positive cells | | | | 7.80E−02 |
| Mean IC50 (ug/mL) HER2 negative cells | | | | 9.40E+00 |
| IC50 (M) | 5.86E−10 | 4.49E−10 | 6.24E−08 | >3.32E−07 |
| Mean IC50 (M) HER2 positive cells | | | | 5.18E−10 |
| Mean IC50 (M) HER2 negative cells | | | | 6.24E−08 |

To graphically compare the cytotoxicity of the mAb Trastuzumab, alone with that of the conjugate ADC3, histograms showing the percentages of cell survival after treatment of the different cell lines with the mAb alone (10 µg/mL) or ADC3 at 10 or 1 µg/mL, are shown in FIG. 8, which shows the cytotoxic activity of Trastuzumab vs ADC3 against different breast human cancer cell lines.

At an equal concentration of 10 µg/mL, trastuzumab, alone, showed no cytotoxicity against none of the cell lines tested, independently of their HER2 status. In contrast, ADC3 conjugate showed a potent cytotoxicity against the HER2 expressing cells, HCC-1954 and SK-BR-3. In these cell lines, ADC3 exerted an inhibition of the cell survival of 83% and 84%, respectively, as compared to the control cells. At this concentration, ADC3 also had some effect on HER2 negative cells, MCF-7 and MDA-MB-231, producing a slight inhibition of cell survival of 33% and 20%, respectively. At a concentration of 1 µg/mL, ADC3 conjugate showed a similar cytotoxicity against the HER2 positive cells than that observed at 10 µg/mL, but without detectable effects on HER2 negative cells (FIG. 8). These results clearly demonstrated the remarkable cytotoxicity and specificity of ADC3 against HER2 expressing human tumor cells in vitro.

Bioactivity Example 4—Cytotoxicity of ADC4 and Related Reagents Against HER2 Positive and Negative Breast Cancer Cells The in vitro cytotoxicity of ADC4, along with the parent cytotoxic Compounds 13 and 4 and the mAb Trastuzumab was evaluated against different human breast cancer cell lines expressing or not the HER2 receptor, including HCC-1954 and SK-BR-3 (HER2 positive cells) and MDA-MB-231 and MCF-7 (HER2 negative cells). Standard dose-response (DR) curves for 72 hours were performed.

Cytotoxicity of Compound 4

The cytotoxicity of the parent Compound 4 was assayed in DR curves using ten serial dilutions (1/2.5 ratio) from 1E-01 to 2.6E-05 µg/mL (1.5E-07 to 3.0E-11 M)

The cytotoxicity of Compound 4, in two independent experiments, was homogenous along the different cell lines tested, with $IC_{50}$ values in the low nanomolar range, from 2.43E-04 to 4.45E-04 µg/mL (3.6E-10 to 6.7E-10 M), with the mean $IC_{50}$ value across the whole cell panel 3.3E-04 µg/mL (equivalent to 4.98E-10 M). Thus, the cytotoxicity of Compound 4 was independent of the HER2 status of the tumor cell lines (Table 13).

TABLE 13

Summary data of the in vitro cytotoxicity of Compound 4

| | Compound 4 | | | |
|---|---|---|---|---|
| | Breast cells | | | |
| | HER2+ | | HER2− | |
| | HCC1954 | SK-BR3 | MCF7 | MDA-MB-231 |
| IC50 (Mg/mL) | 2.98E−04 | 2.43E−04 | 4.45E−04 | 3.35E−04 |
| IC50 (Molar) | 4.49E−10 | 3.66E−10 | 6.71E−10 | 5.05E−10 |

Cytotoxicity of Compound 13

The activity of Compound 13, the modified Compound 4 carrying the thiol containing group, was assayed in the same conditions than above, from 1E-01 to 2.6E-05 µg/mL (1.3E-07 to 2.0E-11 M)

The cytotoxic activity of Compound 13, in two independent experiments, was also relatively homogenous along the different cell lines tested, with $IC_{50}$ values in the low nanomolar range, from 7.95E-04 to 2.63E-03 µg/mL (1.OE-09 to 3.5E-09 M), being the mean $IC_{50}$ value across the whole cell panel 1.83E-03 µg/mL (2.44E-09 M) (Table 14). The presence of the thiol containing tail in Compound 13 slightly decreased (about 5 fold) the cytotoxic activity of the compound as compared to Compound 4. Also, the cytotoxicity of Compound 13 seemed to be independent of the HER2 status of the tumor cell lines (Table 14).

TABLE 14

Summary data of the in vitro cytotoxicity of Compound 13

| | Compound 13 Breast cells | | | |
|---|---|---|---|---|
| | HER2+ | | HER2− | |
| | HCC1954 | SK-BR3 | MCF7 | MDA-MB-231 |
| IC50 (Mg/mL) | 1.49E−03 | 7.95E−04 | 2.43E−03 | 2.63E−03 |
| IC50 (Molar) | 1.98E−09 | 1.06E−09 | 3.23E−09 | 3.50E−09 |

Cytotoxicity of ADC4

Figure 9:
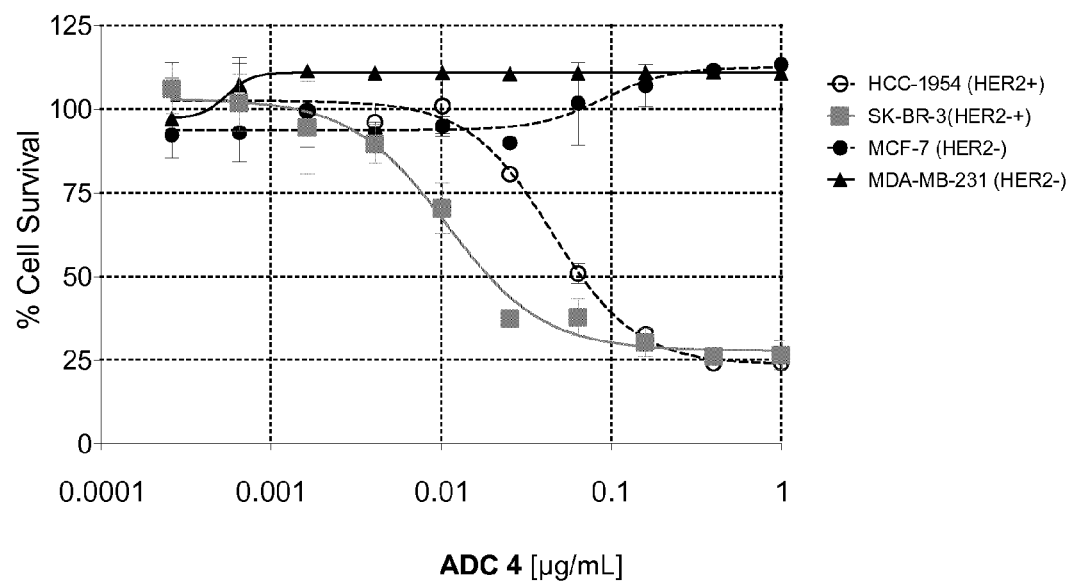
FIG. 9 is a representative dose response curves for ADC4 against various cancer cell lines.

The cytotoxicity of the ADC4 was assayed against the different cell lines. Just to assure the appropriate range of concentrations, the conjugate was assayed in four different concentration ranges, each in triplicate DR curves (ten serial dilutions, 1/2.5 ratio) starting from 50, 10, 1 and 0.1 µg/mL, in two independent experiments. A representative DR curve is shown in FIG. 9. After adjusting all the different DR curves, the mean $IC_{50}$ values calculated for ADC4 against the different cell lines tested are shown in Table 15.

The conjugate ADC4 showed specificity against the HER2+ expressing cells, HCC-1954 and SK-BR-3, in which the compound demonstrated a potent cytotocixity similar to that of the parent Compounds 4 and 13, with mean $IC_{50}$ values of 1.17E-01 and 4.80E-02 µg/mL, respectively. The two HER negative cell lines, MCF-7 and MDA-MB-231, showed a significant lower sensitivity against ADC4, with mean $IC_{50}$ values of 5.35E+00 and 6.50E+00 µg/mL, respectively. It seemed that the conjugate was preferentially acting through the interaction of the mAb with the membrane associated HER2 receptor on tumor cells, and subsequent intracellular delivery of the cytotoxic drug into the target tissue.

TABLE 15

Summary data of the in vitro cytotoxicity of ADC4.
ADC 4

| | HER2 status | | | |
|---|---|---|---|---|
| | HER2+ | | HER2− | |
| Cell line | HCC1954 | SK-BR3 | MCF7 | MDA-MB-231 |
| IC50 (µg/mL) | 1.17E−01 | 4.80E−02 | 5.35E+00 | 6.50E+00 |
| Mean IC50 (Mg/mL) HER2 positive cells | | | 8.24E−02 | |
| Mean IC50 (Mg/mL) HER2 negative cells | | | 5.93E+00 | |

Figure 10:
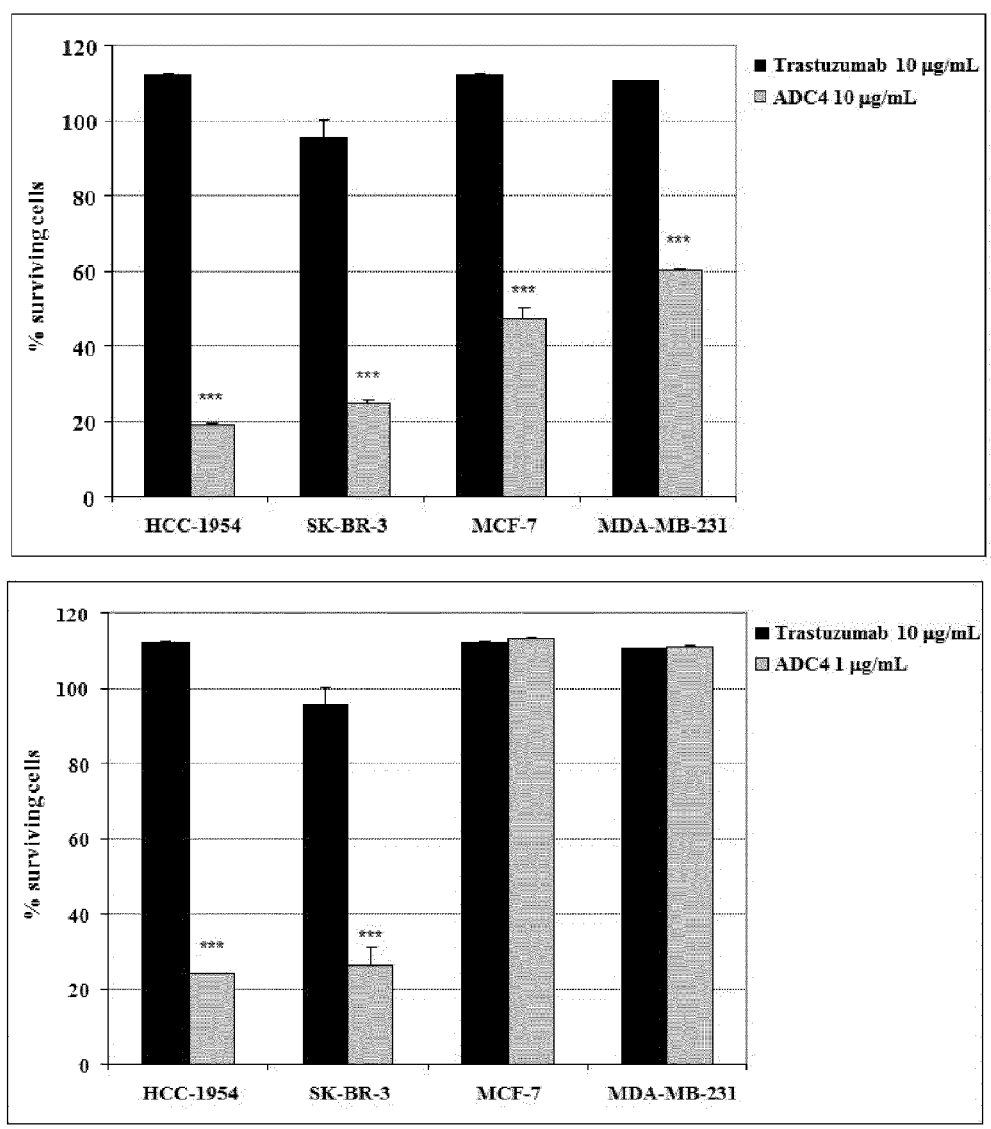
FIG. 10 shows histograms showing the percentages of cell survival after treatment of the different cell lines with the mAb alone (10 µg/mL) or ADC4 at 10 or 1 µg/mL.

To graphically compare the cytotoxicity of the mAb Trastuzumab, alone with that of the conjugate ADC4, histograms showing the percentages of cell survival after treatment of the different cell lines with the mAb alone (10 Mg/mL) or ADC4 at 10 or 1 µg/mL, are shown in FIG. 10. At a concentration of 10 Mg/mL, the mAb trastuzumab alone, showed no cytotoxicity against any of the cell lines tested, independently of their HER2 status. In contrast, ADC4 conjugate presented a significant and specific cytotoxicity against the HER2 expressing cells, HCC-1954 and SK-BR-3, inducing a mean inhibition of the cell survival of 80% and 75%, respectively, as compared to the control cells. At this concentration, ADC4 also had effect on HER2 negative cells, MCF-7 and MDA-MB-231, producing an inhibition of cell survival of 53% and 40%, respectively. At a concentration of 1 Mg/mL, the ADC4 conjugate showed a somewhat similar cytotoxicity against the HER2 positive cells than that observed at 10 Mg/mL, but without detectable effects on HER2 negative cells (FIG. 10). These results clearly demonstrated the remarkable cytotoxicity and specificity of ADC4 conjugate against HER2 expressing human tumor cells in vitro.

Bioactivity Example 5—Cytotoxicity of ADC5 and Related Reagents Against HER2 Positive and Negative Breast Cancer Cells The in vitro cytotoxicity of ADC5 along with the parent cytotoxic Compounds 15 and 40, was evaluated against different human breast cancer cell lines expressing or not the HER2 receptor, including HCC-1954 and SK-BR-3 (HER2 positive cells) and MDA-MB-231 and MCF-7 (HER negative cells).

Cytotoxicity of Compound 40

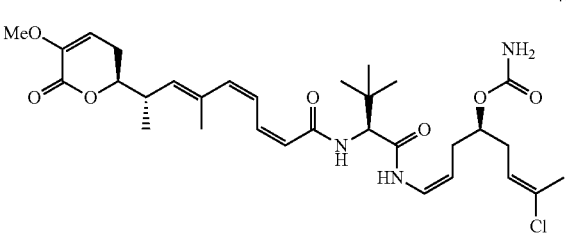

40

Compound 40 was prepared as described in WO20071 44423 (Compound 1 in such patent application), the contents of which are incorporated herein by reference.

The cytotoxicity of the parent Compound 40 was assayed in DR curves using ten serial dilutions (1/2.5 ratio) from 1E-02 to 2.6E-06 µg/mL (1.65E-08 to 4.29E-12 M).

The cytotoxicity of Compound 40, in two independent experiments, was very homogenous along the different cell lines tested, with $IC_{50}$ values in the low nanomolar range, from 4.90E-05 to 1.73E-04 µg/mL (8.1 OE-1 1 to 2.84E-1 0 M), being the mean $IC_{50}$ value across the whole cell panel 1.06E-04 µg/mL (equivalent to 1.75E-10 M). Thus the cytotoxicity of Compound 40 was independent of the HER2 status of the tumor cell lines (Table 16).

TABLE 16

Summary data of the in vitro cytotoxicity of Compound 40.

| | Compound 40 Breast cells | | | |
|---|---|---|---|---|
| | HER2+ | | HER2− | |
| | HCC1954 | SK-BR3 | MCF7 | MDA-MB-231 |
| IC50 (Mg/mL) | 7.05E−05 | 4.90E−05 | 1.32E−04 | 1.73E−04 |
| IC50 (Molar) | 1.16E−10 | 8.10E−11 | 2.18E−10 | 2.84E−10 |

Cytotoxicity of Compound 15

The activity of Compound 15, the modified Compound 40 carrying the thiol containing group, was assayed in the same conditions than above, from 1E-01 to 2.6E-05 µg/mL (1.47E-07 to 3.82E-1 1 M).

The cytotoxicity of Compound 15, in two independent experiments, was also quite homogenous along the different cell lines tested, with $IC_{50}$ values in the nanomolar range, from 4.80E-04 to 1.49E-03 µg/mL (7.06E-10 to 2.19E-09 M), being the mean $IC_{50}$ value across the whole cell panel 1.03E-03 µg/mL (1.51 E-09 M). The presence of the thiol containing tail in Compound 15 slightly decreased (about 8 fold) the cytotoxic activity of the compound as compared to Compound 40. Also, the cytotoxicity of Compound 15 was independent of the HER2 status of the tumor cell lines. (Table 17)

TABLE 17

Summary data of the in vitro cytotoxicity of Compound 15

| | Compound 15 Breast cells | | | |
|---|---|---|---|---|
| | HER2+ | | HER2− | |
| | HCC1954 | SK-BR3 | MCF7 | MDA-MB-231 |
| IC50 (Mg/mL) | 6.75E−04 | 4.80E−04 | 1.45E−03 | 1.49E−03 |
| IC50 (Molar) | 9.94E−10 | 7.06E−10 | 2.14E−09 | 2.19E−09 |

Cytotoxicity of ADC 5

Figure 11:
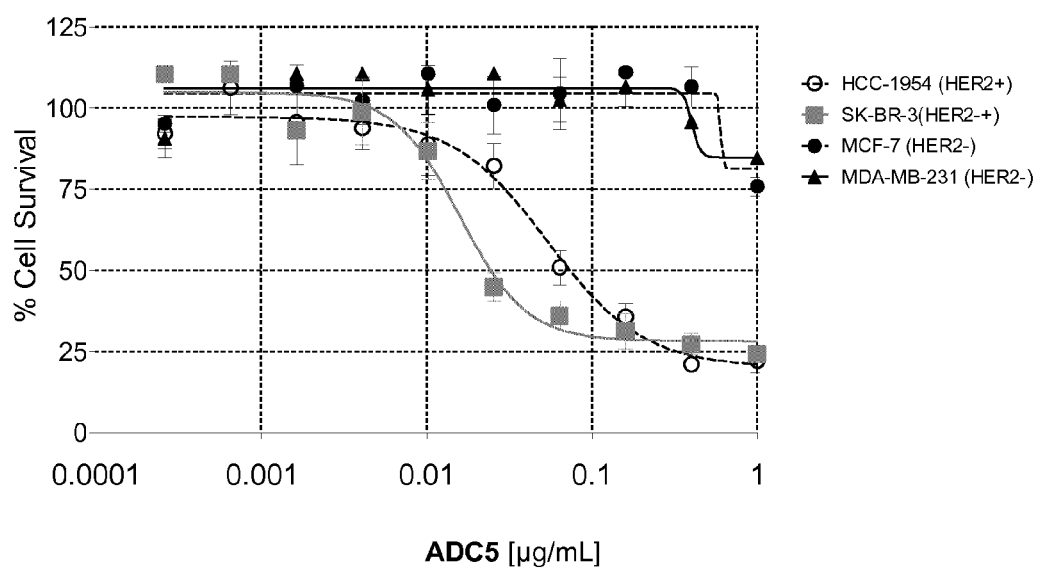
FIG. 11 is a representative dose response curves of ADC5 against various cancer cell lines.

The cytotoxicity of the ADC5 was assayed against the different cell lines. Just to assure the appropriate range of concentrations, the conjugate was assayed in four different concentration ranges, each in triplicate DR curves (ten serial dilutions, 1/2.5 ratio) starting from 50, 10, 1 and 0.1 μg/mL, in two independent experiments. A representative DR curve (starting concentration 1 μg/mL) is shown in FIG. 11. After adjusting all the different DR curves, the mean $IC_{50}$ values calculated for the ADC5 against the different cell lines tested are shown in Table 18.

The conjugate ADC5 showed specificity against the HER2+ expressing cells, HCC-1954 and SK-BR-3, in which the compound demonstrated a cytotoxic activity similar to that of the parent compounds Compound 40 and Compound 15, with mean $IC_{50}$ values of 1.13E-01 and 4.61 E-02 μg/mL, respectively. The two HER negative cell lines, MCF-7 and MDA-MB-231, showed a significantly lower sensitivity against ADC5, with mean $IC_{50}$ values of 1.23E+00 and 1.45E+00 μg/mL, respectively.

It seemed that the conjugate ADC5 was preferentially acting through the interaction of the mAb with the membrane associated HER2 receptor on tumor cells, and subsequent intracellular delivery of the cytotoxic drug into the target tissue.

TABLE 18

Summary data of the in vitro cytotoxicity of ADC5.

| | ADC5 | | | |
|---|---|---|---|---|
| | HER2 status | | | |
| | HER2+ | | HER2− | |
| Cell line | HCC1954 | SK-BR3 | MCF7 | MDA-MB-231 |
| IC50 (μg/mL) | 1.13E−01 | 4.61E−02 | 1.23E+00 | 1.45E+00 |
| Mean IC50 (Mg/mL) HER2 positive cells | | | 7.96E−02 | |
| Mean IC50 (Mg/mL) HER2 negative cells | | | 1.34E+00 | |

Figure 12:
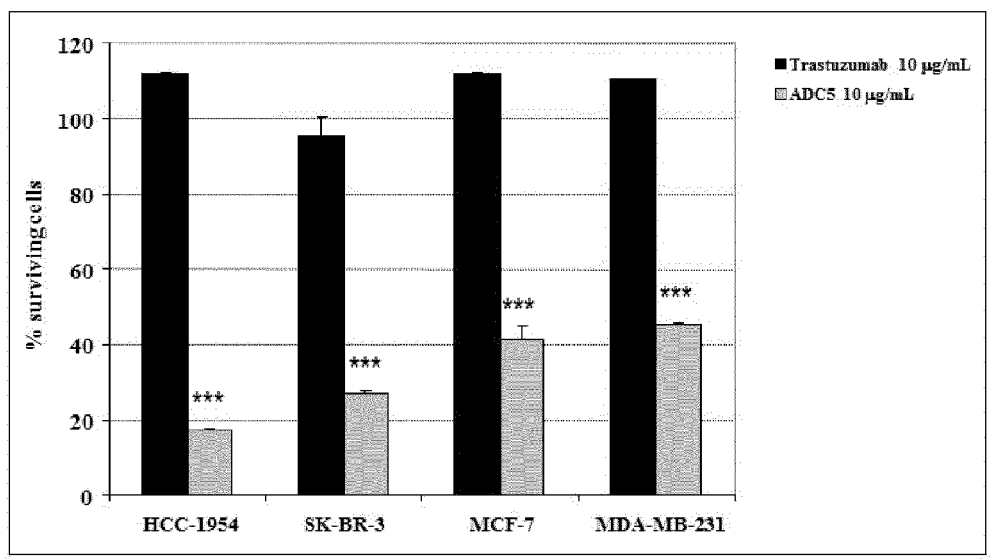
FIG. 12 shows histograms showing the percentages of cell survival after treatment of the different cell lines with the mAb alone (10 µg/mL) or ADC5 at 10 or 1 µg/mL.
Figure 12:
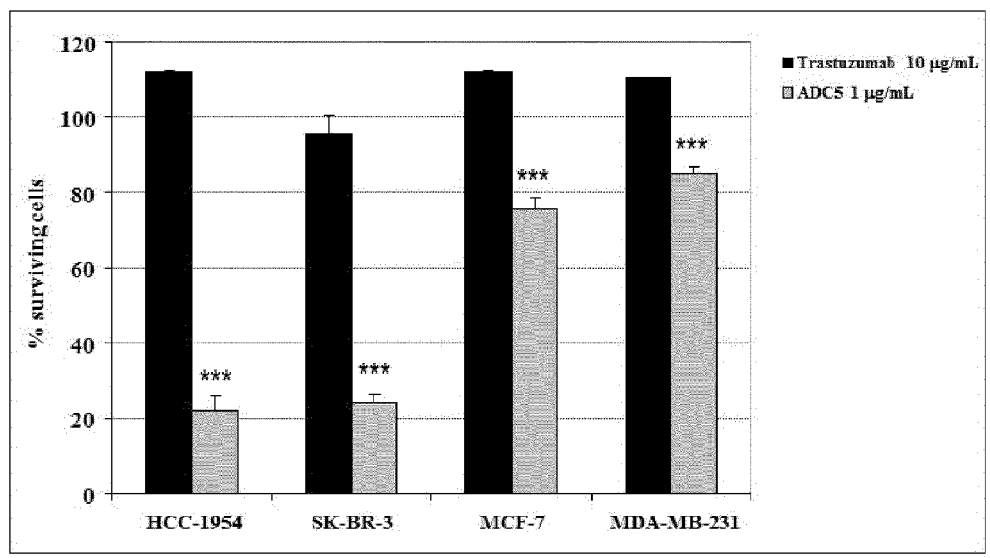

To graphically compare the cytotoxic activity of the mAb Trastuzumab alone with that of the conjugate ADC5, histograms showing the percentages of cell survival after treatment of the different cell lines with the mAb alone (10 Mg/mL) or ADC5 at 10 μg/mL or 1 Mg/mL, are shown in FIG. 12. At a concentration of 10 Mg/mL, the mAb trastuzumab alone showed no cytotoxicity activity against any of the cell lines tested, independently of their HER2 status. In contrast, ADC5 conjugate presented a significant and specific cytotoxicity against HER2 expressing cells, HCC-1954 and SK-BR-3, inducing a mean inhibition of the cell survival of 82% and 72%, respectively, as compared to the control cells. At this concentration, ADC5 also had effect on HER2 negative cells, MCF-7 and MDA-MB-231, producing a inhibition of cell survival of 58% and 54%, respectively. At a concentration of 1 Iv/mL, the ADC5 conjugate showed a relatively similar cytotoxic activity against the HER2 positive cells than that observed at 10 Mg/mL (77% and 75%, respectively), but much less activity against HER2 negative cells, with an inhibition of cell survival of 24% and 15%, respectively (FIG. 12). These results demonstrated the remarkable cytotoxic activity and relative specificity of ADC5 conjugate against HER2 expressing human tumor cells in vitro.

Bioactivity Example 6—Cytotoxicity of ADC6 and Related Reagents Against HER2 Positive and Negative Breast Cancer Cells The in vitro cytotoxicity of ADC6 along with the parent cytotoxic Compounds 18 and 8 was evaluated against different human breast cancer cell lines expressing or not the HER2 receptor, including HCC-1954 and SK-BR-3 (HER2 positive cells) and MDA-MB-231 and MCF-7 (HER2 negative cells). Standard dose-response (DR) curves for hours were performed.

Cytotoxicity of Compound 8

The cytotoxicity of the parent Compound 8 was assayed in DR curves using ten serial dilutions (1/2.5 ratio) from 1E+00 to 2.6E-04 μg/mL (1.59E-06 to 4.13E-10 M). The cytotoxic activity of this compound, in two independent experiments, was relatively homogenous across the different cell lines tested (slightly more active against SK-BR-3 cells), with $IC_{50}$ values in the low nanomolar range, from 1.85E-03 to 9.50E-03 μg/mL (2.94E-09 to 1.51 E-08 M), being the mean $IC_{50}$ value across the whole cell panel 5.45E-03 μg/mL (equivalent to 8.67E-09 M). Thus, the cytotoxicity of Compound 8 seemed to be independent of the HER2 status of the tumor cell lines (Table 19).

TABLE 19

Summary data of the in vitro cytotoxicity of Compound 8

| | Compound 8 Breast cells | | | |
|---|---|---|---|---|
| | HER2+ | | HER2− | |
| | HCC1954 | SK-BR3 | MCF7 | MDA-MB-231 |
| IC50 (Mg/mL) | 5.20E−03 | 1.85E−03 | 9.50E−03 | 5.25E−03 |
| IC50 (Molar) | 8.27E−09 | 2.94E−09 | 1.51E−08 | 8.35E−09 |

Cytotoxicity of Compound 18

The activity of Compound 18, the modified Compound 8 carrying the thiol containing group, was assayed in the same conditions than above, from 1E+00 to 2.6E-04 μg/mL (1.39E-06 to 3.63E-10 M). The cytotoxicity of this compound, in two independent experiments, was also quite homogenous across the different cell lines tested, with $IC_{50}$ values in the nanomolar range, from 4.40E-03 to 1.85E-02 μg/mL (6.14E-09 to 2.58E-08 M), being the mean $IC_{50}$ value across the whole cell panel 1.06E-02 μg/mL (1.48E-08 M). The presence of the thiol containing tail in Compound 18 had little effect on the activity of the compound, as compared to Compound 8. Also, the cytotoxicity of Compound 18 seemed to be rather independent of the HER2 status of the tumor cell line (Table 20).

TABLE 20

Summary data of the in vitro cytotoxicity of Compound 18

| | Compound 18 Breast cells | | | |
|---|---|---|---|---|
| | HER2+ | | HER2- | |
| | HCC1954 | SK-BR3 | MCF7 | MDA-MB-231 |
| IC50 (Mg/mL) | 8.05E−03 | 4.40E−03 | 1.85E−02 | 1.15E−02 |
| IC50 (Molar) | 1.12E−08 | 6.14E−09 | 2.58E−08 | 1.60E−08 |

Cytotoxicity of ADC6

Figure 13:
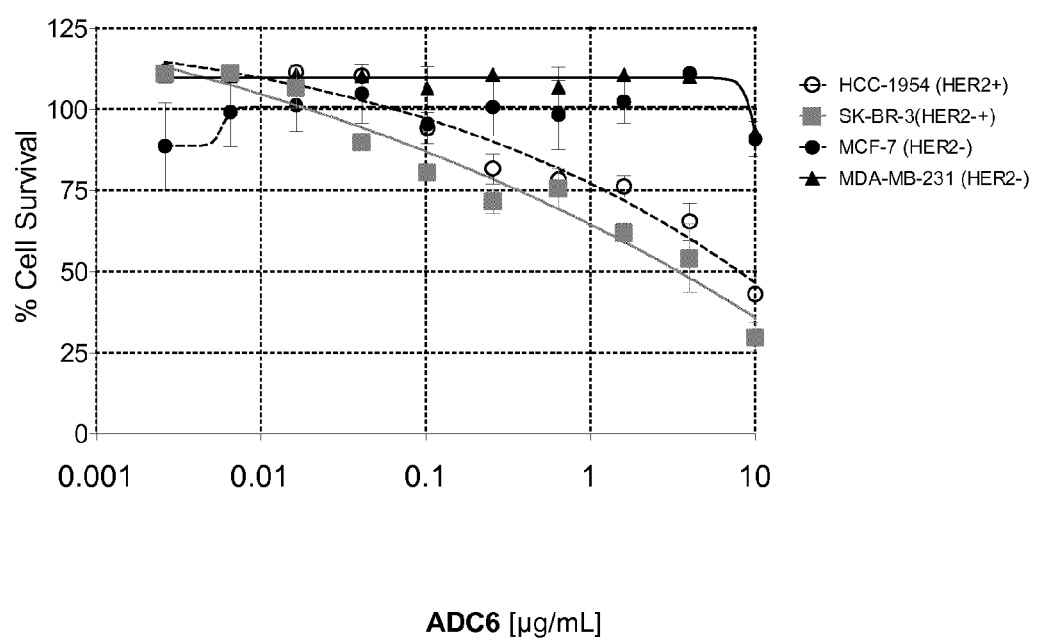
FIG. 13 is a representative dose response curves of ADC6 against various cancer cell lines.

The cytotoxicity of the ADC6 was assayed against the different cell lines. Just to assure the appropriate range of concentrations, the conjugate was assayed in four different concentration ranges, each in triplicate DR curves (ten serial dilutions, 1/2.5 ratio) starting from 50, 10, 1 and 0.1 μg/mL, in two independent experiments. A representative DR is shown in FIG. 13. After adjusting all the different DR curves, the mean $IC_{50}$ values calculated for ADC6 against the different cell lines tested are shown in Table 21.

The conjugate ADC6, although limited, showed some specificity towards HER2+ expressing cells, HCC-1954 and SK-BR-3. In these cell lines, the conjugate was slightly less cytotoxic than the parent Compounds 8 and 18 alone (5.6 and 3.2 times respectively), with mean $IC_{50}$ values of 1.04 E+01 and 3.80E+00 μg/mL, respectively. The two HER negative cell lines, MCF-7 and MDA-MB-231, showed slightly lower sensitivity against ADC6 (5 fold less), with mean $IC_{50}$ values of 3.50E+01 and 4.40E+01 μg/mL, respectively. It seemed that the conjugate ADC6 had some preference for HER2 expressing cells, acting through the interaction of the mAb with the membrane associated HER2 receptor on tumor cells, and subsequent intracellular delivery of the cytotoxic drug into the target tissue.

TABLE 21

Summary data of the in vitro cytotoxicity of ADC6.
ADC6

| | HER2 status | | | |
|---|---|---|---|---|
| | HER2+ | | HER2- | |
| Cell line | HCC1954 | SK-BR3 | MCF7 | MDA-MB-231 |
| IC50 (μg/mL) | 1.04E+01 | 3.80E+00 | 3.50E+01 | 4.40E+01 |
| Mean IC50 (Mg/mL) HER2 positive cells | | | 7.12E+00 | |
| Mean IC50 (Mg/mL) HER2 negative cells | | | 3.95E+01 | |

Figure 14:
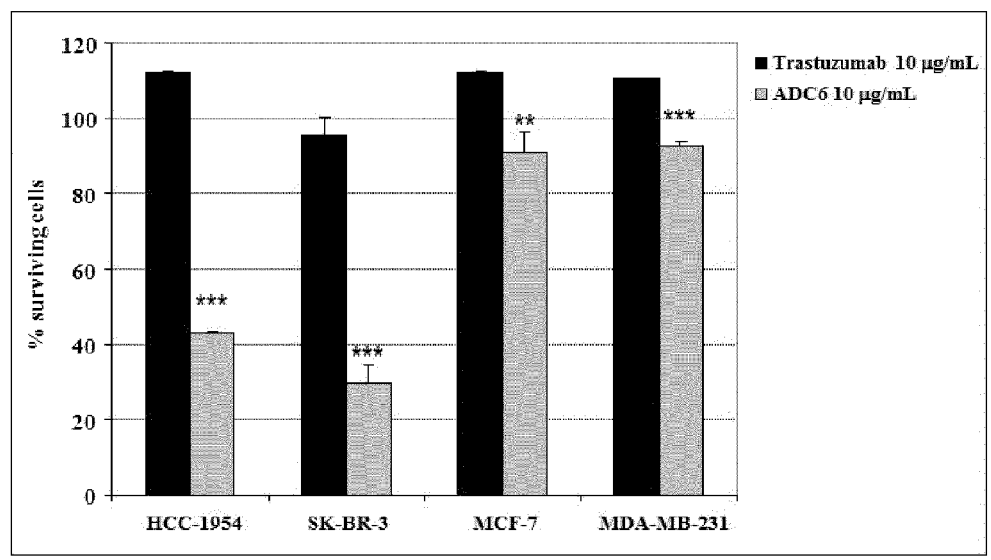
FIG. 14 shows histograms showing the percentages of cell survival after treatment of the different cell lines with the mAb alone (10 µg/mL) or ADC6 at 10 or 1 µg/mL.
Figure 14:
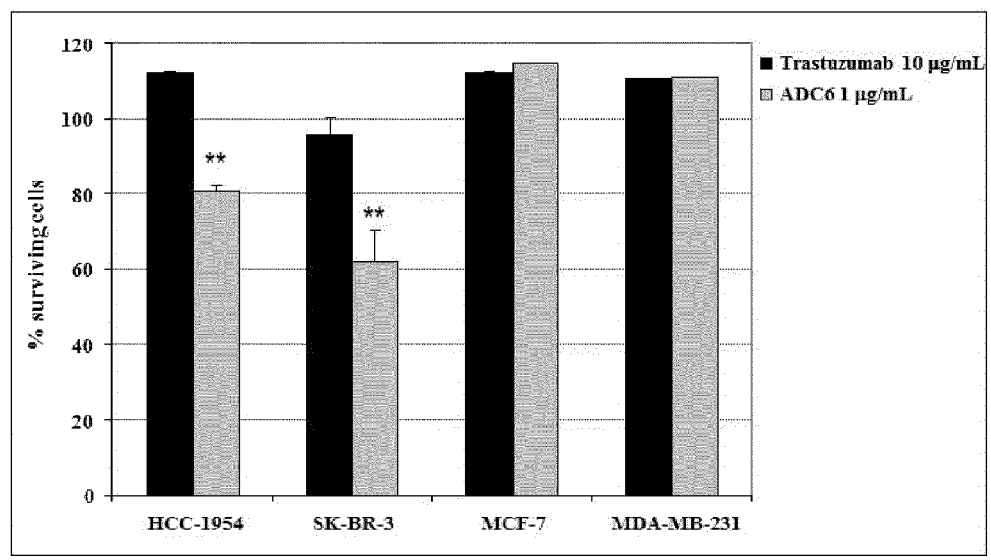

To graphically compare the cytotoxic activity of the mAb Trastuzumab alone with that of the conjugate ADC6, histograms showing the percentages of cell survival after treatment of the different cell lines with the mAb alone (10 Mg/mL) or ADC6 at 10 or 1 Mg/mL, are shown in FIG. 14. At a concentration of 10 Mg/mL, the mAb trastuzumab alone showed no cytotoxic activity against any of the cell lines tested, independently of their HER2 status. In contrast, ADC6 conjugate presented specific cytotoxicity against HER2 expressing cells, HCC-1954 and SK-BR-3, inducing a mean inhibition of the cell survival of 57% and 70%, respectively, as compared to the control cells. At this concentration, ADC6 also had a residual effect on HER2 negative cells, MCF-7 and MDA-MB-231, producing an inhibition of cell survival of 9% and 7%, respectively. At a concentration of 1 Mg/mL, the ADC6 conjugate still had cytotoxic activity against the HER2 positive cells, although less than that observed at 10 Mg/mL (19% and 38%, respectively). At this concentration, ADC6 was completely inactive against HER2 negative cells (FIG. 14). These results demonstrated the preferential cytotoxic activity of ADC6 conjugate against HER2 expressing human tumor cells in vitro.

Bioactivity Example 7—Cytotoxicity of ADC7 and Related Reagents Against HER2 Positive and Negative Breast Cancer Cells The in vitro cytotoxicity of ADC7 along with the parent cytotoxic Compounds 24, 25 and 41 was evaluated against different human breast cancer cell lines expressing or not the HER2 receptor, including HCC-1954 and SK-BR-3 (HER2 positive cells) and MDA-MB-231 and MCF-7 (HER2 negative cells). Standard dose-response (DR) curves for 72 hours were performed.

Cytotoxicity of Compound 41

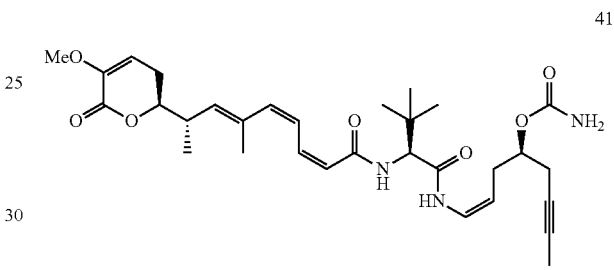

41

Compound 41 was prepared as described in WO 2009/080761 (Compound 72 in such patent application), the contents of which are incorporated herein by reference.

The cytotoxicity of the parent Compound 41 was assayed in DR curves using ten serial dilutions (1/2.5 ratio) from 1E-02 to 2.6E-06 μg/mL (1.8E-08 to 4.6E-12 M). The cytotoxic activity of this compound, in two independent experiments, was homogenous across the different cell lines tested, with $IC_{50}$ values in the low nanomolar range, from 1.OE-04 to 2.6E-04 μg/mL (1.8E-1 0 to 4.6E-1 0 M), being the mean $IC_{50}$ value across the whole cell panel 1.6E-04 μg/mL (equivalent to 2.9E-10 M). Thus, the cytotoxicity of Compound 41 was independent of the HER2 status of the tumor cell lines (Table 22)

TABLE 22

Summary data of the in vitro cytotoxicity of Compound 41.

| | Compound 41 Breast cells | | | |
|---|---|---|---|---|
| | HER2+ | | HER2- | |
| | HCC1954 | SK-BR3 | MCF7 | MDA-MB-231 |
| IC50 (Mg/mL) | 1.04E−04 | 1.10E−04 | 2.65E−04 | 1.80E−04 |
| IC50 (Molar) | 1.83E−10 | 1.93E−10 | 4.65E−10 | 3.16E−10 |

Cytotoxicity of Compound 24

The activity of Compound 24 was assayed in the same conditions than above, from 1E+00 to 2.6E-04 μg/mL (1.6E-06 to 4.1 E-10 M). The cytotoxic activity of this compound, in two independent experiments, was homogeneous across the different cell lines tested, with $IC_{50}$ values in the nanomolar range, from 9.0E-03 to 1.8E-02 g/mL (1.4E-08 to 2.8E-08 M), being the mean $IC_{50}$ value across the whole cell panel 1.5E-02 µg/mL (2.4E-08 M). The presence of the 1,3-propylenediamine group in Compound 24 significantly decreased (about 2 logs) the cytotoxic activity of the compound as compared to Compound 41. Also, the cytotoxicity of Compound 24 seemed to be independent of the HER2 status of the tumor cell lines (Table 23).

TABLE 23

Summary data of the in vitro cytotoxicity of Compound 24.

| | Compound 24 Breast cells | | | |
|---|---|---|---|---|
| | HER2+ | | HER2- | |
| | HCC1954 | SK-BR3 | MCF7 | MDA-MB-231 |
| IC50 (Mg/mL) | 1.80E-02 | 9.00E-03 | 1.65E-02 | 1.75E-02 |
| IC50 (Molar) | 2.87E-08 | 1.44E-08 | 2.63E-08 | 2.79E-08 |

Cytotoxicity of Compound 25

The activity of Compound 25, the modified Compound 24 carrying the MC linker, was assayed in the same conditions than above, from 1E-01 to 2.6E-05 µg/mL (1.2E-07 to 3.2E-1 1 M). The cytotoxic activity of this compound, in two independent experiments, was homogenous across the different cell lines tested, with $IC_{50}$ values in the nanomolar range, from 2.5E-02 to 5.3E-02 µg/mL (3.1 E-08 to 6.5E-08 M), being the mean $IC_{50}$ value across the whole cell panel 4.1 E-02 µg/mL (4.9E-08 M). The presence of the MC linker in Compound 25 very slightly decreased the cytotoxic activity of the compound as compared to Compound 24, particularly in MDA-MB-231 cells. The cytotoxicity of Compound 25 seemed to be independent of the HER2 status of the tumor cell lines (Table 24).

TABLE 24

Summary data of the in vitro cytotoxicity of Compound 25

| | Compound 25 Breast cells | | | |
|---|---|---|---|---|
| | HER2+ | | HER2- | |
| | HCC1954 | SK-BR3 | MCF7 | MDA-MB-231 |
| IC50 (Mg/mL) | 4.40E-02 | 2.55E-02 | 5.30E-02 | >1.0E-01 |
| IC50 (Molar) | 5.37E-08 | 3.11E-08 | 6.46E-08 | >1.22E-07 |

Cytotoxicity of ADC7

Figure 15:
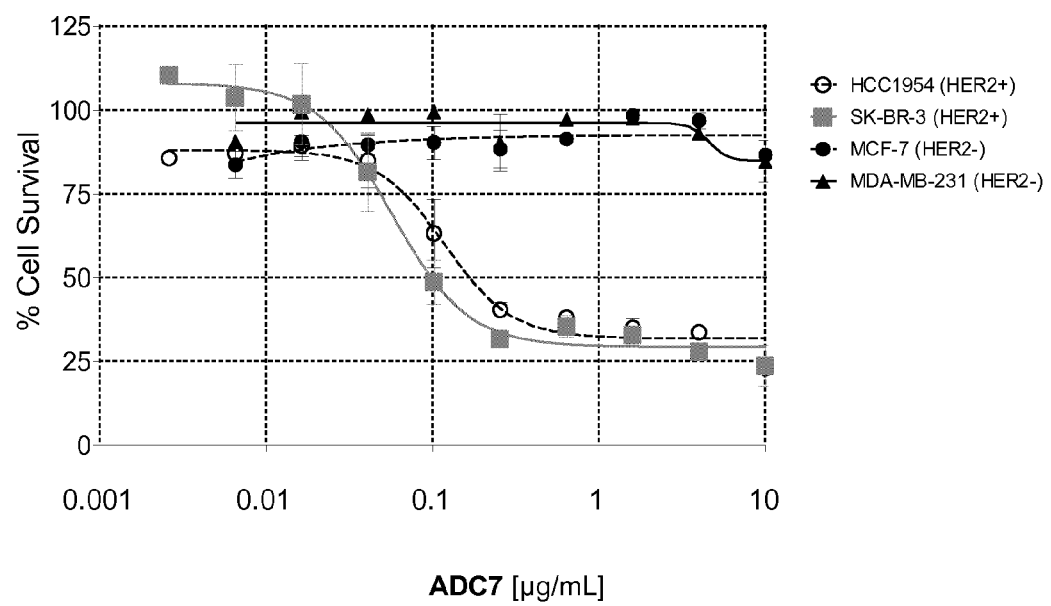
FIG. 15 is a representative dose response curves of ADC7 against various cancer cell lines.

The cytotoxicity of the ADC7 was assayed against the different cell lines. Just to assure the appropriate range of concentrations, the conjugate was assayed in four different concentration ranges, each in triplicate DR curves (ten serial dilutions, 1/2.5 ratio) starting from 50, 10, 1 and 0.1 µg/mL in two independent experiments. A representative DR curve (starting concentration 10 Mg/mL) is shown in FIG. 15. After adjusting all the different DR curves, the mean $IC_{50}$ values calculated for the ADC7 against the difference cell lines tested are shown in Table 25.

The conjugate ADC7 showed specificity against the HER2+ expressing cells, HCC-1954 and SK-BR-3, in which the compound demonstrated a cytotoxic activity nearly similar to that of the parent Compound 41, with mean $IC_{50}$ values of 3.7E-01 and 8.9E-02 µg/mL, respectively. The two HER negative cell lines, MCF-7 and MDA-MB-231, were virtually unresponsive to ADC7. The conjugate seemed to be acting through the interaction of the mAb with the membrane associated HER2 receptor on positive tumor cells, and subsequent intracellular delivery of the cytotoxic drug into the target tissue.

TABLE 25

Summary data of the in vitro cytotoxicity of ADC7
ADC7

| | HER2 status | | | |
|---|---|---|---|---|
| | HER2+ | | HER2- | |
| Cell line | HCC1954 | SK-BR3 | MCF7 | MDA-MB-231 |
| IC50 (µg/mL) | 3.75E-01 | 8.97E-02 | >5.0E+01 | >5.0E+01 |
| Mean IC50 (Mg/mL) HER2 positive cells | | | 2.32E-01 | |
| Mean IC50 (Mg/mL) HER2 negative cells | | | >5.0E+01 | |

Figure 16:
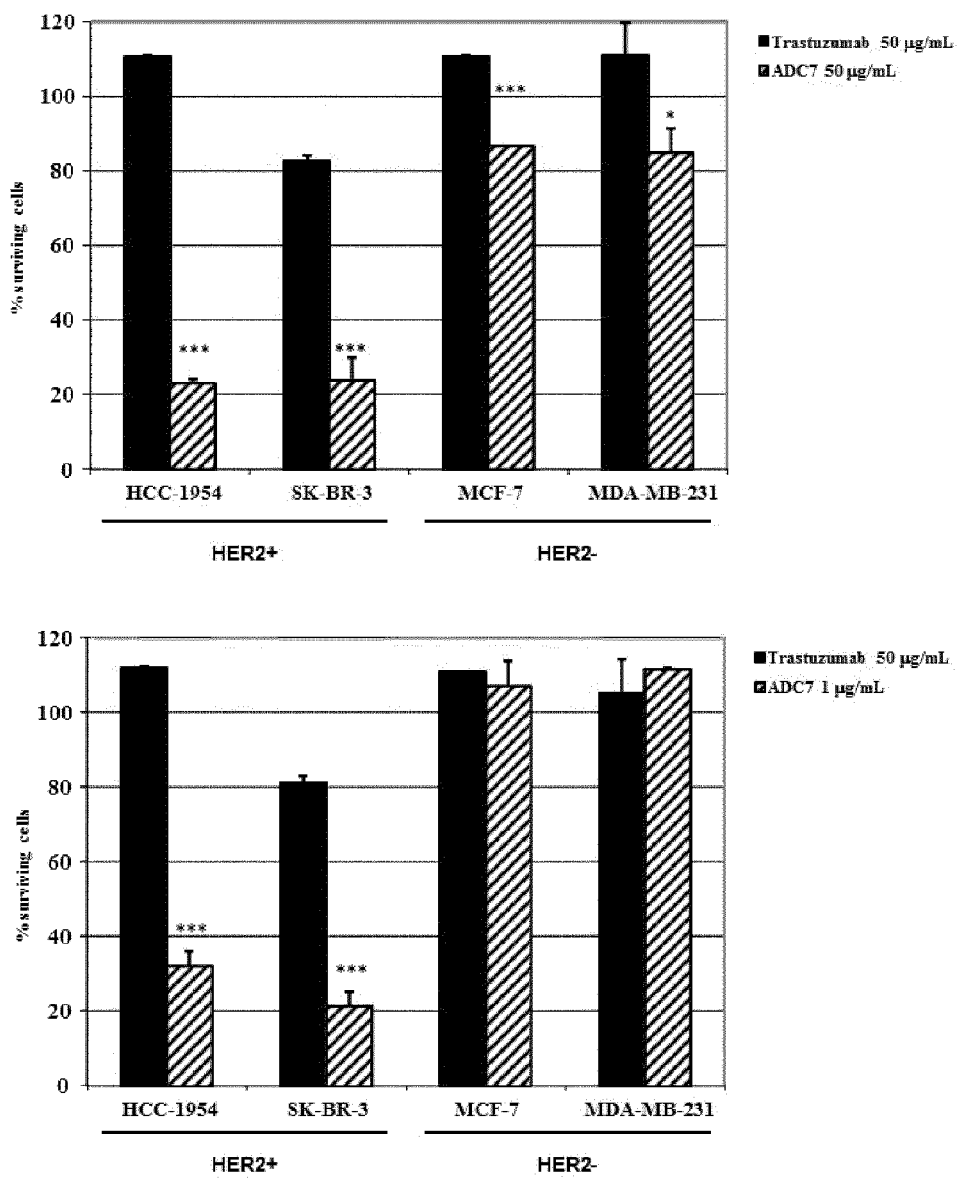
FIG. 16 shows histograms showing the percentage of cell survival after treatment of the different cell lines with the mAb alone (50 µg/mL) or ADC7 at 50 or 1 µg/mL.

To graphically compare the cytotoxic activity of the mAb Trastuzumab alone with that of the conjugate ADC7, histograms showing the percentages of cell survival after treatment of the different cell lines with the mAb alone (50 µg/mL) or ADC7 at 50 or 1 µg/mL, are shown in FIG. 16. At a concentration of 50 µg/mL, the mAb trastuzumab alone, showed no significant cytotoxic activity against any of the cell lines tested, independently of their HER2 status. In contrast, ADC7 conjugate presented a significant and specific cytotoxicity against HER2 expressing cells, HCC-1954 and SK-BR-3, inducing a mean inhibition of the cell survival of 77% and 76%, respectively, as compared to the control cells. At this concentration, ADC7 only had a residual effect on HER2 negative cells, MCF-7 and MDA-MB-231, producing an inhibition of cell survival of 13% and 15%, respectively. A similar activity and specificity was detected at lower concentrations of ADC7 (as low as 1 µg/mL) in HCC-1954 and SK-BR-3 cells, producing an inhibition of the cell survival of 68% and 79%, respectively (FIG. 16). Together, these results clearly demonstrated the remarkable cytotoxic activity and specificity of ADC7 conjugate against HER2 expressing human tumor cells in vitro.

Bioactivity Example 8—Cytotoxicity of ADC8 and Related Reagents Against HER2 Positive and Negative Breast Cancer Cells The in vitro cytotoxic activity of ADC8 along with the parent cytotoxic Compounds 24, 27 and 41, was evaluated against different human breast cancer cell lines expressing or not the HER2 receptor, including HCC-1954 and SK-BR-3 (HER2 positive cells) and MDA-MB-231 and MCF-7 (HER negative cells). Standard dose-response (DR) curves for 72 hours were performed.

Cytotoxicity of Compound 41

The cytotoxic activity of the parent Compound 41 was assayed in DR curves using ten serial dilutions (1/2.5 ratio) from 01E-02 to 2.6E-06 µg/mL (1.8E-08 to 4.6E-12 M). The cytotoxic activity of this compound, in two independent experiments, was homogenous across the different cell lines tested, with $IC_{50}$ values in the low nanomolar range, from 7.5E-05 to 1.4E-04 µg/mL (1.3E-10 to 2.4E-1 0 M), being the mean $IC_{50}$ value across the whole cell panel 1.1 E-04 µg/mL (equivalent to 1.9E-10 M). Thus, the cytotoxicity of Compound 41 was independent of the HER2 status of the tumor cell lines (Table 26).

TABLE 26

Summary data of the in vitro cytotoxicity of Compound 41

| | Compound 41 Breast cells | | | |
|---|---|---|---|---|
| | HER2+ | | HER2− | |
| | HCC1954 | SK-BR3 | MCF7 | MDA-MB-231 |
| $IC_{50}$ (μg/mL) | 7.55E−05 | 8.05E−05 | 1.39E−04 | 1.35E−04 |
| $IC_{50}$ (Molar) | 1.33E−10 | 1.41E−10 | 2.44E−10 | 2.36E−10 |

Cytotoxicity of Compound 24

The activity of Compound 24 (was assayed in the same conditions than above, from 01E+00 to 2.6E−04 μg/mL (1.6E-06 to 4.1 E-10 M). The cytotoxic activity of this compound, in two independent experiments, was homogenous across the different cell lines tested, with $IC_{50}$ values in the nanomolar range, from 9.0E-03 to 1.8E-02 μg/mL (1.4E-08 to 2.9E-08 M), being the mean $IC_{50}$ value across the whole cell panel 1.5E-02 μg/mL (2.4E-08 M). The presence of the 1,3-propylenediamine group in Compound 24 significantly decreased (about 2 logs) the cytotoxic activity of the compound as compared to Compound 41. The cytotoxicity of Compound 24 seemed to be independent of the HER2 status of the tumor cell lines (Table 27).

TABLE 27

Summary data of the in vitro cytotoxicity of Compound 24

| | Compound 24 Breast cells | | | |
|---|---|---|---|---|
| | HER2+ | | HER2− | |
| | HCC1954 | SK-BR3 | MCF7 | MDA-MB-231 |
| $IC_{50}$ (μg/mL) | 1.80E−02 | 9.00E−03 | 1.65E−02 | 1.75E−02 |
| $IC_{50}$ (Molar) | 2.87E−08 | 1.44E−08 | 2.63E−08 | 2.79E−08 |

Cytotoxicity of Compound 27

The activity of Compound 27 was assayed in DR curves using ten serial dilutions (1/2.5 ratio) from 01E+00 to 2.6E−04 μg/mL (1.4E-06 to 3.6E-10 M). The cytotoxic activity of Compound 27, in two independent experiments, was homogenous across the different cell lines tested, with $IC_{50}$ values in the micromolar range, from 1.05E-02 to 3.9E-02 μg/mL (1.5E-08 to 5.5E-08 M), being the mean $IC_{50}$ value across the whole cell panel 2.5E-02 μg/mL (3.5E-08 M). The presence of the MPA linker in Compound 27 had no significant effect on the cytotoxic activity of the compound as compared to Compound 24. The activity of Compound 27 was independent of the HER2 status of the tumor cell lines (Table 28).

TABLE 28

Summary data of the in vitro cytotoxicity of Compound 27

| | Compound 27 Breast cells | | | |
|---|---|---|---|---|
| | HER2+ | | HER2− | |
| | HCC1954 | SK-BR3 | MCF7 | MDA-MB-231 |
| $IC_{50}$ (μg/mL) | 1.65E−02 | 1.05E−02 | 3.90E−02 | 3.45E−02 |
| $IC_{50}$ (Molar) | 2.31E−08 | 1.47E−08 | 5.46E−08 | 4.83E−08 |

Cytotoxicity of ADC8

Figure 17:
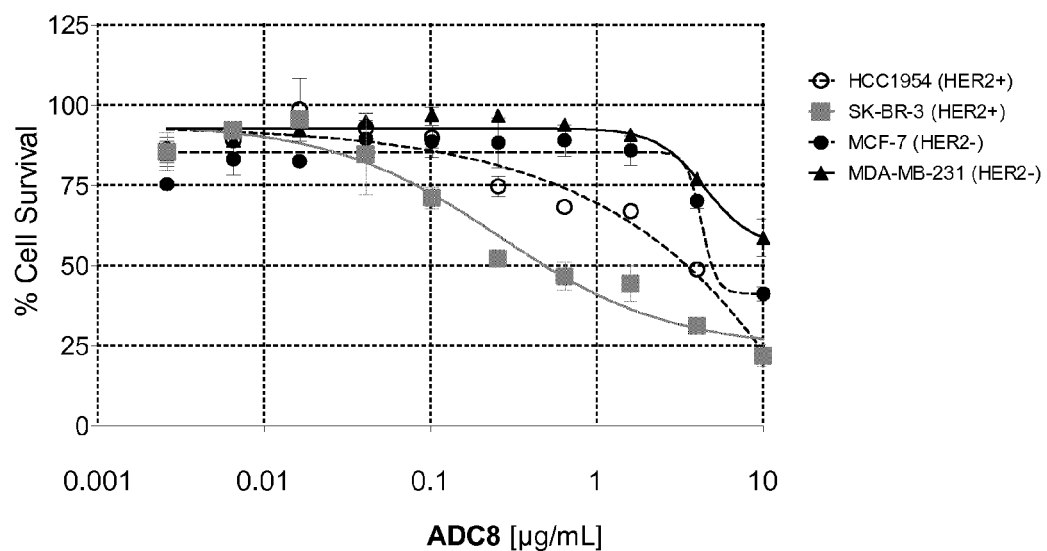
FIG. 17 is a representative dose response curves of ADC8 against various cancer cell lines.

The cytotoxic activity of the ADC8 was assayed against the different cell lines. The conjugate was assayed in four different concentration ranges, each in triplicate DR curves (ten serial dilutions, 1/2.5 ratio) starting from 50, 10, 1 and 0.1 μg/mL, in two independent experiments. A representative DR curve (maximum concentration of 10 g/mL) is shown in FIG. 17. ADC8 showed some specificity against the HER2+ expressing cells, particularly in SK-BR-3, the most sensitive cell line. Except for these cells, which are around 4 times more sensitive than HER2 negative cells ($IC_{50}$ 2.3E-09M), ADC8 showed, similar cytotoxic activity, HER2 independent, than the parent Compound 27, with $IC_{50}$ values in the nanomolar range (Table 29).

TABLE 29

Summary data of the in vitro cytotoxicity of ADC8

| | ADC8 Breast cells | | | |
|---|---|---|---|---|
| | HER2+ | | HER2− | |
| | HCC1954 | SK-BR3 | MCF7 | MDA-MB-231 |
| $IC_{50}$ (μg/mL) | 3.83E+00 | 6.37E−01 | 7.75E+00 | 1.02E+01 |
| Mean $IC_{50}$ (μg/mL) HER2 positive cells | | | 2.23E+00 | |
| Mean $IC_{50}$ (μg/mL) HER2 negative cells | | | 8.98E+00 | |

Figure 18:
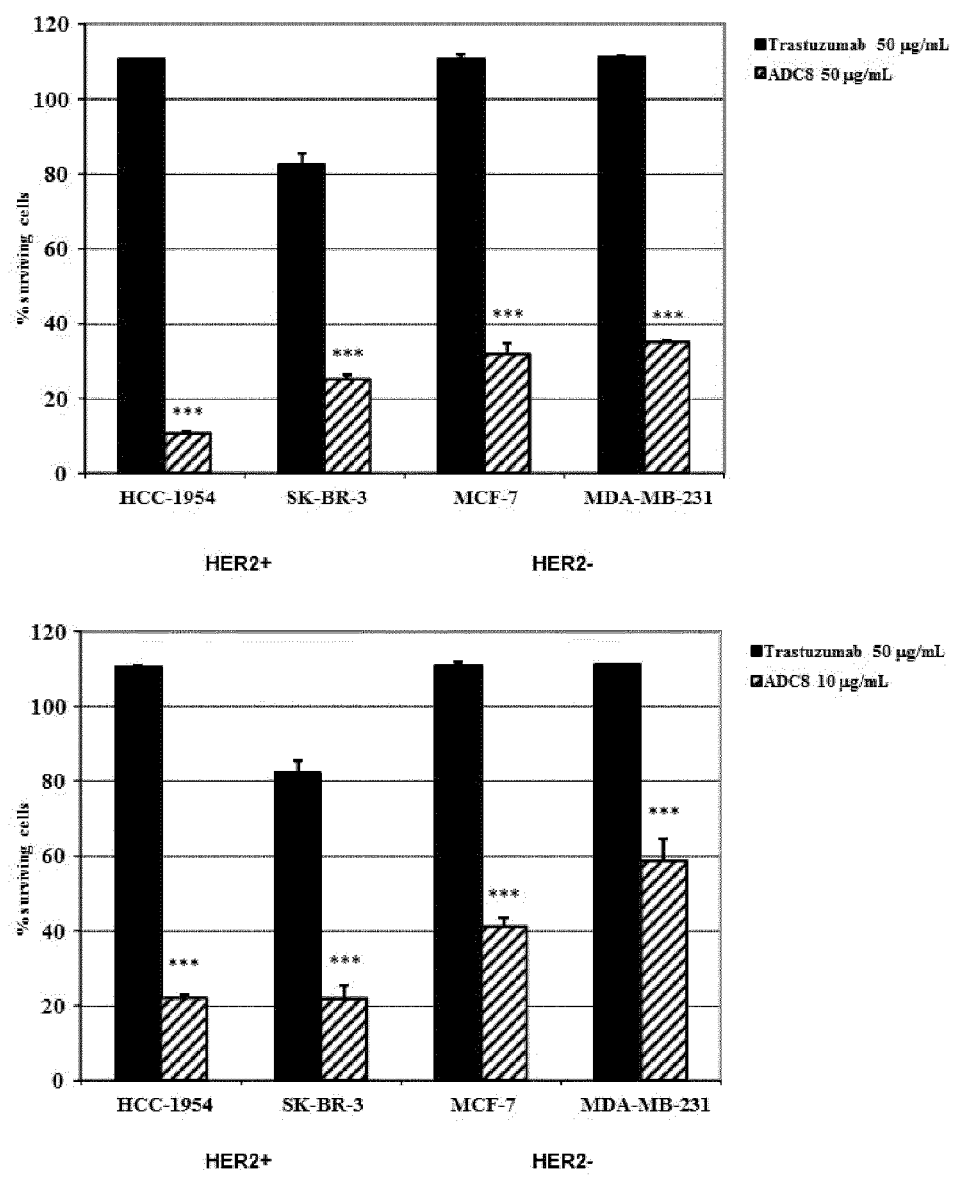
FIG. 18 shows histograms showing the percentage of cell survival after treatment of the different cell lines with the mAb alone (50 µg/mL) or ADC8 at 50 or 10 µg/mL.

To graphically compare the cytotoxic activity of the mAb Trastuzumab alone with that of the conjugate ADC8, histograms showing the percentages of cell survival after treatment of the different cell lines with the mAb alone (50 μg/mL) or ADC8 (50 or 10 g/mL), are shown in FIG. 18. At 50 μg/mL, the mAb alone had no activity in any of the cell lines tested, except for SK-BR-3, in which it produced an inhibition of cell survival of less than 20%. ADC8, in turn, showed no significant specificity for the HER2+ cell lines, producing a strong inhibition of cell survival of more than 60% in all the cells analyzed. At a concentration of 10 μg/mL, ADC8 showed some, but little, specificity against HER2+ cells, producing a 78% inhibition of cell survival in HCC-1954 and SK-BR-3 cells, both HER2 positive, while having a smaller effect on HER2 negative cells, 59% and 41%, in MCF7 and MDA-MB-231, respectively. HER2 positive cells were, roughly, between 1.5 and 2 times more sensitive to ADC8 than HER2 negative cells.

Bioactivity Example 9—Cytotoxicity of ADC9 and Related Reagents Against CD13 Positive and Negative Human Tumor Cells The in vitro cytotoxic activity of ADC9 along with the parent cytotoxic Compounds 1 and 4, was evaluated against different human tumor cell lines expressing or not the CD13 receptor, including NB4 and U937 (CD13 positive cells) and Raji and RPMI-8226 (CD13 negative cells). Standard dose-response (DR) curves for 72 hours were performed.

Cytotoxicity of the Anti-CD13 Mouse Monoclonal Antibody

First of all, the in vitro cytotoxic activity of the anti-CD13 mouse mAb alone was assayed against the different tumor cell lines. In triplicate DR curves ranging from 5.0E+01 to 1.3E-02 μg/mL (3.3E-07-8.7E-1 1 M), in two independent experiments, the antibody was virtually inactive, not reaching the $IC_{50}$ in any of the cell lines tested, independently of their CD13 status (Table 30).

TABLE 30

Summary data of the in vitro cytotoxic activity of the antiCD13 mouse mAb

| | antiCD13 mouse mAb Cell lines | | | |
|---|---|---|---|---|
| | CD13+ | | CD13− | |
| | NB-4 | U937 | Raji | RPMI18226 |
| $IC_{50}$ (µg/mL) | >5.0E+01 | >5.0E+01 | >5.0E+01 | >5.0E+01 |
| $IC_{50}$ (Molar) | >3.33E−07 | >3.33E−07 | >3.33E−07 | >3.33E−07 |

Cytotoxicity of Compound 4

The cytotoxic activity of Compound 4 was assayed in DR curves using ten serial dilutions (1/2.5 ratio) from 01E-02 to 2.6E-06 µg/mL (1.5E-08 to 4.0E-12 M). The cytotoxic activity of Compound 4, in two independent experiments, was very homogenous across the different cell lines tested, with $IC_{50}$ values in the low nanomolar range, from 7.9E-05 to 2.65E-03 µg/mL (1.2E-10 to 4.0E-09 M), being the mean $IC_{50}$ value across the whole cell panel 8.4E-04 µg/mL (equivalent to 1.2E-09 M). Thus, the cytotoxicity of Compound 4 was rather independent of the CD13 status of the tumor cell lines (Table 31).

TABLE 31

Summary data of the in vitro cytotoxicity of Compound 4

| | Compound 4 Cell lines | | | |
|---|---|---|---|---|
| | CD13+ | | CD13− | |
| | NB-4 | U937 | Raji | RPMI18226 |
| $IC_{50}$ (µg/mL) | 7.93E−05 | 2.78E−04 | 2.65E−03 | 3.58E−04 |
| $IC_{50}$ (Molar) | 1.20E−10 | 4.19E−10 | 4.00E−09 | 5.39E−10 |

Cytotoxicity of Compound 1

The activity of the Compound 1 was assayed in DR curves using ten serial dilutions (1/2.5 ratio) from 01E-01 to 2.6E-05 µg/mL (1.1 E-07 to 3.0E-1 1 M). The cytotoxic activity of Compound 1, in two independent experiments, was somewhat homogenous across the different cell lines tested, with $IC_{50}$ values in the nanomolar range, from 8.0E-04 to 6.3E-03 µg/mL (9.4E-10 to 7.3E-09 M), being the mean $IC_{50}$ value across the whole cell panel 2.8E-03 µg/mL (3.3E-09 M). The presence of the maleimide linker in Compound 1 does not alter very significantly the cytotoxic activity of the compound, as compared to Compound 4. In addition, the cytotoxicity of the compound was not related to the CD13 status of the tumor cell lines (Table 32).

TABLE 32

Summary data of the in vitro cytotoxicity of Compound 1

| | Compound 1 Cell lines | | | |
|---|---|---|---|---|
| | CD13+ | | CD13− | |
| | NB-4 | U937 | Raji | RPM1 18226 |
| $IC_{50}$ (µg/mL) | 8.05E−04 | 1.65E−03 | 6.25E−03 | 2.50E−03 |
| $IC_{50}$ (Molar) | 9.39E−10 | 1.93E−09 | 7.31E−09 | 2.92E−09 |

Cytotoxicity of ADC9

Figure 19:
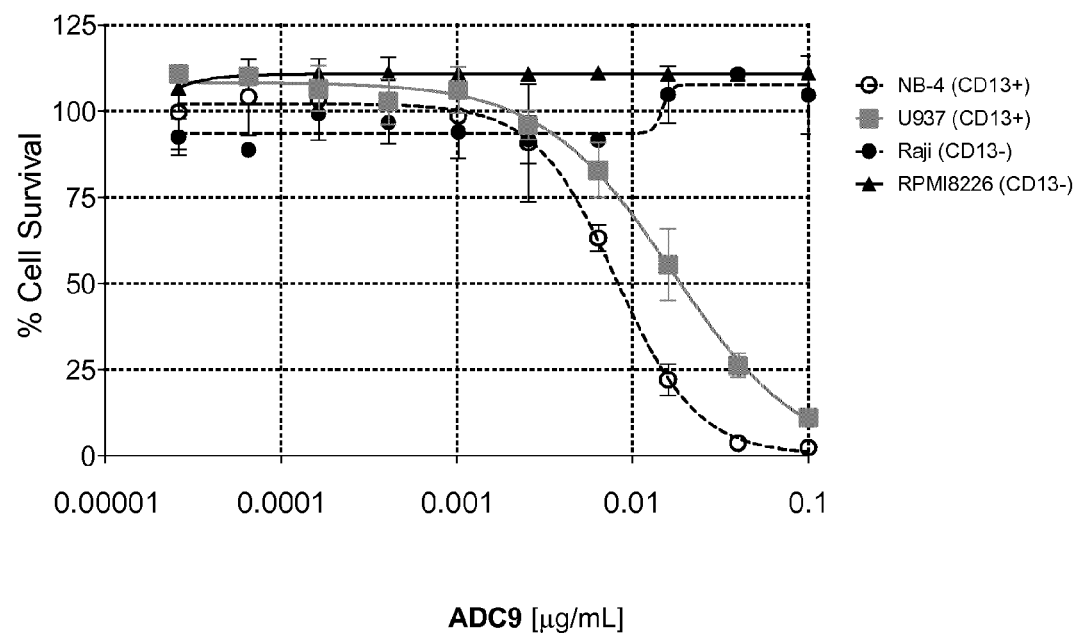
FIG. 19 is a representative dose response curves of ADC9 against various cancer cell lines.

The cytotoxic activity of the ADC9 was assayed against the different cell lines. The conjugate was assayed in four different concentration ranges, each in triplicate DR curves (ten serial dilutions, 1/2.5 ratio) starting from 50, 10, 1 and 0.1 µg/mL, in two independent experiments. A representative DR curve (maximum concentration 0.1 µg/mL) is shown in FIG. 19.

The conjugate ADC9 showed a significant specificity against CD13+ expressing cells, in which the compound demonstrated a cytotoxic activity similar, or slightly higher, to that of the parent Compounds 4 and 1. Both CD13+ cell lines, NB4 and U937, showed a comparable sensitivity against ADC9, with mean $IC_{50}$ values of 8.7E-03 and 2.4E-02 µg/mL, respectively. The two CD13 negative cell lines, Raji and RPMI-8226, showed a significantly lower sensitivity against ADC9, with mean $IC_{50}$ values of 1.6E+00 and 5.9E-01 µg/mL, respectively. Average, CD13+ cell lines (mean $IC_{50}$ 1.66E-02 µg/mL) were around 65 times more sensitive to ADC9 than the CD13− cells (mean $IC_{50}$ 1.08E+00 µg/mL). Comparing the activity of ADC9 in NB4 cells (the most sensitive) vs Raji cells (the least sensitive); it was found a difference of around 180 times. These results clearly showed the specificity of the conjugate against the CD13 expressing cells (Table 33). We assume, therefore, that the ADC9 was, at least in part, acting through the interaction of the mAb with the membrane associated CD13 receptor on tumor cells, and subsequent intracellular delivery of the cytotoxic drug into the target tissue.

TABLE 33

Summary data of the in vitro cytotoxicity of ADC9

| | ADC9 Cell lines | | | |
|---|---|---|---|---|
| | CD13+ | | CD13− | |
| | NB-4 | U937 | Raji | RPMI18226 |
| $IC_{50}$ (µg/mL) | 8.75E−03 | 2.44E−02 | 1.57E+00 | 5.92E−01 |
| Mean $IC_{50}$ (µg/mL) CD13 positive cells | | | | 1.66E−02 |
| Mean $IC_{50}$ (µg/mL) CD13 negative cells | | | | 1.08E+00 |

Figure 20:
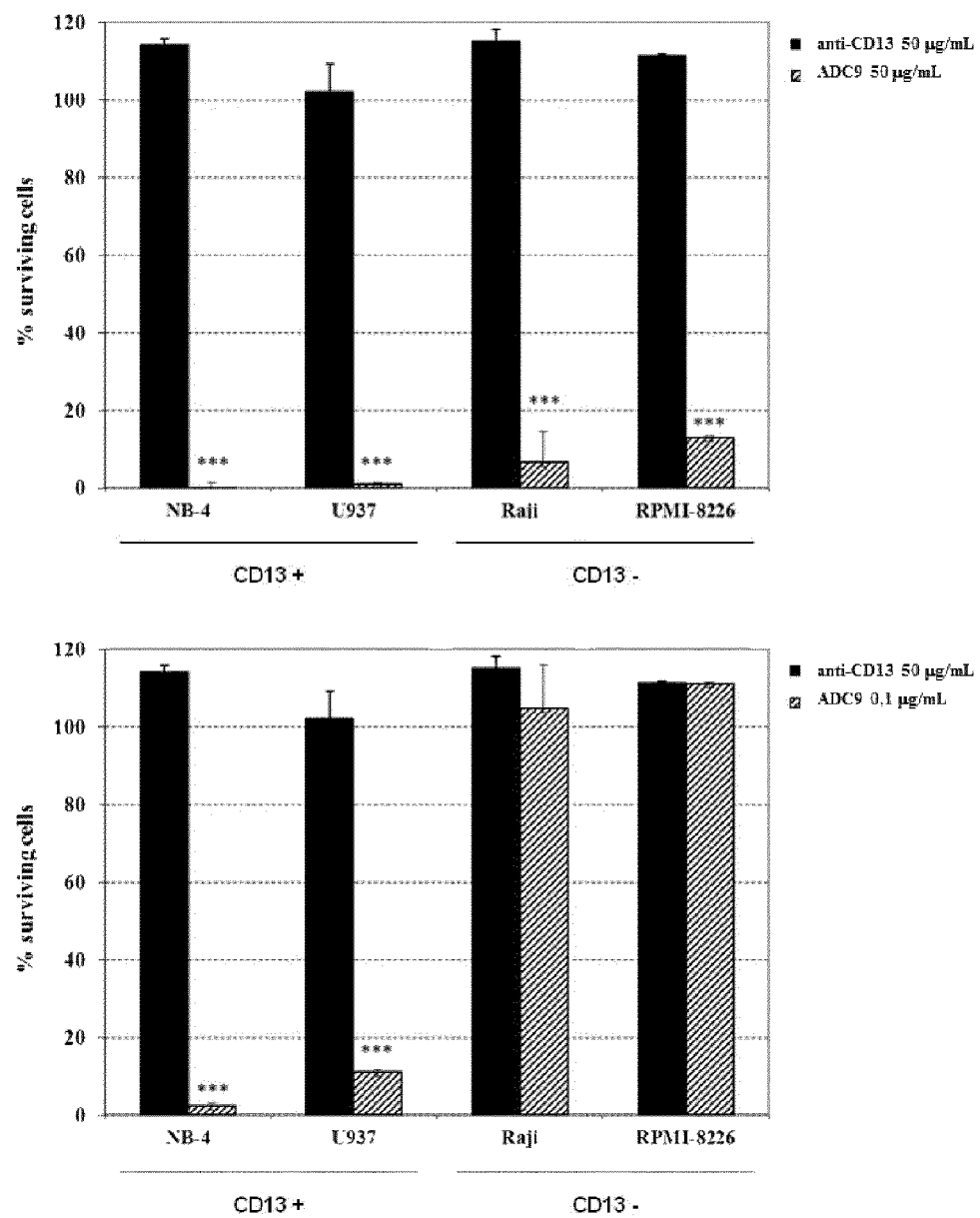
FIG. 20 shows histograms showing the percentage of cell survival after treatment of the different cell lines with the mAb alone (50 µg/mL) or ADC9 at 50 or 0.1 µg/mL.

To graphically compare the cytotoxic activity of the mAb alone with that of the conjugate ADC9, histograms showing the percentages of cell survival after treatment of the different cell lines with the mAb alone (50 µg/mL) or the ADC at 50 or 0.1 µg/η1 L, are shown in FIG. 20. At an equal concentration of 50 µg/η1 L, the anti-CD13 antibody alone, showed no cytotoxic activity against any of the cell lines tested, independently of their CD13 status. In contrast, ADC9 conjugate showed a potent cytotoxic activity against all the cell lines, inducing an inhibition of the cell survival of more than 80%. At a concentration of 0.1 µg/mL, the conjugate ADC9 showed a similar cytotoxic activity against the CD13 positive cells than that observed at 50 µg/mL, but without any detectable effect on CD13 negative cells. These results further demonstrated the remarkable cytotoxic activity and specificity of ADC9 against CD13 expressing human tumor cells in vitro.

Bioactivity Example 10—Cytotoxicity of ADC10 and Related Reagents Against CD13 Positive and Negative Human Tumor Cells The in vitro cytotoxic activity of ADC10 along with the parent cytotoxic Compounds 12 and 4, was evaluated against different human tumor cell lines expressing or not the CD13 receptor, including NB4 and U937 (CD13 positive cells) and Raji and RPMI-8226 (CD13 negative cells). Standard dose-response (DR) curves for 72 hours were performed.

Cytotoxicity of Compound 4

The cytotoxic activity of Compound 4 was assayed in DR curves using ten serial dilutions (1/2.5 ratio) from 01E-02 to 2.6E-06 µg/mL (1.5E-08 to 4.0E-12 M). The cytotoxic activity of Compound 4, in two independent experiments, was very homogenous across the different cell lines tested, with $IC_{50}$ values in the low nanomolar range, from 7.9E-05 to 2.65E-03 µg/mL (1.2E-10 to 4.0E-09 M), being the mean $IC_{50}$ value across the whole cell panel 8.4E-04 µg/mL (equivalent to 1.2E-09 M). Thus, the cytotoxicity of Compound 4 was rather independent of the CD13 status of the tumor cell lines (Table 34).

TABLE 34

Summary data of the in vitro cytotoxicity of Compound 4

| | Compound 4 Cell lines | | | |
|---|---|---|---|---|
| | CD13+ | | CD13− | |
| | NB-4 | U937 | Raji | RPM1 18226 |
| $IC_{50}$ (µg/mL) | 7.93E−05 | 2.78E−04 | 2.65E−03 | 3.58E−04 |
| $IC_{50}$ (Molar) | 1.20E−10 | 4.19E−10 | 4.00E−09 | 5.39E−10 |

Cytotoxicity of Compound 12

The activity of the Compound 12 was assayed in DR curves using ten serial dilutions (1/2.5 ratio) from 01E+00 to 2.6E-04 µg/mL (7.9E-07 to 2.0E-10 M). The cytotoxic activity of Compound 12, in two independent experiments, was somewhat homogenous across the different cell lines tested, with $IC_{50}$ values in the nanomolar range, from 4.4E-03 to 4.8E-02 µg/mL (3.5E-09 to 3.8E-08 M), being the mean $IC_{50}$ value across the whole cell panel 2.0E-02 µg/mL (1.6E-08 M). The presence of the long linker in Compound 12 decreased (aprox 1 log) the cytotoxic activity of the compound, as compared to Compound 4. In addition, the cytotoxicity of the compound was not related to the CD13 status of the tumor cell lines (Table 35).

TABLE 35

Summary data of the in vitro cytotoxicity of Compound 12

| | Compound 12 Cell lines | | | |
|---|---|---|---|---|
| | CD13+ | | CD13− | |
| | NB-4 | U937 | Raji | RPMI18226 |
| $IC_{50}$ (µg/mL) | 4.45E−03 | 1.07E−02 | 4.80E−02 | 1.90E−02 |
| $IC_{50}$ (Molar) | 3.53E−09 | 8.44E−09 | 3.80E−08 | 1.51E−08 |

Cytotoxicity of ADC10

Figure 21:
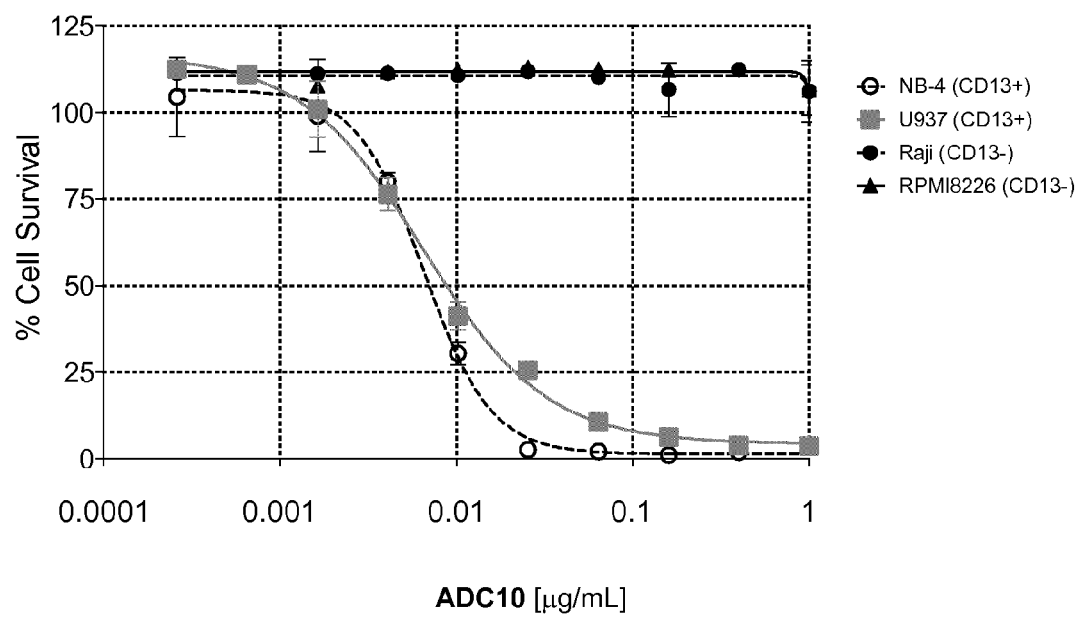
FIG. 21 is a representative dose response curves of ADC10 against various cancer cell lines.

The cytotoxic activity of the ADC10 was assayed against the different cell lines. The conjugate was assayed in four different concentration ranges, each in triplicate DR curves (ten serial dilutions, 1/2.5 ratio) starting from 50, 10, 1 and 0.1 µg/mL, in two independent experiments. A representative DR curve (maximum concentration 1 µg/mL) is shown in FIG. 21.

The conjugate ADC10 showed a significant specificity against CD13+ expressing cells, in which the compound demonstrated a cytotoxic activity similar, or slightly higher, to that of the parent Compounds 4 and 12. Both CD13+ cell lines, NB4 and U937, showed a comparable sensitivity against ADC10, with mean $IC_{50}$ values of 7.2E-03 and 9.8E-03 µg/mL, respectively. The two CD13 negative cell lines, Raji and RPMI-8226, showed a significantly lower sensitivity against ADC10, with mean $IC_{50}$ values of 1.0E+01 and 5.3E+00 µg/mL, respectively. Average, CD13+ cell lines (mean $IC_{50}$ 8.50E-03 µg/mL) were around 900 times more sensitive to ADC10 than the CD13− cells (mean $IC_{50}$ 7.83E+00 µg/mL). Comparing the activity of ADC10 in NB4 cells (the most sensitive) vs Raji cells (the least sensitive); it was found a difference of around 1440 times. These results clearly showed the specificity of ADC10 against CD13 expressing cells (Table 36). We assume, therefore, that the ADC10 was, at least in part, acting through the interaction of the mAb with the membrane associated CD13 receptor on tumor cells, and subsequent intracellular delivery of the cytotoxic drug into the target tissue.

TABLE 36

Summary data of the in vitro cytotoxicity of ADC10

| | ADC10 Cell lines | | | |
|---|---|---|---|---|
| | CD13+ | | CD13− | |
| | NB-4 | U937 | Raji | RPMI18226 |
| $IC_{50}$ (µg/mL) | 7.18E−03 | 9.81E−03 | 1.04E+01 | 5.30E+00 |
| Mean $IC_{50}$ (pg/mL) CD13 positive cells | | 8.50E−03 | | |
| Mean $IC_{50}$ (pg/mL) CD13 negative cells | | 7.83E+00 | | |

Figure 22:
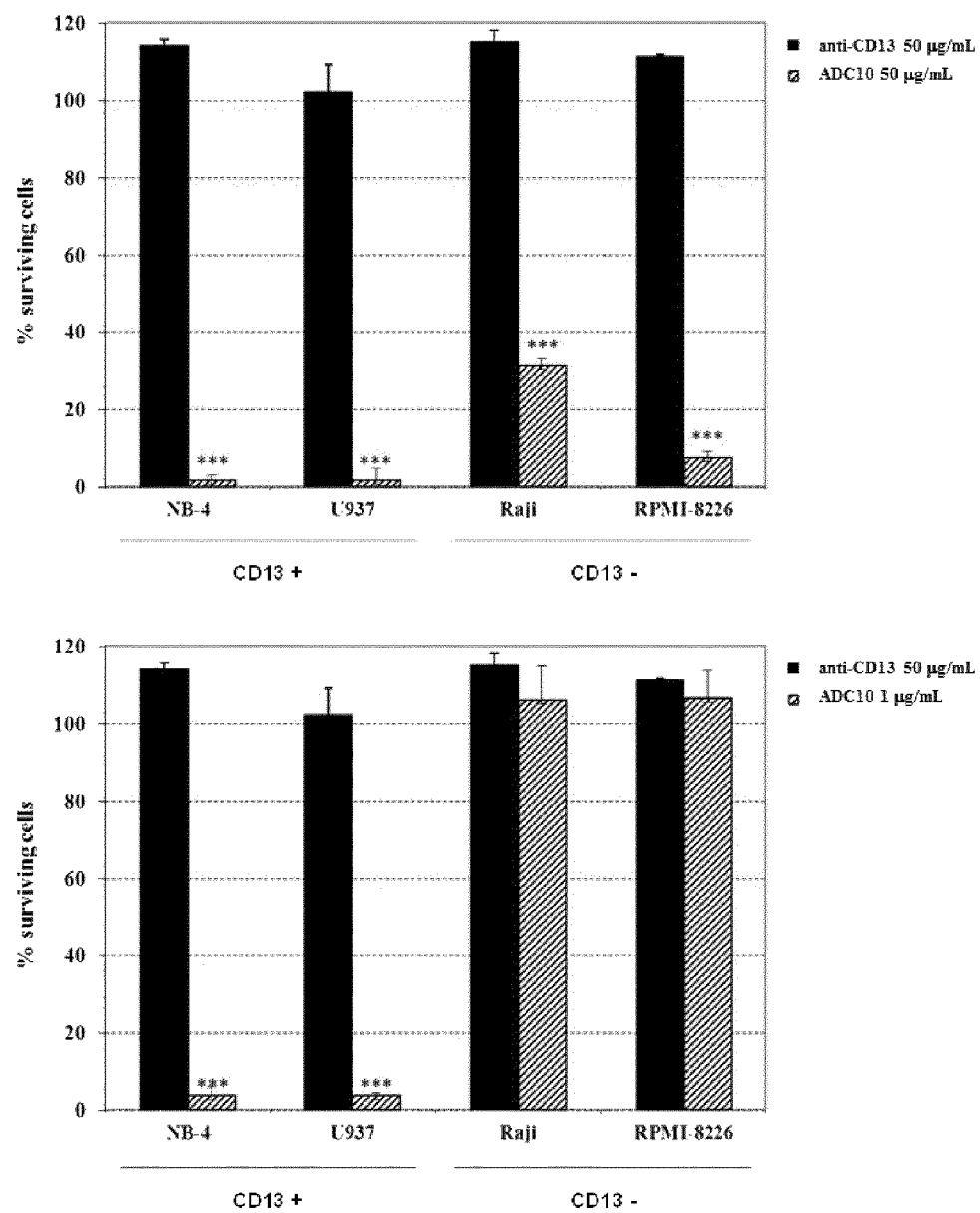
FIG. 22 shows histograms showing the percentage of cell survival after treatment of the different cell lines with the mAb alone (50 µg/mL) or ADC10 at 50 or 1 µg/mL.

To graphically compare the cytotoxic activity of the mAb alone with that of the conjugate ADC10, histograms showing the percentages of cell survival after treatment of the different cell lines with the mAb alone (50 µg/mL) or the ADC at 50 or 1 µg/mL, are shown in FIG. 22. At an equal concentration of 50 µg/mL, the anti-CD13 antibody alone, showed no cytotoxic activity against any of the cell lines tested, independently of their CD13 status. In contrast, ADC10 conjugate showed a potent cytotoxic activity against all the cell lines, inducing an inhibition of the cell survival of more than 80%, except for Raji cells, in which it produced a lower, but still important, inhibition of around 70%. At a concentration of 1 µg/mL, ADC10 showed a similar cytotoxic activity against the CD13 positive cells than that observed at 50 g/mL, but without any detectable effect on CD13 negative cells. These results further demonstrated the remarkable cytotoxic activity and specificity of ADC10 against CD13 expressing human tumor cells in vitro.

Bioactivity Example 11—Cytotoxicity of ADC11 and Related Reagents Against CD13 Positive and Negative Human Tumor Cells The in vitro cytotoxic activity of ADC11 along with the parent cytotoxic Compounds 13 and 40, was evaluated against different human tumor cell lines expressing or not the CD13 receptor, including NB4 and U937 (CD13 positive cells) and Raji and RPMI-8226 (CD13 negative cells). Standard dose-response (DR) curves for 72 hours were performed.

Cytotoxicity of Compound 40

The cytotoxic activity of Compound 40 was assayed in DR curves using ten serial dilutions (1/2.5 ratio) from 01E-03 to 2.6E-07 µg/mL (1.7E-09 to 4.3E-13 M). The cytotoxic activity of Compound 40, in two independent experiments, was homogenous across the different cell lines tested, with $IC_{50}$ values in the low picomolar range, from 3.1 E-05 to 1.7E-04 µg/mL (5.2E-1 1 to 2.8E-10 M), being the mean $IC_{50}$ value across the whole cell panel 8.6E-05 µg/mL (equivalent to 1.4E-10 M). The cytotoxicity of Compound 40 was independent of the CD13 expression levels on the tumor cell lines (Table 37).

TABLE 37

Summary data of the in vitro cytotoxicity of Compound 40

| | Compound 40 Cell lines | | | |
|---|---|---|---|---|
| | CD13+ | | CD13- | |
| | NB-4 | U937 | Raji | RPMI18226 |
| $IC_{50}$ (µg/mL) | 3.15E-05 | 7.10E-05 | 1.70E-04 | 7.05E-05 |
| $IC_{50}$ (Molar) | 5.20E-11 | 1.17E-10 | 2.80E-10 | 1.16E-10 |

Cytotoxicity of Compound 13

The activity of the Compound 13 was assayed in DR curves using ten serial dilutions (1/2.5 ratio) from 01E-01 to 2.6E-05 µg/mL (1.3E-07 to 3.4E-1 1 M). The cytotoxic activity of Compound 13, in two independent experiments, was somewhat homogenous across the different cell lines tested, with $IC_{50}$ values in the nanomolar range, from 1.7E-03 to 1.0E-02 µg/mL (2.7E-09 to 1.4E-08 M), being the mean $IC_{50}$ value across the whole cell panel 4.3E-03 µg/mL (5.7E-09 M). The presence of the thiol containing tail in Compound 13 reduced (less than 1 log) the cytotoxic activity of the compound, as compared to Compound 40. The cytotoxicity of the compound was rather independent of the CD13 status of the tumor cell lines (Table 38).

TABLE 38

Summary data of the in vitro cytotoxicity of Compound 13

| | Compound 13 Cell lines | | | |
|---|---|---|---|---|
| | CD13+ | | CD13- | |
| | NB-4 | U937 | Raji | RPMI18226 |
| $IC_{50}$ (µg/mL) | 1.70E-03 | 2.85E-03 | 1.03E-02 | 2.30E-03 |
| $IC_{50}$ (Molar) | 2.26E-09 | 3.80E-09 | 1.37E-08 | 3.06E-09 |

Figure 23:
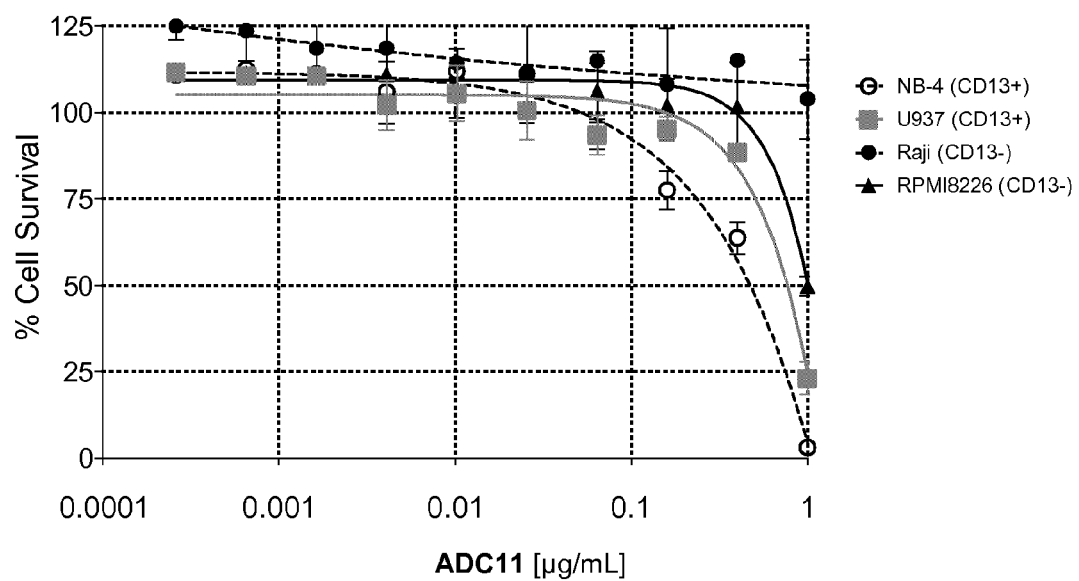
FIG. 23 is a representative dose response curves of ADC11 against various cancer cell lines.

Cytotoxicity of ADC1 1 The cytotoxic activity of the ADC11 was assayed against the different cell lines. The conjugate was assayed in four different concentration ranges, each in triplicate DR curves (ten serial dilutions, 1/2.5 ratio) starting from 50, 10, 1 and 0.1 µg/mL, in two independent experiments. A representative DR curve (maximum concentration of 1 g/mL) is shown in FIG. 23. ADC11 showed some, but little, specificity against the CD13 expressing cells. The conjugate had rather similar cytotoxic activity, except for Raji cells, which are slightly less sensitive, in all the cell lines tested. The activity of ADC11 was comparable to that of the parent Compound 13, with $IC_{50}$ values in the low nanomolar range (Table 39).

TABLE 39

Summary data of the in vitro cytotoxicity of ADC11

| | ADC11 Cell lines | | | |
|---|---|---|---|---|
| | CD13+ | | CD13- | |
| | NB-4 | U937 | Raji | RPMI 18226 |
| $IC_{50}$ (µg/mL) | 2.27E-01 | 6.77E-01 | 3.48E+00 | 6.95E-01 |
| Mean $IC_{50}$ ^g/mL) CD1 3 positive cells | | | | 4.52E-01 |
| Mean $IC_{50}$ ^g/mL) CD1 3 negative cells | | | | 2.09E+00 |

Figure 24:
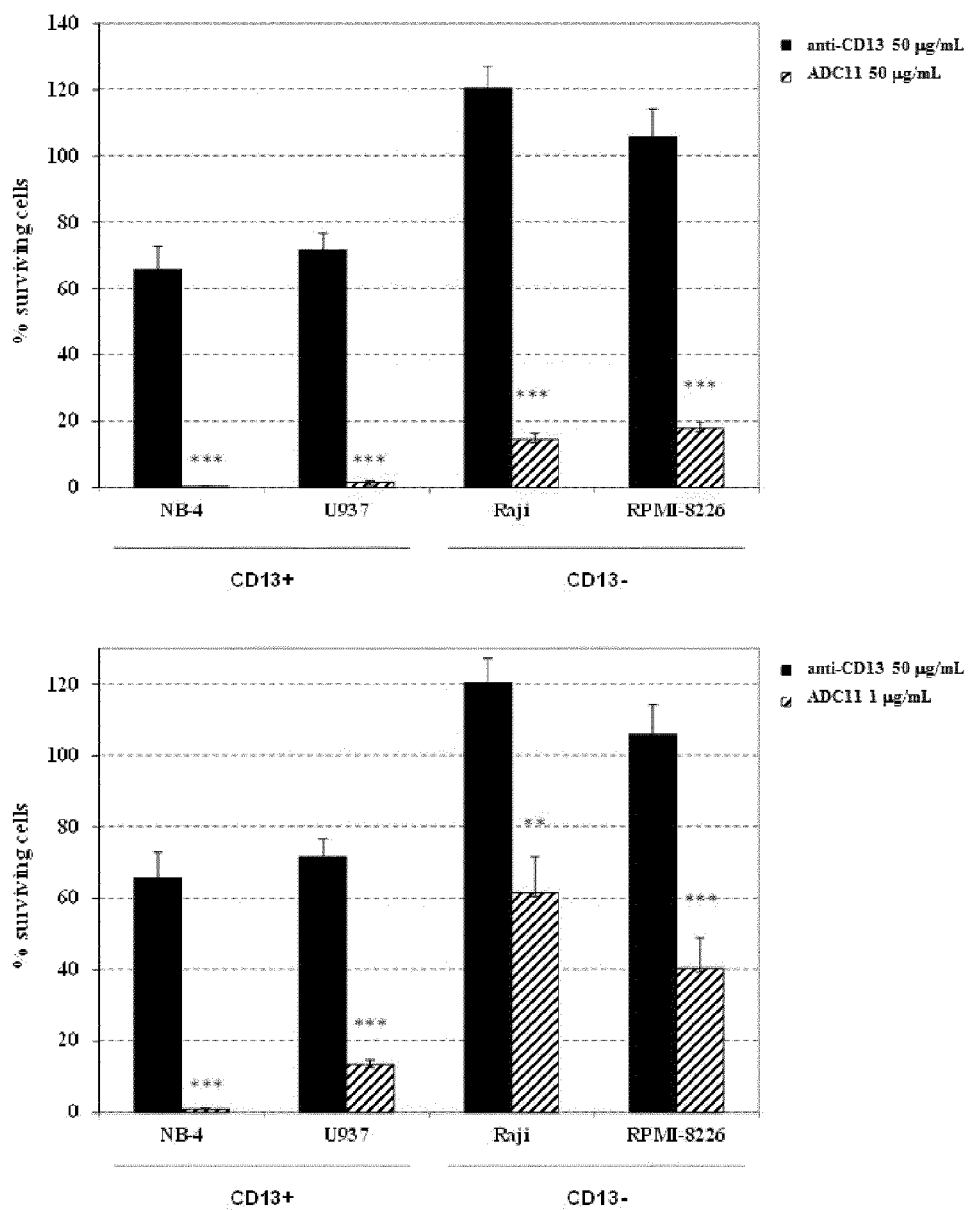
FIG. 24 shows histograms showing the percentage of cell survival after treatment of the different cell lines with the mAb alone (50 µg/mL) or ADC11 at 50 or 1 µg/mL.

To graphically compare the cytotoxic activity of the Anti-CD13 mAb alone with that of the conjugate ADC11, histograms showing the percentages of cell survival after treatment of the different cell lines with the mAb alone (50 µg/mL) or the ADC11 (50 or 1 µg/mL), are shown in FIG. 24. At a concentration of 50 µg/mL, the anti-CD13 antibody alone, showed some cytotoxic activity against CD13+ cell lines, producing an inhibition of cell survival of around 30%. In CD13- cells, the antibody was virtually inactive. At the same concentration, ADC1 1 conjugate showed a potent cytotoxic activity against all the cell lines, with some, but very little, specificity against CD13 expressing cells, in which it induced a reduction of cell survival of nearly 100%. In CD13- cells, ADC1 1 induced more than 80% reduction in cell survival. At a concentration of 1 µg/mL, ADC11 showed more specificity against CD13+ cells, NB-4 and U937, in which it induced a reduction of cell survival of 99 and 85%, respectively. In CD13- cells, Raji and RPMI8226, the conjugate induced a reduction of cell survival of 38 and 60%, respectively.

Bioactivity Example 12—Cytotoxicity of ADC12 and Related Reagents Against CD20 Positive and Negative Human Tumor Cells The in vitro cytotoxic activity of ADC12 along with the parent cytotoxic Compounds 1, 4, and 40, was evaluated was assayed against different human cancer cell lines expressing or not the CD20 antigen, including Raji (CD20 positive cells); RPMI-8226 and Karpas-299 (CD20 negative cells). Standard dose-response (DR) curves for 72 hours were performed.

Cytotoxicity of Rituximab

First of all, the in vitro cytotoxic activity of the mAb alone Rituximab was assayed against different human cancer cell lines expressing or not the CD20 antigen, including Raji (CD20 positive cells); RPMI-8226 and Karpas-299 (CD20 negative cells). In triplicate DR curves spanning from 5.0E+ 01 to 2.62E-05 µg/mL (3.4E-07 to 1.7E-13 M), the antibody was rather inactive, not reaching the $IC_{50}$ in any of the cell lines tested, independently of their CD20 status (Table 40).

TABLE 40

Summary data of the in vitro cytotoxicity of Rituximab

| | Rituximab | | |
|---|---|---|---|
| | CD20+ | CD20- | |
| | Raji Burkitt's Lymphoma | RPMI-8226 Multiple Myeloma | Karpas-299 NHL |
| $IC_{50}$ (µg/mL) | >5.0E+01 | >5.0E+01 | >5.0E+01 |
| $IC_{50}$ (Molar) | >3.48E-07 | >3.48E-07 | >3.48E-07 |

Cytotoxicity of Compound 40

The cytotoxic activity of the parent Compound 40 was assayed in DR curves using ten serial dilutions (1/2.5 ratio) from 01E-03 to 2.6E-07 µg/mL (1.7E-09 to 4.3E-13 M). The cytotoxic activity of Compound 40 was very homogenous across the different cell lines tested, with $IC_{50}$ values in the low subnanomolar range, from 8.6E-05 to 1.1 E-04 µg/mL (1.4E-10 to 1.9E-10 M), being the mean $IC_{50}$ value across the whole cell panel 9.6E-05 µg/mL (equivalent to 1.6E-10 M). The cytotoxicity of Compound 40 was independent of the CD20 status of the tumor cell lines (Table 41).

TABLE 41

Summary data of the in vitro cytotoxicity of Compound 40

| | Compound 40 | | |
|---|---|---|---|
| | CD20+ | CD20− | |
| | Raji Burkitt's Lymphoma | RPMI-8226 Multiple Myeloma | Karpas-299 NHL |
| $IC_{50}$ (µg/mL) | 1.15E−04 | 8.65E−05 | 8.60E−05 |
| $IC_{50}$ (Molar) | 1.90E−10 | 1.43E−10 | 1.42E−10 |

Cytotoxicity of Compound 4

The cytotoxic activity of Compound 4 was assayed in DR curves using ten serial dilutions (1/2.5 ratio) from 01E-02 to 2.6E-06 µg/mL (1.5E-08 to 4.0E-12 M). The cytotoxic activity of Compound 4 was homogenous across the different cell lines tested, with $IC_{50}$ values in the nanomolar range, from 5.7E-04 to 1.4E-03 µg/mL (8.6E-10 to 2.1 E-09 M), being the mean $IC_{50}$ value across the whole cell panel 9.7E-04 µg/mL (1.5E-09 M). The presence of the amine containing group in Compound 4 slightly reduced the cytotoxic activity of the compound, as compared to Compound 40. The cytotoxic activity of Compound 4 was also independent of the CD20 status of the tumor cell lines (Table 42).

TABLE 42

Summary data of the in vitro cytotoxicity of Compound 4

| | Compound 4 | | |
|---|---|---|---|
| | CD20+ | CD20− | |
| | Raji Burkitt's Lymphoma | RPMI-8226 Multiple Myeloma | Karpas-299 NHL |
| $IC_{50}$ (µg/mL) | 1.41E−03 | 5.70E−04 | 9.30E−04 |
| $IC_{50}$ (Molar) | 2.12E−09 | 8.59E−10 | 1.40E−09 |

Cytotoxicity of Compound 1

The activity of the Compound 1 was assayed in DR curves using ten serial dilutions (1/2.5 ratio) from 01E-01 to 2.6E-05 µg/mL (1.2E-07 to 3.0E-1 1 M). The cytotoxic activity of Compound 1, in two independent experiments, was very homogenous across the different cell lines tested, with $IC_{50}$ values in the nanomolar range, from 1.6E-03 to 2.8E-03 µg/mL (1.9E-09 to 3.3E-09 M), being the mean $IC_{50}$ value across the whole cell panel 2.1 E-03 µg/mL (2.5E-09 M). The presence of the maleimide linker in Compound 1 does not significantly alter the cytotoxic activity of the compound, as compared to Compound 4. In addition, the cytotoxicity of the compound was also independent of the CD20 status of the tumor cell lines (Table 43).

TABLE 43

Summary data of the in vitro cytotoxicity of Compound 1

| | Compound 1 | | |
|---|---|---|---|
| | CD20+ | CD20− | |
| | Raji Burkitt's Lymphoma | RPMI-8226 Multiple Myeloma | Karpas-299 NHL |
| $IC_{50}$ (µg/mL) | 2.85E−03 | 1.60E−03 | 1.90E−03 |
| $IC_{50}$ (Molar) | 3.33E−09 | 1.87E−09 | 2.22E−09 |

Cytotoxicity of ADC12

Figure 25:
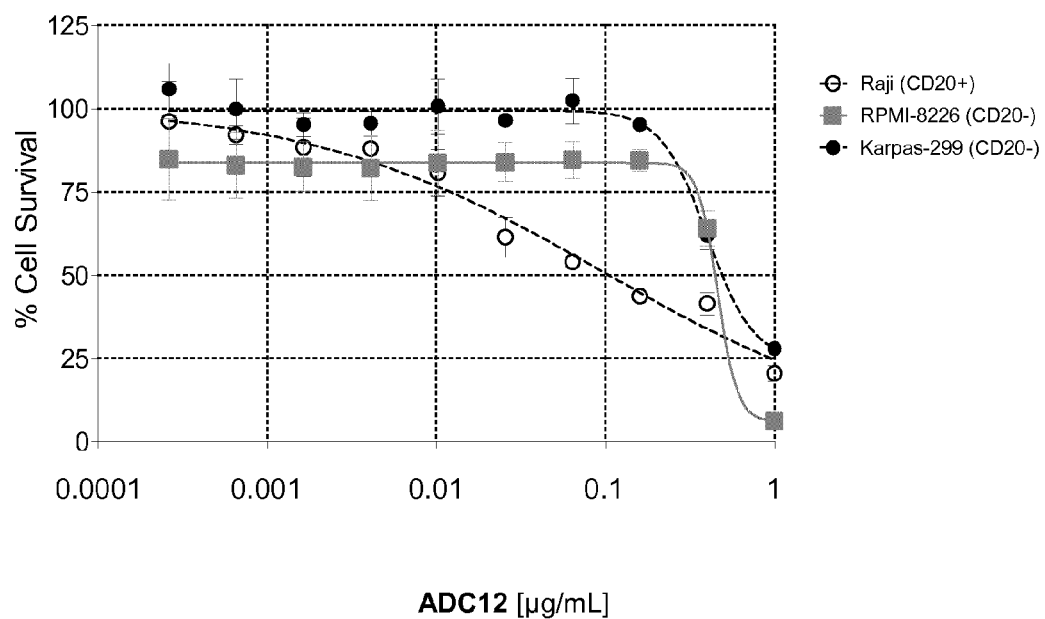
FIG. 25 is a representative dose response curves of ADC12 against various cancer cell lines.

The cytotoxic activity of the ADC12 was assayed against the different tumor cell lines. The conjugate was assayed in four different concentration ranges, each in triplicate DR curves (ten serial dilutions, 1/2.5 ratio) starting from 50, 10, 1 and 0.1 g/mL, respectively. A representative DR curve (starting concentration 1 µg/mL) is shown in FIG. 25. Although higher in CD20 positive Raji cells, ADC12 presented a relatively similar cytotoxic activity, in the nanomolar range, in all the cell lines tested. Raji cells (CD20+), showed a mean $IC_{50}$ value of 9.5E-02 µg/mL, while the respective values for RPMI-8226 and Karpas-299 cells (both CD20−), were 4.0E-01 and 4.1 E-01 µg/mL, respectively (Table 44). Thus, CD20 positive cells were slightly more sensitive (4 fold) to ADC12 than CD20 negative cells.

TABLE 44

Summary data of the in vitro cytotoxicity of ADC12

| | ADC12 | | |
|---|---|---|---|
| | CD20+ | CD20− | |
| | Raji Burkitt's Lymphoma | RPMI-8226 Multiple Myeloma | Karpas-299 NHL |
| $IC_{50}$ (µg/mL) | 9.54E−02 | 3.97E−01 | 4.13E−01 |
| Mean $IC_{50}$ (µg/mL) CD20 positive cells | | | 9.54E−02 |
| Mean $IC_{50}$ (µg/mL) CD20 negative cells | | | 4.05E−01 |

Figure 26:
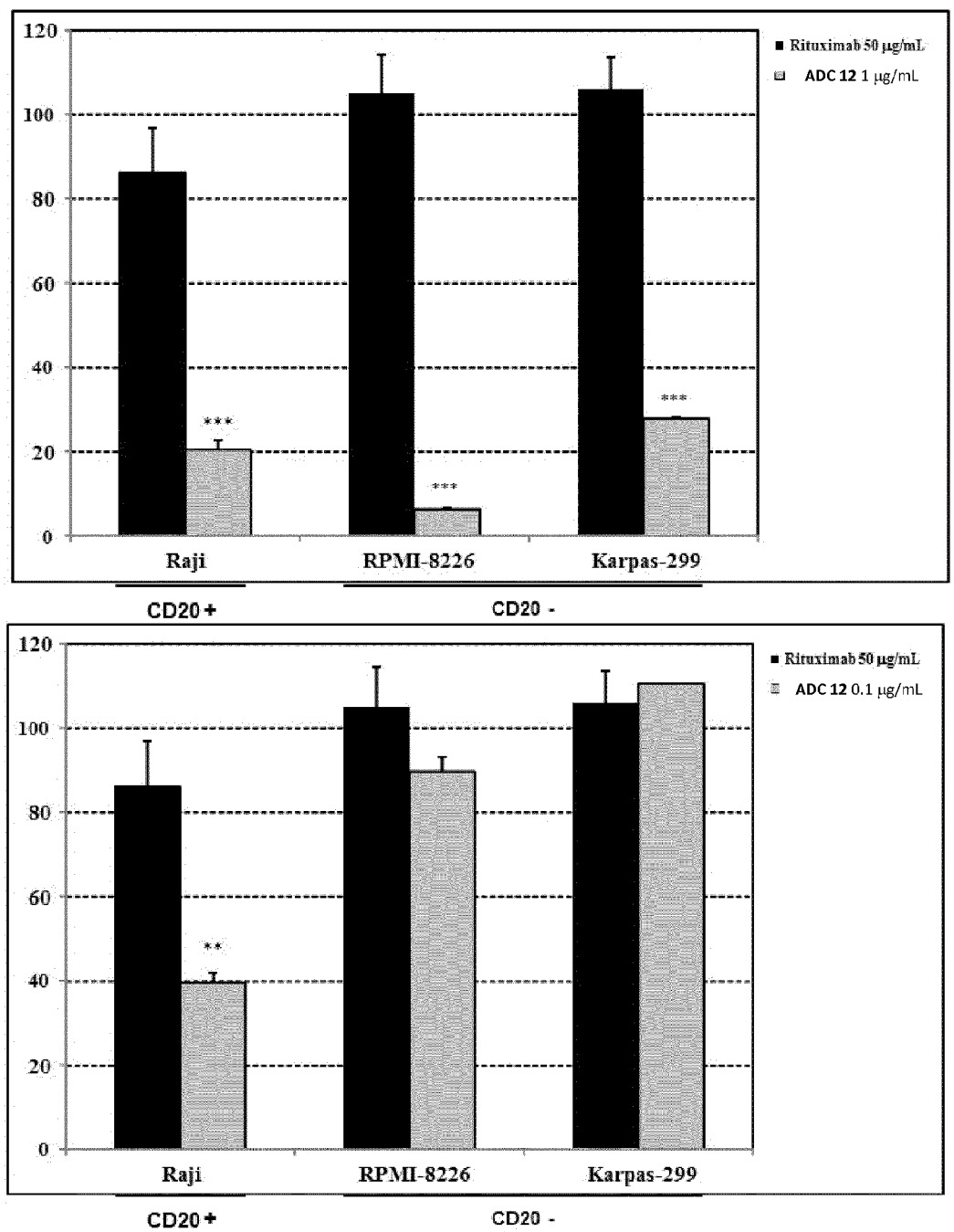
FIG. 26 shows histograms showing the percentage of cell survival after treatment of the different cell lines with the mAb alone (50 µg/mL) or ADC12 at 1 or 0.1 µg/mL.

To graphically compare the cytotoxic activity of the mAb Rituximab alone with that of the conjugate ADC12, histograms showing the percentages of cell survival after treatment of the different cell lines with the mAb alone (50 µg/mL) or ADC12 (1 and 0.1 µg/mL), are shown in FIG. 26. Rituximab alone, at a concentration of 50 g/mL, was virtually inactive in all the cell lines tested, independently of their CD20 status. In contrast, the ADC12, at a concentration of 1 µg/mL, showed potent cytotoxic activity in all the cell lines tested, causing more than 70% reduction in the cell survival after 72 hours of treatment. At a lower concentration, 0.1 µg/mL, ADC12 conjugate showed some specificity, inducing a reduction of cell survival of around 60% in CD20 positive cells (Raji), while being virtually inactive in CD20 negative cells (RPMI-8226 and Karpas-299).

Bioactivity Example 13—Cytotoxicity of ADC13 and Related Reagents Against CD20 Positive and Negative Human Tumor Cells The in vitro cytotoxic activity of ADC13 along with the parent cytotoxic Compounds 1, 4, and 40, was evaluated was assayed against different human cancer cell lines expressing or not the CD20 antigen, including Raji (CD20 positive cells); RPMI-8226 and Karpas-299 (CD20 negative cells). Standard dose-response (DR) curves for 72 hours were performed.

Cytotoxicity of Compound 40

The cytotoxic activity of the parent Compound 40 was assayed in DR curves using ten serial dilutions (1/2.5 ratio) from 01E-03 to 2.6E-07 µg/mL (1.7E-09 to 4.3E-13 M). The cytotoxic activity of Compound 40 was very homogenous across the different cell lines tested, with $IC_{50}$ values in the low subnanomolar range, from 8.6E-05 to 1.1 E-04 µg/mL (1.4E-10 to 1.9E-10 M), being the mean $IC_{50}$ value across the whole cell panel 9.6E-05 µg/mL (equivalent to 1.6E-10 M). The cytotoxicity of Compound 40 was independent of the CD20 status of the tumor cell lines (Table 45).

TABLE 45

Summary data of the in vitro cytotoxicity of Compound 40

| | Compound 40 | | |
|---|---|---|---|
| | CD20+ | CD20− | |
| | Raji Burkitt's Lymphoma | RPMI-8226 Multiple Myeloma | Karpas-299 NHL |
| $IC_{50}$ (µg/mL) | 1.15E−04 | 8.65E−05 | 8.60E−05 |
| $IC_{50}$ (Molar) | 1.90E−10 | 1.43E−10 | 1.42E−10 |

Cytotoxicity of Compound 4

The cytotoxic activity of Compound 4 was assayed in DR curves using ten serial dilutions (1/2.5 ratio) from 01E-02 to 2.6E-06 µg/mL (1.5E-08 to 4.0E-12 M). The cytotoxic activity of Compound 4 was homogenous across the different cell lines tested, with $IC_{50}$ values in the nanomolar range, from 5.7E-04 to 1.4E-03 µg/mL (8.6E-10 to 2.1 E-09 M), being the mean $IC_{50}$ value across the whole cell panel 9.7E-04 µg/mL (1.5E-09 M). The presence of the amine containing group in Compound 4 slightly reduced the cytotoxic activity of the compound, as compared to Compound 40. The cytotoxic activity of Compound 4 was also independent of the CD20 status of the tumor cell lines (Table 46).

TABLE 46

Summary data of the in vitro cytotoxicity of Compound 4

| | Compound 4 | | |
|---|---|---|---|
| | CD20+ | CD20− | |
| | Raji Burkitt's Lymphoma | RPMI-8226 Multiple Myeloma | Karpas-299 NHL |
| $IC_{50}$ (µg/mL) | 1.41E−03 | 5.70E−04 | 9.30E−04 |
| $IC_{50}$ (Molar) | 2.12E−09 | 8.59E−10 | 1.40E−09 |

Cytotoxicity of Compound 12

The activity of the Compound 12 was assayed in DR curves using ten serial dilutions (1/2.5 ratio) from 01E+00 to 2.6E-04 µg/mL (7.9E-07 to 2.1 E-10 M). The cytotoxic activity of Compound 12, in two independent experiments, was very homogenous across the different cell lines tested, with $IC_{50}$ values in the nanomolar range, from 2.2E-02 to 6.7E-02 µg/mL (1.8E-08 to 5.5E-08 M), being the mean $IC_{50}$ value across the whole cell panel 3.9E-02 µg/mL (3.1 E-08 M). The presence of the maleimide linker in Compound 12 reduced the cytotoxic activity of the compound, as compared to Compound 4 and Compound 40. In addition, the cytotoxicity of the compound was also independent of the CD20 status of the tumor cell lines (Table 47).

TABLE 47

Summary data of the in vitro cytotoxicity of Compound 12

| | Compound 12 | | |
|---|---|---|---|
| | CD20+ | CD20− | |
| | Raji Burkitt's Lymphoma | RPMI-8226 Multiple Myeloma | Karpas-299 NHL |
| $IC_{50}$ (µg/mL) | 6.95E−02 | 2.25E−02 | 2.50E−02 |
| $IC_{50}$ (Molar) | 5.51E−08 | 1.78E−08 | 1.98E−08 |

Cytotoxicity of ADC13

Figure 27:
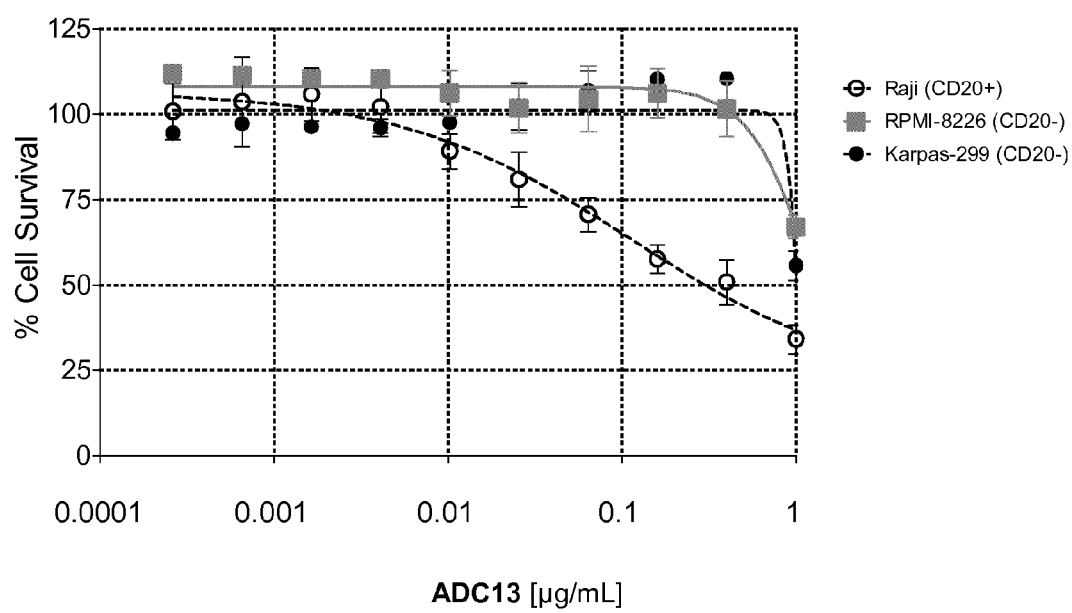
FIG. 27 is a representative dose response curves of ADC13 against various cancer cell lines.

The cytotoxic activity of the ADC13 was assayed against the different tumor cell lines. The conjugate was assayed in four different concentration ranges, each in triplicate DR curves (ten serial dilutions, 1/2.5 ratio) starting from 50, 10, 1 and 0.1 µg/mL, respectively. A representative DR curve (starting concentration 1 µg/mL) is shown in FIG. 27. Although higher in CD20 positive Raji cells, ADC13 presented a rather similar cytotoxic activity, in the nanomolar range, in all the cell lines tested. Raji cells (CD20+), showed a mean $IC_{50}$ value of 2.5E-01 µg/mL, while the respective values for RPMI-8226 and Karpas-299 cells (both CD20−), were 1.1 E+00 g/mL (Table 48). Thus, CD20 positive cells were slightly more sensitive (about 5 fold) to ADC13 than CD20 negative cells.

TABLE 48

Summary data of the in vitro cytotoxicity of ADC13

| | ADC13 | | |
|---|---|---|---|
| | CD20+ | CD20− | |
| | Raji Burkitt's Lymphoma | RPMI-8226 Multiple Myeloma | Karpas-299 NHL |
| $IC_{50}$ (µg/mL) | 2.53E−01 | 1.08E+00 | 1.07E+00 |
| Mean $IC_{50}$ (µg/mL) CD20 positive cells | | | 2.53E−01 |
| Mean $IC_{50}$ (µg/mL) CD20 negative cells | | | 1.07E+00 |

Figure 28:
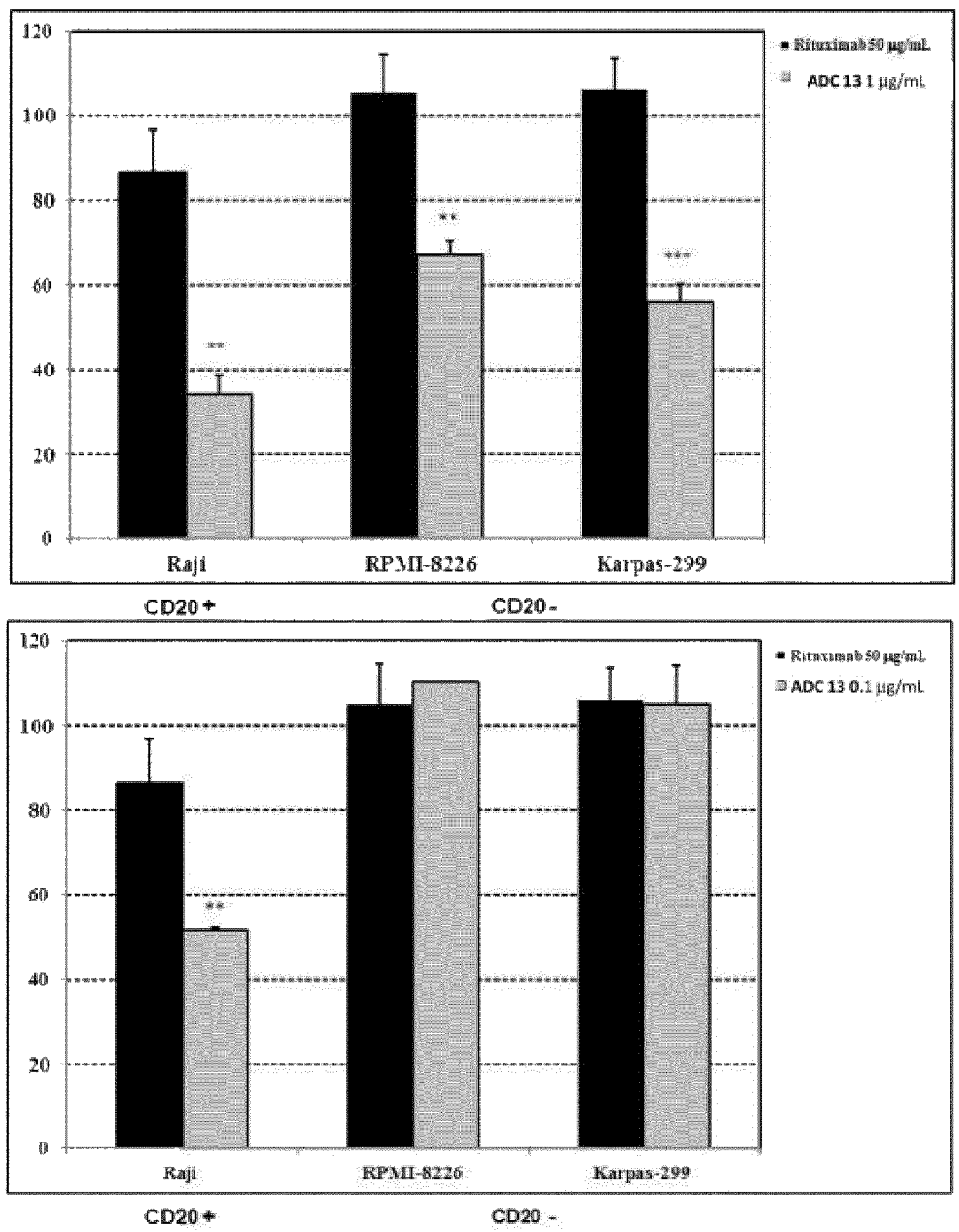
FIG. 28 shows histograms showing the percentage of cell survival after treatment of the different cell lines with the mAb alone (50 µg/mL) or ADC13 at 1 or 0.1 µg/mL.

To graphically compare the cytotoxic activity of the mAb Rituximab alone with that of the conjugate ADC13, histograms showing the percentages of cell survival after treatment of the different cell lines with the mAb alone (50 µg/mL) or ADC13 (1 and 0.1 µg/mL), are shown in FIG. 28. Rituximab alone, at a concentration of 50 g/mL, was virtually inactive in all the cell lines tested, independently of their CD20 status. In contrast, ADC13 showed, at both 1 and 0.1 µg/mL, cytotoxic activity, with some specificity for CD20 expressing Raji cells. At 1 µg/mL, ADC13 caused, after 72 hours of treatment, more than 65% reduction in the cell survival of Raji cells (CD20+) while inducing a 35-45% in RPMI-8226 and Karpas-299 cells (CD20−), respectively. At 0.1 µg/mL, ADC13 conjugate showed more clear specificity, inducing a reduction of cell survival of around 50% in CD20+ cells, while being inactive in CD20− cells.

Bioactivity Example 14—Cytotoxicity of ADC14 and Related Reagents Against CD5 Positive and Negative Human Tumor Cells The in vitro cytotoxic activity of ADC14 along with the parent cytotoxic Compounds 1, 4, and 40, was evaluated against different human cancer cell lines expressing or not the CD5 antigen, including Karpas-299 and MOLT-4 (both CD5+); Raji and RPMI-8226 (both CD5−). Standard dose-response (DR) curves for 72 hours were performed.

Cytotoxicity of Anti-CD5 mAb

First of all, the in vitro cytotoxic activity of the anti-CD5 mouse mAb alone was assayed against different human cancer cell lines expressing or not the CD5 antigen, including Karpas-299 and MOLT-4 (both CD5+); Raji and RPMI-8226 (both CD5−). In triplicate DR curves spanning from 5.0E+01 to 1.3E-02 µg/mL (3.3E-07 to 8.7E-1 1 M), in two independent experiments, the antibody was virtually inactive, not reaching the $IC_{50}$ in any of the cell lines tested, independently of their CD5 status (Table 49).

TABLE 49

Summary data of the in vitro cytotoxicity of Anti-CD5 mAb

| | Anti-CD5 mAb Cell lines | | | |
|---|---|---|---|---|
| | CD5+ | | CD5− | |
| | Karpas-299 | MOLT-4 | Raji | RPMI18226 |
| $IC_{50}$ (µg/mL) | >5.0E+01 | >5.0E+01 | >5.0E+01 | >5.0E+01 |
| $IC_{50}$ (Molar) | >3.3E−07 | >3.3E−07 | >3.3E−07 | >3.3E−07 |

Cytotoxicity of Compound 40

The cytotoxic activity of the parent Compound 40 was assayed in DR curves using ten serial dilutions (1/2.5 ratio) from 01E-03 to 2.6E-07 µg/mL (1.7E-09 to 4.3E-13 M). The cytotoxic activity of Compound 40 was very homogenous across the different cell lines tested, with $IC_{50}$ values in the low subnanomolar range, from 7.5E-05 to 3.6E-04 µg/mL (1.2E-10 to 5.9E-10 M), being the mean $IC_{50}$ value across the whole cell panel 1.6E-04 µg/mL (equivalent to 2.6E-10 M). The cytotoxicity of Compound 40 was independent of the CD5 expression levels in the tumor cell lines (Table 50).

TABLE 50

Summary data of the in vitro cytotoxicity of Compound 40

| | Compound 40 Cell lines | | | |
|---|---|---|---|---|
| | CD5+ | | CD5− | |
| | Karpas-299 | MOLT-4 | Raji | RPM1 18226 |
| ICso (µg/mL) | 1.12E−04 | 9.35E−05 | 3.60E−04 | 7.55E−05 |
| IC50 (Molar) | 1.85E−10 | 1.54E−10 | 5.94E−10 | 1.25E−10 |

Cytotoxicity of Compound 4

The cytotoxic activity of Compound 4 was assayed in DR curves using ten serial dilutions (1/2.5 ratio) from 01E-02 to 2.6E-06 µg/mL (1.5E-08 to 4.0E-12 M). The cytotoxic activity of Compound 4 was homogenous across the different cell lines tested, with $IC_{50}$ values in the nanomolar range, from 6.3E-04 to 2.7E-03 µg/mL (9.5E-10 to 4.1 E-09 M), being the mean $IC_{50}$ value across the whole cell panel 1.3E-03 µg/mL (1.9E-09 M). The presence of the amine containing group in Compound 4 reduced the cytotoxic activity of the compound (around 1 log), as compared to Compound 40 The cytotoxic activity of Compound 4 was also independent of the CD5 expression levels in the tumor cell lines (Table 51).

TABLE 51

Summary data of the in vitro cytotoxicity of Compound 4

| | Compound 4 Cell lines | | | |
|---|---|---|---|---|
| | CD5+ | | CD5− | |
| | Karpas-299 | MOLT-4 | Raji | RPMI18226 |
| $IC_{50}$ (µg/mL) | 9.15E−04 | 9.10E−04 | 2.70E−03 | 6.30E−04 |
| $IC_{50}$ (Molar) | 1.38E−09 | 1.37E−09 | 4.07E−09 | 9.50E−10 |

Cytotoxicity of Compound 1

The activity of Compound 1 was assayed in DR curves using ten serial dilutions (1/2.5 ratio) from 01E-01 to 2.6E-05 µg/mL (1.2E-07 to 3.0E-1 1 M). The cytotoxic activity of Compound 1 was nearly homogenous across the different cell lines tested, except for Raji cells in which the compound was less active, with $IC_{50}$ values in the nanomolar range, from 1.8E-03 to 1.1 E-02 µg/mL (2.2E-09 to 1.3E-09 M), being the mean $IC_{50}$ value across the whole cell panel 4.6E-03 µg/mL (5.3E-09 M). The presence of the maleimide containing linker in Compound 1 did not alter the cytotoxic activity of the compound, as compared to Compound 4. The cytotoxicity of the compound was also independent of the CD5 expression levels in the tumor cell lines (Table 52).

TABLE 52

Summary data of the in vitro cytotoxicity of Compound 1

| | Compound 1 Cell lines | | | |
|---|---|---|---|---|
| | CD5+ | | CD5− | |
| | Karpas-299 | MOLT-4 | Raji | RPMI18226 |
| $IC_{50}$ (µg/mL) | 2.15E−03 | 3.35E−03 | 1.09E−02 | 1.85E−03 |
| $IC_{50}$ (Molar) | 2.51E−09 | 3.91E−09 | 1.28E−08 | 2.16E−09 |

Cytotoxicity of ADC14

Figure 29:
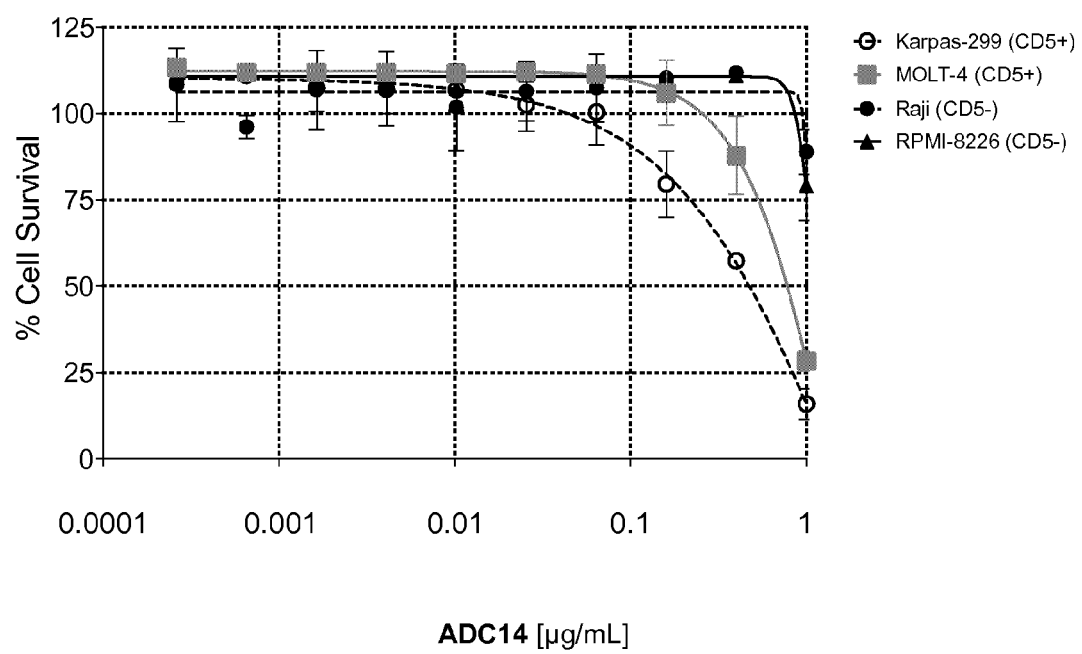
FIG. 29 is a representative dose response curves of ADC14 against various cancer cell lines.

The cytotoxic activity of the ADC14 was assayed against the different tumor cell lines. The conjugate was assayed in four different concentration ranges, each in triplicate DR curves (ten serial dilutions, 1/2.5 ratio) starting from 50, 10, 1 and 0.1 µg/mL, respectively. A representative DR curve (starting concentration 1 µg/mL) is shown in FIG. 29. ADC14 showed some trend of selectivity against CD5 positive cells, although the mean $IC_{50}$ values, in the medium nanomolar range, were relatively similar for all the cell lines tested, independently of the CD5 status (Table 53).

TABLE 53

Summary data of the in vitro cytotoxicity of ADC14

| | ADC14 Cell lines | | | |
|---|---|---|---|---|
| | CD5+ | | CD5− | |
| | Karpas-299 | MOLT-4 | Raji | RPMI18226 |
| $IC_{50}$ (µg/mL) | 5.56E−01 | 6.18E−01 | 4.23E+00 | 5.47E+00 |
| Mean $IC_{50}$ (µg/mL) CD5 positive cells | | | | 5.87E−01 |
| Mean $IC_{50}$ (µg/mL) CD5 negative cells | | | | 2.39E+00 |

Figure 30:
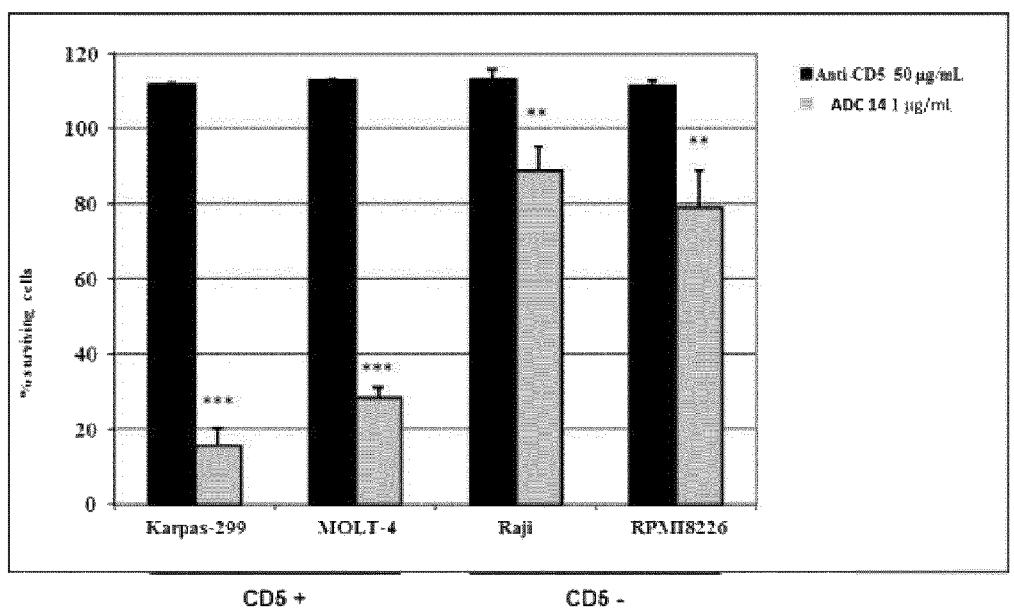
FIG. 30 shows histograms showing the percentage of cell survival after treatment of the different cell lines with the mAb alone (50 µg/mL) or ADC14 at 1 µg/mL.

To graphically compare the cytotoxic activity of the anti-CD5 mAb alone with that of the conjugate ADC14, histograms showing the percentages of cell survival after treatment of the different cell lines with the mAb alone (50 µg/mL) or ADC14 (1 µg/πιL), are shown in FIG. 30. The anti-CD5 mAb alone, at a concentration of 50 µg/mL, was virtually inactive in all the cell lines tested. ADC14, at a concentration of 1 µg/mL, showed specific cytotoxic activity against the CD5 positive cells, Karpas-299 and MOLT-4, inducing an inhibition in cell survival of around 84% and 70%, respectively, while being virtually inactive against CD5 negative cells (FIG. 30).

Bioactivity Example 15—Cytotoxicity of ADC16 and Related Reagents Against CD4 Positive and Negative Human Tumor Cells The in vitro cytotoxic activity of ADC16 along with the parent cytotoxic Compounds 1, 4, and 40, was evaluated against different human cancer cell lines expressing or not the CD4 antigen, including Karpas-299 and U937 (both CD4+); Raji and RPMI-8226 (both CD4−). Standard dose-response (DR) curves for 72 hours were performed.

Cytotoxicity of Anti-CD4 mAb

First of all, the in vitro cytotoxic activity of the anti-CD4 mouse mAb alone was assayed against different human cancer cell lines expressing or not the CD4 antigen, including Karpas-299 and U937 (both CD4+); Raji and RPMI-8226 (both CD4−). In triplicate DR curves spanning from 5.0E+01 to 1.3E-02 µg/mL (3.3E-07 to 8.7E-1 1 M), in two independent experiments, the antibody was virtually inactive, not reaching the $IC_{50}$ in any of the cell lines tested, independently of their CD4 status (Table 54).

TABLE 54

Summary data of the in vitro cytotoxicity of Anti-CD4 mAb

| | Anti-CD4 mAb Cell lines | | | |
|---|---|---|---|---|
| | CD4+ | | CD4− | |
| | Karpas-299 | U937 | RPMI18226 | Raji |
| $IC_{50}$ (µg/mL) | >5.0E+01 | >5.0E+01 | >5.0E+01 | >5.0E+01 |
| $IC_{50}$ (Molar) | >3.3E−07 | >3.3E−07 | >3.3E−07 | >3.3E−07 |

Cytotoxicity of Compound 40

The cytotoxic activity of the parent Compound 40 was assayed in DR curves using ten serial dilutions (1/2.5 ratio) from 01E-03 to 2.6E-07 µg/mL (1.7E-09 to 4.3E-1 3 M). The cytotoxic activity of Compound 40 was homogenous across the different cell lines tested, with $IC_{50}$ values in the low subnanomolar range, from 7.9E-os to 2.8E-04 µg/mL (1.3E-10 to 4.7E-10 M), being the mean $IC_{50}$ value across the whole cell panel 1.5E-04 µg/mL (equivalent to 2.5E-10 M). The cytotoxicity of Compound 40 was independent of the CD4 expression levels in the tumor cell lines (Table 55).

TABLE 55

Summary data of the in vitro cytotoxicity of Compound 40

| | Compound 40 Cell lines | | | |
|---|---|---|---|---|
| | CD4+ | | CD4− | |
| | Karpas-299 | U937 | RPMI18226 | Raji |
| $IC_{50}$ (µg/mL) | 1.30E−04 | 7.90E−05 | 1.20E−04 | 2.85E−04 |
| $IC_{50}$ (Molar) | 2.15E−10 | 1.31E−10 | 1.98E−10 | 4.70E−10 |

Cytotoxicity of Compound 4

The cytotoxic activity of Compound 4 was assayed in DR curves using ten serial dilutions (1/2.5 ratio) from 01E-02 to 2.6E-06 µg/mL (1.5E-08 to 4.0E-12 M). The cytotoxic activity of Compound 4 was also homogenous across the different cell lines tested, with $IC_{50}$ values in the nanomolar range, from 6.1 E-04 to 2.7E-03 µg/mL (9.2E-10 to 4.1 E-09 M), being the mean $IC_{50}$ value across the whole cell panel 1.2E-03 µg/mL (1.8E-09 M). The presence of the amine containing group in Compound 4 reduced the cytotoxic activity of the compound, as compared to Compound 40. The cytotoxic activity of Compound 4 was also independent of the CD4 expression levels in the tumor cell lines (Table 56).

TABLE 56

Summary data of the in vitro cytotoxicity of Compound 4

| | Compound 40 Cell lines | | | |
|---|---|---|---|---|
| | CD4+ | | CD4− | |
| | Karpas-299 | U937 | RPM1 18226 | Raji |
| $IC_{50}$ (µg/mL) | 9.10E−04 | 6.10E−04 | 6.35E−04 | 2.75E−03 |
| $IC_{50}$ (Molar) | 1.38E−09 | 9.20E−10 | 9.60E−10 | 4.15E−09 |

Cytotoxicity of Compound 1

The activity of the Compound 1 was assayed in DR curves using ten serial dilutions (1/2.5 ratio) from 01E-01 to 2.6E-05 µg/mL (1.2E-07 to 3.0E-1 1 M). The cytotoxic activity of Compound 1 was also homogenous across the different cell lines tested, with $IC_{50}$ values in the nanomolar range, from 1.5E-03 to 7.3E-03 µg/mL (1.7E-09 to 8.6E-09 M), being the mean $IC_{50}$ value across the whole cell panel 3.4E-03 µg/mL (3.9E-09 M). The presence of the maleimide containing linker in Compound 1 did not alter the cytotoxic activity of the compound, as compared to Compound 4. The cytotoxicity of the compound was also independent of the CD4 expression levels in the tumor cell lines (Table 57).

TABLE 57

Summary data of the in vitro cytotoxicity of Compound 1

| | Compound 1 Cell lines | | | |
|---|---|---|---|---|
| | CD4+ | | CD4− | |
| | Karpas-299 | U937 | RPMI18226 | Raji |
| $IC_{50}$ (µg/mL) | 2.35E−03 | 1.50E−03 | 2.30E−03 | 7.35E−03 |
| $IC_{50}$ (Molar) | 2.75E−09 | 1.75E−09 | 2.69E−09 | 8.57E−09 |

Cytotoxicity of ADC16

Figure 31:
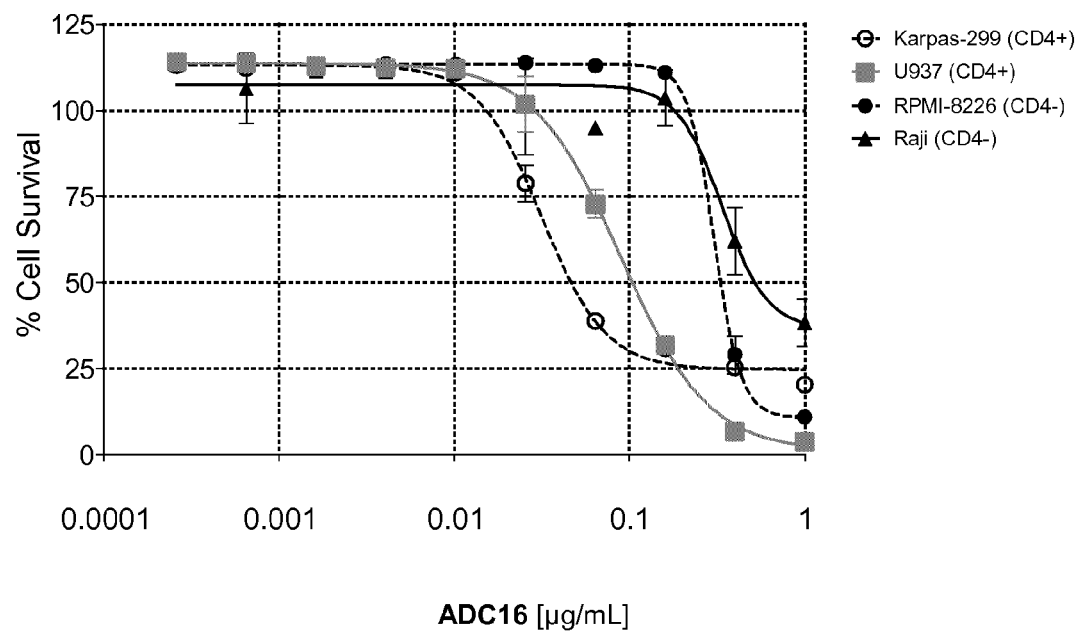
FIG. 31 is a representative dose response curves of ADC16 against various cancer cell lines.

The cytotoxic activity of the ADC16 was assayed against the different tumor cell lines. The conjugate was assayed in four different concentration ranges, each in triplicate DR curves (ten serial dilutions, 1/2.5 ratio) starting from 50, 10, 1 and 0.1 µg/mL, respectively. A representative DR curve (starting concentration 1 µg/mL) is shown in FIG. 31. ADC16 presented some specificity against CD4 positive cells, although the mean difference in sensitivity with respect to the CD4 negative cells was relatively low, approximately 7 fold (being the maximum difference between the less and the most sensitive cell line, Raji and Karpas-299, respectively, was around 14 times) (Table 58). Although showing a small therapeutic window, it was likely that, at least part of the cytotoxicity of ADC16 observed was mediated by the interaction of the mAb and the CD4 glycoprotein in the cell membrane of tumor cells.

TABLE 58

Summary data of the in vitro cytotoxicity of ADC16

| | ADC 16 Cell lines | | | |
|---|---|---|---|---|
| | CD4+ | | CD4− | |
| | Karpas-299 | U937 | RPM1 18226 | Raji |
| IC$_{50}$ (µg/mL) | 4.70E−02 | 8.18E−02 | 2.60E−01 | 6.74E−01 |
| Mean IC$_{50}$ (µg/mL) CD4 positive cells | | 6.44E−02 | | |
| Mean IC$_{50}$ (µg/mL) CD4 negative cells | | | | 4.67E−01 |

Figure 32:
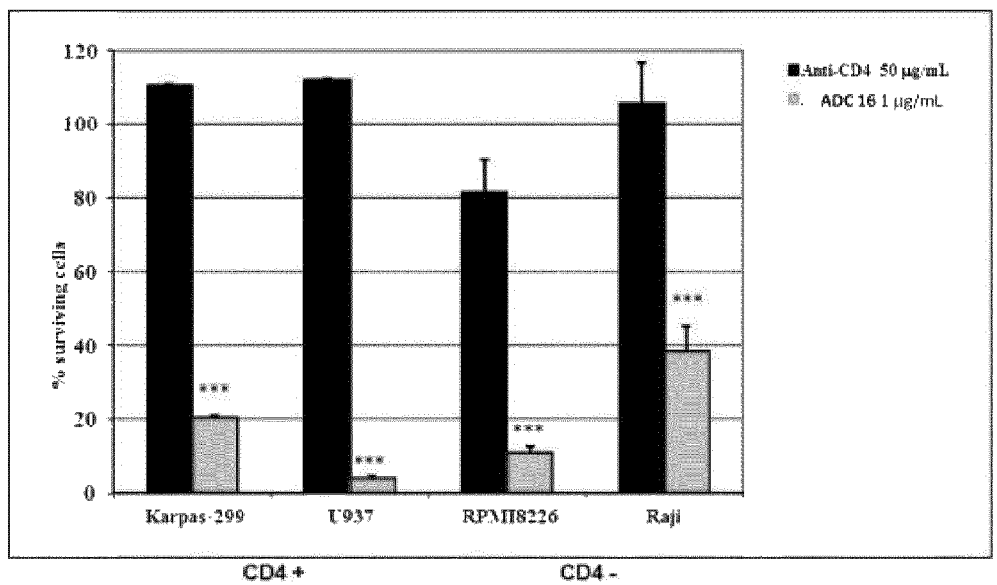
FIG. 32 shows histograms showing the percentage of cell survival after treatment of the different cell lines with the mAb alone (50 µg/mL) or ADC16 at 1 µg/mL and 0.1 µg/mL.
Figure 32:
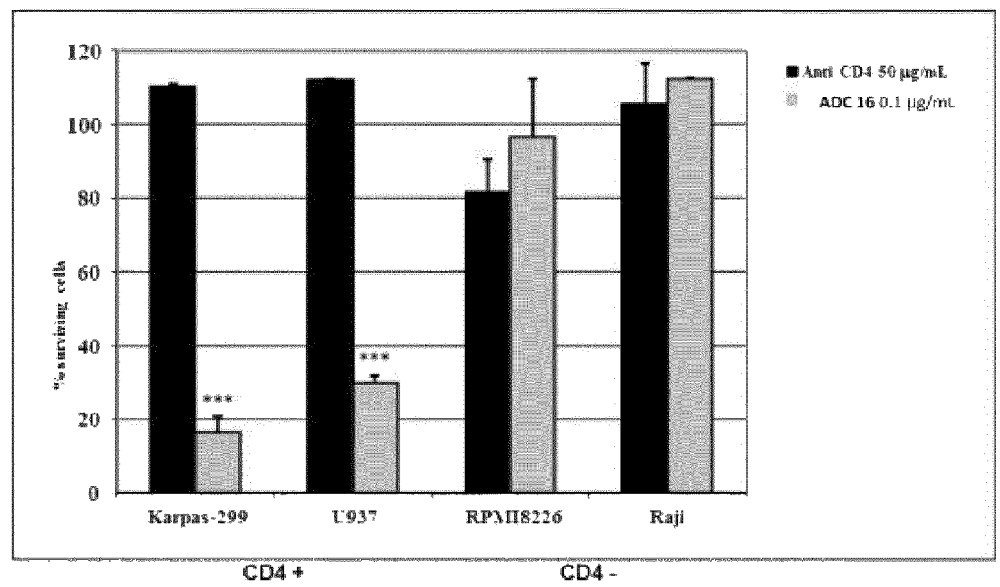

To graphically compare the cytotoxic activity of the anti-CD4 mAb alone with that of the conjugate ADC16, histograms showing the percentages of cell survival after treatment of the different cell lines with the mAb alone (50 µg/mL) or ADC16 (1 and 0.1 µg/mL), are shown in FIG. 32. The anti-CD4 mAb alone, at a concentration of 50 µg/mL, was virtually inactive in all the cell lines tested. In contrast, ADC16, at a concentration of 1 µg/mL, showed potent cytotoxic activity in all the cell lines tested, independently of their CD4 status, causing more than 60% reduction (range 60-90%) in the cell survival after 72 hours of treatment. Even at a concentration of 0.1 µg/mL, ADC16 showed specific cytotoxic activity against the CD4 positive cells, Karpas-299 and U937, inducing an inhibition in cell survival of around 80% and 70%, respectively, while being inactive against CD4 negative cells (FIG. 32).

Bioactivity Example 16—Cytotoxicity of ADC17 and Related Reagents Against CD4 Positive and Negative Human Tumor Cells The in vitro cytotoxic activity of ADC17 along with the parent cytotoxic Compounds 12, 4, and 40, was evaluated against different human cancer cell lines expressing or not the CD4 antigen, including Karpas-299 and U937 (both CD4+); Raji and RPMI-8226 (both CD4−). Standard dose-response (DR) curves for 72 hours were performed.

Cytotoxicity of Compound 40

The cytotoxic activity of the parent Compound 40 was assayed in DR curves using ten serial dilutions (1/2.5 ratio) from 01E−03 to 2.6E−07 µg/mL (1.7E−09 to 4.3E−13 M). The cytotoxic activity of Compound 40 was homogenous across the different cell lines tested, with IC$_{50}$ values in the low subnanomolar range, from 7.9E−05 to 2.8E−04 µg/mL (1.3E−10 to 4.7E−1 0 M), being the mean IC$_{50}$ value across the whole cell panel 1.5E−04 µg/mL (equivalent to 2.5E−1 0 M). The cytotoxicity of Compound 40 was independent of the CD4 expression levels in the tumor cell lines (Table 59).

TABLE 59

Summary data of the in vitro cytotoxicity of Compound 40

| | Compound 40 Cell lines | | | |
|---|---|---|---|---|
| | CD4+ | | CD4− | |
| | Karpas-299 | U937 | RPMI18226 | Raji |
| IC$_{50}$ (µg/mL) | 1.30E−04 | 7.90E−05 | 1.20E−04 | 2.85E−04 |
| IC$_{50}$ (Molar) | 2.15E−10 | 1.31E−10 | 1.98E−10 | 4.70E−10 |

Cytotoxicity of Compound 4

The cytotoxic activity of Compound 4 was assayed in DR curves using ten serial dilutions (1/2.5 ratio) from 01E−02 to 2.6E−06 µg/πη¹ L (1.5E−08 to 4.0E−12 M). The cytotoxic activity of Compound 4 was also homogenous across the different cell lines tested, with IC$_{50}$ values in the nanomolar range, from 6.1 E−04 to 2.7E−03 µg/mL (9.2E−10 to 4.1 E−09 M), being the mean IC$_{50}$ value across the whole cell panel 1.2E−03 µg/mL (1.8E−09 M). The presence of the amine containing group in Compound 4 reduced the cytotoxic activity of the compound, as compared to Compound 40. The cytotoxic activity of Compound 4 was also independent of the CD4 expression levels in the tumor cell lines (Table 60).

TABLE 60

Summary data of the in vitro cytotoxicity of Compound 4

| | Compound 4 Cell lines | | | |
|---|---|---|---|---|
| | CD4+ | | CD4− | |
| | Karpas-299 | U937 | RPMI18226 | Raji |
| IC$_{50}$ (µg/mL) | 9.10E−04 | 6.10E−04 | 6.35E−04 | 2.75E−03 |
| IC$_{50}$ (Molar) | 1.38E−09 | 9.20E−10 | 9.60E−10 | 4.15E−09 |

Cytotoxicity of Compound 12

The activity of the Compound 12 was assayed in DR curves using ten serial dilutions (1/2.5 ratio) from 01E+00 to 2.6E−04 µg/mL (7.9E−07 to 2.1 E−10 M). The cytotoxic activity of Compound 12, in two independent experiments, was relatively homogenous across the different cell lines tested, with IC$_{50}$ values in the nanomolar range, from 7.3E−02 to 4.1 E−01 µg/mL (5.8E−08 to 3.2E−07 M), being the mean IC$_{50}$ value across the whole cell panel 1.7E−01 µg/mL (1.3E−07 M). The presence of the long maleimide containing linker in Compound 12 strongly reduced the cytotoxic activity of the compound, as compared to Compound 40 (nearly 3 log) and Compound 4 (nearly 2 log). In addition, the cytotoxicity of the compound was also independent of the CD4 expression levels of the tumor cell lines (Table 61).

TABLE 61

Summary data of the in vitro cytotoxicity of Compound 12

| | Compound 12 Cell lines | | | |
|---|---|---|---|---|
| | CD4+ | | CD4− | |
| | Karpas-299 | U937 | RPMI18226 | Raji |
| IC$_{50}$ (µg/mL) | 7.65E−02 | 7.30E−02 | 1.15E−01 | 4.15E−01 |
| IC$_{50}$ (Molar) | 6.07E−08 | 5.79E−08 | 9.11E−08 | 3.29E−07 |

Cytotoxicity of ADC1 7

Figure 33:
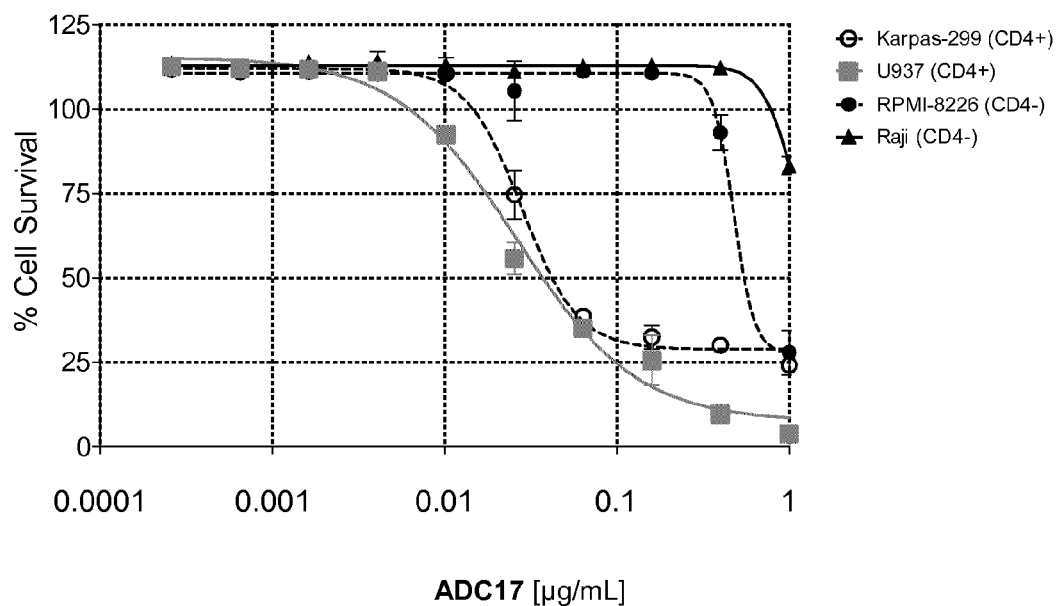
FIG. 33 is a representative dose response curves of ADC17 against various cancer cell lines.

The cytotoxic activity of the ADC17 was assayed against the different tumor cell lines. The conjugate was assayed in four different concentration ranges, each in triplicate DR curves (ten serial dilutions, 1/2.5 ratio) starting from 50, 10, 1 and 0.1 µg/mL, respectively. A representative DR curve (starting concentration 1 µg/mL) is shown in FIG. 33. ADC17 presented specificity against CD4 positive cells, with a mean difference in sensitivity with respect to the CD4 negative cells around 40 fold (range between 11-64 fold) (Table 62). It was likely that a major part of the cytotoxic activity of ADC17 observed was mediated by the interaction of the mAb and the CD4 glycoprotein in the cell membrane of tumor cells.

TABLE 62

Summary data of the in vitro cytotoxicity of ADC17

| | ADC 17 Cell lines | | | |
|---|---|---|---|---|
| | CD4+ | | CD4− | |
| | Karpas-299 | U937 | RPM1 18226 | Raji |
| IC$_{50}$ (μg/mL) | 4.50E−02 | 3.86E−02 | 5.24E−01 | 2.90E+00 |
| Mean IC$_{50}$ (μg/mL) CD4 positive cells | | | | 4.18E−02 |
| Mean IC$_{50}$ (μg/mL) CD4 negative cells | | | | 1.71E+00 |

Figure 34:
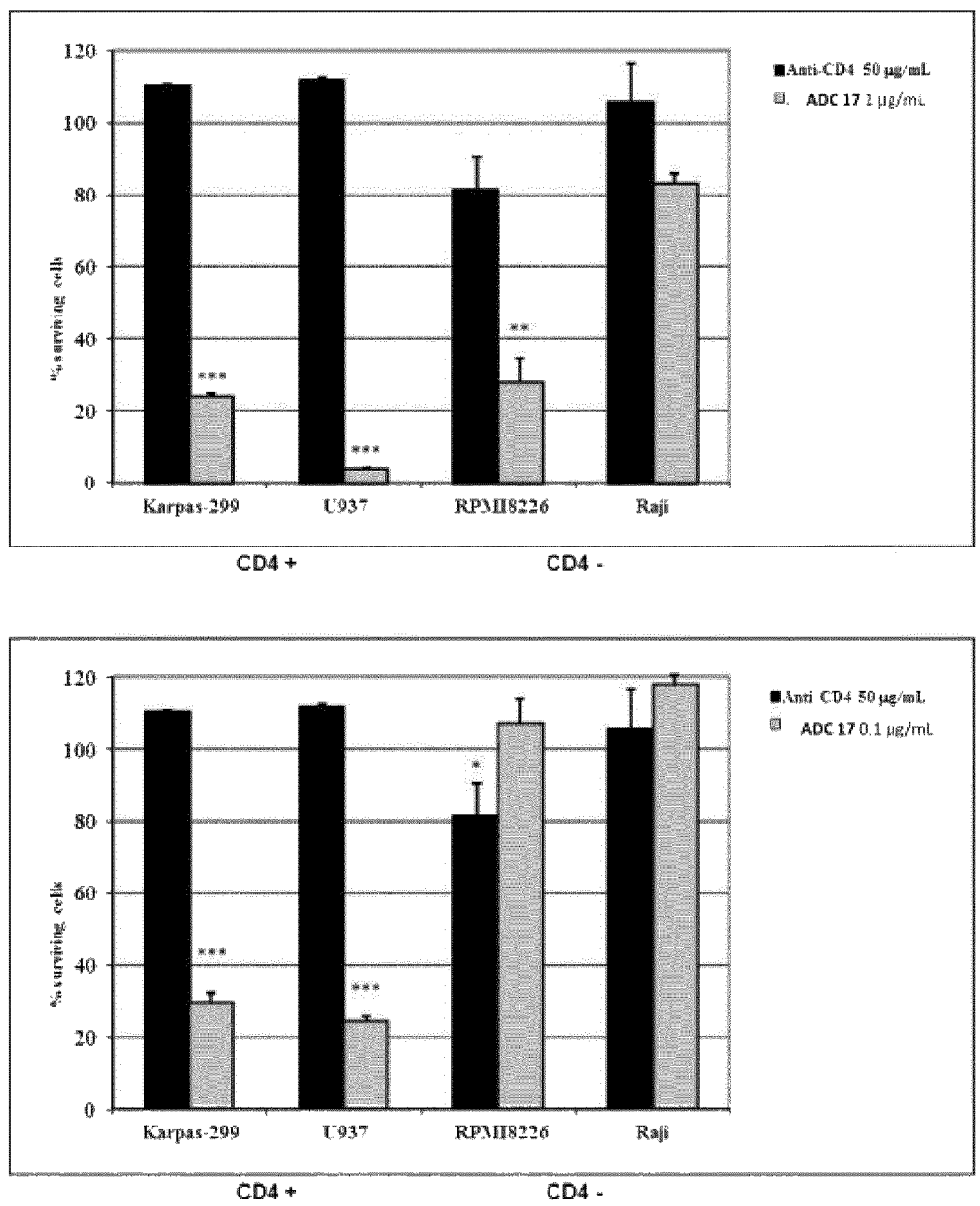
FIG. 34 shows histograms showing the percentage of cell survival after treatment of the different cell lines with the mAb alone (50 µg/mL) or ADC17 at 1 µg/mL and 0.1 µg/mL.

To graphically compare the cytotoxic activity of the anti-CD4 mAb alone with that of the conjugate ADC17, histograms showing the percentages of cell survival after treatment of the different cell lines with the mAb alone (50 μg/mL) or ADC17 (1 and 0.1 μg/mL), are shown in FIG. 34. Anti-CD4 mAb alone, at a concentration of 50 μg/mL, was virtually inactive in all the cell lines tested. In contrast, ADC17, at a concentration of 1 ug/mL, showed potent cytotoxic activity in three out of the four cell lines tested (except Raji cells), causing more than 70% reduction (range 72-95%) in the cell survival after 72 hours of treatment. Even at a concentration of 0.1 μg/mL, ADC17 showed specific cytotoxic activity against the CD4 positive cells, Karpas-299 and U937, inducing an inhibition in cell survival of around 70% and 75%, respectively, while being quite inactive against CD4 negative cells (FIG. 34).

Bioactivity Example 17—Cytotoxicity of ADC14 and Related Reagents Against Raji Cell Clones with High or Null CD5 Expression The in vitro cytotoxic activity of ADC14 along with the parent cytotoxic Compounds 1, 4, and 40, was evaluated against Raji cell clones expressing or not the CD5 antigen. Stand and dose-response (DR) curves for 72 hours were performed.

Cytotoxicity of Anti-CD5 mAb

The in vitro cytotoxic activity of the anti-CD5 mouse mAb alone was assayed against Raji cell clones expressing (C #10) or not (C #18) the CD5 antigen. In triplicate DR curves ranging from 5.0E+01 to 1.3E−02 μg/mL (3.3E-07-8.7E-1 1 M), in two independent experiments, the antibody was virtually inactive, not reaching the IC$_{50}$ in any of the cell lines tested, independently of their CD5 status (Table 63).

TABLE 63

Summary data of the in vitro cytotoxicity of Anti-CD5 mAb

| | Anti-CD5 mAb Raji cells | |
|---|---|---|
| | C#10 (high CD5) | C#18 (null CD5) |
| IC$_{50}$ (μg/mL) | >5.0E+01 | >5.0E+01 |
| IC50 (Molar) | >3.3E−07 | >3.3E−07 |

Cytotoxicity of Compound 40

The cytotoxic activity of the parent Compound 40 was assayed in DR curves using ten serial dilutions (1/2.5 ratio) from 01E-03 to 2.6E-07 μg/mL (1.7E-09 to 4.3E-13 M). The cytotoxic activity of Compound 40 was relatively similar between the CD5 expressing (clone #10) and non expressing (clone #18) Raji cells, with mean IC$_{50}$ values in the sub-nanomolar range, 4.95E−04 and 8.90E−04 μg/mL (equivalent to 8.17E-10 and 1.47E-09 M), respectively. Although slightly higher in CD5 positive cells, the cytotoxicity of Compound 40 seemed to be rather independent of the CD5 expression levels in the tumor cell lines (Table 64)

TABLE 64

Summary data of the in vitro cytotoxicity of Compound 40

| | Compound 40 Raji cells | |
|---|---|---|
| | C#10 (high CD5) | C#18 (null CD5) |
| IC$_{50}$ (μg/mL) | 4.95E−04 | 8.90E−04 |
| IC$_{50}$ (Molar) | 8.17E−10 | 1.47E−09 |

Cytotoxicity of Compound 4

The cytotoxic activity of Compound 4 was assayed in DR response curves using ten serial dilutions (1/2.5 ratio) from 01E-02 to 2.6E-06 μg/mL (1.5E-08 to 4.0E-12 M). The cytotoxic activity of Compound 4 was relatively similar between the CD5 expressing (clone #10) and non expressing (clone #18) Raji cells, although in the null cells the compound did not reach the IC$_{50}$ value. In the CD5 positive cells, the compound showed a mean IC$_{50}$ value of 9.9E-03 μg/mL (equivalent to 1.57E-08 M). Although slightly higher in CD5 positive cells, the cytotoxicity of Compound 4 seemed to be rather independent of the CD5 expression levels in the tumor cells lines (see IC$_2$o values in Table 65 as a reference).

TABLE 65

Summary data of the in vitro cytotoxicity of Compound 4

| | Compound 4 Raji cells | |
|---|---|---|
| | C#10 (high CD5) | C#18 (null CD5) |
| IC$_{20}$ (μg/mL) | 4.65E−03 | 6.77E−03 |
| IC$_{20}$ (Molar) | 7.01E−09 | 1.02E−08 |
| IC$_{50}$ (μg/mL) | 9.90E−03 | >1.00E−02 |
| IC$_{50}$ (Molar) | 1.49E−08 | >1.51E−08 |

Cytotoxicity of Compound 1

The activity of Compound 1 was assayed in DR curves using ten serial dilutions (1/2.5 ratio) from 01E-01 to 2.6E-05 μg/mL (1.2E-07 to 3.0E-1 1 M). The cytotoxic activity of Compound 1 differs between the two Raji cell clones, being more active (around 1 log) in CD5 overexpressing cells (clone #10) than in CD5 null cells (clone #18), with mean IC$_{50}$ values of 2.9E-03 and 3.8E-02 μg/mL (equivalent to 3.4E-09 and 4.4E-08 M), respectively (Table 66). In this case the cytotoxicity of Compound 1 seemed not to be independent of the CD5 status of the tumor cell lines.

TABLE 66

Summary data of the in vitro cytotoxicity of Compound 1

| | Compound 1 Raji cells | |
|---|---|---|
| | C#10 (high CD5) | C#18 (null CD5) |
| $IC_{50}$ (μg/mL) | 2.90E-03 | 3.80E-02 |
| $IC_{50}$ (Molar) | 3.39E-09 | 4.44E-08 |

Cytotoxicity of ADC14

Figure 35:
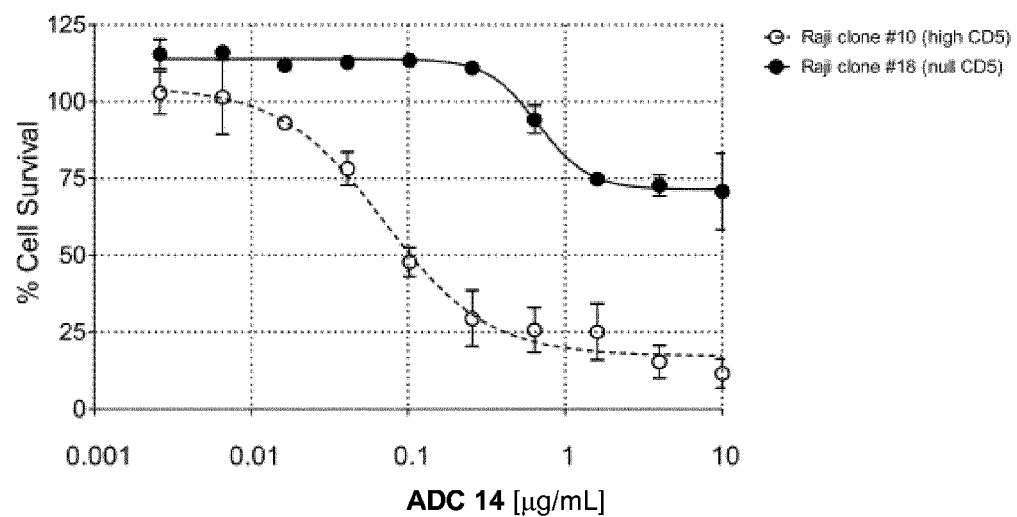
FIG. 35 is a representative dose response curves of ADC14 against two Raji cell clones.

The cytotoxic activity of the ADC14 was assayed against the two Raji clones. The conjugated was assayed in three different concentration ranges, each in triplicate DR curves (ten serial dilutions, 1/2.5 ratio) starting from 10, 1 and 0.1 μg/mL. A representative DR curve (starting concentration 10 μg/mL) is shown in FIG. 35. ADC 14 showed specificity against CD5 overexpressing cells (clone #10), in which the compound demonstrated a cytotoxic activity similar to, or even higher than, that of the parent Compounds 1, 4 and 40. In CD5 expressing Raji cells, the conjugate showed a mean $IC_{50}$ value of 1.6E-01 μg/mL. In CD5 null cells the conjugate was more than 50 fold less active than in CD5 positive cells, showing a mean $IC_{50}$ value of 9.0E+00 μg/mL. Although with some reservations, due to some differential sensitivity observed between the two Raji cell clones against some parent compounds, these results indicated that ADC14 has specifity against CD5 expressing cells (Table 67). We assume, therefore, that ADC14 was, at least partially, acting through the interaction of the mAb with the membrane associated CD5 receptor on tumor cells, and subsequent intracellular delivery of the cytotoxic drug into the target tissue.

TABLE 67

Summary data of the in vitro cytotoxicity of ADC14

| | ADC14 Raji Cells | |
|---|---|---|
| | C#10 (high CD5) | C#18 (null CD5) |
| $IC_{50}$ (μg/mL) | 1.65E-01 | 9.00E+00 |

Figure 36:
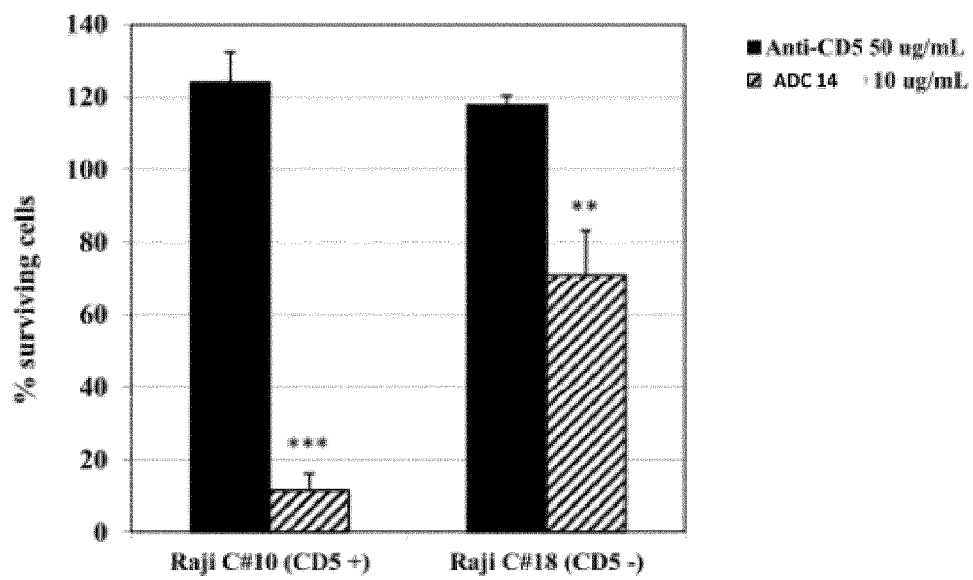
FIG. 36 shows histograms showing the percentage of cell survival after treatment of the different cell lines with the mAb alone (50 µg/mL) or ADC14 at 10 µg/mL.

To graphically compare the cytotoxic activity of the anti-CD5 mAb alone with that of the conjugate ADC14, histograms showing the percentages of cell survival after treatment of the different cell lines with the mAb alone (50 μg/mL) or ADC14 (10 μg/mL), are shown in FIG. 36. Anti-CD5 mAb alone, at a concentration of 50 μg/mL, was inactive against the two Raji cell clones, independently of their CD5 status. On the contrary ADC14, at a concentration of 10 μg/mL, showed potent and somehow selective cytotoxic activity against CD5 positive Raji cells (clone #10), causing a nearly 90% reduction in their cell survival after 72 hours of treatment. Under the same conditions, ADC14 caused a 30% reduction in the cell survival of CD5 null cells (clone #18) (FIG. 36).

Bioactivity Example 18—Cytotoxicity of ADC15 and Related Reagents Against Raji Cell Clones with High or Null CD5 Expression The in vitro cytotoxic activity of ADC15 along with the parent cytotoxic Compounds 12, 4, and 40, was evaluated against Raji cell clones expressing or not the CD5 antigen. Standard dose-response (DR) curves for 72 hours were performed.

Cytotoxicity of Compound 40

The cytotoxic activity of the parent Compound 40 was assayed in DR curves using ten serial dilutions (1/2.5 ratio) from 01E-03 to 2.6E-07 μg/mL (1.7E-09 to 4.3E-13 M). The cytotoxic activity of Compound 40 was relatively similar between the CD5 expressing (clone #10) and non expressing (clone #18) Raji cells, with mean $IC_{50}$ values in the sub-nanomolar range, 4.95E-04 and 8.90E-04 μg/mL (equivalent to 8.17E-10 and 1.47E-09 M), respectively. Although slightly higher in CD5 positive cells, the cytotoxicity of Compound 40 seemed to be rather independent of the CD5 expression levels in the tumor cell lines (Table 68).

TABLE 68

Summary data of the in vitro cytotoxicity of Compound 40

| | Compound 40 Raji cells | |
|---|---|---|
| | C#10 (high CD5) | C#18 (null CD5) |
| $IC_{50}$ (μg/mL) | 4.95E-04 | 8.90E-04 |
| $IC_{50}$ (Molar) | 8.17E-10 | 1.47E-09 |

Cytotoxicity of Compound 4

The cytotoxic activity of Compound 4 was assayed in DR response curves using ten serial dilutions (1/2.5 ratio) from 01E-02 to 2.6E-06 μg/mL (1.5E-08 to 4.0E-12 M). The cytotoxic activity of Compound 4 was relatively similar between the CD5 expressing (clone #10) and non expressing (clone #18) Raji cells, although in the null cells the compound did not reach the $IC_{50}$ value. In the CD5 positive cells, the compound showed a mean $IC_{50}$ value of 9.9E-03 μg/mL (equivalent to 1.57E-08 M). Although slightly higher in CD5 positive cells, the cytotoxicity of Compound 4 seemed to be rather independent of the CD5 expression levels in the tumor cell lines (see $IC_{2}0$ values in Table 69 as a reference).

TABLE 69

Summary data of the in vitro cytotoxicity of Compound 4

| | Compound 4 Raji cells | |
|---|---|---|
| | C#10 (high CD5) | C#18 (null CD5) |
| $IC_{20}$ (μg/mL) | 4.65E-03 | 6.77E-03 |
| $IC_{20}$ (Molar) | 7.01E-09 | 1.02E-08 |
| IC50 (μg/mL) | 9.90E-03 | >1.00E-02 |
| ICso (Molar) | 1.49E-08 | >1.51E-08 |

Cytotoxicity of Compound 12

The activity of Compound 12 was assayed in DR curves using ten serial dilutions (1/2.5 ratio) from 01 E+00 to 2.6E-4 μg/mL (7.9E-07 to 2.1 E-10 M). The cytotoxic activity of Compound 12 was relatively similar between the CD5 expressing (clone #10) and non expressing (clone #18) Raji cells, although in the null cells the compound did not reach the $IC_{50}$ value. In the CD5 positive cells, the compound showed a mean $IC_{50}$ value of 2.7E-01 μg/mL (equivalent to 2.15E-07 M). Although slightly higher in CD5 positive cells, the cytotoxicity of Compound 12 seemed to be rather independent of the CD5 expression levels in the tumor cell lines (see IC20 values in Table 70 as reference).

TABLE 70

Summary data of the in vitro cytotoxicity of Compound 12

| | Compound 12 Raji cells | |
|---|---|---|
| | C#10 (high CD5) | C#18 (null CD5) |
| $IC_{20}$ (µg/mL) | 1.50E−01 | 2.00E−01 |
| $IC_{20}$ (Molar) | 1.19E−07 | 1.59E−07 |
| $IC_{50}$ (µg/mL) | 2.70E−01 | >1.00E+00 |
| $IC_{50}$ (Molar) | 2.14E−07 | >7.92E−07 |

Cytotoxicity of ADC1 5

Figure 37:
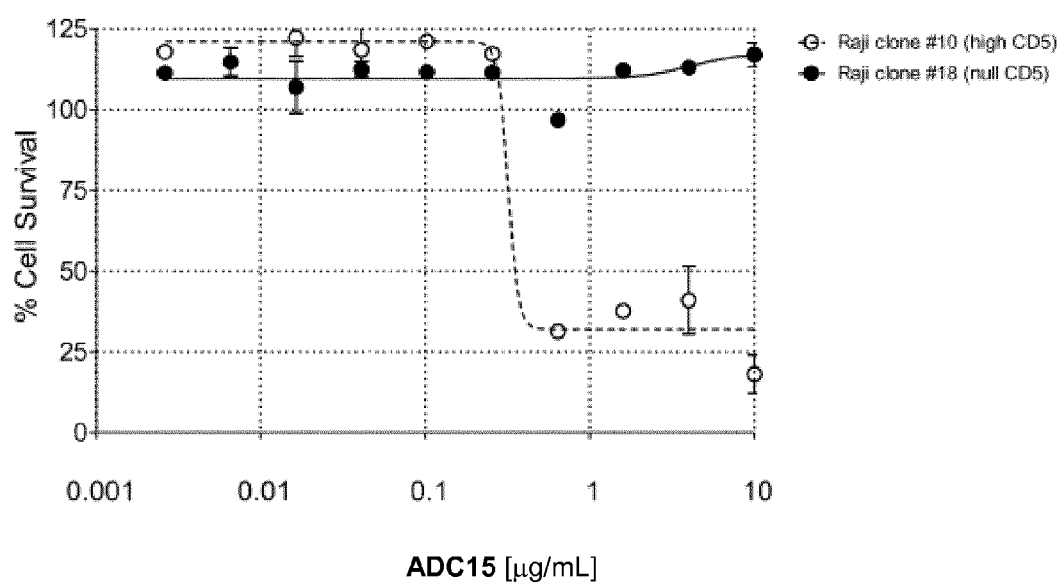
FIG. 37 is a representative dose response curves of ADC15 against two Raji cell clones.

The cytotoxic activity of the ADC15 was assayed against the two Raji clones. The conjugate was assayed in three different concentration ranges, each in triplicate DR curves (ten serial dilutions, 1/2.5 ratio) starting from 10, 1 and 0.1 µg/mL. A representative DR curve (starting concentration 10 µg/mL) is shown in FIG. 37. ADC15 showed significant specificity against CD5 overexpressing cells (clone #10), in which the compound demonstrated a cytotoxic activity similar to that of the parent compound 40 and even higher than that of Compounds 4 and 12. In CD5 expressing Raji cells, the conjugate showed a mean $IC_{50}$ value of 9.3E−01 µg/mL. In CD5 null cells the conjugate was much more than 10 fold less active than in CD5 positive cells, not reaching the $IC_{50}$ value. Although with reservations, due to the potential sensitivity observed between the two Raji cell clones against the parent Compounds 4 and 12, these results indicate that ADC15 has specificity against CD5 expressing cells (Table 71). We can assume that ADC15 was, at least partially, acting through the interaction of the mAb with the membrane associated CD5 receptor on tumor cells, and subsequent intracellular delivery of the cytotoxic drug into the target tissue.

TABLE 71

Summary data of the in vitro cytotoxicity of ADC15

| | ADC15 Raji Cells | |
|---|---|---|
| | C#10 (high CD5) | C#18 (null CD5) |
| $IC_{50}$ (µg/mL) | 9.30E−01 | >1.0E+01 |

Figure 38:
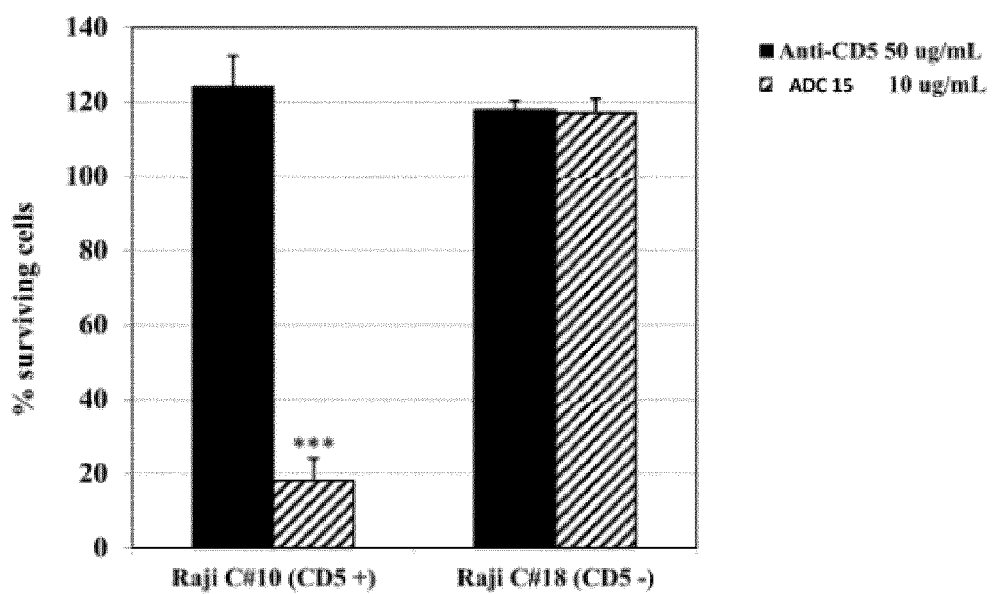
FIG. 38 shows histograms showing the percentage of cell survival after treatment of the different cell lines with the mAb alone (50 µg/mL) or ADC15 at 10 µg/mL.

To graphically compare the cytotoxicity activity of the anti-CD5 mAb alone with that of the conjugate ADC15, histograms showing the percentages of cell survival after treatment of the different cell lines with the mAb alone (50 µg/mL) or ADC15 (10 µg/mL), are shown in FIG. 38. Anti-CD5 mAb alone, at a concentration of 50 µg/mL, was inactive against the two Raji cell clones, independently of their CD5 status. On the contrary, ADC15 at a concentration of 10 µg/mL showed potent and selective cytotoxic activity against CD5 positive Raji cells (clone #10), causing a 80% reduction in their cell survival after 72 hours of treatment. Under the same conditions, ADC15 was inactive on CD5 null cells (clone #18) (FIG. 38).

The invention claimed is:

1. A compound of formula D-X-$(AA)_w$-$L_1$ or of formula D-X-$(AA)_w$—H, wherein:

$L_1$ is a linker selected from the group of formulas consisting of: of formula

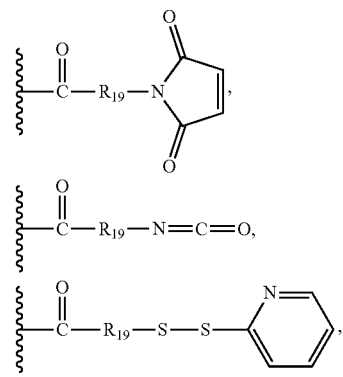

wherein the wavy line indicates the point of covalent attachment to $(AA)_w$ if any, or to X;

$R_{19}$ is selected from —$C_1$-$C_{12}$ alkylene-, —$C_3$-$C_8$ carbocyclo, —O—($C_1$-$C_{12}$ alkylene), —$C_6$-$C_{18}$ arylene in one or more rings which may optionally be substituted with one or more substituents $R_x$, —$C_1$-$C_{12}$ alkylene-$C_6$-$C_{18}$ arylene- wherein the arylene group is in one or more rings which may optionally be substituted with one or more substituents $R_x$, —$C_6$-$C_{18}$ arylene-$C_1$-$C_{12}$ alkylene- wherein the arylene group is in one or more rings which may optionally be substituted with one or more substituents $R_x$, —$C_1$-$C_{12}$ alkylene-($C_3$-$C_8$ carbocyclo)-, —($C_3$-$C_8$ carbocyclo)-$C_1$-$C_{12}$ alkylene-, —$C_5$-$C_{14}$ heterocyclo- wherein said heterocyclo group may be a saturated or unsaturated group having one or more rings and comprising at least one oxygen, nitrogen or sulphur atom in said ring(s), said group optionally being substituted with one or more substituents $R_x$, —$C_1$-$C_{12}$ alkylene-($C_5$-$C_{14}$ heterocyclo)- wherein said heterocyclo group may be a saturated or unsaturated group having one or more rings and comprising at least one oxygen, nitrogen or sulphur atom in said ring(s), said group optionally being substituted with one or more substituents $R_x$, —($C_5$-$C_{14}$ heterocyclo)-$C_1$-$C_{12}$ alkylene-, wherein said heterocyclo group may be a saturated or unsaturated group having one or more rings and comprising at least one oxygen, nitrogen or sulphur atom in said ring(s), said group optionally being substituted with one or more substituents $R_x$, —$(OCH_2CH_2)_r$- and —$CH_2$—$(OCH_2CH_2)_r$-, wherein each of the above alkylene substituents whether alone or attached to another moiety the carbon chain may optionally be substituted by one or more substituents $R_x$;

r is an integer ranging from 1-10;

D is a drug moiety selected from formulas (Ia) and (Ib), or a pharmaceutically acceptable salt, ester, solvate, tautomer or stereoisomer thereof, (Ia)

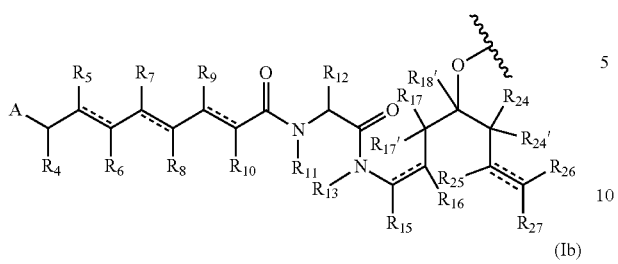

(Ib)

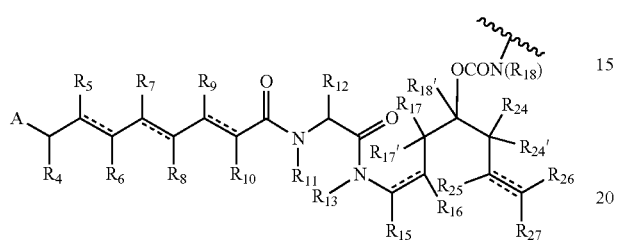

wherein the wavy lines of (Ia) and (Ib) indicate the point of covalent attachment to X;

A is

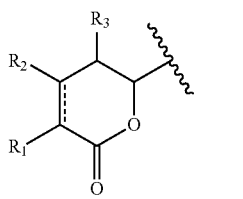

wherein the wavy line of the moiety A indicates the point of covalent attachment to the rest of the drug moiety;

each of $R_1$, $R_2$ and $R_3$ is independently selected from hydrogen and $OR_a$;

each of $R_4$, $R_5$, $R_6$, $R_7$, $R_8$, $R_9$, $R_{10}$ and $R_{12}$ is independently selected from the group consisting of hydrogen and substituted or unsubstituted $C_1$-$C_{12}$ alkyl, wherein the optional substituents are one or more substituents $R_x$;

$R_{11}$ is hydrogen;

$R_{13}$ is hydrogen;

each of $R_{15}$, $R_{16}$, $R_{17}$, $R_{17'}$, $R_{18'}$, $R_{24}$, $R_{24'}$, $R_{25}$ and $R_{26}$ is independently selected from the group consisting of hydrogen and substituted or unsubstituted $C_1$-$C_{12}$ alkyl, wherein the optional substituents are one or more substituents $R_x$;

$R_{18}$ is hydrogen;

$R_{27}$ is selected from hydrogen, substituted or unsubstituted $C_1$-$C_{12}$ alkyl and halogen, wherein the optional substituents are one or more substituents $R_x$;

$R_a$ is selected from the group consisting of hydrogen and substituted or unsubstituted $C_1$-$C_{12}$ alkyl, wherein the optional substituents are one or more substituents $R_x$;

and each dotted line represents an optional additional bond, but when a triple bond exists between the C atom to which $R_{25}$ is attached and the C atom to which $R_{26}$ and $R_{27}$ are attached, then $R_{25}$ and either $R_{26}$ or $R_{27}$ are absent;

$(AA)_w$ is of formula (II):

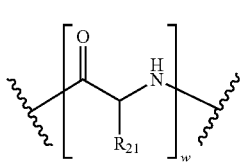

(II)

wherein the wavy lines indicate the point of covalent attachments to X (the wavy line to the left) and to $L_1$ or to a hydrogen atom (the wavy line to the right);

$R_{21}$ is, at each occurrence, selected from the group consisting of hydrogen, methyl, isopropyl, isobutyl, sec-butyl, benzyl, p-hydroxybenzyl, —$CH_2OH$, —CH(OH) $CH_3$, —$CH_2CH_2SCH_3$, —$CH_2CONH_2$, —$CH_2COOH$, —$CH_2CH_2CONH_2$, —$CH_2CH_2COOH$, —$(CH_2)$ $3NHC(=NH)$ $NH_2$, —$(CH_2)_3NH_2$, —$(CH_2)_3NHCOCH_3$, —$(CH_2)_3NHCHO$, —$(CH_2)_4NHC(=NH)$ $NH_2$, —$(CH_2)_4NH_2$, —$(CH_2)_4NHCOCH_3$, —$(CH_2)_4NHCHO$, —$(CH_2)_3NHCONH2$, —$(CH_2)_4NHCONH_2$, —$CH_2CH_2CH(OH)$ $CH_2NH_2$, 2-pyridylmethyl-, 3-pyridylmethyl-, 4-pyridylmethyl-phenyl, cyclohexyl,

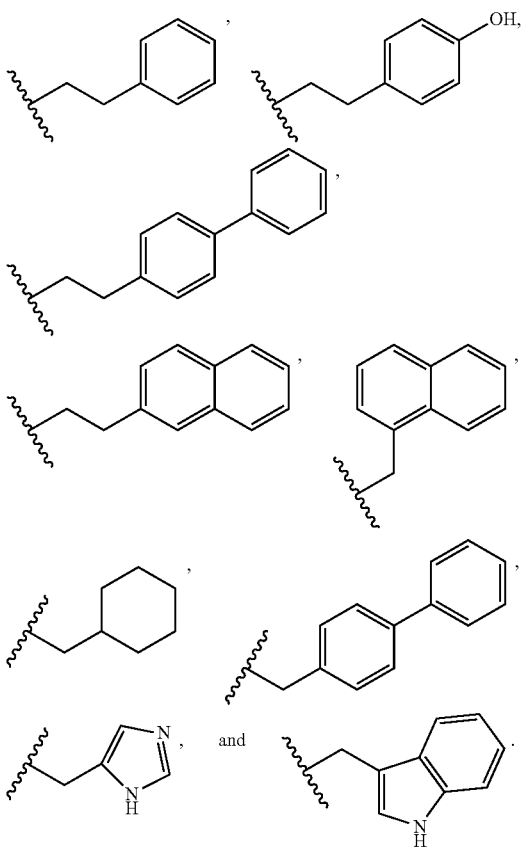

and w is an integer ranging from 0 to 12;

X is selected from the group consisting of: —CONH—($C_1$-$C_6$ alkylene) NH—; —COO—$CH_2$-(phenylene which may optionally be substituted with one or more substituents $R_x$)—NH—; —CONH—($C_1$-$C_6$ alkylene)

NH—COO—CH$_2$-(phenylene which may optionally be substituted with one or more substituents R$_x$)—NH—; —CH$_2$-(phenylene which may optionally be substituted with one or more substituents R$_x$)—NH—; —COCH$_2$NH—COCH$_2$—NH—; —COCH$_2$NH—; —CONH—(C$_1$-C$_6$ alkylene)S—; —CONH—(C$_1$-C$_6$ alkylene) NHCO(C$_1$-C$_6$ alkylene)S—; —(C$_1$-C$_6$ alkylene) NHCO(C$_1$-C$_6$ alkylene)S—; —(C$_1$-C$_6$ alkylene)S—; —(C$_1$-C$_6$ alkylene) NH—; and —(C$_1$-C$_6$ alkylene) NH—COO—CH$_2$-(phenylene which may optionally be substituted with one or more substituents R$_x$)—NH—;

substituents R$_x$ are selected from the group consisting of C$_1$-C$_{12}$ alkyl groups which may be optionally substituted with at least one group R$_y$, C$_2$-C$_{12}$ alkenyl groups which may be optionally substituted with at least one group R$_y$, C$_2$-C$_{12}$ alkynyl groups which may be optionally substituted with at least one group R$_y$, halogen atoms, oxo groups, thio groups, cyano groups, nitro groups, OR$_y$, OCOR$_y$, OCOOR$_y$, COR$_y$, COOR$_y$, OCONR$_y$R$_z$, CONR$_y$R$_z$, S(O) R$_y$, SO$_2$R$_y$, P(O) (R$_y$) OR$_z$, NR$_y$R$_z$, NR$_y$COR$_z$, NR$_y$C(=O) NR$_y$R$_z$, NR$_y$C(=NR$_y$) NR$_y$R$_z$, aryl groups having from 6 to 18 carbon atoms in one or more rings which may optionally be substituted with one or more substituents which may be the same or different selected from the group consisting of R$_y$, OR$_y$, OCOR$_y$, OCOOR$_y$, NR$_y$R$_z$, NR$_y$COR$_z$ and NR$_y$C(=NR$_y$) NR$_y$R$_z$, aralkyl groups comprising an alkyl group having from 1 to 12 carbon atoms substituted with an optionally substituted aryl group as defined above, aralkyloxy groups comprising an alkoxy group having from 1 to 12 carbon atoms substituted with an optionally substituted aryl group as defined above, and a 5- to 14-membered saturated or unsaturated heterocyclic group having one or more rings and comprising at least one oxygen, nitrogen or sulphur atom in said ring(s), said heterocyclic group optionally being substituted with one or more substituents R$_y$, and where there is more than one optional substituent on any given group the optional substituents R$_y$ may be the same or different;

each R$_y$ and R$_z$ is independently selected from the group consisting of hydrogen, C$_1$-C$_{12}$ alkyl groups, C$_1$-C$_{12}$ alkyl groups that are substituted with at least one halogen atom, aralkyl groups comprising a C$_1$-C$_{12}$ alkyl group that is substituted with an aryl group having from 6 to 18 carbon atoms in one or more rings and heterocycloalkyl groups comprising a C$_1$-C$_{12}$ alkyl group that is substituted with a 5- to 14-membered unsaturated or saturated heterocyclic group having one or more rings and comprising at least one oxygen, nitrogen or sulphur atom in said ring(s).

2. The compound of formula D-X-(AA)$_w$-L$_1$ or of formula D-X-(AA)$_w$-H according to claim 1, wherein:

R$_{19}$ is selected from —C$_1$-C$_{12}$ alkylene-, —O—(C$_1$-C$_{12}$ alkylene), —C$_6$-C$_{12}$ arylene in one or more rings which may optionally be substituted with one or more substituents R$_x$, —C$_1$-C$_{12}$ alkylene-C$_6$-C$_{12}$ arylene- wherein the arylene group is in one or more rings which may optionally be substituted with one or more substituents R$_x$, —C$_6$-C$_{12}$ arylene-C$_1$-C$_{12}$ alkylene- wherein the arylene group is in one or more rings which may optionally be substituted with one or more substituents R$_x$, —C$_5$-C$_{12}$ heterocyclo- wherein said heterocyclo group may be a saturated or unsaturated group having one or more rings and comprising at least one oxygen, nitrogen or sulphur atom in said ring(s), said group optionally being substituted with one or more substituents R$_x$, —C$_1$-C$_{12}$ alkylene-(C$_5$-C$_{12}$ heterocyclo)- wherein said heterocyclo group may be a saturated or unsaturated group having one or more rings and comprising at least one oxygen, nitrogen or sulphur atom in said ring(s), said group optionally being substituted with one or more substituents R$_x$, —(C$_5$-C$_{12}$ heterocyclo)-C$_1$-C$_{12}$ alkylene- wherein said heterocyclo group may be a saturated or unsaturated group having one or more rings and comprising at least one oxygen, nitrogen or sulphur atom in said ring(s), said group optionally being substituted with one or more substituents R$_x$, —(OCH$_2$CH$_2$)$_r$- and —CH$_2$—(OCH$_2$CH$_2$)$_r$-, wherein each of the above alkylene substituents whether alone or attached to another moiety the carbon chain may optionally be substituted by one or more substituents R$_x$;

r is an integer ranging from 1-6.

3. The compound of formula D-X-(AA)$_w$-L$_1$ or of formula D-X-(AA)$_w$-H according to claim 1 wherein:

R$_{19}$ is selected from —C$_1$-C$_8$alkylene-, —O—(C$_1$-C$_8$alkylene), —C$_1$-C$_8$alkylene-C$_6$-C$_{12}$ arylene- wherein the arylene group is in one or more rings which may optionally be substituted with one or more substituents R$_x$, —C$_6$-C$_{12}$ arylene-C$_1$-C$_8$ alkylene- wherein the arylene group is in one or more rings which may optionally be substituted with one or more substituents R$_x$, wherein each of the above alkylene substituents whether alone or attached to another moiety the carbon chain may optionally be substituted by one or more substituents R$_x$;

(AA)$_w$ is of formula (II):

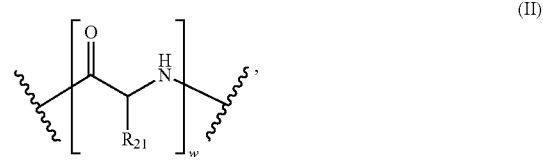

(II)

wherein the wavy lines indicate the point of covalent attachments to X (the wavy line to the left) and to L$_1$ or to a hydrogen atom (the wavy line to the right);

wherein R$_{21}$ is selected, at each occurrence, from the group consisting of hydrogen, methyl, isopropyl, sec-butyl, benzyl, indolylmethyl, —(CH$_2$)$_3$NHCONH$_2$, —(CH$_2$)$_4$NH$_2$, —(CH$_2$)$_3$NHC(=NH) NH$_2$ and —(CH$_2$)$_4$NHC—(=NH) NH$_2$, and w is an integer from 0 to 6;

X is an extending group selected from the group consisting of —CONH—(C$_2$-C$_4$ alkylene) NH—, COO—CH$_2$-phenylene-NH, wherein said phenylene group may optionally be substituted with from one to four substituents R$_x$ selected from the group consisting of alkyl groups having from 1 to 6 carbon atoms, alkoxy groups having from 1 to 6 carbon atoms, halogen atoms, nitro groups and cyano groups, —CONH—(C$_2$-C$_4$ alkylene) NH—COO—CH$_2$-(phenylene which may optionally be substituted with from one to four substituents R$_x$ selected from the group consisting of alkyl groups having from 1 to 6 carbon atoms, alkoxy groups having from 1 to 6 carbon atoms, halogen atoms, nitro groups and cyano groups)-NH—, —COCH$_2$NH—COCH$_2$—NH—, —CONH—(C$_2$-C$_4$ alkylene)S—, —CONH—(C$_2$-C$_4$ alkylene)-NHCO(C$_1$-C$_3$ alkylene)

S—, —($C_2$-$C_4$ alkylene) NHCO($C_1$-$C_3$ alkylene)S—, —($C_2$-$C_4$ alkylene)S—, —($C_2$-$C_4$ alkylene) NH— and —($C_2$-$C_4$ alkylene) NH—COO—$CH_2$-(phenylene which may optionally be substituted with from one to four substituents $R_x$ selected from the group consisting of alkyl groups having from 1 to 6 carbon atoms, alkoxy groups having from 1 to 6 carbon atoms, halogen atoms, nitro groups and cyano groups)-NH—;

D is a drug moiety of formula (Ia) or (Ib), or a pharmaceutically acceptable salt, ester, solvate, tautomer or stereoisomer thereof, wherein

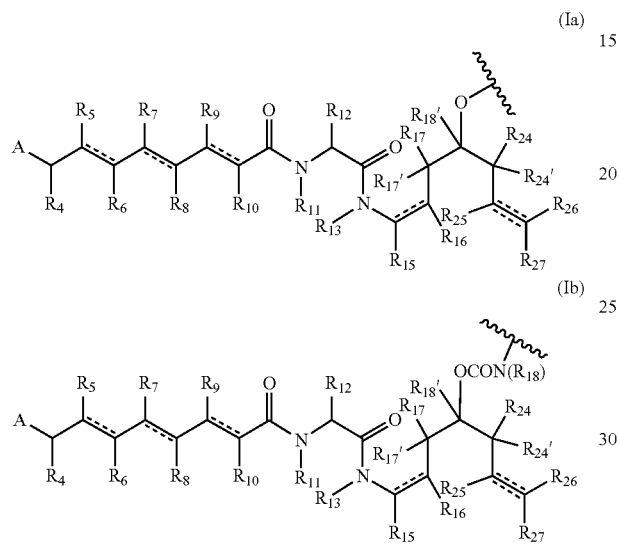

$R_1$ is selected from hydrogen and $OR_a$, wherein $R_a$ is selected from hydrogen and substituted or unsubstituted $C_1$-$C_6$ alkyl, wherein the optional substituents are one or more substituents $R_x$;

$R_2$ and $R_3$ are hydrogen;

each of $R_4$, $R_5$, $R_6$, $R_7$, $R_8$, $R_9$, $R_{10}$ and $R_{12}$ is independently selected from hydrogen and substituted and unsubstituted $C_1$-$C_6$ alkyl, wherein the optional substituents are one or more substituents $R_x$;

each of $R_{15}$, $R_{16}$, $R_{17}$, $R_{17'}$, $R_{18'}$, $R_{24}$, $R_{24'}$, $R_{25}$ and $R_{26}$ is independently selected from the group consisting of: hydrogen and substituted or unsubstituted $C_1$-$C_6$ alkyl groups wherein the optional substituents are selected from the group consisting of alkoxy groups having from 1 to 6 carbon atoms, hydroxyl groups, oxo groups, halogen atoms, $OCOR_y$, $OCOOR_y$, $COR_y$, $COOR_y$, $OCONR_yR_z$, $CONR_yR_z$, $NR_yR_z$, $NR_yCOR_z$ wherein each of $R_y$ and $R_z$ is selected from hydrogen atoms and alkyl groups having from 1 to 6 carbon atoms;

$R_{27}$ is selected from hydrogen, halogen and substituted or unsubstituted $C_1$-$C_6$ alkyl, wherein the optional substituents are one or more substituents $R_x$.

4. The compound of formula D-X-$(AA)_w$-$L_1$ or of formula D-X-$(AA)_w$-H according to claim 1 wherein:

$R_{19}$ is selected from —$C_1$-$C_6$ alkylene-, phenylene-$C_1$-$C_6$ alkylene- wherein the phenylene group may optionally be substituted with one or more substituents $R_x$ selected from the group consisting of alkyl groups having from 1 to 6 carbon atoms, alkoxy groups having from 1 to 6 carbon atoms, halogen atoms, nitro groups and cyano groups, wherein each of the above alkylene substituents whether alone or attached to another moiety in the carbon chain may optionally be substituted by one or more substituents $R_x$ selected from the group consisting of alkyl groups having from 1 to 6 carbon atoms, alkoxy groups having from 1 to 6 carbon atoms, aryl groups having from 6 to 12 carbon atoms, halogen atoms, nitro groups and cyano groups;

w is 0 or 2, and where w is 2, then $(AA)_w$ is of formula (III):

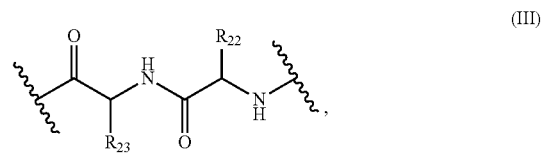

wherein the wavy lines indicate the point of covalent attachments to X (the wavy line to the left) and to $L_1$ or to a hydrogen atom (the wavy line to the right);

$R_{22}$ is selected from methyl, benzyl, isopropyl, sec-butyl and indolylmethyl;

$R_{23}$ is selected from methyl, —$(CH_2)_4NH_2$, —$(CH_2)_3NHCONH_2$ and —$(CH_2)_3NHC(=NH) NH_2$;

X is an extending group selected from —CONH—($C_2$-$C_4$ alkylene) NH—, —CONH($C_2$-$C_4$ alkylene) NHCOO—$CH_2$-(phenylene which may optionally be substituted with one or more substituents $R_x$ selected from the group consisting of alkyl groups having from 1 to 6 carbon atoms, alkoxy groups having from 1 to 6 carbon atoms, halogen atoms, nitro groups and cyano groups)-NH, —CONH—($C_2$-$C_4$ alkylene)S—, —CONH—($C_2$-$C_4$ alkylene) NHCO—($C_1$-$C_3$ alkylene)S—, —($C_2$-$C_4$ alkylene) NHCO($C_1$-$C_3$ alkylene)S—, —($C_2$-$C_4$ alkylene)S—, —($C_2$-$C_4$ alkylene) NH— and —($C_2$-$C_4$ alkylene) NH—COO—$CH_2$-(phenylene which may optionally be substituted with from one to four substituents $R_x$ selected from the group consisting of alkyl groups having from 1 to 6 carbon atoms, alkoxy groups having from 1 to 6 carbon atoms, halogen atoms, nitro groups and cyano groups)-NH; and D is a drug moiety of formula (Ia) or (Ib) or a pharmaceutically acceptable salt, ester, solvate, tautomer or stereoisomer thereof, wherein each of $R_5$, $R_7$, $R_8$, $R_9$ and $R_{10}$ is hydrogen;

each of $R_4$ and $R_6$ is methyl;

$R_{12}$ is isopropyl, tert-butyl or benzyl;

each of $R_{15}$, $R_{16}$, $R_{17}$, $R_{17'}$, $R_{18'}$, $R_{24}$, $R_{24'}$, $R_{25}$ and $R_{26}$ is independently selected from the group consisting of hydrogen and $C_1$-$C_6$ alkyl group;

$R_{27}$ is hydrogen or halogen.

5. The compound of formula D-X-$(AA)_w$-$L_1$ or of formula D-X-$(AA)_w$-H according to claim 1 wherein:

$R_{19}$ is —$C_3$-$C_6$ alkylene-;

w is 0 or 2, and where w is 2, then $(AA)_w$ is of formula (III):

(Ia)

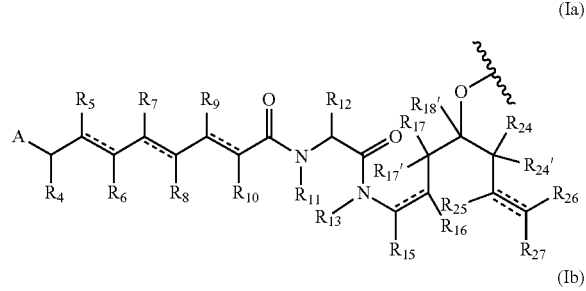

(Ib)

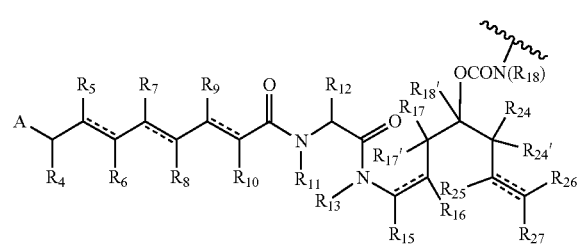

$R_1$ is hydrogen or methoxy;

(III)

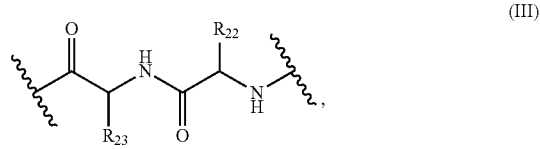

$R_{22}$ is isopropyl, $R_{23}$ is —$(CH_2)_3NHCONH_2$, wherein the wavy lines indicate the point of covalent attachments to X (the wavy line to the left) and to $L_1$ or to a hydrogen atom (the wavy line to the right);

X is an extending group selected from the group consisting of —CONH—($C_2$-$C_4$ alkylene) NH—, COO—$CH_2$-phenylene-NH—, wherein said phenylene group may optionally be substituted with from one to four substituents $R_x$ selected from the group consisting of alkyl groups having from 1 to 6 carbon atoms, alkoxy groups having from 1 to 6 carbon atoms, halogen atoms, nitro groups and cyano groups, —CONH—($C_2$-$C_4$ alkylene) NH—COO—$CH_2$-(phenylene which may optionally be substituted with from one to four substituents $R_x$ selected from the group consisting of alkyl groups having from 1 to 6 carbon atoms, alkoxy groups having from 1 to 6 carbon atoms, halogen atoms, nitro groups and cyano groups)-NH—, —CONH—($C_2$-$C_4$ alkylene)S—, —CONH—($C_2$-$C_4$ alkylene) NHCO($C_1$-$C_3$ alkylene)S—, —($C_2$-$C_4$ alkylene) NHCO($C_1$-$C_3$ alkylene)S—, —($C_2$-$C_4$ alkylene)S—, —($C_2$-$C_4$ alkylene) NH— and —($C_2$-$C_4$ alkylene) NH—COO—$CH_2$-(phenylene which may optionally be substituted with from one to four substituents $R_x$ selected from the group consisting of alkyl groups having from 1 to 6 carbon atoms, alkoxy groups having from 1 to 6 carbon atoms, halogen atoms, nitro groups and cyano groups)-NH—; and D is a drug moiety of formula (Ia) or formula (Ib), or a pharmaceutically acceptable salt, ester, solvate, tautomer or stereoisomer thereof selected from the following group:

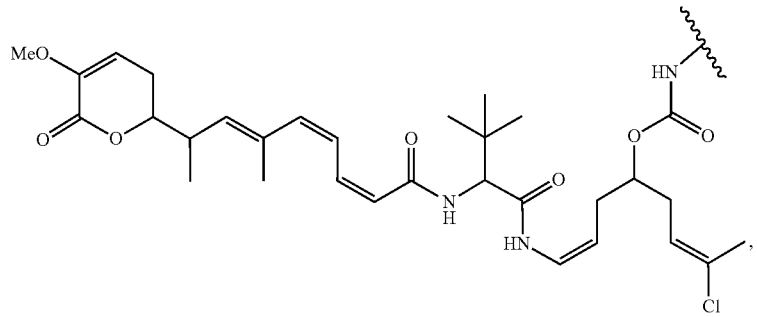

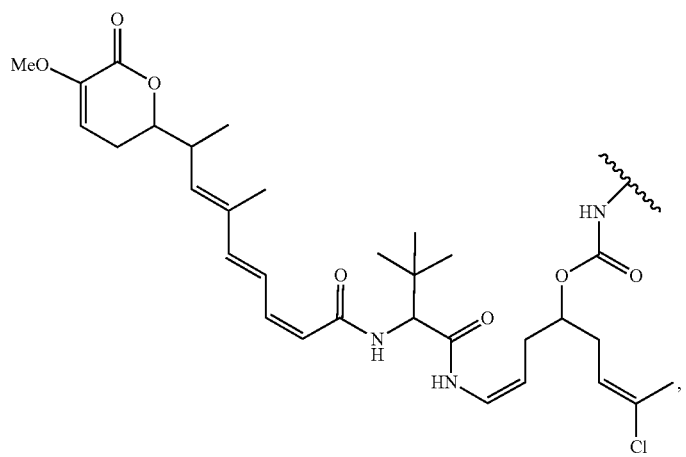

-continued
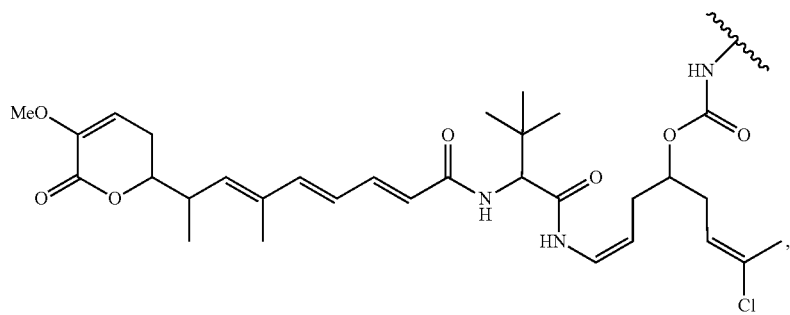
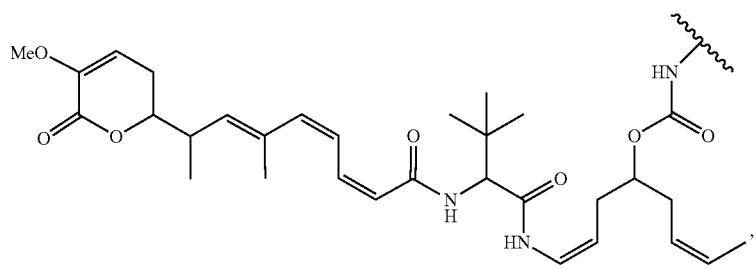
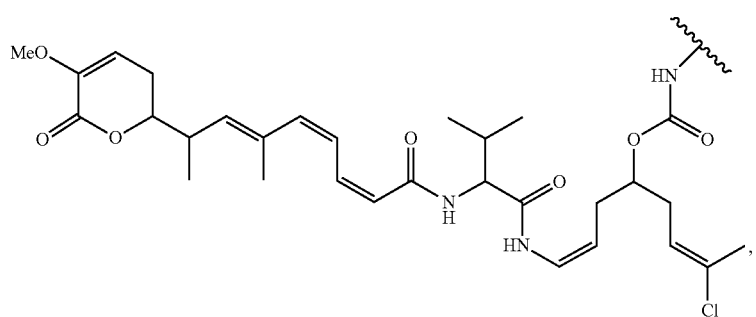
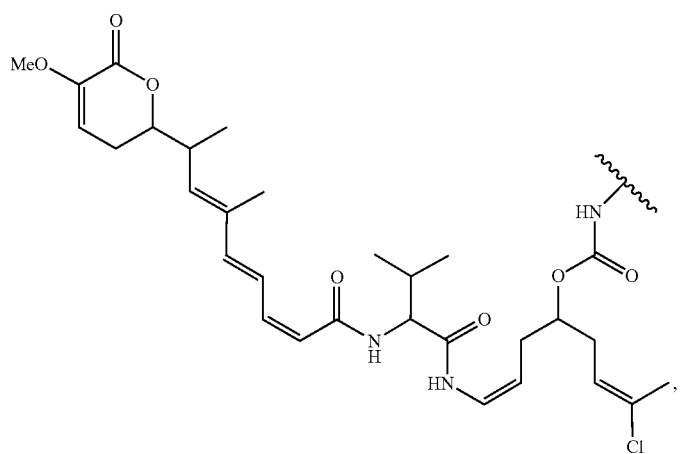
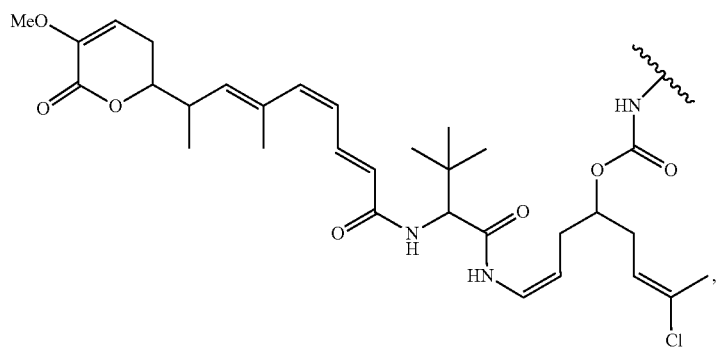

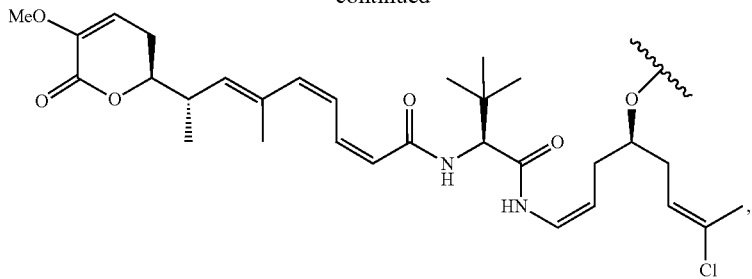
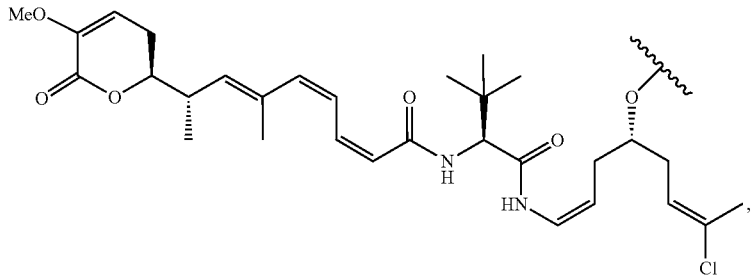
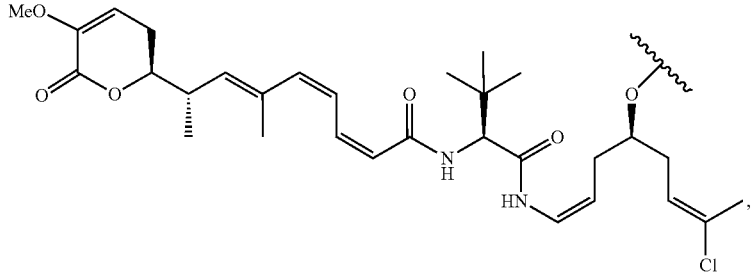
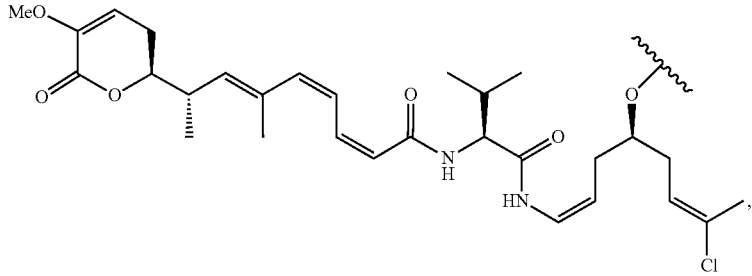
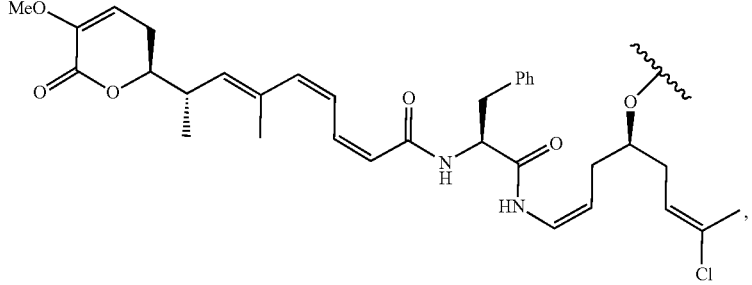
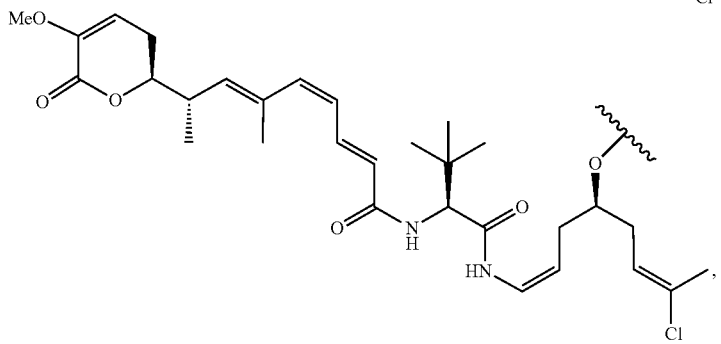

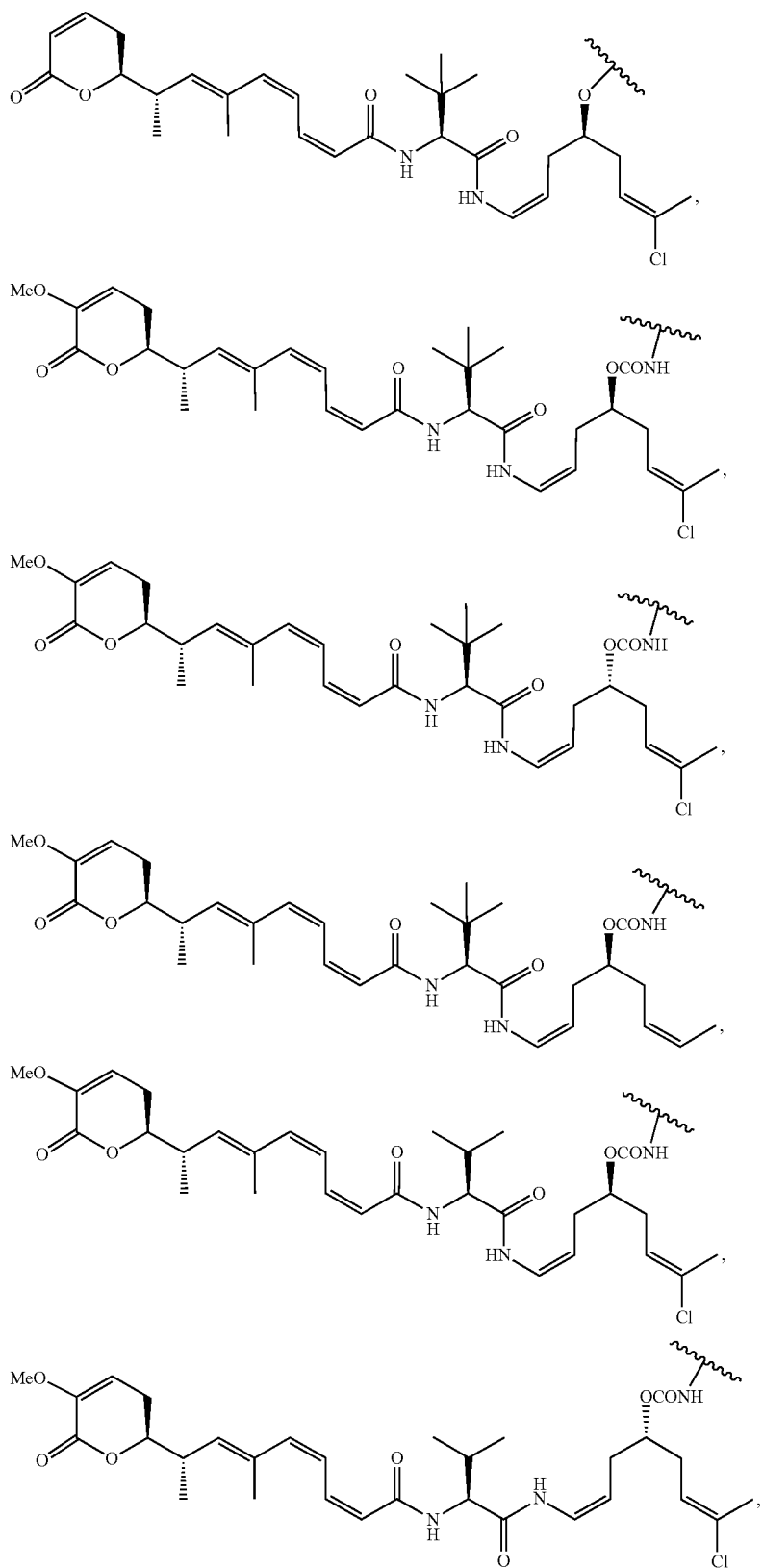

-continued
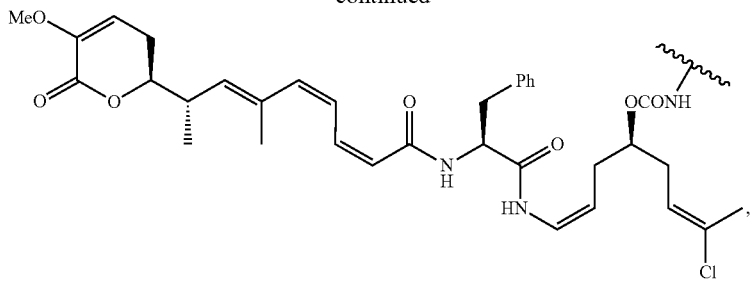
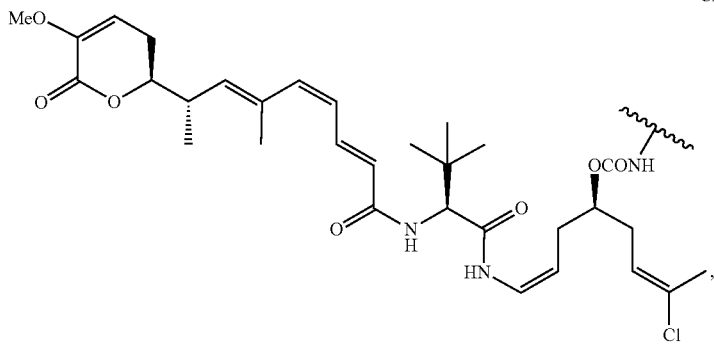
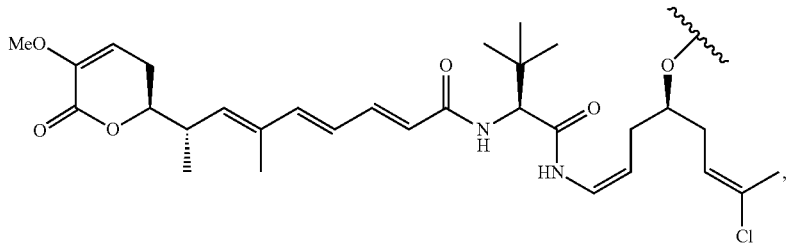
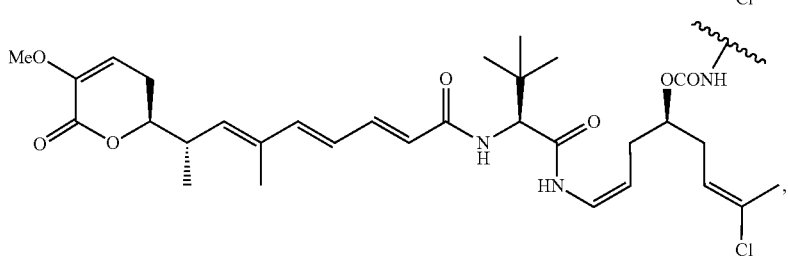
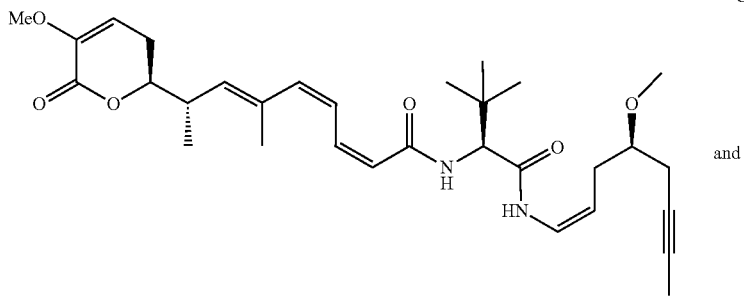
and
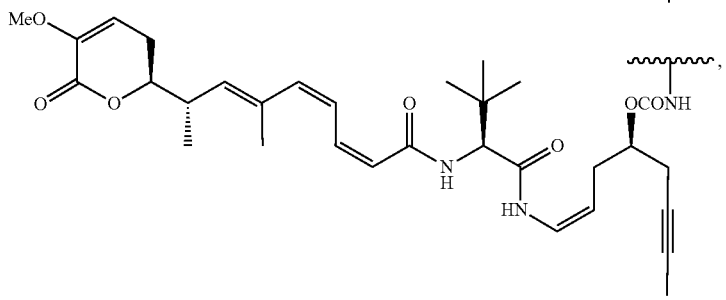

wherein the wavy line indicates the point of covalent attachment to X.

6. The compound of formula D-X-(AA)$_w$-L$_1$ or of formula D-X-(AA)$_w$-H according to claim 1 wherein:
R$_{19}$ is —C$_5$ alkylene-;
w is 0 or 2, and where w is 2, then (AA)$_w$ is of formula (III):

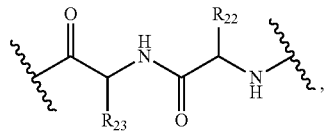

(III)

wherein R$_{22}$ is isopropyl, R$_{23}$ is —(CH$_2$)$_3$NHCONH$_2$, wherein the wavy lines indicate the point of covalent attachments to X (the wavy line to the left) and to L$_1$ or to a hydrogen atom (the wavy line to the right);
X is an extending group selected from —CONH(CH$_2$)$_3$NHCOOCH$_2$-phenylene-NH—, —CONH(CH$_2$)$_3$NH—, —CONH(CH$_2$)$_3$—S— and —CONH(CH$_2$)$_3$NHCO(CH$_2$)$_2$S—; and
D is a drug moiety of formula (Ia), or a pharmaceutically acceptable salt, ester, solvate, tautomer or stereoisomer thereof selected from:

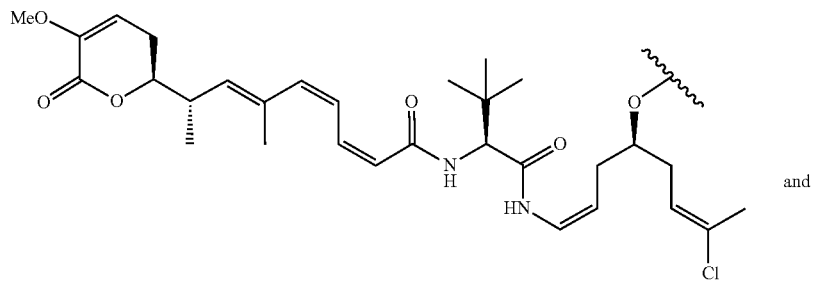

and

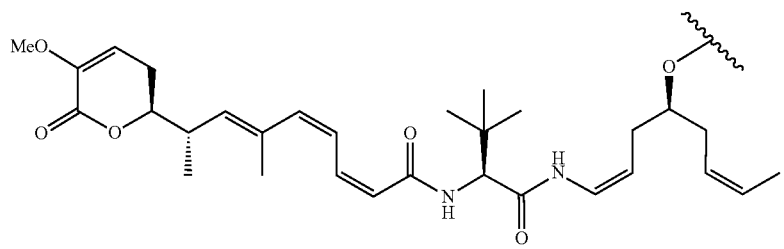

wherein the wavy line indicates the point of covalent attachment to X.

7. The compound of formula D-X-(AA)$_w$-L$_1$ according to claim 1 selected from:

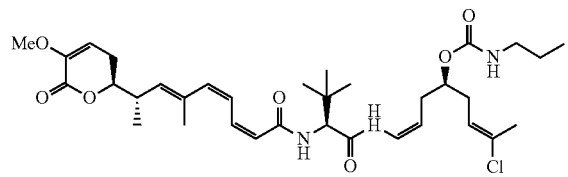

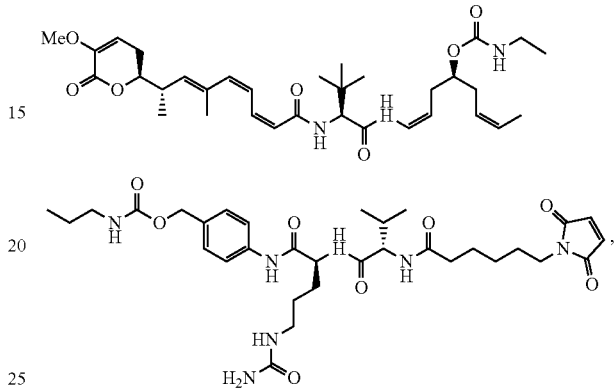

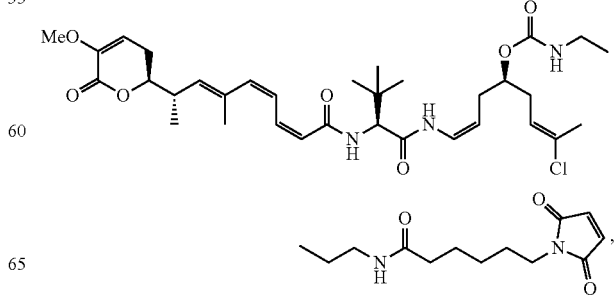

229
-continued
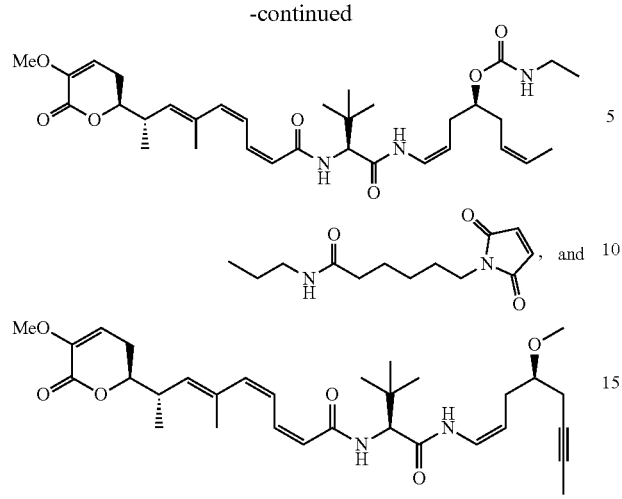
, and
230
-continued
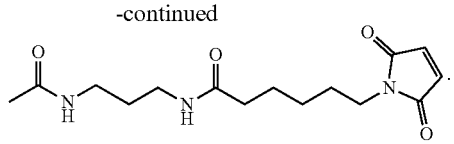
8. A compound of formula D-X-(AA)$_w$-H according to claim 1 selected from:
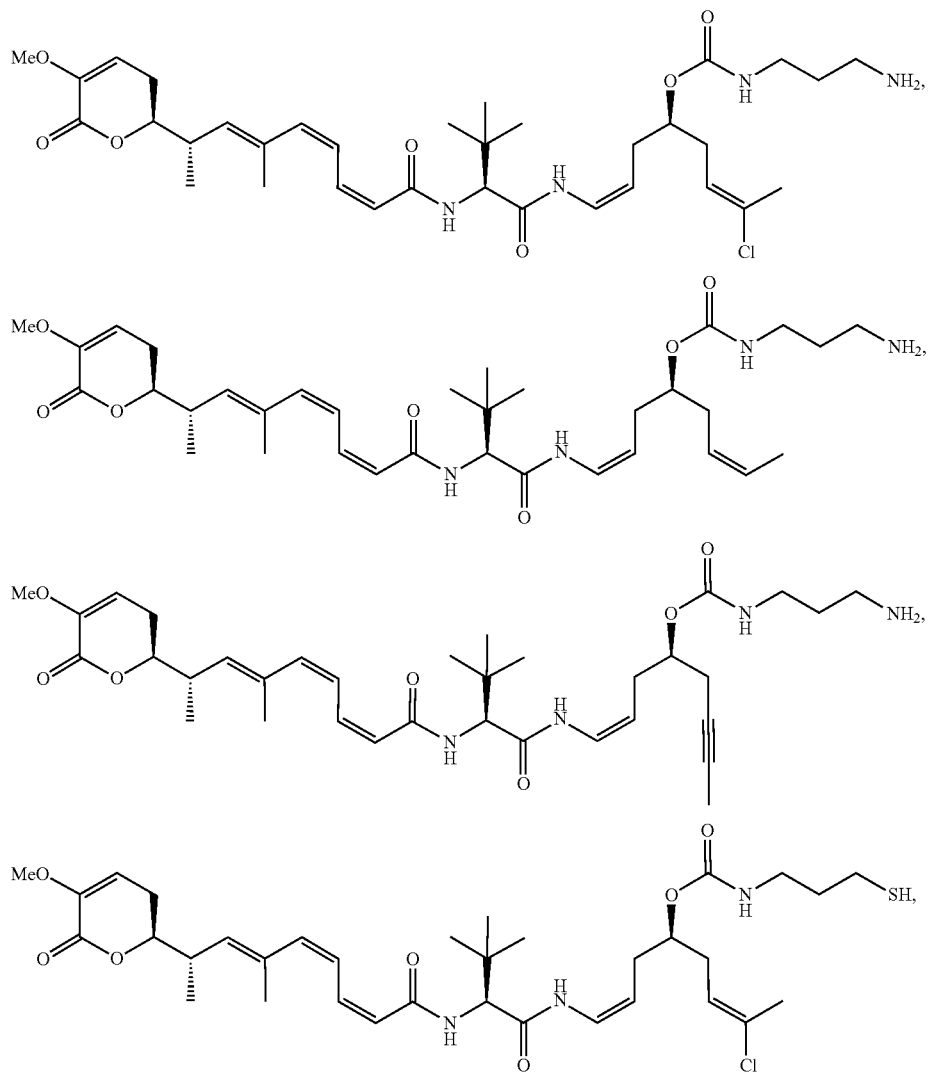

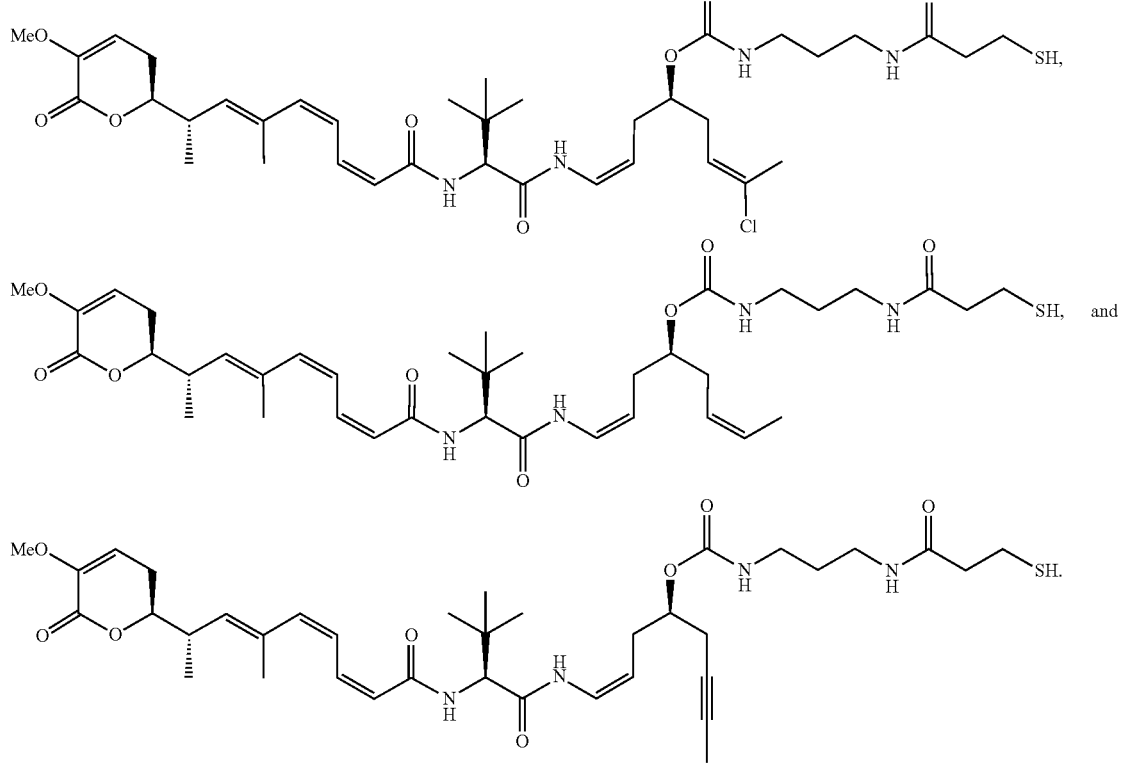

UNITED STATES PATENT AND TRADEMARK OFFICE
CERTIFICATE OF CORRECTION

| | | |
|---|---|---|
| PATENT NO. | : 12,410,148 B2 | Page 1 of 1 |
| APPLICATION NO. | : 17/553745 | |
| DATED | : September 9, 2025 | |
| INVENTOR(S) | : Carmen Cuevas Marchante et al. | |

It is certified that error appears in the above-identified patent and that said Letters Patent is hereby corrected as shown below:

On the Title Page

Item (71) Applicant, please change PARMA MAR, S.A. to read as -- PHARMA MAR, S.A --.

Signed and Sealed this
Twenty-first Day of October, 2025

John A. Squires
*Director of the United States Patent and Trademark Office*